United States Patent
Toure et al.

(10) Patent No.: US 12,012,398 B2
(45) Date of Patent: Jun. 18, 2024

(54) BICYCLIC COMPOUNDS AS ANDROGEN RECEPTOR MODULATORS

(71) Applicant: NIDO BIOSCIENCES, INC., Cambridge, MA (US)

(72) Inventors: Bakary-Barry Toure, Weston, MA (US); Mark Andrew Gallop, San Francisco, CA (US)

(73) Assignee: NIDO BIOSCIENCES, INC., Watertown, MA (US)

( * ) Notice: Subject to any disclaimer, the term of this patent is extended or adjusted under 35 U.S.C. 154(b) by 0 days.

(21) Appl. No.: 17/811,731

(22) Filed: Jul. 11, 2022

(65) Prior Publication Data

US 2023/0039586 A1  Feb. 9, 2023

Related U.S. Application Data

(60) Provisional application No. 63/235,468, filed on Aug. 20, 2021, provisional application No. 63/220,763, filed on Jul. 12, 2021.

(51) Int. Cl.
| | |
|---|---|
| *C07D 405/14* | (2006.01) |
| *C07D 209/42* | (2006.01) |
| *C07D 307/85* | (2006.01) |
| *C07D 401/12* | (2006.01) |
| *C07D 403/04* | (2006.01) |
| *C07D 403/12* | (2006.01) |
| *C07D 405/12* | (2006.01) |
| *C07D 413/12* | (2006.01) |
| *C07D 471/04* | (2006.01) |
| *C07D 495/04* | (2006.01) |

(52) U.S. Cl.
CPC ......... *C07D 405/14* (2013.01); *C07D 209/42* (2013.01); *C07D 307/85* (2013.01); *C07D 401/12* (2013.01); *C07D 403/04* (2013.01); *C07D 403/12* (2013.01); *C07D 405/12* (2013.01); *C07D 413/12* (2013.01); *C07D 471/04* (2013.01); *C07D 495/04* (2013.01)

(58) Field of Classification Search
CPC .. C07D 401/12; C07D 403/04; C07D 403/12; C07D 405/12; C07D 413/12
See application file for complete search history.

(56) References Cited

FOREIGN PATENT DOCUMENTS

| EP | 4008718 A1 | 6/2022 | | |
|---|---|---|---|---|
| JP | 2012107001 A | * | 6/2012 | |
| WO | WO-2005097129 A2 | * | 10/2005 | ........... C07D 471/04 |
| WO | WO 2008/075196 A1 | | 6/2008 | |
| WO | WO 2009/158375 A1 | | 12/2009 | |
| WO | WO 2014/037900 A1 | | 3/2014 | |
| WO | WO-2014037900 A1 | * | 3/2014 | ........... A61K 31/404 |
| WO | WO 2015/150097 A1 | | 10/2015 | |
| WO | WO 2018/189553 A1 | | 10/2018 | |
| WO | WO 2021/060890 A1 | | 4/2021 | |

OTHER PUBLICATIONS

CAS Abstract of RN 2345115-29-7 (Year: 2019).*
CAS Abstract of RN 2338919-85-8 (Year: 2019).*
CAS Abstract of RN 1901955-74-5 (Year: 2016).*
CAS Abstract of RN 1899979-27-1 (Year: 2016).*
CAS Abstract of RN 1795082-31-3 (Year: 2015).*
CAS Abstract of RN 1209542-75-5 (Year: 2010).*
CAS Abstract of RN 91822-76-3 (Year: 2010).*
CAS Abstract of RN 313966-55-1 (Year: 2001).*
Saturated Bioisosteres of ortho-Substituted Benzenes Angew. Chem. Int. Ed. 2020, 59, 20515-20521 (Year: 2020).*
Ban et al., "Discovery of 1 H-Indole-2-carboxamides as Novel Inhibitors of the Androgen Receptor Binding Function 3 (BF3)", *Journal of Medicinal Chemistry* 57(15):6867-6872 (2014).
International Search Report and Written Opinion for International Application No. PCT/US2022/036682, dated Dec. 5, 2022, 24 pages.
Diana et al., "Synthesis of the New Ring System Pyrrolizino[2,3-b]indol-4(5H)-one", *Tetrahedron* 67(19):3374-3379 (2011).
La Regina et al., "Synthesis, structure-activity relationships and molecular modeling studies of new indole inhibitors of monoamine oxidases A and B", *Bioorganic & Medicinal Chemistry* 16(22):9729-9740 (2008).
Zhang et al., "Supporting Information Copper-Mediated Cascade C—H/N—H Annulation of Indolocarboxamides with Arynes: Construction of Tetracyclic Indoloquinoline Alkaloids Contents", *Organic Letters*, 8 (2017).

* cited by examiner

*Primary Examiner* — Theodore R. Howell
*Assistant Examiner* — Pierre P Eleniste
(74) *Attorney, Agent, or Firm* — Lathrop GPM LLP; Brian C. Trinque; Nicole Sassu

(57) ABSTRACT

Provided herein are compounds that bind to BF3 of an androgen receptor (AR), which can modulate the AR for the treatment of Kennedy's disease.

12 Claims, No Drawings

BICYCLIC COMPOUNDS AS ANDROGEN RECEPTOR MODULATORS

RELATED APPLICATIONS

This application claims priority to U.S. Provisional Application No. 63/220,763 filed on Jul. 12, 2021, and to U.S. Provisional Application No. 63/235,468 filed on Aug. 20, 2021, the contents of which are hereby incorporated in their entirety.

BACKGROUND

Prostate cancer is the second leading cause of male cancer-related death in Western countries (Damber, J. E. and Aus, G. *Lancet* (2008) 371:1710-1721). Numerous studies have shown that the androgen receptor (AR) is central not only to the development of prostate cancer, but also the progression of the disease to the castration resistance state (Taplin, M. E. et al. J. Clin. Oncol. (2003) 21:2673-8; and Tilley, W. D. et al. Cancer Res. (1994) 54:4096-4102). Thus, effective inhibition of human AR remains one of the most effective therapeutic approaches to the treatment of advanced, metastatic prostate cancer.

Androgen receptor activity is also liked to Kennedy's disease, also referred to as Spinal Bulbar Muscular Atrophy (SBMA). Kennedy's disease is an x-linked recessive motor neuron disease resulting from disruptions in the transmission of nerve cell signals in the brain stem and spinal cord. The motor neuron disruptions are more noticeable relative to other cells because of the higher number of the androgen receptors residing in nerve cells. The nerve cells in a Kennedy's patient gradually become increasingly dysfunctional and eventually die, leaving the muscles unable to contract, resulting in atrophy of the muscles throughout the body, but most noticeably in the extremities, face and throat. The binding of testosterone to the AR is thought to cause the disease.

There remains a need for effective treatments for both prostate cancer and Kennedy's disease.

SUMMARY

Provided herein are compounds that modulate androgen receptor (AR) activity. In particular, the compounds disclosed herein show inhibition of Androgen Receptor Binding Function-3 (BF3).

In an aspect, provided herein is a compound of Formula I:

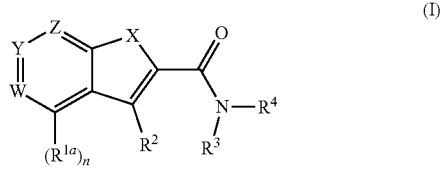

(I)

or a pharmaceutically acceptable salt thereof; wherein the variables are defined herein.

In another aspect, provided herein is a compound of Formula II:

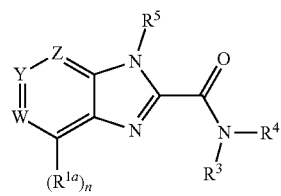

(II)

or a pharmaceutically acceptable salt thereof; wherein the variables are defined herein.

In yet another aspect, provided herein is a compound of Formula III:

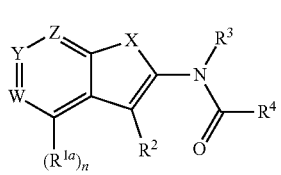

(III)

or a pharmaceutically acceptable salt thereof; wherein the variables are defined herein.

In another aspect, provided herein is a pharmaceutical composition comprising a compound of any one of the compounds disclosed herein and a pharmaceutically acceptable carrier.

In yet another aspect, provided herein is a method of treating a neurodegenerative disorder in a subject in need thereof comprising administering to the subject a therapeutically effective amount of a compound disclosed herein. In an embodiment of the methods, the neurodegenerative disorder is spinal bulbar muscular atrophy (SBMA).

In still another aspect, provided herein is a method of modulating androgen receptor (AR) activity in a subject in need thereof comprising administering to the subject a therapeutically effective amount of a compound disclosed herein.

In another aspect, provided herein is a method of treating cancer in a subject in need thereof comprising administering to the subject a therapeutically effective amount of a compound disclosed herein. In an embodiment, the cancer is prostate cancer.

DETAILED DESCRIPTION

Androgens play a role in a wide range of developmental and physiological responses, for example, male sexual differentiation, maintenance of spermatogenesis, and male gonadotropin regulation (Ross, R. K., et al., *Eur. Urol.* 35, 355-361 (1999); Thomson, A. A., *Reproduction* 121, 187-195 (2001); Tanji, N., et al., *Arch. Androl.* 47, 1-7 (2001)). Androgens are also associated with the development of prostate carcinogenesis. Induction of prostatic carcinogenesis in rodent models has been associated with androgens (R. L. Noble, *Cancer Res.* 37, 1929-1933 (1977); R. L. Noble, *Oncology* 34, 138-141 (1977)), and men receiving androgens in the form of anabolic steroids are reported to have a higher incidence of prostate cancer (Roberts, J. T., and Essenhigh, D. M., *Lancet* 2, 742 (1986); Jackson, J. A., et al., Arch. Intern. Med. 149, 2365-2366 (1989); Guinan, P. D., et al., Am. J. Surg. 131, 599-600 (1976)). Furthermore, prostate cancer does not develop if humans or dogs are castrated before puberty (Wilson, J. D., and Roehrborn, C., J. Clin. Endocrinol. Metab. 84, 4324-4331 (1999); G. Wilding, Cancer Surv. 14, 113-130 (1992)). Castration of adult males causes involution of the prostate and apoptosis of prostatic epithelium (Bruckheimer, E. M., and Kyprianou, N., Cell Tissue Res. 301, 153-162 (2000); J. T. Isaacs, Prostate 5, 545-557 (1984)). This dependency on androgens provides the underlying rationale for treating prostate cancer with chemical or surgical castration (i.e., androgen ablation).

The AR possesses a modular organization characteristic of all nuclear receptors. It is comprised of an N-terminal domain, a central DNA binding domain, a short hinge region, and C-terminal domain that contains a hormone ligand binding pocket and the Activation Function-2 (AF2) site (Gao, W. Q. et al. Chem. Rev. (2005) 105:3352-3370). The latter represents a hydrophobic groove on the AR surface which is flanked with regions of positive and negative charges, "charge clamps," that are significant for binding AR activation factors (Zhou, X. E. et al. J. Biol. Chem. (2010) 285:9161-9171). Recent studies have identified a novel site on the AR called Binding Function 3 (BF3) that is involved into AR transcriptional activity.

It has been proposed that a small molecule bound to the BF3 site could cause the AR protein to undergo an allosteric modification that prevents AR interactions with co-activators. Importantly, the BF3 site is located near, but distinct from, the ligand-binding site that is normally targeted by conventional anti-androgen drugs. Compounds such as flufenamic acid (FLU F), thriiodothyronine (T3) and 3,3',5-triiodo thyroacetic acid (TRIAC) can bind to the BF3 cleft, inhibit AF2 interactions, and interfere with AR activity (Estebanez-Perpina, E. et al. Proc. Natl. Acad. Sci. USA (2007) 104:16074-16079). While these compounds revealed the importance of the BF3 site, they have shown a low potency ($I_{50}$>50 µM) and were found to bind non-specifically to the AR.

The activation of AR follows a well-characterized pathway: in the cytoplasm, the receptor is associated with chaperone proteins that maintain agonist binding conformation of the AR (Georget, V. et al. Biochemistry (2002) 41:11824-11831). Upon binding of an androgen, the AR undergoes a series of conformational changes, disassociation from chaperones, dimerization and translocation into the nucleus (Fang, Y. F. et al. J. Biol. Chem. (1996) 271: 28697-28702; and Wong, C. I. et al. J. Biol. Chem. (1993) 268:19004-19012) where it further interacts with co-activator proteins at the AF2 site (Zhou, X. E. et al. J. Biol. Chem. (2010) 285:9161-9171). This event triggers the recruitment of RNA polymerase II and other factors to form a functional transcriptional complex with the AR.

Notably, the current anti-androgens such as bicalutamide, flutamide, nilutamide and MDV3100, all target this particular process. However, instead of affecting the AR-cofactor interaction directly, these anti-androgens act indirectly, by binding to the AR ligand binding site. Thus, by preventing androgens from binding they also prevent conformational changes of the receptor that are necessary for co-activator interactions. While treatment with these AR inhibitors can initially suppress prostate cancer growth, long term hormone therapy becomes progressively less effective (Taplin, M. E. et al. J. Clin. Oncol. (2003) 21:2673-8; and Tilley, W. D. et al. Cancer Res. (1994) 54:4096-4102). Factors that make the AR less sensitive to conventional anti-androgens include resistance mutations at the ligand binding site that can even lead AR antagonists to act as agonists further contributing to cancer progression (Chen, Y. et al. Lancet Oncol. (2009) 10:981-991).

Androgens also play a role in female cancers. One example is ovarian cancer where elevated levels of androgens are associated with an increased risk of developing ovarian cancer (K. J. Helzlsouer, et al., JAMA 274, 1926-1930 (1995); R. J. Edmondson, et al, Br J Cancer 86, 879-885 (2002)). The AR has been detected in a majority of ovarian cancers (H. A. Risch, J. Natl. Cancer Inst. 90, 1774-1786 (1998); B. R. Rao & B. J. Slotman, Endocr. Rev. 12, 14-26 (1991); G. M. Clinton & W. Hua, Crit. Rev. Oncol. Hematol. 25, 1-9 (1997)), whereas estrogen receptor-alpha (ERα) and the progesterone receptor are detected in less than 50% of ovarian tumors.

Spinal and bulbar muscular atrophy (SBMA), popularly known as Kennedy's disease, is a progressive debilitating neurodegenerative disorder resulting in muscle cramps and progressive weakness due to degeneration of motor neurons in the brainstem and spinal cord. The condition is associated with mutation of the androgen receptor (AR) gene and is inherited in an X-linked recessive manner. As with many genetic disorders, no cure is known, although research continues. Because of its endocrine manifestations related to the impairment of the AR gene, SBMA can be viewed as a variation of the disorders of the androgen insensitivity syndrome (AIS). It is also related to other neurodegenerative diseases caused by similar mutations, such as Huntington's disease.

The BF3 site is an attractive target for direct inhibition of the AR co-activation.

Definitions

It is appreciated that certain features of the present disclosure, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like. The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —$OCH_2CH_2O$— and $OCH_2CH_2CH_2O$—. In some embodiments, the two 0 atoms of a C n-m dialkoxy group may be attached to the same B atom to form a 5- or 6-membered heterocycloalkyl group. The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "aromatic" refers to a carbocycle or heterocycle having one or more polyunsaturated rings having aromatic character (i.e., having (4n+2) delocalized □ (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thio-phenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazabicyclo[2.2.1]-heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound," as used herein, is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds provided herein, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences,* 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use,* (Wiley, 2002). In some embodiments, the compounds described herein include the N-oxide forms.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

Compounds as described herein may be administered to a subject. As used herein, a "subject" may be a human, non-human primate, rat, mouse, cow, horse, pig, sheep, goat, dog, cat, etc. In an embodiment, the subject is human.

Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK).

Some compounds and compositions as described herein may interfere with a mechanism specific to ligand-dependent activation (e.g., accessibility of the ligand binding domain (LBD) to androgen) or to ligand-independent activation of the AR.

Various alternative embodiments and examples of the invention are described herein. These embodiments and examples are illustrative and should not be construed as limiting the scope of the invention.

Compounds

In an aspect, provided herein is a compound of Formula I:

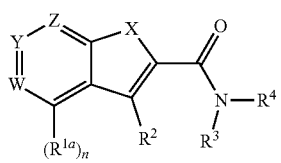

(I)

or a pharmaceutically acceptable salt thereof;
wherein
X is O, S, or $NR^5$;
W, Y, and Z are each independently selected from the group consisting of CH, $CR^1$, and N;
each $R^1$ is independently selected from the group consisting of halo, CN, $C_{1-6}$ alkyl, $C_{1-6}$ haloalkyl, $C_{1-6}$ alkoxy, $C_{1-6}$ alkyl-$NH_2$, $C_{3-10}$ cycloalkyl, $O(C_{3-10}$ cycloalkyl), $NH_2$, $NH(C_{1-6}$ alkyl), and $N(C_{1-6}$ alkyl)$_2$;
$R^{1a}$ is selected from the group consisting of halo, CN, $C_{1-6}$ alkyl, $C_{1-6}$ haloalkyl, $C_{1-6}$ alkoxy, $C_{1-6}$ alkyl-$NH_2$, $C_{3-10}$ cycloalkyl, $O(C_{3-10}$ cycloalkyl), $NH_2$, $NH(C_{1-6}$ alkyl), and $N(C_{1-6}$ alkyl)$_2$;
$R^2$ is selected from the group consisting of H, halo, $C_{1-6}$ alkyl, 5-10 membered heteroaryl, $C_{3-10}$ cycloalkyl, $C_{6-10}$ aryl, wherein heteroaryl, cycloalkyl, and aryl are each optionally substituted one, two, or three times with $R^6$;
$R^3$ is selected from the group consisting of H, $C_{1-6}$ alkyl, 3-10 membered heterocycloalkyl, wherein $C_{1-6}$ alkyl is optionally substituted one, two, or three times with $R^7$;
$R^4$ is selected from the group consisting of $C_{1-6}$ alkyl, $C_{6-10}$ aryl, 5-10 membered heteroaryl, $C_{3-10}$ cycloalkyl, and 3-10 membered heterocycloalkyl, wherein alkyl, aryl, heteroaryl, cycloalkyl, and heterocycloalkyl are each optionally substituted one, two, three, or four times with $R^8$;
alternatively, $R^3$ and $R^4$, together with the nitrogen atom to which they are attached, form a 3-10 membered heterocycloalkyl;
$R^5$ is selected from the group consisting of H, $C_{1-6}$ alkyl, $C_{1-6}$ alkyl-O—$C_{1-6}$ alkyl-TMS, $C_{1-6}$ alkyl-$C_{3-10}$ cycloalkyl, $C_{1-6}$ alkyl-OH, $C_{1-6}$ alkyl-O—$C_{1-6}$ alkyl, $C_{1-6}$ alkyl-(3-10 membered heterocycloalkyl), and $C_{1-6}$ alkyl-$NH_2$;
alternatively, when Z is $CR^1$, then $R^5$ and $R^1$, together with the atoms to which they are attached, optionally form a 4-7 membered heterocyclic ring;
each $R^6$ is independently selected from the group consisting of $C_{1-6}$ alkyl, $NH_2$, $NH(C_{1-6}$ alkyl), and $N(C_{1-6}$ alkyl)$_2$;
each $R^7$ is independently selected from the group consisting of O—$C_{1-6}$ alkyl, $NH_2$, $NH(C_{1-6}$ alkyl), $N(C_{1-6}$ alkyl)$_2$, and $C_{3-10}$ cycloalkyl;
each $R^8$ is independently selected from the group consisting of 5-10 membered heteroaryl, 3-10 membered heterocycloalkyl, $C_{3-10}$ cycloalkyl, CN, halo, $C_{1-6}$ alkyl, and OH, wherein heteroaryl is optionally substituted with $C_{1-4}$ alkyl; and
n is 0 or 1.
In an embodiment,
X is $NR^5$;
W, Y, and Z are each independently selected from the group consisting of CH, $CR^1$, and N;
each $R^1$ is independently selected from the group consisting of halo, CN, and $C_{1-6}$ alkoxy;
$R^{1a}$ is halo;
$R^2$ is H;
$R^3$ is selected from the group consisting of H, $C_{1-6}$ alkyl, 3-10 membered heterocycloalkyl, wherein $C_{1-6}$ alkyl is optionally substituted one, two, or three times with $R^7$;
$R^4$ is selected from the group consisting of $C_{1-6}$ alkyl, $C_{6-10}$ aryl, 5-10 membered heteroaryl, $C_{3-10}$ cycloalkyl, and 3-10 membered heterocycloalkyl, wherein alkyl, aryl, heteroaryl, cycloalkyl, and heterocycloalkyl are each optionally substituted one, two, three, or four times with $R^8$;
alternatively, $R^3$ and $R^4$, together with the nitrogen atom to which they are attached, form a 4-6 membered heterocycloalkyl;
$R^5$ is H or $C_{1-6}$ alkyl;
each $R^7$ is independently selected from the group consisting of O—$C_{1-6}$ alkyl, $NH_2$, $NH(C_{1-6}$ alkyl), $N(C_{1-6}$ alkyl)$_2$, and $C_{3-10}$ cycloalkyl;

each $R^8$ is independently selected from the group consisting of 5-10 membered heteroaryl, 3-10 membered heterocycloalkyl, $C_{3-10}$ cycloalkyl, CN, halo, $C_{1-6}$ alkyl, and OH, wherein heteroaryl is optionally substituted with 014 alkyl; and n is 0 or 1.

In another embodiment,

X is $NR^5$;

W is CH;

Y is N;

Z is $CR^1$;

$R^1$ is independently selected from the group consisting of halo, CN, and $C_{1-6}$ alkoxy;

$R^2$ is H;

$R^3$ is H or $C_{1-6}$ alkyl, wherein $C_{1-6}$ alkyl is optionally substituted one, two, or three times with $R^7$;

$R^4$ is selected from the group consisting of $C_{1-6}$ alkyl, phenyl, 5-6 membered heteroaryl, $C_{3-7}$ cycloalkyl, and 3-7 membered heterocycloalkyl, wherein alkyl, phenyl, heteroaryl, cycloalkyl, and heterocycloalkyl are each optionally substituted one, two, three, or four times with $R^8$;

alternatively, $R^3$ and $R^4$, together with the nitrogen atom to which they are attached, form a 3-10 membered heterocycloalkyl;

$R^5$ is H or $C_{1-6}$ alkyl;

each $R^7$ is independently selected from the group consisting of O—$C_{1-6}$ alkyl, $NH_2$, and cyclopropyl;

each $R^8$ is independently selected from the group consisting of 5-6 membered heteroaryl, 3-7 membered heterocycloalkyl, $C_{3-7}$ cycloalkyl, CN, halo, $C_{1-6}$ alkyl, and OH, wherein heteroaryl is optionally substituted with $C_{1-4}$ alkyl; and n is 0.

In another embodiment,

X is $NR^5$;

W is CH;

Y is CH;

Z is $CR^1$;

$R^1$ is independently selected from the group consisting of halo, CN, and $C_{1-6}$ alkoxy;

$R^2$ is H;

$R^3$ is H or $C_{1-6}$ alkyl, wherein $C_{1-6}$ alkyl is optionally substituted one, two, or three times with $R^7$;

$R^4$ is selected from the group consisting of $C_{1-6}$ alkyl, phenyl, 5-6 membered heteroaryl, $C_{3-7}$ cycloalkyl, and 3-7 membered heterocycloalkyl, wherein alkyl, phenyl, heteroaryl, cycloalkyl, and heterocycloalkyl are each optionally substituted one, two, three, or four times with $R^8$;

alternatively, $R^3$ and $R^4$, together with the nitrogen atom to which they are attached, form a 3-10 membered heterocycloalkyl;

$R^5$ is H or $C_{1-6}$ alkyl;

each $R^7$ is independently selected from the group consisting of O—$C_{1-6}$ alkyl, $NH_2$, and cyclopropyl;

each $R^8$ is independently selected from the group consisting of 5-6 membered heteroaryl, 3-7 membered heterocycloalkyl, $C_{3-7}$ cycloalkyl, CN, halo, $C_{1-6}$ alkyl, and OH, wherein heteroaryl is optionally substituted with $C_{1-4}$ alkyl; and n is 0.

In another embodiment,

X is $NR^5$;

W is CH;

Y is CH or $CR^1$;

Z is $CR^1$;

$R^1$ is independently selected from the group consisting of halo, CN, and $C_{1-6}$ alkoxy;

$R^2$ is H;

$R^3$ is H or $C_{1-6}$ alkyl, wherein $C_{1-6}$ alkyl is optionally substituted one, two, or three times with $R^7$;

$R^4$ is selected from the group consisting of $C_{1-6}$ alkyl, phenyl, 5-6 membered heteroaryl, $C_{3-7}$ cycloalkyl, and 3-7 membered heterocycloalkyl, wherein alkyl, phenyl, heteroaryl, cycloalkyl, and heterocycloalkyl are each optionally substituted one, two, three, or four times with $R^8$;

alternatively, $R^3$ and $R^4$, together with the nitrogen atom to which they are attached, form a 3-10 membered heterocycloalkyl;

$R^5$ is H or $C_{1-6}$ alkyl;

each $R^7$ is independently selected from the group consisting of O—$C_{1-6}$ alkyl, $NH_2$, and cyclopropyl;

each $R^8$ is independently selected from the group consisting of 5-6 membered heteroaryl, 3-7 membered heterocycloalkyl, $C_{3-7}$ cycloalkyl, CN, halo, $C_{1-6}$ alkyl, and OH, wherein heteroaryl is optionally substituted with $C_{1-4}$ alkyl; and n is 0.

In yet another embodiment, each $R^1$ is independently selected from the group consisting of halo, CN, $C_{1-4}$ haloalkyl, $C_{1-3}$ alkoxy, $O(C_{3-6}$ cycloalkyl), $N(C_{1-4}$ alkyl$)_2$, and $NH(C_{1-4}$ alkyl). In still another embodiment, each $R^1$ is independently selected from the group consisting of halo, CN, and $C_{1-6}$ alkoxy.

In an embodiment, $R^{1a}$ is halo. In another embodiment, n is 0.

In yet another embodiment, $R^2$ is H. In still another embodiment, $R^2$ is selected from the group consisting of halo, $C_{1-3}$ alkyl, $C_{3-6}$ cycloalkyl, 5-membered heteroaryl, and phenyl, wherein heteroaryl is optionally substituted with $C_{1-3}$ alkyl.

In an embodiment, $R^3$ is H or $C_{1-4}$ alkyl, wherein $C_{1-4}$ alkyl is optionally substituted one, two, or three times with $R^7$. In another embodiment, $R^3$ is selected from the group consisting of $C_{1-6}$ alkyl-O—$C_{1-3}$ alkyl, $C_{1-6}$ alkyl-$NH_2$, $C_{1-6}$ alkyl-$C_{3-6}$ cycloalkyl, and 5-membered heteroaryl.

In yet another embodiment, $R^4$ is selected from the group consisting of $C_{1-6}$ alkyl, phenyl, 5-6 membered heteroaryl, $C_{3-7}$ cycloalkyl, and 3-7 membered heterocycloalkyl, wherein alkyl, phenyl, heteroaryl, cycloalkyl, and heterocycloalkyl are each optionally substituted one, two, three, or four times with $R^8$.

In still another embodiment, $R^4$ is selected from the group consisting of $C_{1-4}$ alkyl, $C_{1-4}$ alkyl-(5-6 membered heteroaryl), $C_{1-4}$ alkyl-(5-7 membered heterocycloalkyl), $C_{1-4}$ alkyl-($C_{3-6}$ cycloalkyl), phenyl, 5-6 membered heteroaryl, $C_{3-7}$ cycloalkyl, and 3-6 membered heterocycloalkyl, wherein phenyl, heteroaryl, cycloalkyl, and heterocycloalkyl are each optionally substituted with one, two, three, or four substituents selected from the group consisting of CN, halo, $C_{1-4}$ alkyl, and OH.

In an embodiment, $R^3$ and $R^4$, together with the nitrogen atom to which they are attached, form 5-membered heterocycloalkyl.

In another embodiment, $R^5$ is H or $C_{1-6}$ alkyl. In yet another embodiment, $R^5$ is selected from the group consisting of $C_{1-3}$ alkyl-O—$C_{1-3}$ alkyl-TMS, $C_{1-3}$ alkyl-cyclopropyl, $C_{1-3}$ alkyl-OH, $C_{1-3}$ alkyl-O—$C_{1-3}$ alkyl, $C_{1-3}$ alkyl(5-7 membered heterocycloalkyl), and $C_{1-3}$ alkyl-$NH_2$.

In yet another embodiment, the compound of Formula I is a compound of Formula Ia:

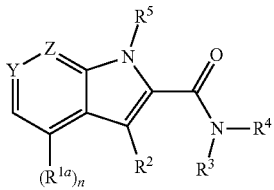

(Ia)

or a pharmaceutically acceptable salt thereof.

In still another embodiment, the compound of Formula I is a compound of Formula Ib:

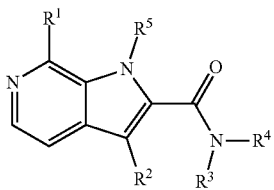

(Ib)

or a pharmaceutically acceptable salt thereof.

In an embodiment, the compound of Formula I is a compound of Formula Ic:

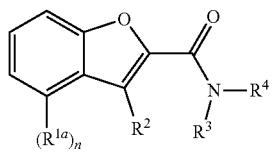

(Ic)

or a pharmaceutically acceptable salt thereof.

In another embodiment, the compound of Formula I is selected from the group consisting of a compound from Table 1, or a pharmaceutically acceptable salt thereof.

In another aspect, provided herein is a compound of Formula II:

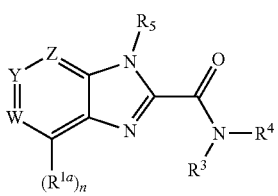

(II)

or a pharmaceutically acceptable salt thereof;
wherein
W, Y, and Z are each independently selected from the group consisting of CH, $CR^1$, and N;
each $R^1$ is independently selected from the group consisting of halo, CN, $C_{1-6}$ alkyl, $C_{1-6}$ haloalkyl, $C_{1-6}$ alkoxy, $C_{1-6}$ alkyl-$NH_2$, $C_{3-10}$ cycloalkyl, $O(C_{3-10}$ cycloalkyl), $NH_2$, $NH(C_{1-6}$ alkyl), and $N(C_{1-6}$ alkyl)$_2$;

$R^{1a}$ is selected from the group consisting of halo, CN, $C_{1-6}$ alkyl, $C_{1-6}$ haloalkyl, $C_{1-6}$ alkoxy, $C_{1-6}$ alkyl-$NH_2$, $C_{3-10}$ cycloalkyl, $O(C_{3-10}$ cycloalkyl), $NH_2$, $NH(C_{1-6}$ alkyl), and $N(C_{1-6}$ alkyl)$_2$;

$R^3$ is selected from the group consisting of H, $C_{1-6}$ alkyl, 3-10 membered heterocycloalkyl, wherein $C_{1-6}$ alkyl is optionally substituted one, two, or three times with $R^7$;

$R^4$ is selected from the group consisting of $C_{1-6}$ alkyl, $C_{6-10}$ aryl, 5-10 membered heteroaryl, $C_{3-10}$ cycloalkyl, and 3-10 membered heterocycloalkyl, wherein alkyl, aryl, heteroaryl, cycloalkyl, and heterocycloalkyl are each optionally substituted one, two, three, or four times with $R^8$;

alternatively, $R^3$ and $R^4$, together with the nitrogen atom to which they are attached, form a 3-10 membered heterocycloalkyl;

$R^5$ is selected from the group consisting of H, $C_{1-6}$ alkyl, $C_{1-6}$ alkyl-O—$C_{1-6}$ alkyl, $C_{1-6}$ alkyl-O—$C_{1-6}$ alkyl-TMS, $C_{1-6}$ alkyl-$C_{3-10}$ cycloalkyl, $C_{1-6}$ alkyl-OH, $C_{1-6}$ alkyl-O—$C_{1-6}$ alkyl, $C_{1-6}$ alkyl-(3-10 membered heterocycloalkyl), and $C_{1-6}$ alkyl-$NH_2$;

alternatively, when Z is $CR^1$, then $R^5$ and $R^1$, together with the atoms to which they are attached, optionally form a 4-7 membered heterocyclic ring;

each $R^7$ is independently selected from the group consisting of O—$C_{1-6}$ alkyl, $NH_2$, $NH(C_{1-6}$ alkyl), $N(C_{1-6}$ alkyl)$_2$, and $C_{3-10}$ cycloalkyl;

each $R^8$ is independently selected from the group consisting of 5-10 membered heteroaryl, 3-10 membered heterocycloalkyl, $C_{3-10}$ cycloalkyl, CN, halo, $C_{1-6}$ alkyl, and OH, wherein heteroaryl is optionally substituted with O14 alkyl; and n is 0 or 1.

In an embodiment of Formula II,
W, Y, and Z are each independently selected from the group consisting of CH, $CR^1$, and N;
each $R^1$ is independently selected from the group consisting of halo, CN, and $C_{1-6}$ alkoxy;
$R^{1a}$ is halo;
$R^3$ is selected from the group consisting of H, $C_{1-6}$ alkyl, 3-10 membered heterocycloalkyl, wherein $C_{1-6}$ alkyl is optionally substituted one, two, or three times with $R^7$;
$R^4$ is selected from the group consisting of $C_{1-6}$ alkyl, $C_{6-10}$ aryl, 5-10 membered heteroaryl, $C_{3-10}$ cycloalkyl, and 3-10 membered heterocycloalkyl, wherein alkyl, aryl, heteroaryl, cycloalkyl, and heterocycloalkyl are each optionally substituted one, two, three, or four times with $R^8$;
alternatively, $R^3$ and $R^4$, together with the nitrogen atom to which they are attached, form a 4-6 membered heterocycloalkyl;
$R^5$ is H or $C_{1-6}$ alkyl;
each $R^7$ is independently selected from the group consisting of O—$C_{1-6}$ alkyl, $NH_2$, $NH(C_{1-6}$ alkyl), $N(C_{1-6}$ alkyl)$_2$, and $C_{3-10}$ cycloalkyl;
each $R^8$ is independently selected from the group consisting of 5-10 membered heteroaryl, 3-10 membered heterocycloalkyl, $C_{3-10}$ cycloalkyl, CN, halo, $C_{1-6}$ alkyl, and OH, wherein heteroaryl is optionally substituted with $C_{1-4}$ alkyl; and
n is 0 or 1.

In another embodiment, the compound of Formula II is a compound of Formula IIa:

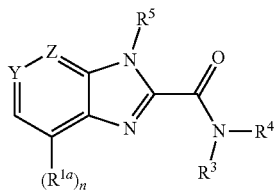

(IIa)

or a pharmaceutically acceptable salt thereof; wherein

Y and Z are each independently CH or CR$^1$.

In yet another embodiment, the compound of Formula II is selected from the group consisting of

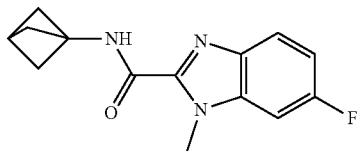

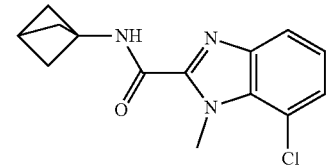

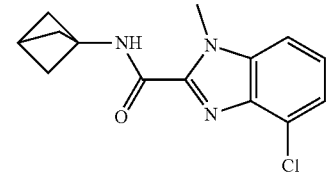

or a pharmaceutically acceptable salt thereof.

In yet another aspect, provided herein is a compound of Formula III:

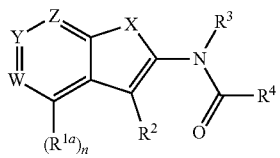

(III)

or a pharmaceutically acceptable salt thereof; wherein

X is O, S, or NR$^5$;

W, Y, and Z are each independently selected from the group consisting of CH, CR$^1$, and N;

each R$^1$ is independently selected from the group consisting of halo, CN, C$_{1-6}$ alkyl, C$_{1-6}$ haloalkyl, C$_{1-6}$ alkoxy, C$_{1-6}$ alkyl-NH$_2$, C$_{3-10}$ cycloalkyl, O(C$_{3-10}$ cycloalkyl), NH$_2$, NH(C$_{1-6}$ alkyl), and N(C$_{1-6}$ alkyl)$_2$;

R$^{1a}$ is selected from the group consisting of halo, CN, C$_{1-6}$ alkyl, C$_{1-6}$ haloalkyl, C$_{1-6}$ alkoxy, C$_{1-6}$ alkyl-NH$_2$, C$_{3-10}$ cycloalkyl, O(C$_{3-10}$ cycloalkyl), NH$_2$, NH(C$_{1-6}$ alkyl), and N(C$_{1-6}$ alkyl)$_2$;

R$^2$ is selected from the group consisting of H, halo, C$_{1-6}$ alkyl, 5-10 membered heteroaryl, C$_{3-10}$ cycloalkyl, C$_{6-10}$ aryl, wherein heteroaryl, cycloalkyl, and aryl are each optionally substituted one, two, or three times with R$^6$;

R$^3$ is selected from the group consisting of H, C$_{1-6}$ alkyl, 3-10 membered heterocycloalkyl, wherein C$_{1-6}$ alkyl is optionally substituted one, two, or three times with R$^7$;

R$^4$ is selected from the group consisting of C$_{1-6}$ alkyl, C$_{6-10}$ aryl, 5-10 membered heteroaryl, C$_{3-10}$ cycloalkyl, and 3-10 membered heterocycloalkyl, wherein alkyl, aryl, heteroaryl, cycloalkyl, and heterocycloalkyl are each optionally substituted one, two, three, or four times with R$^8$;

alternatively, R$^3$ and R$^4$, together with the nitrogen atom to which they are attached, form a 3-10 membered heterocycloalkyl;

R$^5$ is selected from the group consisting of H, C$_{1-6}$ alkyl, C$_{1-6}$ alkyl-O—C$_{1-6}$ alkyl, C$_{1-6}$ alkyl-O—C$_{1-6}$ alkyl-TMS, C$_{1-6}$ alkyl-C$_{3-10}$ cycloalkyl, C$_{1-6}$ alkyl-OH, C$_{1-6}$ alkyl-O—C$_{1-6}$ alkyl, C$_{1-6}$ alkyl-(3-10 membered heterocycloalkyl), and C$_{1-6}$ alkyl-NH$_2$;

alternatively, when Z is CR$^1$, then R$^5$ and R$^1$, together with the atoms to which they are attached, optionally form a 4-7 membered heterocyclic ring;

each R$^6$ is independently selected from the group consisting of C$_{1-6}$ alkyl, NH$_2$, NH(C$_{1-6}$ alkyl), and N(C$_{1-6}$ alkyl)$_2$;

each R$^7$ is independently selected from the group consisting of O—C$_{1-6}$ alkyl, NH$_2$, NH(C$_{1-6}$ alkyl), N(C$_{1-6}$ alkyl)$_2$, and C$_{3-10}$ cycloalkyl;

each R$^8$ is independently selected from the group consisting of 5-10 membered heteroaryl, 3-10 membered heterocycloalkyl, C$_{3-10}$ cycloalkyl, CN, halo, C$_{1-6}$ alkyl, and OH, wherein heteroaryl is optionally substituted with 014 alkyl; and n is 0 or 1.

In an embodiment, the compound of Formula III is a compound of Formula IIIa:

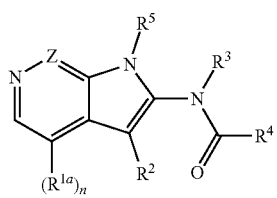

(IIIa)

or a pharmaceutically acceptable salt thereof.

In an embodiment of any of the formulae disclosed herein, R$^4$ is

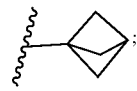

wherein R$^4$ is optionally substituted with one, two, three, or four substituents selected from the group consisting of CN, halo, C$_{1-4}$ alkyl, and OH.

In another embodiment, the compound of Formula III is

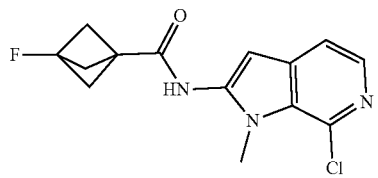 [SMILES: Cn1c(NC(=O)C23CC(F)(C2)C3)cc2ccnc(Cl)c21]

or a pharmaceutically acceptable salt thereof.

In an aspect, provided herein is a pharmaceutical composition comprising a compound provided herein, or a pharmaceutically acceptable salt thereof, and a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a 2H (i.e., deuterium) isotope.

In still another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds disclosed herein can be used in a method of treating a disease or condition in a subject, said method comprising administering to the subject a compound provided herein, or a pharmaceutical composition comprising the compound, and a pharmaceutically acceptable carrier.

In still another aspect, provided herein is a method of treating cancer in a subject in need thereof, comprising administering to the subject a therapeutically effective amount of a compound of Formula I or Formula II.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers. In an embodiment, the cancer is prostate cancer. In another embodiment, the cancer is ovarian cancer.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In an embodiment, the cancer is selected from the group consisting of hematological cancers, sarcomas, lung cancers, gastrointestinal cancers, genitourinary tract cancers, liver cancers, bone cancers, nervous system cancers, gynecological cancers, and skin cancers.

In an embodiment, the cancer is selected from the group consisting of pancreatic cancer, cervical cancer, colon cancer, ovarian cancer, breast cancer, pancreatic cancer, carcinoma, and adenocarcinoma.

In another embodiment, the cancer is pancreatic cancer. In yet another embodiment, the cancer is a solid tumor.

In an aspect, provided herein is a method of treating a neurodegenerative disorder in a subject in need thereof comprising administering to the subject a therapeutically effective amount of a compound of Formula I or II, or a pharmaceutically acceptable salt thereof.

In an embodiment, the neurodegenerative disorder is an x-linked recessive disorder. In another embodiment, the neurodegenerative disorder is spinal bulbar muscular atrophy (SBMA).

In another aspect, provided herein is a method of modulating androgen receptor (AR) activity in a subject in need thereof comprising administering to the subject a therapeutically effective amount of a compound of Formula I or II, or a pharmaceutically acceptable salt thereof.

In an embodiment, the androgen receptor (AR) undergoes allosteric modulation. In another embodiment, modulating androgen receptor (AR) activity treats spinal bulbar muscular atrophy (SBMA) in the subject.

In an embodiment of the methods, the subject is human.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Administration/Dosage/Formulations

In another aspect, provided herein is a pharmaceutical composition comprising at least one compound provided herein, together with a pharmaceutically acceptable carrier. Actual dosage levels of the active ingredients in the pharmaceutical compositions discussed herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated as pharmaceutical compositions using one or more pharmaceutically acceptable excipients or carriers. In one embodiment, the pharmaceutical compositions comprise a therapeutically effective amount of a disclosed compound and a pharmaceutically acceptable carrier.

Routes of administration of any of the compositions disclosed herein include oral, nasal, rectal, intravaginal, parenteral, buccal, sublingual or topical. The compounds disclosed herein may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present application as set forth.

EXAMPLES

Example A: Synthetic Procedures

Abbreviations

ACN acetonitrile
AcOH acetic acid
DCM dichloromethane
DMF dimethylformamide
dppf 1,1'-bis(diphenylphosphino)ferrocene
EtOAc ethyl acetate
FC flash chromatography
MeOH methanol
MTBE methyl tert-butyl ether
PE petroleum ether
TEA triethylamine Intermediate C1

3-[5-[(tert-butoxycarbonyl)amino]-6-methylpyridin-2-yl]-6-fluoro-1H-indole-2-carboxylic acid

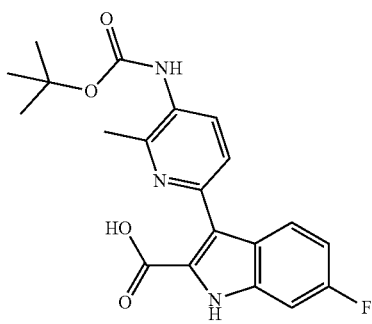 [SMILES: Cc1nc(-c2c(C(=O)O)[nH]c3cc(F)ccc23)ccc1NC(=O)OC(C)(C)C]

Step 1: To a solution of 6-fluoro-1H-indole-2-carboxylic acid (2.00 g, 11.20 mmol) in dichloromethane (10 mL) and methanol (1 mL) was added (trimethylsilyl)diazomethane (8 mL, 16.00 mmol, 2 mol/L in hexane) dropwise at 0° C. The resulting solution was stirred at 0° C. for 2 h. The residue was concentrated and purified by FC with 0-25% ethyl acetate in petroleum ether to afford methyl 6-fluoro-1H-indole-2-carboxylate (1.60 g, 74%) as a yellow solid. MS m/z 194.1 [M+1]$^+$.

Step 2: To a solution of methyl 6-fluoro-1H-indole-2-carboxylate (1.60 g, 8.30 mmol) in tetrahydrofuran (5 mL) was added N-bromosuccinimide (1.50 g, 8.30 mmol). The resulting solution was stirred at room temperature for 2 h. The resulting solution was extracted with ethyl acetate, dried over sodium sulfate, filtered, and concentrated under vacuum to afford methyl 3-bromo-6-fluoro-1H-indole-2-carboxylate (2.20 g, crude) as a yellow solid. MS m/z 272.0 [M+1]$^+$.

Step 3: To a solution of methyl 3-bromo-6-fluoro-1H-indole-2-carboxylate (2.20 g, 8.10 mmol) in dichloromethane (8.00 mL) were added di(tert-butyl) carbonate (2.10 g, 9.70 mmol), triethylamine (2.40 g, 24.20 mmol) and 4-dimethylaminopyridine (98 mg, 0.80 mmol). The resulting solution was stirred at room temperature for 2 h. The mixture was concentrated under vacuum. The residue was purified by FC with 0-20% ethyl acetate in petroleum ether to afford 1-tert-butyl 2-methyl 3-bromo-6-fluoroindole-1,2-dicarboxylate (2.90 g, 96%) as a yellow solid. MS m/z 372.0 [M+1]$^+$.

Step 4: To a solution of 1-tert-butyl 2-methyl 3-bromo-6-fluoroindole-1,2-dicarboxylate (2.90 g, 7.80 mmol) in dioxane (8 mL) was added bis(pinacolato)diboron (5.90 g, 23.30 mmol), potassium acetate (2.30 g, 23.30 mmol) and [1,1'-bis(diphenylphosphino)ferrocene]dichloropalladium (II) (570 mg, 0.70 mmol) under nitrogen atmosphere. The resulting solution was stirred at 80° C. overnight. The reaction mixture was concentrated under vacuum. The residue was purified by FC with 0-25% ethyl acetate in petroleum ether to afford 1-tert-butyl 2-methyl 6-fluoro-3-(4,4,5,5-tetramethyl-1,3,2-dioxaborolan-2-yl)indole-1,2-dicarboxylate (3.20 g, 97%) as a yellow solid. MS m/z 420.2 [M+1]$^+$.

Step 5: To a solution of 1-tert-butyl 2-methyl 6-fluoro-3-(4,4,5,5-tetramethyl-1,3,2-dioxaborolan-2-yl)indole-1,2-dicarboxylate (2.00 g, 4.70 mmol) in dioxane (8 mL) and water (0.5 mL) was added tert-butyl N-(6-bromo-2-methylpyridin-3-yl)carbamate (1.40 g, 4.70 mmol), 2-(dicyclohexylphosphino)-2',4',6'-triisopropylbiphenyl (227 mg, 0.40 mmol), tripotassium orthophosphate (3.00 g, 14.30 mmol) and chloro(2-dicyclohexylphosphino-2',4',6'-triisopropyl-1,1'-biphenyl)[2-(2'-amino-1,1'-biphenyl)]palladium(II) (375 mg, 0.40 mmol) under nitrogen atmosphere. The resulting solution was stirred at 100° C. for 3 h. The reaction mixture was concentrated under vacuum. The residue was purified by FC with 0-20% ethyl acetate in petroleum ether to afford 1-tert-butyl 2-methyl 3-[5-[(tert-butoxycarbonyl)amino]-6-methylpyridin-2-yl]-6-fluoroindole-1,2-dicarboxylate (1.40 g, 58%) as a yellow solid. MS m/z 500.2 [M+1]$^+$.

Step 6: To a solution of 1-tert-butyl 2-methyl 3-[5-[(tert-butoxycarbonyl)amino]-6-methylpyridin-2-yl]-6-fluoroindole-1,2-dicarboxylate (1.20 g, 2.40 mmol) in tetrahydrofuran (5 mL) and water (5 mL) was added lithium hydroxide (230 mg, 9.60 mmol). The resulting solution was stirred at 55° C. overnight. The reaction mixture was acidified with HCl (conc.) to pH 4. The resulting solution was extracted with ethyl acetate. The organic layer was dried over sodium sulfate, filtered and concentrated under vacuum to afford 3-[5-[(tert-butoxycarbonyl)amino]-6-methylpyridin-2-yl]-6-fluoro-1H-indole-2-carboxylic acid (C$_1$) (500 mg, 54%) as a yellow solid. MS m/z 386.1 [M+1]$^+$. $^1$H NMR (400 MHz, DMSO-d$_6$) δ 12.31 (s, 1H), 9.20 (s, 1H), 8.32-8.07 (m, 3H), 7.30 (dd, J=9.4, 2.4 Hz, 1H), 7.14 (td, J=9.2, 2.4 Hz, 1H), 2.56 (s, 3H), 1.52 (s, 9H).

Intermediate C3

7-bromo-1-benzofuran-2-carboxylic acid

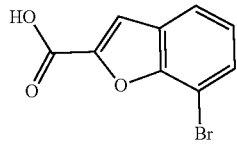 [SMILES: O=C(O)c1cc2cccc(Br)c2o1]

Step 1: To a solution of 2-bromophenol (10.00 g, 57.80 mmol) and magnesium chloride (8.25 g, 86.70 mmol) in acetonitrile (100 mL) were added triethylamine (11.69 g, 115.60 mmol) and paraformaldehyde (12.14 g, 404.60 mmol) at room temperature. The mixture was stirred at 80° C. for 16 h. The mixture was concentrated under vacuum. The residue was diluted by ethyl acetate and washed by water. The organic layer was dried over anhydrous sodium sulfate, filtered and concentrated under vacuum to afford 3-bromo-2-hydroxybenzaldehyde (13.00 g, crude) as an off-white solid, which was used directly without purification. MS m/z 200.9 [M+1]$^+$.

Step 2: To a solution of 3-bromo-2-hydroxybenzaldehyde (5.00 g, 24.87 mmol) and potassium carbonate (10.31 g, 74.62 mmol) in N,N-dimethylformamide (35 mL) was added ethyl bromoacetate (6.23 g, 37.31 mmol). The mixture was stirred at 90° C. for 16 h. The mixture was diluted by water and extracted with ethyl acetate. The organic layer was dried over sodium sulfate, filtered, and concentrated under vacuum. The residue was purified by FC with 0-80% ethyl acetate in petroleum ether to afford ethyl 7-bromo-1-benzofuran-2-carboxylate (2.37 g, 30% over two steps) as a light-yellow solid. MS m/z 269.0 [M+1]$^+$.

Step 3: A mixture of ethyl 7-bromo-1-benzofuran-2-carboxylate (2.00 g, 7.43 mmol) and lithium hydroxide (0.96 g, 40.08 mmol) in tetrahydrofuran (10 mL) and water (10 mL) was stirred at room temperature for 2 h. The organic solvent was removed under vacuum. The remaining aqueous solution was acidified with HCl (aq., 2N) and extracted with ethyl acetate. The combined organic layers were washed with brine, dried over anhydrous sodium sulfate, filtered, and concentrated under vacuum to afford 7-cyano-1-benzofuran-2-carboxylic acid (C3) (2.05 g, crude) as a white solid. MS m/z 241.0 [M+1]$^+$.

Intermediate C4

7-(trifluoromethyl)benzofuran-2-carboxylic acid

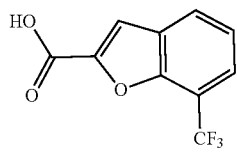

Step-1: To a solution of 2-hydroxy-3-(trifluoromethyl) benzaldehyde (1.00 g, 5.26 mmol) in N,N-dimethylformamide (10.00 mL) was added ethyl bromoacetate (1.05 g, 6.31 mmol). The mixture was stirred at room temperature for 20 min, this was followed by the addition of potassium carbonate (1.45 g, 10.52 mmol) at room temperature. Then the mixture was heated at 100° C. for 16 h. The mixture was diluted by water and extracted with ethyl acetate. The organic layer was dried over sodium sulfate, filtered, and concentrated under vacuum. The residue was purified by FC with 0-50% ethyl acetate in petroleum ether to afford ethyl 7-(trifluoromethyl)benzofuran-2-carboxylate (0.50 g, 36%) as a white oil. MS m/z 259.1 [M+1]$^+$.

Step-2: A mixture of ethyl 7-(trifluoromethyl)-1-benzofuran-2-carboxylate (500 mg, 1.93 mmol) and lithium hydroxide (46 mg, 1.94 mmol) in tetrahydrofuran (2.80 mL) and water (2.80 mL) was stirred at room temperature for 2 h. The mixture was acidified by HCl (aq., 2N) and extracted with ethyl acetate. The combined organic layers were washed with brine, dried over anhydrous sodium sulfate, filtered, and concentrated under vacuum. The residue was purified by reverse-phase FC with 20-60% acetonitrile in water to afford 7-(trifluoromethyl)benzofuran-2-carboxylic acid (C4) (290 mg, 65%) as a white solid. MS m/z 229.1 [M–1]$^-$.

Intermediate C5

6-fluoro-1-(phenylsulfonyl)-1H-indole-2-carboxylic acid

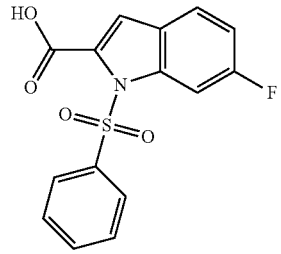

Step-1: To a mixture of 6-fluoro-1H-indole-2-carboxylic acid (5.00 g, 27.93 mmol) in methanol (50 mL) was added concentrated sulfuric acid (1 mL). The mixture was stirred at 40° C. for 2 h. The mixture was diluted with ethyl acetate and washed with saturated sodium bicarbonate aqueous solution. The organic layer was dried over anhydrous sodium sulfate, filtered, and concentrated under vacuum to afford methyl 6-fluoro-1H-indole-2-carboxylate (5.30 g, crude) as a brown solid. MS m/z 194.2 [M+1]$^+$.

Step-2: To a stirred solution of methyl 6-fluoro-1H-indole-2-carboxylate (5.00 g, 25.88 mmol) in N,N-dimethylformamide (50 mL) was added sodium hydride (930 mg, 23.25 mmol, 60% in mineral oil) at 5° C. The mixture was warmed to room temperature and then stirred for 30 min before benzenesulfonyl chloride (4.60 g, 25.88 mmol) was added dropwise at room temperature. The resulting mixture was stirred for 2 h before the reaction was quenched using water and extracted with ethyl acetate. The organic layer was washed with brine, dried over anhydrous sodium sulfate, filtered, and concentrated under vacuum. The residue was purified by FC with 0-60% ethyl acetate in petroleum ether to afford methyl 6-fluoro-1-(phenylsulfonyl)-1H-indole-2-carboxylate (3.30 g, 36% over two steps) as a yellow solid. MS m/z 334.0 [M+1]⁺.

Step-3: A mixture of methyl 6-fluoro-1-(phenylsulfonyl)-1H-indole-2-carboxylate (3.00 g, 9.88 mmol) and potassium hydroxide (2.00 g, 35.71 mmol) in tetrahydrofuran (18 mL), ethanol (18 mL) and water (18 mL) was stirred at room temperature for 2 h. The aqueous solution was acidified with HCl (2 N) to pH 3~4. The mixture was extracted with ethyl acetate. The organic layer was washed with brine, dried over anhydrous sodium sulfate, filtered, and concentrated under vacuum to afford 6-fluoro-1-(phenylsulfonyl)-1H-indole-2-carboxylic acid (C5) (2.70 g, crude) as a yellow solid. MS m/z 320.1 [M+1]⁺.

Intermediate C6

7-chloro-1-{[2-(trimethylsilyl)ethoxy]methyl}indole-2-carboxylic acid

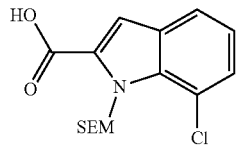

Step-1: To a mixture of 7-chloro-1H-indole-2-carboxylic acid (1 g, 5.1 mmol) in MeOH (10 mL) was added H$_2$SO$_4$ (752 mg, 7.7 mmol) at 0° C. The resulting mixture was stirred at room temperature overnight. The residue was basified to pH 8 with saturated NaHCO$_3$ (aq.). The resulting mixture was extracted with EtOAc. The combined organic layers were washed with brine, dried over anhydrous Na$_2$SO$_4$. After filtration, the filtrate was concentrated under reduced pressure. The resulting mixture was concentrated under vacuum. This resulted in methyl 7-chloro-1H-indole-2-carboxylate (1 g, 93.3%) as a brown solid. MS m/z 210.0 [M+1]⁺

Step-2: To a mixture of methyl 7-chloro-1H-indole-2-carboxylate (1 g, 4.770 mmol) in DMF (5 mL) was added NaH (229 mg, 9.541 mmol). The resulting mixture was stirred at 0° C. for 30 min under nitrogen atmosphere. To the above mixture was added SEMCl (1.59 g, 9.541 mmol). The resulting mixture was brought to room temperature and stirred for 2 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-30% ethyl acetate in PE to afford methyl 7-chloro-1-[[2-(trimethylsilyl)ethoxy]methyl]indole-2-carboxylate (1.4 g, 86.35%) as a brown oil. MS m/z 340.1 [M+1]⁺

Step-3: To a mixture of methyl 7-chloro-1-{[2-(trimethylsilyl)ethoxy]methyl}indole-2-carboxylate (1.4 g, 4.1 mmol) in THF (5 mL) was added H$_2$O (5 mL) was added LiOH (294 mg, 12.3 mmol). The resulting mixture was stirred at room temperature overnight. The aqueous solution was acidified with HCl (2 N) to pH 3~4. This resulted in 7-chloro-1-{[2-(trimethylsilyl)ethoxy]methyl}indole-2-carboxylic acid (C6) (1.3 g, crude) as a white solid. MS m/z 326.1 [M+1]⁺

Intermediate C7

7-chloro-1H-pyrrolo[2,3-c]pyridine-2-carboxylic acid

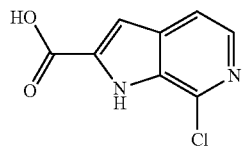 [SMILES: O=C(O)c1cc2ccnc(Cl)c2[nH]1]

To a mixture of ethyl 7-chloro-1H-pyrrolo[2,3-c]pyridine-2-carboxylate (300 mg, 1.34 mmol) in THF (2 mL) and H$_2$O (2 mL) was added LiOH (160 mg, 6.677 mmol). The resulting mixture was stirred at room temperature for 2 h. The aqueous solution was acidified with HCl (2 N) to pH 3~4. The resulting mixture was concentrated under vacuum. The residue was purified by reverse-phase FC with 0-20% ACN in H$_2$O to afford 7-chloro-1H-pyrrolo[2,3-c]pyridine-2-carboxylic acid (C7) (170 mg, 64.75%) as a yellow solid. MS m/z 197.0 [M+1]⁺

Intermediate C8

7-methoxy-1H-pyrrolo[2,3-c]pyridine-2-carboxylic acid

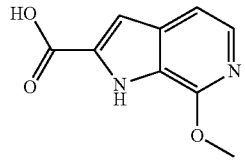

Step-1: To a mixture of ethyl 7-chloro-1H-pyrrolo[2,3-c]pyridine-2-carboxylate (400 mg, 1.781 mmol) in toluene (5 mL) were added MeOH (1 mL), Cs$_2$CO$_3$ (870 mg, 2.671 mmol), t-BuBrettPhos (86 mg, 0.178 mmol) and [Pd(allyl)Cl]$_2$ (26 mg, 0.071 mmol). The resulting mixture was stirred at 80° C. for 1 h under nitrogen atmosphere. The resulting mixture was concentrated under vacuum. The residue was purified by FC with 0-50% ethyl acetate in petroleum ether to afford methyl 7-methoxy-1H-pyrrolo[2,3-c]pyridine-2-carboxylate (240 mg, 65.37%) as a yellow solid. MS m/z 207.1 [M+1]⁺

Step-2: To a mixture of methyl 7-methoxy-1H-pyrrolo[2,3-c]pyridine-2-carboxylate (210 mg, 1.018 mmol) in THF (2 mL) and H$_2$O (2 mL) was added LiOH (122 mg, 5.092 mmol) at 0° C. The resulting mixture was stirred at room temperature for 2 h. The aqueous solution was acidified with HCl (2 N) to pH 3~4. The resulting mixture was concentrated under vacuum. The residue was purified by reverse-phase FC with 0-20% ACN in H$_2$O to afford 7-methoxy-1H-pyrrolo[2,3-c]pyridine-2-carboxylic acid (C8) (150 mg, 76.64%) as a yellow solid. MS m/z 193.1 [M+1]⁺

Intermediate C9

7-chloro-1-[[2-(trimethylsilyl)ethoxy]methyl]pyrrolo[2,3-c]pyridine-2-carboxylic acid

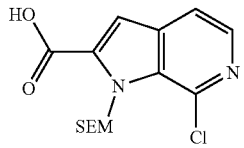 [SMILES: C[Si](C)(C)CCOCn1c(C(=O)O)cc2ccnc(Cl)c21]

Step-1: To a mixture of ethyl 7-chloro-1H-pyrrolo[2,3-c]pyridine-2-carboxylate (500 mg, 2.226 mmol) in DMF (10 mL) was added $K_2CO_3$ (922 mg, 6.677 mmol) and SEMCl (742 mg, 4.452 mmol). The resulting mixture was heated to 80° C. for 1 h. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% ethyl acetate in PE to afford ethyl 7-chloro-1-[[2-(trimethylsilyl)ethoxy]methyl]pyrrolo[2,3-c]pyridine-2-carboxylate (650 mg, 74.06%) as a yellow oil. MS m/z 355.1 [M+1]+

Step-2: To a mixture of ethyl 7-chloro-1-[[2-(trimethylsilyl)ethoxy]methyl]pyrrolo[2,3-c]pyridine-2-carboxylate (600 mg, 1.691 mmol) in THF (6 mL) and $H_2O$ (6 mL) was added LiOH (202 mg, 8.453 mmol). The resulting mixture was stirred at room temperature overnight. The aqueous solution was acidified with HCl (2 N) to pH 3~4. The resulting mixture was concentrated under vacuum. This resulted in 7-chloro-1-[[2-(trimethylsilyl)ethoxy]methyl]pyrrolo[2,3-c]pyridine-2-carboxylic acid (C9) (600 mg, crude) as a white solid. MS m/z 327.1 [M+1]+

Intermediate C10

1H-pyrrolo[2,3-c]pyridine-2-carboxylic acid

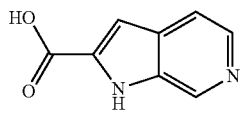 [SMILES: O=C(O)c1cc2ccncc2[nH]1]

To a mixture of ethyl 1H-pyrrolo[2,3-c]pyridine-2-carboxylate (200 mg, 1.05 mmol) in THF (5 mL) and $H_2O$ (5 mL) was added LiOH (126 mg, 5.25 mmol). The resulting mixture was stirred at room temperature overnight. The aqueous solution was acidified with HCl (2 N) to pH 3~4. The resulting mixture was concentrated under vacuum. This resulted 1H-pyrrolo[2,3-c]pyridine-2-carboxylic acid (C10) (150 mg, crude) as a white solid. MS m/z 163.0 [M+1]+

Intermediate C11

7-chloro-3-cyclopropyl-1H-indole-2-carboxylic acid

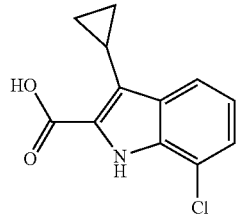 [SMILES: O=C(O)c1[nH]c2c(Cl)cccc2c1C1CC1]

Step-1: To a mixture of methyl 7-chloro-1H-indole-2-carboxylate (1 g, 4.770 mmol) in THF (10 mL) was added NBS (0.85 g, 4.770 mmol). The resulting mixture was stirred at room temperature for 1 h followed by extraction with EtOAc. The combined organic layers were washed with brine, dried over anhydrous $Na_2SO_4$. After filtration, the filtrate was concentrated under reduced pressure. The resulting mixture was concentrated under vacuum. This resulted in methyl 3-bromo-7-chloro-1H-indole-2-carboxylate (1.2 g, 87%) as a brown solid. MS m/z 287.9 [M+1]+

Step-2: To a mixture of methyl 3-bromo-7-chloro-1H-indole-2-carboxylate (400 mg, 1.386 mmol) and cyclopropylboronic acid (119 mg, 1.386 mmol) in dioxane (5 mL) and $H_2O$ (0.5 mL) were added $K_2CO_3$ (383 mg, 2.773 mmol) and Pd(dppf)Cl₂ (101 mg, 0.139 mmol). The resulting mixture was stirred at 100° C. overnight under nitrogen atmosphere. The resulting mixture was concentrated under vacuum. The residue was purified by FC with 0-50% ethyl acetate in PE to afford methyl 7-chloro-3-cyclopropyl-1H-indole-2-carboxylate (194 mg, 56.04%) as a yellow solid. MS m/z 250.1 [M+1]+

Step-3: To a mixture of methyl 7-chloro-3-cyclopropyl-1H-indole-2-carboxylate (180 mg, 0.721 mmol) in THF (4 mL) and $H_2O$ (4 mL) was added LiOH (86 mg, 3.604 mmol). The resulting mixture was stirred at room temperature overnight. The aqueous solution was acidified with HCl (2 N) to pH 3~4. The resulting mixture was concentrated under vacuum. This resulted in 7-chloro-3-cyclopropyl-1H-indole-2-carboxylic acid (C11) (160 mg, crude) as a yellow solid. MS m/z 236.0 [M+1]+

Intermediate C12

3,7-dichloro-1H-indole-2-carboxylic acid

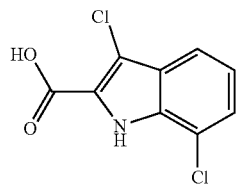

Step-1: To a mixture of 7-chloro-1H-indole-2-carboxylate (140 mg, 0.665 mmol) in THF (3 mL) were added NCS (64 mg, 0.477 mmol) at 0° C. The resulting mixture was stirred at 80° C. overnight. The mixture was concentrated under vacuum. The residue was purified by FC with 0-50% ethyl acetate in PE to afford 3,7-dichloro-1H-indole-2-carboxylate (180 mg, 38.65%) as a white solid MS m/z 244.0. [M−1]⁻.

Step-2: To a mixture of 3,7-dichloro-1H-indole-2-carboxylate (150 mg, 0.615 mmol) in THF (2 mL) and H$_2$O (2 mL) was added LiOH (73 mg, 3.073 mmol) at 0° C. The resulting mixture was stirred at room temperature overnight. The aqueous solution was acidified with HCl (2 N) to pH 3~4. The resulting mixture was concentrated under vacuum. This resulted in 3,7-dichloro-1H-indole-2-carboxylic acid (C12) (180 mg, crude) as a white solid. MS m/z 231.0. [M+1]⁺

Intermediate C13

7-chloro-3-(1-methylpyrazol-3-yl)-1H-indole-2-carboxylic acid

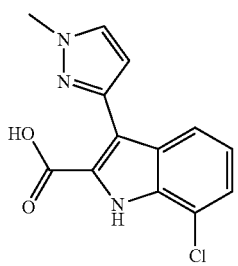 [SMILES: Cn1ccc(-c2c(C(=O)O)[nH]c3c(Cl)cccc23)n1]

Step-1: To a mixture of methyl 3-bromo-7-chloro-1H-indole-2-carboxylate (400 mg, 1.386 mmol) and 1-methyl-3-(4,4,5,5-tetramethyl-1,3,2-dioxaborolan-2-yl)pyrazole (289 mg, 1.386 mmol) in dioxane (5 mL) and H$_2$O (1 mL) were added K$_2$CO$_3$ (575 mg, 4.159 mmol) and Pd(dppf)Cl$_2$ (203 mg, 0.277 mmol). The resulting mixture was stirred at 100° C. for 1 h under nitrogen atmosphere. The mixture was concentrated under vacuum. The residue was purified by FC with 0-25% EtOAc in PE to afford methyl 7-chloro-3-(1-methylpyrazol-3-yl)-1H-indole-2-carboxylate (320 mg, 79.67%) as a light yellow solid. MS m/z 290.0 [M+1]⁺

Step-2: To a mixture of methyl 7-chloro-3-(1-methylpyrazol-3-yl)-1H-indole-2-carboxylate (200 mg, 0.690 mmol) in THF (3 mL) and H$_2$O (3 mL) was added LiOH (50 mg, 2.071 mmol) at 0° C. The resulting mixture was stirred at room temperature overnight. The aqueous solution was acidified with HCl (2 N) to pH 3~4. The resulting mixture was concentrated under vacuum. This resulted in 7-chloro-3-(1-methylpyrazol-3-yl)-1H-indole-2-carboxylic acid (C13) (170 mg, crude) as a light yellow solid. MS m/z 276.0 [M+1]⁺

Intermediate C14

7-chloro-3-phenyl-1H-indole-2-carboxylic acid

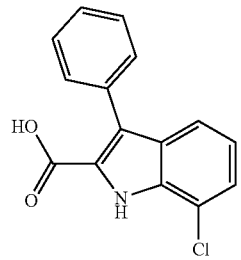 [SMILES: O=C(O)c1[nH]c2c(Cl)cccc2c1-c1ccccc1]

Step-1: To a mixture of methyl 3-bromo-7-chloro-1H-indole-2-carboxylate (350 mg, 1.213 mmol) and phenyl boronic acid (148 mg, 1.213 mmol) in dioxane (5 mL) and H$_2$O (1 mL) were added K$_2$CO$_3$ (503 mg, 3.639 mmol) and Pd(dppf)Cl$_2$ (178 mg, 0.243 mmol). The resulting mixture was stirred at 100° C. for 1 h under nitrogen atmosphere. The mixture was concentrated under vacuum. The residue was purified by FC with 0-50% EtOAc in PE to afford methyl 7-chloro-3-phenyl-1H-indole-2-carboxylate (160 mg, 46.16%) as a light yellow solid. MS m/z 284.0 [M−1]⁻

Step-2: To a mixture of methyl 7-chloro-3-phenyl-1H-indole-2-carboxylate (160 mg, 0.560 mmol) in THF (3 mL) and H$_2$O (3 mL) was added LiOH (41 mg, 1.680 mmol) at 0° C. The resulting mixture was stirred at room temperature overnight. The aqueous solution was acidified with HCl (2 N) to pH 3~4. The resulting mixture was concentrated under vacuum. This resulted in 7-chloro-3-phenyl-1H-indole-2-carboxylic acid (C14) (120 mg, crude) as a light yellow solid. MS m/z 270.0 [M−1]⁻

Intermediate C15

7-chloro-1-methylpyrrolo[2,3-c]pyridine-2-carboxylic acid

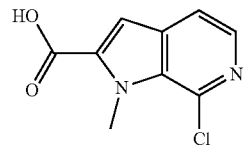

Step-1: To a mixture of ethyl 7-chloro-1H-pyrrolo[2,3-c]pyridine-2-carboxylate (400 mg, 1.781 mmol) in DMF (3 mL) was added NaH (85 mg, 3.562 mmol). The resulting mixture was stirred at 0° C. for 30 min under nitrogen atmosphere. To the above mixture was added CH$_3$I (303 mg, 2.137 mmol). The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford ethyl 7-chloro-1-methylpyrrolo[2,3-c]pyridine-2-carboxylate (277 mg, 65.18%) as a white solid. MS m/z 239.1 [M+1]⁺

Step-2: To a mixture of ethyl 7-chloro-1-methylpyrrolo[2,3-c]pyridine-2-carboxylate (150 mg, 0.628 mmol) in THF (2 mL) and H$_2$O (2 mL) was added LiOH (75 mg, 3.142 mmol). The resulting mixture was stirred at room temperature for 1 h. The aqueous solution was acidified with HCl (2 N) to pH 3~4. The resulting mixture was concentrated under vacuum. This resulted 7-chloro-1-methylpyrrolo[2,3-c]pyridine-2-carboxylic acid (C15) (130 mg, crude) as a yellow solid. MS m/z 211.0 [M+1]$^+$ Intermediate C16

7-chloro-1-ethylpyrrolo[2,3-c]pyridine-2-carboxylic acid

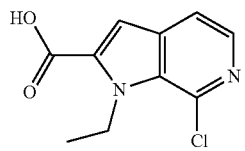

Step-1: To a mixture of ethyl 7-chloro-1H-pyrrolo[2,3-c]pyridine-2-carboxylate (400 mg, 1.781 mmol) in DMF (3 mL) was added NaH (85 mg, 3.562 mmol). The resulting mixture was stirred at 0° C. for 30 min under nitrogen atmosphere. To the above mixture was added CH$_3$CH$_2$I (333 mg, 2.137 mmol). The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford ethyl 7-chloro-1-ethylpyrrolo[2,3-c]pyridine-2-carboxylate (323 mg, 71.78%) as a white solid. MS m/z 253.1 [M+1]$^+$ Step-2: To a mixture of ethyl 7-chloro-1-ethylpyrrolo[2,3-c]pyridine-2-carboxylate (150 mg, 0.594 mmol) in THF (2 mL) and H$_2$O (2 mL) was added LiOH (75 mg, 3.142 mmol). The resulting mixture was stirred at room temperature for 1 h. The aqueous solution was acidified with HCl (2 N) to pH 3~4. The resulting mixture was concentrated under vacuum. This resulted 7-chloro-1-ethylpyrrolo[2,3-c]pyridine-2-carboxylic acid in acid (C16) (130 mg, crude) as a yellow solid. MS m/z 225.0 [M+1]$^+$ Intermediate C17

7-chloro-1-isopropylpyrrolo[2,3-c]pyridine-2-carboxylic acid

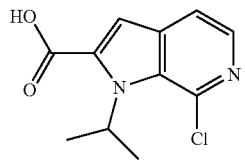 [SMILES: CC(C)n1c(C(=O)O)cc2ccnc(Cl)c21]

Step-1: To a mixture of ethyl 7-chloro-1H-pyrrolo[2,3-c]pyridine-2-carboxylate (300 mg, 1.335 mmol) in DMF (5 mL) was added K$_2$CO$_3$ (554 mg, 4.005 mmol) and 2-iodopropane (1.1 g, 6.675 mmol). The resulting mixture was stirred at 80° C. for 1 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% EtOAc in PE to afford ethyl 7-chloro-1-isopropylpyrrolo[2,3-c]pyridine-2-carboxylate (70 mg, 19.65%) as a yellow oil. MS m/z 266.9 [M+1]$^+$ Step-2: To a mixture of ethyl 7-chloro-1-isopropylpyrrolo[2,3-c]pyridine-2-carboxylate (70 mg, 0.262 mmol) in THF (3 mL) and H$_2$O (3 mL) was added LiOH (32 mg, 1.310 mmol) at 0° C. The resulting mixture was stirred at room temperature overnight. The aqueous solution was acidified with HCl (2 N) to pH 3~4. The resulting mixture was concentrated under vacuum. The residue was purified reverse FC with 0-20% ACN in H$_2$O to afford 7-chloro-1-isopropylpyrrolo[2,3-c]pyridine-2-carboxylic acid (C17) (50 mg, 79.83%) as a white solid. MS m/z 239.0 [M+1]$^+$ Intermediate C18

7-chloro-1-(cyclopropylmethyl)pyrrolo[2,3-c]pyridine-2-carboxylic acid

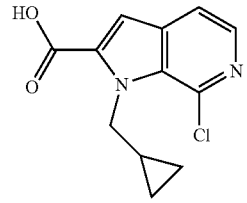 [SMILES: O=C(O)c1cc2ccnc(Cl)c2n1CC1CC1]

Step-1: To a mixture of ethyl 7-chloro-1H-pyrrolo[2,3-c]pyridine-2-carboxylate (400 mg, 1.781 mmol) in DMF (5 mL) was added K$_2$CO$_3$ (739 mg, 5.342 mmol) and (bromomethyl)cyclopropane (241 mg, 1.781 mmol). The resulting mixture was stirred at 80° C. for 1 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% EtOAc in PE to afford ethyl 7-chloro-1-(cyclopropylmethyl)pyrrolo[2,3-c]pyridine-2-carboxylate (380 mg, 76.56%) as a white solid. MS m/z 279.1 [M+1]$^+$ Step-2: To a mixture of ethyl 7-chloro-1-(cyclopropylmethyl)pyrrolo[2,3-c]pyridine-2-carboxylate (180 mg, 0.646 mmol) in THF (3 mL) and H$_2$O (3 mL) was added LiOH (78 mg, 3.230 mmol) at 0° C. The resulting mixture was stirred at room temperature overnight. The aqueous solution was acidified with HCl (2 N) to pH 3~4. The resulting mixture was concentrated under vacuum. The residue was purified by reverse FC with 0-30% ACN in H$_2$O to afford 7-chloro-1-(cyclopropylmethyl)pyrrolo[2,3-c]pyridine-2-carboxylic acid (C18) (120 mg, 74.13%) as a white solid. MS m/z 251.1 [M+1]$^+$ Intermediate C19

7-chloro-1-methylindole-2-carboxylic acid

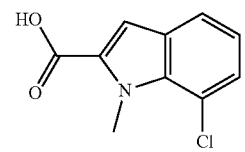

Step-1: To mixture of 7-chloro-1H-indole-2-carboxylic acid (1 g, 5.112 mmol) in MeOH (20 mL) was added H$_2$SO$_4$ (0.50 g, 5.112 mmol). The resulting mixture was stirred at 70° C. overnight. The resulting mixture was extracted with EtOAc. The combined organic layers were washed with brine, dried over anhydrous Na$_2$SO$_4$. This resulted in methyl 7-chloro-1H-indole-2-carboxylate (1 g, 93.31%) as a yellow solid. MS m/z 208.0 [M−1]$^-$ Step-2: To a mixture of 7-chloro-1H-indole-2-carboxylate (400 mg, 1.908 mmol) in DMF (5 mL) were added NaH (92 mg, 3.816 mmol) at 0° C. The resulting mixture was stirred at 0° C. for 30 min under nitrogen atmosphere. To the above mixture was added CH$_3$I (541 mg, 3.816 mmol). The resulting mixture was stirred at room temperature for 1 h. The reaction was then quenched by the addition of water. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford methyl 7-chloro-1-methylindole-2-carboxylate (130 mg, 30.46%) as a white solid. MS m/z 224.0 [M+1]$^+$ Step-3: To a mixture of methyl 7-chloro-1-methylindole-2-carboxylate (110 mg, 0.492 mmol) in THF (2 mL) and H$_2$O (2 mL) was added LiOH (59 mg, 2.460 mmol) at 0° C. The resulting mixture was stirred at room temperature overnight. The aqueous solution was acidified with HCl (2 N) to pH 3~4. The resulting mixture was concentrated under vacuum. This resulted in 7-chloro-1-methylindole-2-carboxylic acid (C19) (200 mg, crude) as a white solid. MS m/z 210.0 [M+1]$^+$ Intermediate C20

7-methoxy-1-methylpyrrolo[2,3-c]pyridine-2-carboxylic acid

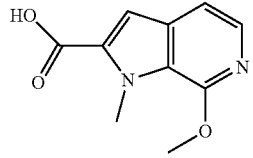

Step-1: To a mixture of ethyl 7-chloro-1-methylpyrrolo[2,3-c]pyridine-2-carboxylate (300 mg, 1.257 mmol) in toluene (5 mL) were added methanol (1.5 mL), Cs$_2$CO$_3$ (614 mg, 1.885 mmol), t-BuBrettPhos (61 mg, 0.126 mmol) and [Pd(allyl)Cl]$_2$ (18 mg, 0.05 mmol). The resulting mixture was stirred at 80° C. for 1 h under nitrogen atmosphere. The residue was purified by FC with 0-20% ethyl acetate in PE to afford methyl 7-methoxy-1-methylpyrrolo[2,3-c]pyridine-2-carboxylate (240 mg, 86.70%) as a white solid. MS m/z 221.1 [M+1]$^+$ Step-2: To a mixture of methyl 7-methoxy-1-methylpyrrolo[2,3-c]pyridine-2-carboxylate (150 mg, 0.681 mmol) in THF (3 mL) and H$_2$O (3 mL) were added LiOH (82 mg, 3.405 mmol). The resulting mixture was stirred at room temperature overnight. The aqueous solution was acidified with HCl (2 N) to pH 3~4. The resulting mixture was concentrated under vacuum. The residue was purified by reverse-phase FC with 0-20% ACN in H$_2$O to afford 7-methoxy-1-methylpyrrolo[2,3-c]pyridine-2-carboxylic acid (C20) (100 mg, 71.20%) as a white solid. MS m/z 207.1 [M+1]$^+$ Intermediate C21

7-cyclopropoxy-1-methylpyrrolo[2,3-c]pyridine-2-carboxylic acid

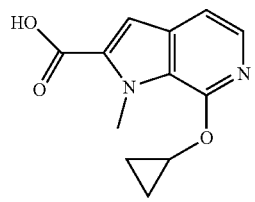 [SMILES: Cn1c(C(=O)O)cc2ccnc(OC3CC3)c21]

Step-1: To a mixture of ethyl 7-chloro-1-methylpyrrolo[2,3-c]pyridine-2-carboxylate (250 mg, 1.047 mmol) and cyclopropanol (608 mg, 10.47 mmol) in toluene (6 mL) were added Cs$_2$CO$_3$ (512 mg, 1.571 mmol), t-BuBrettPhos (51 mg, 0.105 mmol) and [Pd(allyl)Cl]$_2$ (16 mg, 0.042 mmol). The resulting mixture was stirred at 80° C. for 1 h under nitrogen atmosphere. The resulting mixture was concentrated under reduced pressure. The residue was purified by FC with 0-50% ethyl acetate in PE to afford ethyl 7-cyclopropoxy-1-methylpyrrolo[2,3-c]pyridine-2-carboxylate (50 mg, 16.50%) as a white solid. MS m/z 261.1 [M+1]$^+$ Step-2: To a mixture of ethyl 7-cyclopropoxy-1-methylpyrrolo[2,3-c]pyridine-2-carboxylate (50 mg, 0.192 mmol) in THF (5 mL) and H$_2$O (5 mL) was added LiOH (23 mg, 0.96 mmol). The resulting mixture was stirred at room temperature overnight. The aqueous solution was acidified with HCl (2 N) to pH 3~4. The resulting mixture was concentrated under vacuum. This resulted in 7-cyclopropoxy-1-methylpyrrolo[2,3-c]pyridine-2-carboxylic acid (C21) (50 mg, crude) as a white solid. MS m/z 233.1 [M+1]$^+$ Intermediate C22

7-cyclopropyl-1-methylpyrrolo[2,3-c]pyridine-2-carboxylic acid

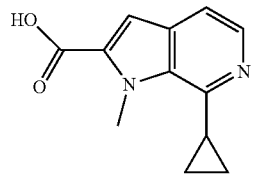 [SMILES: Cn1c(C(=O)O)cc2ccnc(C3CC3)c21]

Step-1: To a mixture of ethyl 7-chloro-1-methylpyrrolo[2,3-c]pyridine-2-carboxylate (300 mg, 1.335 mmol) and cyclopropylboronic acid (115 mg, 1.335 mmol) in dioxane (5 mL) and H$_2$O (0.5 mL) were added K$_2$CO$_3$ (369 mg, 2.670 mmol) and Pd(dppf)Cl$_2$ (98 mg, 0.134 mmol). The resulting mixture was stirred at 100° C. overnight under nitrogen atmosphere. The reaction was concentrated. The residue was purified by FC with 0-50% ethyl acetate in PE to afford ethyl 7-cyclopropyl-1-methylpyrrolo[2,3-c]pyridine-2-carboxylate (270 mg, 82.76%) as a white solid. MS m/z 245.1 [M+1]$^+$ Step-2: To a mixture of ethyl 7-cyclopropyl-1-methylpyrrolo[2,3-c]pyridine-2-carboxylate (180 mg, 0.754 mmol) in THF (2 mL) and H$_2$O (2 mL) was added LiOH (89 mg, 3.771 mmol). The resulting mixture was stirred at room temperature for 1 h. The aqueous solution was acidified with HCl (2 N) to pH 3~4. The precipitated solids were collected by filtration. This resulted in 7-cyclopropyl-1-methylpyrrolo[2,3-c]pyridine-2-carboxylic acid (C22) (160 mg, 98.15%) as a white solid. MS m/z 217.1 [M+1]⁺

Intermediate C23

7-methoxy-1H-pyrrolo[2,3-c]pyridine-2-carboxylic acid

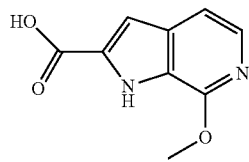

Step-1: To a mixture of ethyl 7-chloro-1-methylpyrrolo[2,3-c]pyridine-2-carboxylate (600 mg, 2.514 mmol) in toluene (5 mL) were added MeOH (2 mL), Cs₂CO₃ (1.3 g, 3.987 mmol), t-BuBrettPhos (122 mg, 0.251 mmol) and [Pd(allyl)Cl]₂ (37 mg, 0.101 mmol). The resulting mixture was stirred at 80° C. for 1 h. The residue was purified by FC with 0-50% ethyl acetate in PE to afford methyl 7-methoxy-1-methylpyrrolo[2,3-c]pyridine-2-carboxylate (350 mg, 63.22%) as a yellow solid. MS m/z 207.1 [M+1]⁺

Step-2: To a mixture of methyl 7-hydroxy-1H-pyrrolo[2,3-c]pyridine-2-carboxylate (250 mg, 1.301 mmol) in THF (2 mL) and H₂O (2 mL) were added LiOH (156 mg, 6.505 mmol). The resulting mixture was stirred at room temperature overnight. The aqueous solution was acidified with HCl (2 N) to pH 3~4. The resulting mixture was concentrated under vacuum. The residue was purified by reverse-phase FC with 0-20% ACN in H₂O to afford 7-methoxy-1H-pyrrolo[2,3-c]pyridine-2-carboxylic acid (C23) (155 mg, 62.00%) as a white solid. MS m/z 193.1 [M+1]⁺

Intermediate C24

7-cyclopropoxy-1-{[2-(trimethylsilyl)ethoxy]methyl}pyrrolo[2,3-c]pyridine-2-carboxylic acid

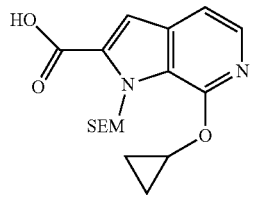 [SMILES: C[Si](C)(C)CCOCn1c(C(=O)O)cc2ccnc(OC3CC3)c21]

Step-1: To a mixture of ethyl 7-chloro-1H-pyrrolo[2,3-c]pyridine-2-carboxylate (600 mg, 2.671 mmol) in DMF (6 mL) were added K₂CO₃ (1.1 g, 8.013 mmol) and SEMCl (891 mg, 5.342 mmol). The resulting mixture was stirred at 80° C. for 1 h. The resulting mixture was extracted with EtOAc. The combined organic layers were washed with brine, dried over anhydrous Na₂SO₄. After filtration, the filtrate was concentrated under reduced pressure. The residue was purified by FC with 0-20% EtOAc in PE to afford ethyl 7-chloro-1-{[2-(trimethylsilyl)ethoxy]methyl}pyrrolo[2,3-c]pyridine-2-carboxylate (860 mg, 90.72%) as a light yellow oil. MS m/z 355.1 [M+1]⁺.

Step-2: To a mixture of ethyl 7-chloro-1-{[2-(trimethylsilyl)ethoxy]methyl}pyrrolo[2,3-c]pyridine-2-carboxylate (600 mg, 1.691 mmol) and cyclopropanol (982 mg, 16.906 mmol) in toluene (6 mL) were added Cs₂CO₃ (827 mg, 2.536 mmol), t-BuBrettPhos (82 mg, 0.169 mmol) and [Pd(allyl)Cl]₂ (25 mg, 0.068 mmol). The resulting mixture was stirred at 80° C. for 1 h under nitrogen atmosphere. The resulting mixture was concentrated under vacuum. The residue was purified by FC with 0-30% EtOAc in PE to afford ethyl 7-cyclopropoxy-1-{[2-(trimethylsilyl)ethoxy]methyl}pyrrolo[2,3-c]pyridine-2-carboxylate (220 mg, 34.56%) as a yellow oil. MS m/z 377.2 [M+1]⁺

Step-3: To a mixture of ethyl 7-cyclopropoxy-1-{[2-(trimethylsilyl)ethoxy]methyl}pyrrolo[2,3-c]pyridine-2-carboxylate (220 mg, 0.584 mmol) in THF (4 mL) and H₂O (4 mL) was added LiOH (70 mg, 2.920 mmol) at 0° C. The resulting mixture was stirred at room temperature overnight. The aqueous solution was acidified with HCl (2 N) to pH 3~4. The resulting mixture was concentrated under vacuum. The residue was purified by reverse-phase column chromatography with 0-20% ACN in H₂O to afford 7-cyclopropoxy-1-{[2-(trimethylsilyl)ethoxy]methyl}pyrrolo[2,3-c]pyridine-2-carboxylic acid (C24) (200 mg, 98.23%) as a yellow solid. MS m/z 349.2 [M+1]⁺.

Intermediate C25

1-methyl-7-(methylamino)pyrrolo[2,3-c]pyridine-2-carboxylic acid

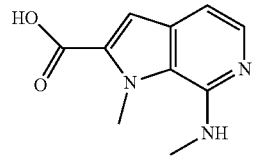

Step-1: To a mixture of ethyl 7-chloro-1-methylpyrrolo[2,3-c]pyridine-2-carboxylate (150 mg, 0.628 mmol) and methanamine hydrochloride (213 mg, 3.140 mmol) in DMSO (5 mL) were added K₂CO₃ (263 mg, 1.884 mmol), L-Proline (29 mg, 0.251 mmol) and copper(I) iodide (24 mg, 0.126 mmol). The resulting mixture was stirred at 100° C. for 1 h under nitrogen atmosphere. The resulting mixture was extracted with EtOAc. The combined organic layers were washed with brine, dried over anhydrous Na₂SO₄. After filtration, the filtrate was concentrated under reduced pressure. The residue was purified by FC with 0-50% EtOAc in PE to afford ethyl 1-methyl-7-(methylamino)pyrrolo[2,3-c]pyridine-2-carboxylate (35 mg, 23.87%) as a yellow solid. MS m/z 234.1 [M+1]⁺

Step-2: To a mixture of ethyl 1-methyl-7-(methylamino)pyrrolo[2,3-c]pyridine-2-carboxylate (35 mg, 0.150 mmol) in THF (3 mL) and H₂O (3 mL) was added LiOH (18 mg, 0.750 mmol). The resulting mixture was stirred at room temperature overnight. The aqueous solution was acidified with HCl (2 N) to pH 3~4. The resulting mixture was concentrated under vacuum. The residue was purified by reverse-phase column chromatography with 0-20% ACN in H₂O to afford 1-methyl-7-(methylamino)pyrrolo[2,3-c]pyridine-2-carboxylic acid (C25) (30 mg, 97.43%) as a yellow solid. MS m/z 206.1 [M+1]⁺

Intermediate C26

7-(dimethylamino)-1-methylpyrrolo[2,3-c]pyridine-2-carboxylic acid

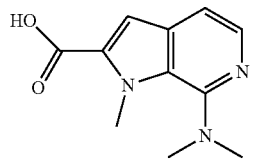 [SMILES: CN(C)c1nccc2cc(C(=O)O)n(C)c12]

Step-1: To a mixture of ethyl 7-chloro-1-methylpyrrolo[2,3-c]pyridine-2-carboxylate (300 mg, 1.257 mmol) and dimethylamine hydrochloride (308 mg, 3.771 mmol) in DMSO (5 mL) were added $K_2CO_3$ (525 mg, 3.771 mmol), L-Proline (58 mg, 0.503 mmol) and copper(I) iodide (48 mg, 0.251 mmol). The resulting mixture was stirred at 100° C. for 1 h under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by FC with 0-20% EtOAc in PE to afford ethyl 7-(dimethylamino)-1-methylpyrrolo[2,3-c]pyridine-2-carboxylate (200 mg, 64.34%) as a light yellow oil. MS m/z 248.1 [M+1]$^+$.

Step-2: To a mixture of ethyl 7-(dimethylamino)-1-methylpyrrolo[2,3-c]pyridine-2-carboxylate (100 mg, 0.404 mmol) in THF (3 mL) and $H_2O$ (3 mL) was added LiOH (49 mg, 2.020 mmol) at 0° C. The resulting mixture was stirred at room temperature overnight. The aqueous solution was acidified with HCl (2 N) to pH 3~4. The resulting mixture was concentrated under vacuum. The residue was purified by reverse-phase column chromatography with 0-20% ACN in $H_2O$ to afford 7-(dimethylamino)-1-methylpyrrolo[2,3-c]pyridine-2-carboxylic acid (C26) (60 mg, 67.68%) as a white solid. MS m/z 220.1 [M+1]$^+$

Intermediate C27

7-chloro-1,3-dimethylpyrrolo[2,3-c]pyridine-2-carboxylic acid

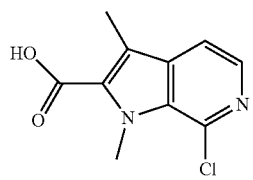

Step-1: To a mixture of ethyl 7-chloro-1-methylpyrrolo[2,3-c]pyridine-2-carboxylate (300 mg, 1.257 mmol) in $CH_3CN$ (6 mL) was added NBS (224 mg, 1.257 mmol) at 0° C. The resulting mixture was stirred at room temperature for 2 h. The resulting mixture was extracted with EtOAc. The combined organic layers were washed with brine, dried over anhydrous $Na_2SO_4$. After filtration, the filtrate was concentrated under reduced pressure. This resulted in ethyl 3-bromo-7-chloro-1-methylpyrrolo[2,3-c]pyridine-2-carboxylate (400 mg, 80.17%) as a white solid. MS m/z 317.0 [M+1]$^+$ Step-2: To a mixture of ethyl 3-bromo-7-chloro-1-methylpyrrolo[2,3-c]pyridine-2-carboxylate (400 mg, 1.26 mmol) and methylboronic acid (151 mg, 2.52 mmol) in dioxane (6 mL) and $H_2O$ (0.6 mL) were added $K_2CO_3$ (523 mg, 3.78 mmol) and Pd(dppf)$Cl_2$ (92 mg, 0.126 mmol). The resulting mixture was stirred at 100° C. overnight under nitrogen atmosphere. The resulting mixture was concentrated under reduced pressure. The residue was purified by FC with 0-35% ethyl acetate in PE to afford ethyl 7-chloro-1,3-dimethylpyrrolo[2,3-c]pyridine-2-carboxylate (140 mg, 35.19%) as a white solid. MS m/z 253.0 [M+1]$^+$ Step-3: To a mixture of ethyl 7-chloro-1,3-dimethylpyrrolo[2,3-c]pyridine-2-carboxylate (120 mg, 0.475 mmol) in THF (5 mL) and $H_2O$ (5 mL) was added LiOH (57 mg, 2.375 mmol). The resulting mixture was stirred at room temperature overnight. The aqueous solution was acidified with HCl (2 N) to pH 3~4. The precipitated solids were collected by filtration. This resulted in 7-chloro-1,3-dimethylpyrrolo[2,3-c]pyridine-2-carboxylic acid (C27) (60 mg, 45.00%) as a white solid. MS m/z 225.1 [M+1]$^+$

Intermediate C28

1,7-dimethylpyrrolo[2,3-c]pyridine-2-carboxylic acid

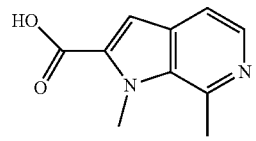

Step-1: To a mixture of ethyl 7-chloro-1-methylpyrrolo[2,3-c]pyridine-2-carboxylate (200 mg, 0.83 mmol) and methylboronic acid (401 mg, 6.704 mmol) in dioxane (2 mL) and $H_2O$ (0.2 mL) were added Pd(dppf)$Cl_2$ (61 mg, 0.084 mmol) and $K_2CO_3$ (347 mg, 2.514 mmol). The resulting mixture was stirred at 100° C. overnight under nitrogen atmosphere. The reaction was concentrated. The residue was purified by FC with 0-50% ethyl acetate in PE to afford ethyl 1,7-dimethylpyrrolo[2,3-c]pyridine-2-carboxylate (90 mg, 59.05%) as a brown solid. MS m/z 219.1 [M+1]$^+$ Step-2: To a mixture of ethyl 1,7-dimethylpyrrolo[2,3-c]pyridine-2-carboxylate (90 mg, 0.41 mmol) in $H_2O$ (2 mL) and THF (2 mL) was added LiOH (49 mg, 2.05 mmol). The resulting mixture was stirred at room temperature for 1 h. The aqueous solution was acidified with HCl (2 N) to pH 3~4. The precipitated solids were collected by filtration and washed with water. This resulted in 1,7-dimethylpyrrolo[2,3-c]pyridine-2-carboxylic acid (C28) (130 mg, 81.81%) as a white solid. MS m/z 191.1 [M+1]$^+$

Intermediate C29

1-{2-[(tert-butoxycarbonyl)amino]ethyl}-7-chloro-pyrrolo[2,3-c]pyridine-2-carboxylic acid

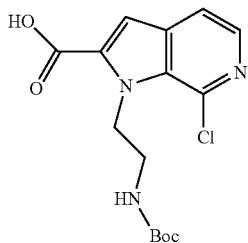 [SMILES: CC(C)(C)OC(=O)NCCn1c(C(=O)O)cc2ccnc(Cl)c21]

Step-1: To a mixture ethyl 7-chloro-1H-pyrrolo[2,3-c]pyridine-2-carboxylate (350 mg, 1.558 mmol) in DMF (3 mL) was added K$_2$CO$_3$ (431 mg, 3.116 mmol) and tert-butyl N-(2-chloroethyl)carbamate (1.4 g, 7.79 mmol). The resulting mixture was stirred at 80° C. overnight. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford ethyl 1-{2-[(tert-butoxycarbonyl)amino]ethyl}-7-chloropyrrolo[2,3-c]pyridine-2-carboxylate (558 mg, 97.37%) as a white solid. MS m/z 368.1 [M+1]$^+$ Step-2: To a mixture of ethyl 1-{2-[(tert-butoxycarbonyl)amino]ethyl}-7-chloropyrrolo[2,3-c]pyridine-2-carboxylate (238 mg, 0.647 mmol) in THF (2 mL) and H$_2$O (2 mL) was added LiOH (77 mg, 3.235 mmol) at 0° C. The resulting mixture was stirred at room temperature for 1 h. The aqueous solution was acidified with HCl (2 N) to pH 3~4. The resulting mixture was concentrated under vacuum. The residue was purified by reverse-phase column chromatography with 0-20% ACN in H$_2$O to afford 1-{2-[(tert-butoxycarbonyl)amino]ethyl}-7-chloropyrrolo[2,3-c]pyridine-2-carboxylic acid (C29) (120 mg, 54.58%) as a white solid. MS m/z 340.1 [M+1]$^+$

Intermediate C30

1-{2-[(tert-butyldimethylsilyl)oxy]ethyl}-7-chloro-pyrrolo[2,3-c]pyridine-2-carboxylic acid

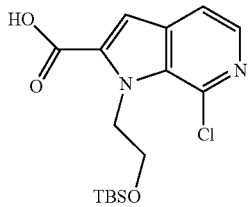 [SMILES: CC(C)(C)[Si](C)(C)OCCn1c(C(=O)O)cc2ccnc(Cl)c21]

Step-1: To a mixture of ethyl 7-chloro-1H-pyrrolo[2,3-c]pyridine-2-carboxylate (400 mg, 1.781 mmol) in DMF (6 mL) was added K$_2$CO$_3$ (739 mg, 5.343 mmol) and (2-bromoethoxy)(tert-butyl)dimethylsilane (512 mg, 2.137 mmol). The resulting mixture was stirred at 80° C. overnight. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-20% EtOAc in PE to afford ethyl 1-{2-[(tert-butyldimethylsilyl)oxy]ethyl}-7-chloropyrrolo[2,3-c]pyridine-2-carboxylate (540 mg, 79.19%) as a colorless oil. MS m/z 383.2 [M+1]$^+$.

Step-2: To a mixture of ethyl 1-{2-[(tert-butyldimethylsilyl)oxy]ethyl}-7-chloropyrrolo[2,3-c]pyridine-2-carboxylate (290 mg, 0.757 mmol) in THF (3 mL) and H$_2$O (3 mL) was added LiOH (91 mg, 3.785 mmol) at 0° C. The resulting mixture was stirred at room temperature overnight. The aqueous solution was acidified with HCl (2 N) to pH 3~4. The resulting mixture was concentrated under vacuum. The residue was purified by reverse column chromatography with 0-100% ACN in H$_2$O to afford 1-{2-[(tert-butyldimethylsilyl)oxy]ethyl}-7-chloropyrrolo[2,3-c]pyridine-2-carboxylic acid (C30) (250 mg, 93.02%) as a white solid. MS m/z 355.1 [M+1]$^+$

Intermediate C31

7-chloro-1-(2-methoxyethyl)pyrrolo[2,3-c]pyridine-2-carboxylic acid

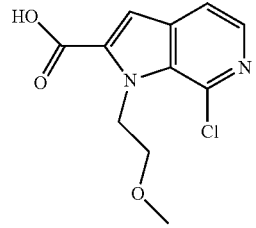 [SMILES: COCCn1c(C(=O)O)cc2ccnc(Cl)c21]

Step-1: To a mixture of ethyl 7-chloro-1H-pyrrolo[2,3-c]pyridine-2-carboxylate (300 mg, 1.335 mmol) in DMF (6 mL) was added K$_2$CO$_3$ (370 mg, 2.670 mmol) and 1-chloro-2-methoxy-ethane (632 mg, 6.675 mmol). The resulting mixture was stirred at 80° C. overnight. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-25% EtOAc in PE to afford ethyl 7-chloro-1-(2-methoxyethyl)pyrrolo[2,3-c]pyridine-2-carboxylate (150 mg, 39.73%) as a light yellow oil. MS m/z 283.1 [M+1]$^+$ Step-2: To a mixture of ethyl 7-chloro-1-(2-methoxyethyl)pyrrolo[2,3-c]pyridine-2-carboxylate (130 mg, 0.460 mmol) in THF (3 mL) and H$_2$O (3 mL) was added LiOH (55 mg, 2.300 mmol) at 0° C. The resulting mixture was stirred at room temperature overnight. The aqueous solution was acidified with HCl (2 N) to pH 3~4. The resulting mixture was concentrated under vacuum. The residue was purified by reverse-phase column chromatography with 0-100% ACN in H$_2$O to afford 7-chloro-1-(2-methoxyethyl)pyrrolo[2,3-c]pyridine-2-carboxylic acid (C31) (100 mg, 85.40%) as a white solid. MS m/z 255.1 [M+1]$^+$

Intermediate C32

7-chloro-3-fluoro-1-methylpyrrolo[2,3-c]pyridine-2-carboxylic acid

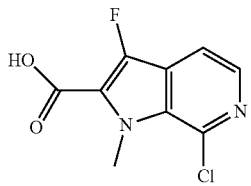

Step-1: To a mixture of ethyl 7-chloro-1-methylpyrrolo[2,3-c]pyridine-2-carboxylate (517 mg, 2.301 mmol) in ACN (6 mL) was added Selectfluor (1223 mg, 3.452 mmol) at 0° C. The resulting mixture was stirred at 60° C. for 1 h. The resulting mixture was concentrated under vacuum. The residue was purified by Prep-HPLC [Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 30% B to 40% B in 8 min, 40% B; Wave Length: 254 nm] to afford ethyl 7-chloro-3-fluoro-1H-pyrrolo[2,3-c]pyridine-2-carboxylate (130 mg, 23.28%) as a white solid. MS m/z 243.0 [M+1]$^+$ Step-2: To a mixture of ethyl 7-chloro-3-fluoro-1H-pyrrolo[2,3-c]pyridine-2-carboxylate (130 mg, 0.536 mmol) in DMF (2 mL) was added K$_2$CO$_3$ (148 mg, 1.072 mmol) and MeI (114 mg, 0.804 mmol). The resulting mixture was stirred at 80° C. for 1 h. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford ethyl 7-chloro-3-fluoro-1-methylpyrrolo[2,3-c]pyridine-2-carboxylate (100 mg, 72.72%) as a white solid. MS m/z 257.0 [M+1]$^+$ Step-3: To a mixture of ethyl 7-chloro-3-fluoro-1-methylpyrrolo[2,3-c]pyridine-2-carboxylate (90 mg, 0.351 mmol) in THF (2 mL) and H$_2$O (2 mL) was added LiOH (42 mg, 1.755 mmol) at 0° C. The resulting mixture was stirred at room temperature overnight. The aqueous solution was acidified with HCl (2 N) to pH 3~4. The precipitated solids were collected by filtration. This resulted in 7-chloro-3-fluoro-1-methylpyrrolo[2,3-c]pyridine-2-carboxylic acid (C32) (80 mg, 99.81%) as a white solid. MS m/z 229.0 [M+1]$^+$

Intermediate C33

7-chloro-1-[2-(morpholin-4-yl)ethyl]pyrrolo[2,3-c]pyridine-2-carboxylic acid

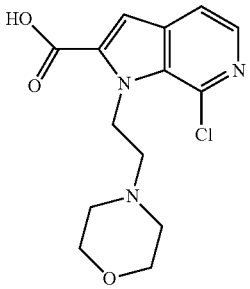 [SMILES: O=C(O)c1cc2ccnc(Cl)c2n1CCN1CCOCC1]

Step-1: To a mixture of ethyl 7-chloro-1H-pyrrolo[2,3-c]pyridine-2-carboxylate (350 mg, 1.558 mmol) in DMF (5 mL) were added NaH (94 mg, 3.895 mmol) at 0° C. The resulting mixture was stirred at 0° C. for 30 min under nitrogen atmosphere. To the above mixture was added 4-(2-chloroethyl)-morpholine (1.17 g, 7.790 mmol). The resulting mixture was stirred at room temperature for 16 h. The reaction was then quenched by water. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-30% ethyl acetate in PE to afford ethyl 7-chloro-1-[2-(morpholin-4-yl)ethyl]pyrrolo[2,3-c]pyridine-2-carboxylate (170 mg, 29.07%) as a yellow solid. MS m/z 338.1 [M+1]$^+$.

Step-2: To a mixture of ethyl 7-chloro-1-[2-(morpholin-4-yl)ethyl]pyrrolo[2,3-c]pyridine-2-carboxylate (150 mg, 0.444 mmol) in THF (3 mL) and H$_2$O (3 mL) was added LiOH (54 mg, 2.225 mmol) at 0° C. The resulting mixture was stirred at room temperature overnight. The aqueous solution was acidified with HCl (2 N) to pH 3~4. The resulting mixture was concentrated under vacuum. The residue was purified by reverse-phase column chromatography with 0-20% ACN in H$_2$O to afford 7-chloro-1-[2-(morpholin-4-yl)ethyl]pyrrolo[2,3-c]pyridine-2-carboxylic acid (C33) (135 mg, 98.15%) as a yellow solid. MS m/z 310.1 [M+1]$^+$

Intermediate C34

6-fluoro-1-methylindole-2-carboxylic acid

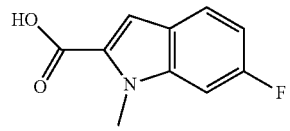

Step-1: To a mixture of 6-fluoro-1H-indole-2-carboxylic acid (1 g, 5.582 mmol) in MeOH (15 mL) was added H$_2$SO$_4$ (0.6 mL) at room temperature. The resulting mixture was stirred at 70° C. overnight. The mixture basified to pH 7 with saturated NaHCO$_3$. The resulting mixture was extracted with EtOAc. The combined organic layers were washed with brine, dried over anhydrous Na$_2$SO$_4$. After filtration, the filtrate was concentrated under reduced pressure. This resulted in methyl 6-fluoro-1H-indole-2-carboxylate (1 g, 92.74%) as a yellow solid. MS m/z 192.1 [M−1]⁻

Step-2: To a mixture of methyl 6-fluoro-1H-indole-2-carboxylate (400 mg, 2.071 mmol) in DMF (2 mL) was added NaH (99 mg, 4.142 mmol). The resulting mixture was stirred at 0° C. for 30 min under nitrogen atmosphere. To the above mixture were added CH₃I (588 mg, 4.142 mmol). The resulting mixture was stirred at room temperature for 1 h. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in PE to afford methyl 6-fluoro-1-methylindole-2-carboxylate (120 mg, 27.97%) as a white solid. MS m/z 208.1 [M+1]⁺

Step-3: To a mixture of methyl 6-fluoro-1-methylindole-2-carboxylate (100 mg, 0.483 mmol) in H₂O (2.5 mL) and THF (2.5 mL) were added LiOH (58 mg, 2.415 mmol) at 0° C. The resulting mixture was stirred at room temperature for 2 h. The aqueous solution was acidified with HCl (2 N) to pH 3~4. The precipitated solids were collected by filtration and washed with water. This resulted in 6-fluoro-1-methyl-indole-2-carboxylic acid (C34) (70 mg, 75.08%) as a white solid. MS m/z 192.1 [M−1]⁻

Intermediate C35

1-methylpyrrolo[2,3-c]pyridine-2-carboxylic acid

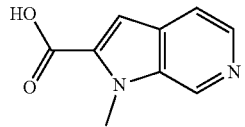

Step-1: To a mixture ethyl 1H-pyrrolo[2,3-c]pyridine-2-carboxylate (250 mg, 1.314 mmol) in DMF (5 mL) were added K₂CO₃ (545 mg, 3.942 mmol) and CH₃I (149 mg, 1.051 mmol) at 0° C. The resulting mixture was stirred at room temperature for 2 h. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in PE to afford ethyl 1-methylpyrrolo[2,3-c]pyridine-2-carboxylate (115 mg, 42.84%) as a white solid. MS m/z 205.1 [M+1]⁺

Step-2: To a mixture of ethyl 1-methylpyrrolo[2,3-c]pyridine-2-carboxylate (105 mg, 0.514 mmol) in THF (2 mL) and H₂O (2 mL) was added LiOH (62 mg, 2.570 mmol) at 0° C. The resulting mixture was stirred at room temperature for 1 h. The aqueous solution was acidified with HCl (2 N) to pH 3~4. The residue was purified by reverse flash chromatography with 0-20% ACN in H₂O to afford 1-methylpyrrolo[2,3-c]pyridine-2-carboxylic acid (C35) (80 mg, 88.32%) as a white solid. MS m/z 177.1 [M+1]⁺

Intermediate C36

6-cyano-1-methylindole-2-carboxylic acid

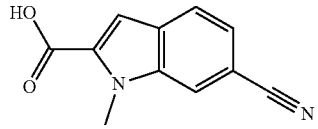

Step-1: To a mixture of methyl 6-cyano-1H-indole-2-carboxylate (200 mg, 0.999 mmol) in DMF (10 mL) were added K₂CO₃ (414 mg, 2.997 mmol) and CH₃I (284 mg, 1.998 mmol). The resulting mixture was stirred at room temperature for 1 h. The resulting mixture was extracted with EtOAc. The combined organic layers were washed with brine, dried over anhydrous Na₂SO₄. After filtration, the filtrate was concentrated under reduced pressure. The residue was purified by flash column chromatography with 0-50% ethyl acetate in PE to afford methyl 6-cyano-1-methylindole-2-carboxylate (200 mg, 84.11%) as a white solid. MS m/z 215.1 [M+1]⁺

Step-2: To a mixture of methyl 6-cyano-1-methylindole-2-carboxylate (170 mg, 0.794 mmol) in THF (5 mL) and H₂O (5 mL) was added LiOH (95 mg, 3.97 mmol) at 0° C. The resulting mixture was stirred at room temperature overnight. The aqueous solution was acidified with HCl (2 N) to pH 3~4. The precipitated solids were collected by filtration and washed with water. This resulted in 6-cyano-1-methylindole-2-carboxylic acid (C36) (150 mg, 84.98%) as a white solid. MS m/z 201.1 [M+1]⁺

Intermediate C37

1-methyl-7-(trifluoromethyl)pyrrolo[2,3-c]pyridine-2-carboxylic acid

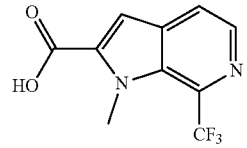 [SMILES: Cn1c(C(=O)O)cc2ccnc(C(F)(F)F)c21]

Step-1: To a mixture of 4-methyl-3-nitro-2-(trifluoromethyl)pyridine (500 mg, 2.426 mmol) in toluene (5 mL) were added EtONa (330 mg, 4.852 mmol) and ethyl oxalate (532 mg, 3.639 mmol). The resulting mixture was stirred at room temperature overnight. The resulting mixture was concentrated under vacuum. The residue was purified by flash column chromatography with 0-10% methanol in dichloromethane to afford ethyl 3-[3-nitro-2-(trifluoromethyl)pyridin-4-yl]-2-oxopropanoate (250 mg, 33.66%) as a yellow solid. MS m/z 307.1 [M+1]⁺

Step-2: To a mixture of ethyl 3-[3-nitro-2-(trifluoromethyl)pyridin-4-yl]-2-oxopropanoate (250 mg, 0.816 mmol) in AcOH (3 mL) was added iron (182 mg, 3.264 mmol). The resulting mixture was stirred at 60° C. for 2 h. The resulting mixture was concentrated under vacuum. The residue was purified by flash column chromatography with 0-50% ethyl acetate to afford ethyl 7-(trifluoromethyl)-1H-pyrrolo[2,3-c]pyridine-2-carboxylate (180 mg, 85.38%) as a yellow solid. MS m/z 259.1 [M+1]⁺

Step-3: To a mixture of ethyl 7-(trifluoromethyl)-1H-pyrrolo[2,3-c]pyridine-2-carboxylate (160 mg, 0.620 mmol) in DMF (3 mL) were added K$_2$CO$_3$ (257 mg, 1.860 mmol) and CH3I (176 mg, 1.240 mmol) at 0° C. The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0-50% ethyl acetate to afford ethyl 1-methyl-7-(trifluoromethyl)pyrrolo[2,3-c]pyridine-2-carboxylate (100 mg, 59.28%) as a white solid. MS m/z 273.1 [M+1]$^+$ Step-4: To a mixture of ethyl 1-methyl-7-(trifluoromethyl)pyrrolo[2,3-c]pyridine-2-carboxylate (90 mg, 0.331 mmol) in H$_2$O (2 mL) and THF (2 mL) was added LiOH (40 mg, 1.655 mmol) at 0° C. The resulting mixture was stirred at room temperature for 2 h. The aqueous solution was acidified with HCl (2 N) to pH 3~4. The resulting mixture was filtered, the filter cake was washed with water. The filtrate was concentrated under reduced pressure. This resulted in 1-methyl-7-(trifluoromethyl)pyrrolo[2,3-c]pyridine-2-carboxylic acid (C37) (80 mg, 99.10%) as a white solid. MS m/z 245.1 [M+1]$^+$ Intermediate D1 isopropyl(1,3-oxazol-2-ylmethyl)amine

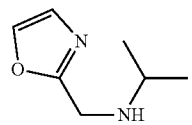

To a solution of 1,3-oxazole-2-carbaldehyde (200 mg, 2.06 mmol) in tetrahydrofuran (2 mL) was added propan-2-amine (121 mg, 2.06 mmol). The mixture was stirred at room temperature for 10 h, this was followed by the addition of sodium borohydride (116 mg, 3.09 mmol) at room temperature. Then the mixture was stirred at room temperature for 3 h. The reaction mixture was quenched by the addition of saturated ammonium chloride aqueous solution. The aqueous solution was extracted with ethyl acetate. The combined organic layers were washed with brine, dried over anhydrous sodium sulfate, filtered, and concentrated under vacuum to afford isopropyl(1,3-oxazol-2-ylmethyl)amine (D1) (340 mg, 47%) as a white oil, which was used directly. MS m/z 141.1 [M+1]$^+$.

Intermediate D2

(furan-2-ylmethyl)(isopropyl)amine

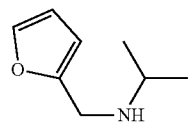

To a solution of furan-2-carbaldehyde (1.00 g, 10.40 mmol) in tetrahydrofuran (5 mL) was added propan-2-amine (0.74 g, 12.40 mmol) at room temperature. After stirring at room temperature for 10 h, sodium borohydride (0.78 g, 20.80 mmol) was added to above mixture. The resulting solution was stirred at room temperature for 3 h. The reaction was then quenched by the addition of water and extracted with ethyl acetate. The combined organic layers were washed with brine, dried over anhydrous sodium sulfate, filtered, and concentrated under vacuum to afford (furan-2-ylmethyl)(isopropyl)amine (D2) (1.00 g, 69%) as a yellow oil, which was used directly. MS m/z 140.1 [M+1]$^+$.

Intermediate D3 isopropyl(oxolan-2-ylmethyl)amine

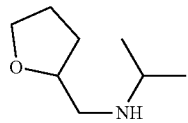

A mixture of 1-(oxolan-2-yl)methanamine (1.00 g, 9.90 mmolv) and acetone (0.62 g, 10.90 mmol) in tetrahydrofuran (10 mL) was stirred at room temperature for 16 h. Then sodium borohydride (0.56 g, 14.80 mmol) was added to the above solution at room temperature. The resulting solution was stirred at room temperature for 2 h. The reaction mixture was quenched by the addition of water and extracted with ethyl acetate. The combined organic layers were washed with brine, dried over anhydrous sodium sulfate, filtered, and concentrated under vacuum to afford isopropyl(oxolan-2-ylmethyl)amine (D3) (1.10 g, 77%) as a light yellow oil, which was used directly without purification. MS m/z 144.1 [M+1]$^+$.

Intermediate D4 isopropyl(1,2-oxazol-3-ylmethyl)amine

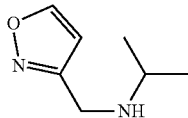

A mixture of 1-(1,2-oxazol-3-yl)methanamine hydrochloride (200 mg, 1.50 mmol), N,N-diisopropylethylamine (288 mg, 2.20 mmol) and acetone (173 mg, 3.00 mmol) in tetrahydrofuran was stirred at 60° C. for 3 h. Then the mixture was cooled at room temperature, sodium borohydride (112 mg, 3.00 mmol) was added to the above mixture at room temperature. The resulting mixture was stirred for additional 1 h at room temperature. The reaction was quenched with water and extracted with ethyl acetate. The combined organic layers were washed with water, dried over anhydrous sodium sulfate. After filtration, the filtrate was concentrated under reduced pressure to afford isopropyl(1,2-oxazol-3-ylmethyl)amine (D4) (75 mg, 36%) as a light yellow oil, which was used directly without purification. MS m/z 141.2 [M+1]$^+$.

Intermediate D5 isopropyl(1,3-oxazol-5-ylmethyl)amine

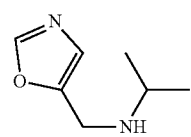

Followed the procedure of Intermediate D4 to afford isopropyl(1,3-oxazol-5-ylmethyl)amine (D5) (85 mg, 40%) as a light yellow oil from 1-(1,3-oxazol-5-yl)methanamine hydrochloride (200 mg, 1.50 mmol). MS m/z 141.0 [M+1]⁺.

Intermediate D6 isopropyl(pyridin-2-ylmethyl)amine

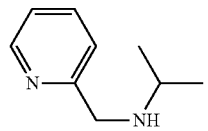

Followed the procedure of Intermediate D4 to afford isopropyl(pyridin-2-ylmethyl)amine (D6) (1.10 g, 78%) as a light yellow oil from 2-formylpyridine (1.00 g, 9.30 mmol). MS m/z 151.2 [M+1]⁺.

Intermediate D7 isopropyl(1,2-oxazol-5-ylmethyl)amine

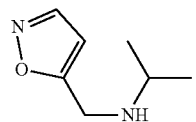

To a solution of 1-(1,2-oxazol-5-yl)methanamine hydrochloride (200 mg, 1.50 mmol) in dichloroethane (2 mL) was added acetone (173 mg, 3.00 mmol). After stirring at room temperature for 10 min, sodium triacetoxyborohydride (630 mg, 3.00 mmol) was added to above mixture. The mixture was stirred at room temperature for 16 h. The reaction was quenched with water and extracted with ethyl acetate. The combined organic layers were washed with water, dried over anhydrous sodium sulfate. After filtration, the filtrate was concentrated under reduced pressure to afford isopropyl(1,2-oxazol-5-ylmethyl)amine (D7) (300 mg, crude) as a yellow oil, which was used directly without purification. MS m/z 141.3 [M+1]⁺.

Intermediate D8 isopropyl(pyridin-3-ylmethyl)amine

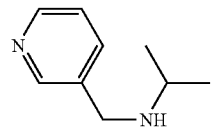

A mixture of 3-pyridinecarboxaldehyde (1.00 g, 9.30 mmol) and propan-2-amine (553 mg, 9.30 mmol) in tetrahydrofuran (10 mL) was stirred at room temperature for 16 h. Then sodium borohydride (530 mg, 14.00 mmol) was added to above mixture at room temperature. The resulting solution was stirred at room temperature for 2 h. The reaction mixture was quenched by the addition of water and extracted with ethyl acetate. The combined organic layers were washed with brine, dried over anhydrous sodium sulfate, filtered, and concentrated under vacuum to afford isopropyl(pyridin-3-ylmethyl)amine (D8) (1.20 g, 85%) as a light yellow oil, which was used directly without purification. MS m/z 151.0 [M+1]⁺.

Intermediate D9 isopropyl(pyridin-4-ylmethyl)amine

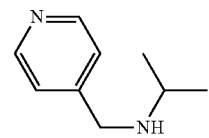

Followed the procedure of Intermediate D8 to afford isopropyl(pyridin-4-ylmethyl)amine (D9) (1.10 g, 78%) as a light yellow oil from 4-formylpyridine (1.00 g, 9.30 mmol). MS m/z 151.1 [M+1]⁺.

Intermediate D10

N-(2-methoxyethyl)aniline

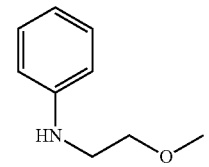

Step 1: To a solution of aniline (1.00 g, 10.70 mmol) and triethylamine (3.30 g, 32.20 mmol) in dichloromethane (10 mL) was added methoxyacetyl chloride (2.30 g, 21.50 mmol) dropwise at 0° C. The resulting solution was stirred at room temperature for 16 h. The resulting mixture was concentrated under vacuum. The residue was purified by FC with 0-70% ethyl acetate in petroleum ether to afford 2-methoxy-N-phenylacetamide (1.20 g, 67%) as a light-yellow oil. MS m/z 166.1 [M+1]⁺.

Step 2: To a solution of 2-methoxy-N-phenylacetamide (1.10 g, 6.60 mmol) in tetrahydrofuran (10 mL) were added boron trifluoride ether complex (1.90 g, 13.30 mmol) and sodium borohydride (0.50 g, 13.30 mmol) at 0° C. The resulting solution was stirred at room temperature for 16 h. The reaction mixture was quenched by the addition of water and extracted with ethyl acetate. The combined organic layers were washed with brine, dried over anhydrous sodium sulfate, filtered, and concentrated under vacuum. The residue was purified by FC with 0-60% ethyl acetate in petroleum ether to afford N-(2-methoxyethyl)aniline (D10) (0.80 g, 79%) as a light-yellow oil. MS m/z 152.1 [M+1]$^+$.

Intermediate D11 tert-butyl N-[2-[(cyclopropylmethyl)amino]ethyl]carbamate

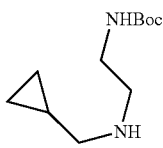 [SMILES: CC(C)(C)OC(=O)NCCNCC1CC1]

A mixture of 1-cyclopropylmethanamine (636 mg, 8.94 mmol), tert-butyl N-(2-bromoethyl)carbamate (1 g, 4.47 mmol) and potassium carbonate (1.85 g, 13.41 mmol) in N,N-dimethylformamide (10 mL) was stirred at 60° C. for 16 h. The mixture was diluted with ethyl acetate, the mixture was washed with brine. The organic layer was dried over anhydrous sodium sulfate, filtered, and concentrated under vacuum. The residue was purified by FC with 0-20% methanol in dichloromethane to afford tert-butyl N-[2-[(cyclopropylmethyl)amino]ethyl]carbamate (D11) (740 mg, 38%) as a yellow semi-solid. MS m/z 215.2 [M+1]$^+$.

Intermediate D12

N-(cyclopropylmethyl)-2-methoxyethanamine

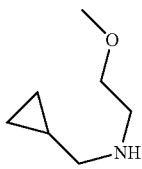

A mixture of 2-methoxyethan-1-amine (2.00 g, 26.67 mmol) and cyclopropanecarbaldehyde (2.00 g, 28.57 mmol) in dichloroethane (10 mL) was stirred at room temperature for 16 h. Then sodium borohydride (2.20 g, 91.67 mmol) and methanol (5 mL) were added to above mixture. The mixture was stirred at room temperature for 2 h. The mixture was diluted with ethyl acetate and washed with brine. The organic layer was dried over anhydrous sodium sulfate, filtered, and concentrated under vacuum. The residue was purified by FC with 0-100% ethyl acetate in petroleum ether to afford N-(cyclopropylmethyl)-2-methoxyethanamine (D12) (193 mg, 5%) as a yellow liquid. MS m/z 130.1 [M+1]$^+$.

Intermediate D13

N-(2-methoxyethyl)-1-methyl-1H-pyrazol-4-amine

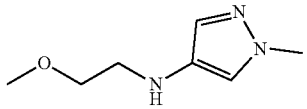

A mixture of 1-methylpyrazol-4-amine (1.00 g, 10.30 mmol), 2-bromoethyl methyl ether (1.00 g, 10.27 mmol) and potassium carbonate (3.00 g, 20.59 mmol) in N,N-dimethylformamide (10 mL) was stirred at room temperature for 16 h. The mixture was diluted with ethyl acetate and washed with brine. The organic layer was dried over anhydrous sodium sulfate, filtered, and concentrated under vacuum. The residue was purified by FC with 0-100% ethyl acetate in petroleum ether to afford N-(2-methoxyethyl)-1-methyl-1H-pyrazol-4-amine (D13) (150 mg, 7%) as a brown oil. MS m/z 156.1 [M+1]$^+$.

Intermediate D14

4-(2-methoxyethylamino)benzonitrile

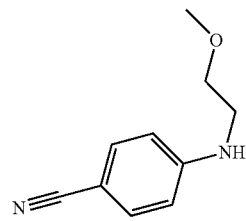

A mixture of 2-methoxyethanamine (2.00 g, 26.67 mmol), 4-fluorobenzonitrile (2.68 g, 22.15 mmol) and caesium carbonate (21.70 g, 66.56 mmol) in methyl sulfoxide (20 mL) was stirred at 60° C. for 2 h. The mixture was diluted with water and extracted with ethyl acetate. The organic layers were washed with brine, dried over anhydrous sodium sulfate, filtered, and concentrated under vacuum. The residue was purified by FC with 0-100% ethyl acetate in petroleum ether to afford 4-(2-methoxyethylamino)benzonitrile (D14) (680 mg, 11%) as a colorless oil. MS m/z 177.2 [M+1]$^+$.

Intermediate D15

6-(2-methoxyethylamino)nicotinonitrile

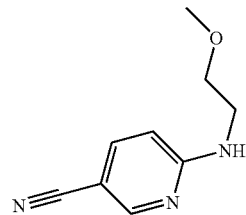

A solution of 2-methoxyethanamine (500 mg, 6.70 mmol), 6-chloronicotinonitrile (770 mg, 5.58 mmol) and caesium carbonate (5.42 g, 16.74 mmol) in methyl sulfoxide (15 mL) was stirred at 60° C. for 2 h. The mixture was diluted with water and extracted with ethyl acetate. The organic layers were washed with brine, dried over anhydrous sodium sulfate, filtered, and concentrated under vacuum. The residue was purified by FC with 0-100% ethyl acetate in petroleum ether to afford 6-(2-methoxyethylamino)nicotinonitrile (D15) (400 mg, 26%) as a yellow solid. MS m/z 178.0 [M+1]+.

Intermediate D16

5-chloro-N-(2-methoxyethyl)pyridin-2-amine

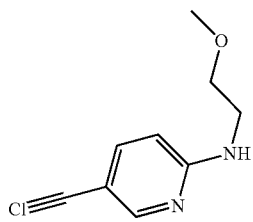

A mixture of 5-chloro-2-fluoropyridine (1.00 g, 7.60 mmol), 2-methoxyethanamine (1.00 g, 15.21 mmol) and N,N-diisopropylethylamine (3.00 g, 22.80 mmol) in ethanol (10 mL) was stirred at 80° C. for 16 h. The mixture was diluted with ethyl acetate and washed with brine. The organic layer was dried over anhydrous sodium sulfate, filtered, and concentrated under vacuum. The residue was purified by FC with 0-80% ethyl acetate in petroleum ether to afford 5-chloro-N-(2-methoxyethyl)pyridin-2-amine (D16) (160 mg, 9%) as a white solid. MS m/z 187.1 [M+1]+.

Intermediate D17

N-(2-methoxyethyl)pyrimidin-2-amine

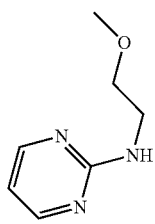

Followed the procedure of Intermediate D16 to afford N-(2-methoxyethyl)pyrimidin-2-amine (D17) (1.00 g, 82%) as a yellow solid. MS m/z 154.1 [M+1]+.

Intermediate D18

4-((cyclopropylmethyl)amino)benzonitrile

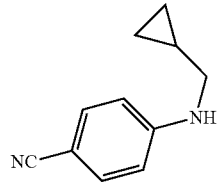 [SMILES: N#Cc1ccc(NCC2CC2)cc1]

A mixture of 4-fluorobenzonitrile (500 mg, 4.13 mmol), cyclopropylmethanamine (587 mg, 8.26 mmol) and potassium carbonate (1.70 g, 12.38 mmol) in acetonitrile (5 mL) was stirred at 55° C. for 16 h. The mixture was diluted with ethyl acetate and washed with brine. The organic layer was dried over anhydrous sodium sulfate, filtered, and concentrated under vacuum. The residue was purified by FC with 0-60% ethyl acetate in petroleum ether to afford 4-((cyclopropylmethyl)amino)benzonitrile (D18) (200 mg, 57%) as a brown oil. MS m/z 173.1 [M+1]+.

Intermediate D19

N-(2-methoxyethyl)-1-methylpyrazol-3-amine

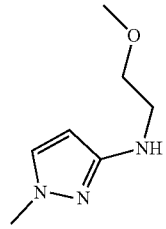

A mixture of 1-methyl-1H-pyrazol-3-amine (200 mg, 2.06 mmol), 1-bromo-2-methoxyethane (286 mg, 2.06 mmol) and potassium carbonate (569 mg, 4.12 mmol) in N,N-dimethylformamide (2 mL) was stirred at room temperature for 16 h. The mixture was diluted with ethyl acetate and washed with brine. The organic layer was dried over anhydrous sodium sulfate, filtered, and concentrated under vacuum. The residue was purified by FC with 0-15% methanol in dichloromethane to afford N-(2-methoxyethyl)-1-methylpyrazol-3-amine (D19) (300 mg, 93%) as a yellow oil. MS m/z 156.1 [M+1]+.

Intermediate D20

N-(4-fluorophenyl)tetrahydrofuran-3-amine

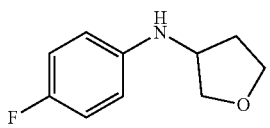 [SMILES: Fc1ccc(NC2CCOC2)cc1]

A degassed mixture of oxolan-3-amine (500 mg, 5.74 mmol), 4-bromofluorobenzene (502 mg, 2.87 mmol), (±)-2, 2'-Bis(diphenylphosphino)-1,1'-binaphthalene (357 mg, 0.57 mmol), tris(dibenzylideneacetone)dipalladium (263 mg, 0.29 mmol) and sodium tert-butoxide (1.10 g, 11.48 mmol) in toluene (5 mL) was stirred at 100° C. for 4 h. The mixture was diluted with ethyl acetate and washed with brine. The organic layer was dried over anhydrous sodium sulfate, filtered, and concentrated under vacuum. The residue was purified by FC with 0-50% ethyl acetate in petroleum ether to afford N-(4-fluorophenyl)tetrahydrofuran-3-amine (D20) (600 mg, 57%) as a brown oil. MS m/z 182.0 [M+1]+.

Intermediate D21

N-(cyclopropylmethyl)pyridin-2-amine

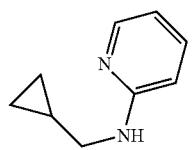

Followed the procedure of Intermediate D20 and purified by FC with 0-55% ethyl acetate in n-hexane to afford N-(cyclopropylmethyl)pyridin-2-amine (D21) (2.30 g, 44%) as a white solid from 2-chloropyridine (2.00 g, 17.61 mmol) and cyclopropylmethanamine (1.38 g, 19.37 mmol). MS m/z 149.1 [M+1]+.

Intermediate D22 isopropyl(1,3-oxazol-5-ylmethyl)amine

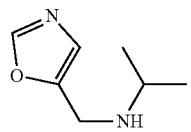

To a mixture of 1,3-oxazol-5-ylmethanamine hydrochloride (200 mg, 1.486 mmol) in DCE (5 mL) were added DIEA (384 mg, 2.972 mmol), acetone (172 mg, 2.972 mmol) and AcOH (0.2 mL). The resulting mixture was stirred at room temperature for 30 min. To the above mixture was added NaBH(OAc)₃ (630 mg, 2.972 mmol) at 0° C. The resulting mixture was stirred at room temperature overnight. The resulting mixture was extracted with EtOAc. The water layers were concentrated under reduced pressure. This resulted in isopropyl(1,3-oxazol-5-ylmethyl)amine (D22) (350 mg, crude) as a brown oil. MS m/z 141.0 [M+1]+

Intermediate D23

N,2,2-trimethyloxan-4-amine

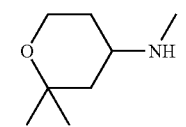

To a mixture of 2,2-dimethyloxan-4-one (500 mg, 3.901 mmol) in DCM (10 mL) was added CH₃NH₂HCl (1.58 g, 23.406 mmol). The resulting mixture was stirred at room temperature for 30 min. To the above mixture was added NaBH(OAc)₃ (4.96 g, 23.406 mmol) at 0° C. The resulting mixture was stirred at room temperature for 1 h. The resulting mixture was concentrated under reduced pressure. This resulted in N,2,2-trimethyloxan-4-amine (D23) (5 g, crude) as a white solid. MS m/z 144.1 [M+1]+

Intermediate D24

4-[(2-methoxyethyl)amino]-2-methylbenzonitrile

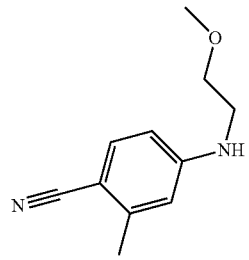

To a mixture of 2-methoxy-ethanamine (1.5 g, 19.97 mmol) in DMSO (20 mL) were added Cs₂CO₃ (9.76 g, 29.955 mmol) and 4-fluoro-2-methylbenzonitrile (2.02 g, 14.978 mmol). The resulting mixture was stirred at 80° C. overnight. The resulting mixture was extracted with EtOAc. The combined organic layers were washed with brine, dried over anhydrous Na₂SO₄. After filtration, the filtrate was concentrated under reduced pressure. The residue was purified by FC with 0-50% ethyl acetate in PE to afford 4-[(2-methoxyethyl)amino]-2-methylbenzonitrile (D24) (500 mg, 11.84%) as a yellow oil. MS m/z 191.1 [M+1]+

Intermediate D25

4-[(2-methoxyethyl)amino]-3-methylbenzonitrile

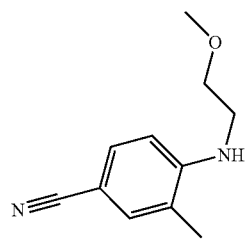

To a mixture of 4-fluoro-3-methylbenzonitrile (1.5 g, 11.100 mmol) and 2-methoxy-ethanamine (1 g, 13.319 mmol) in DMSO (15 mL) were added Cs₂CO₃ (10.85 g, 33.299 mmol). The resulting mixture was stirred at 80° C. overnight. The resulting mixture was extracted with EtOAc. The combined organic layers were washed with brine, dried over anhydrous Na₂SO₄. After filtration, the filtrate was concentrated under reduced pressure. The residue was purified by FC with 0-50% ethyl acetate in PE to afford 4-[(2-methoxyethyl)amino]-3-methylbenzonitrile (D25) (190 mg, 8.10%) as a colorless oil. MS m/z 191.1 [M+1]+

Intermediate D26

2-fluoro-4-[(2-methoxyethyl)amino]benzonitrile

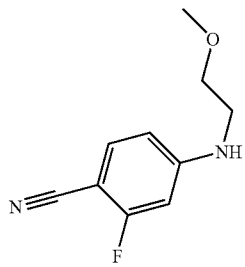

To a mixture of 2-methoxyethanamine (20 mg, 0.266 mmol) and 4-bromo-2-fluorobenzonitrile (160 mg, 0.798 mmol) in DMSO (4 mL) were added L-proline (13 mg, 0.106 mmol), CuI (11 mg, 0.053 mmol) and K$_2$CO$_3$ (111 mg, 0.798 mmol). The resulting mixture was stirred at 100° C. for 1 h under nitrogen atmosphere. The residue was purified by reverse-phase FC with 0-100% ACN in H$_2$O to afford 2-fluoro-4-[(2-methoxyethyl)amino]benzonitrile (D26) (150 mg, 23.21%) as a light yellow solid. MS m/z 195.1 [M+1]$^+$

Intermediate D27

3-fluoro-4-[(2-methoxyethyl)amino]benzonitrile

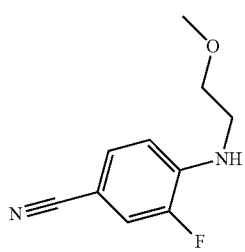

To a mixture of 2-methoxy-ethanamine (2 g, 26.627 mmol) and 4-bromo-3-fluorobenzonitrile (15.98 g, 79.881 mmol) in DMSO (10 mL) were added L-proline (1.23 g, 10.651 mmol), K$_2$CO$_3$ (11.04 g, 79.881 mmol) and CuI (1.01 g, 5.325 mmol). The resulting mixture was stirred at 100° C. for 2 h under nitrogen atmosphere. The residue was purified by reverse-phase FC with 0-100% ACN in H$_2$O to afford 3-fluoro-4-[(2-methoxyethyl)amino]benzonitrile (D27) (190 mg, 3.67%) as a yellow solid. MS m/z 195.1 [M+1]$^+$

Intermediate D28

N,2-dimethyltetrahydrofuran-3-amine

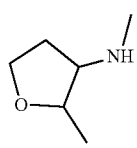

To a mixture of coffee furanone (2.00 g, 19.977 mmol) and in DCM (5 mL) was added CH$_3$NH$_2$HCl (4.05 g, 59.931 mmol). The resulting mixture was stirred at room temperature for 30 min. To the above mixture was added NaBH(OAc)$_3$ (8.47 g, 39.954 mmol) at 0° C. The resulting mixture was stirred at room temperature for 2 h. The resulting mixture was extracted with EtOAc. The combined organic layers were washed with brine, dried over anhydrous Na$_2$SO$_4$. This resulted in methyl N,2-dimethyloxolan-3-amine (D28) (3 g, crude) as a yellow oil. MS m/z 116.1 [M+1]$^+$

Intermediate D29

4-(oxolan-3-ylamino)benzonitrile

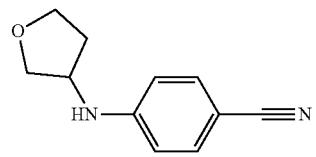 [SMILES: N#Cc1ccc(NC2CCOC2)cc1]

To a mixture of 4-fluoro-benzonitrile (1.11 g, 9.190 mmol) in DMSO (4 mL) were added DIEA (3.56 g, 27.569 mmol) and oxolan-3-amine (800 mg, 9.190 mmol). The resulting mixture was stirred at 120° C. for 16 h. The mixture was concentrated under vacuum. The residue was purified by reverse-phase FC with 0-100% ACN in H$_2$O to afford 4-(oxolan-3-ylamino)benzonitrile (D29) (450 mg, 26.01%) as a yellow oil. MS m/z 189.1 [M+1]$^+$

Intermediate D30

N-(4-fluorophenyl)oxolan-3-amine

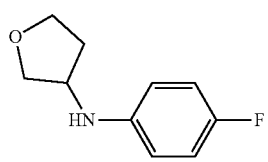 [SMILES: Fc1ccc(NC2CCOC2)cc1]

To a mixture of dihydrofuran-3-one (1 g, 11.616 mmol) and 4-fluoroaniline (1.29 g, 11.616 mmol) in THF (5 mL) were added Ti(Oi-Pr)$_4$ (6.60 g, 23.232 mmol). The resulting mixture was stirred at room temperature for 3 h under nitrogen atmosphere. The resulting mixture was concentrated under vacuum. To the above mixture was added MeOH (5 mL) and NaBH$_3$CN (1.46 g, 23.232 mmol). The resulting mixture was stirred at room temperature overnight. The residue was purified by FC with 0-50% ethyl acetate in PE to afford N-(4-fluorophenyl)oxolan-3-amine (D30) (1.00 g, 45.70%) as a yellow oil. MS m/z 182.1 [M+1]$^+$

Intermediate D31 methyl 3-(methylamino)bicyclo[1.1.1]pentane-1-carboxylate

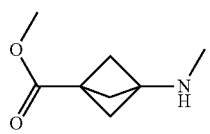

Step-1: To a mixture of 3-[(tert-butoxycarbonyl)amino]bicyclo[1.1.1]pentane-1-carboxylic acid (1 g, 4.4 mmol) in MeOH (5 mL) was added $SOCl_2$ (3.66 g, 30.8 mmol) at 0° C. The resulting mixture was stirred at room temperature overnight The resulting mixture was concentrated under vacuum. This resulted in methyl 3-aminobicyclo[1.1.1]pentane-1-carboxylate (780 mg, crude) as a white solid. MS m/z 142.1 $[M+1]^+$ Step-2: To a mixture of methyl 3-aminobicyclo[1.1.1]pentane-1-carboxylate (500 mg, 3.542 mmol) in DCM (5 mL) was added HCHO (53 mg, 1.771 mmol). The resulting mixture was stirred at room temperature for 30 min. To the above mixture was added $NaBH(OAc)_3$ (1.5 g, 7.084 mmol) at 0° C. The resulting mixture was stirred at room temperature for 2 h. The resulting mixture was filtered, the filter cake was washed with DCM. The filtrate was concentrated under reduced pressure. This resulted in methyl 3-(methylamino)bicyclo[1.1.1]pentane-1-carboxylate (D31) (600 mg, crude) as a white solid. MS m/z 156.1 $[M+1]^+$

Intermediate D32

N-[bicyclo[1.1.1]pentan-1-yl]oxolan-3-amine

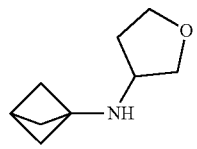

To a mixture of Bicyclo[1.1.1]pentan-1-amine hydrochloride (500 mg, 2.512 mmol) in MeOH (5 mL) were added dihydrofuran-3-one (1.08 g, 12.560 mmol). The resulting mixture was stirred at room temperature for 30 min. $NaBH_3CN$ (789 mg, 12.560 mmol) was added to the above mixture at 0° C. The resulting mixture was stirred at room temperature overnight. The mixture was concentrated under vacuum. This resulted in N-[bicyclo[1.1.1]pentan-1-yl]oxolan-3-amine (D32) (1.6 g, crude) as a yellow oil. MS m/z 154.1 $[M+1]^+$

Intermediate D33 methyl[(4-methyl-1,3-oxazol-5-yl)methyl]amine

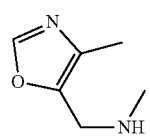

To a mixture of 4-methyl-1,3-oxazole-5-carbaldehyde (200 mg, 1.800 mmol) in MeOH (5 mL) were added $CH_3NH_2HCl$ (608 mg, 9.000 mmol). The resulting mixture was stirred at room temperature for 30 min. To the above mixture was added $NaBH_3CN$ (568 mg, 9.036 mmol). The resulting mixture was stirred at room temperature overnight. The mixture was concentrated under vacuum. This resulted in methyl[(4-methyl-1,3-oxazol-5-yl)methyl]amine (D33) (510 mg, crude) as a yellow oil. MS m/z 127.1 $[M+1]^+$

Example 1

3-(5-amino-6-methylpyridin-2-yl)-6-fluoro-N-(furan-2-ylmethyl)-N-isopropyl-1H-indole-2-carboxamide Step 1: To a solution of 3-[5-[(tert-butoxycarbonyl)amino]-6-methylpyridin-2-yl]-6-fluoro-1H-indole-2-carboxylic acid (250 mg, 0.60 mmol) in N,N-dimethylformamide (5 mL) were added triethylamine (197 mg, 1.90 mmol), N-(3-dimethylaminopropyl)-N'-ethylcarbodiimide hydrochloride (186 mg, 0.90 mmol), 1-hydroxybenzotriazole (131 mg, 0.90 mmol) and (furan-2-ylmethyl)(isopropyl)amine (90 mg, 0.60 mmol) at room temperature. The resulting solution was stirred at room temperature overnight. The mixture was diluted with ethyl acetate and washed with water and brine. The organic layer was dried over anhydrous sodium sulfate, filtered and concentrated under vacuum to afford tert-butyl N-(6-[6-fluoro-2-[(furan-2-ylmethyl)(isopropyl)carbamoyl]-1H-indol-3-yl]-2-methylpyridin-3-yl)carbamate (280 mg, crude) as a yellow solid. MS m/z 507.2 $[M+1]^+$.

Step 2: To a solution of tert-butyl N-(6-[6-fluoro-2-[(furan-2-ylmethyl)(isopropyl)carbamoyl]-1H-indol-3-yl]-2-methylpyridin-3-yl)carbamate (280 mg, 0.50 mmol) in dichloromethane (2 mL) was added trifluoroacetic acid (3 mL). The resulting solution was stirred at room temperature for 2 h. The mixture was basified by saturated sodium bicarbonate aqueous solution. The mixture was extracted with dichloromethane. The organic layer was dried over anhydrous sodium sulfate, filtered and concentrated under vacuum. The crude product was purified by Prep-HPLC with the following conditions: [Column, XBridge Shield RP18 OBD Column, 30*150 mm, 5 um; mobile phase B: acetonitrile, mobile phase A: water, 42% Phase B up to 68% in 6 min] to afford 3-(5-amino-6-methylpyridin-2-yl)-6-fluoro-N-(furan-2-ylmethyl)-N-isopropyl-1H-indole-2-carboxamide (41.6 mg, 18%) as a white solid.

Example 2

6-fluoro-N-isopropyl-N-(1,3-oxazol-2-ylmethyl)-1H-indole-2-carboxamide

To a solution of isopropyl(1,3-oxazol-2-ylmethyl)amine (120 mg, 0.85 mmol) in N,N-dimethylformamide (2.00 mL) was added 6-fluoro-1H-indole-2-carboxylic acid (153 mg, 0.85 mmol). The mixture was stirred at room temperature for 20 min, this was followed by the addition of triethylamine (173 mg, 1.71 mmol), N-(3-dimethylaminopropyl)-N'-ethylcarbodiimide hydrochloride (246 mg, 1.28 mmol) and 1-hydroxybenzotriazole (173 mg, 1.28 mmol) at room temperature. Then the mixture was stirred at room temperature for 3 h. The mixture was diluted by water and extracted with ethyl acetate. The organic layer was dried over anhydrous sodium sulfate, filtered and concentrated under vacuum. The residue was purified by prep-HPLC with the following conditions: [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 8 min] to afford 6-fluoro-N-isopropyl-N-(1,3-oxazol-2-ylmethyl)-1H-indole-2-carboxamide (5.5 mg, 2%) as a white solid.

Example 3

7-cyano-N-(furan-2-ylmethyl)-N-isopropyl-1H-indole-2-carboxamide

To a solution of (furan-2-ylmethyl)(isopropyl)amine (75 mg, 0.50 mmol) in N,N-dimethylformamide (2 mL) were added N-(3-dimethylaminopropyl)-N'-ethylcarbodiimide hydrochloride (155 mg, 0.80 mmol), 1-hydroxybenzotriazole (109 mg, 0.80 mmol), triethylamine (163 mg, 1.62 mmol) and 7-cyano-1H-indole-2-carboxylic acid (100 mg, 0.50 mmol) at room temperature. The resulting solution was stirred at room temperature for 2 h. The mixture was diluted by water and extracted with ethyl acetate. The organic layer was dried over anhydrous sodium sulfate, filtered and concentrated under vacuum. The residue was purified by reverse-phase FC with 5-50% acetonitrile in water to afford 7-cyano-N-(furan-2-ylmethyl)-N-isopropyl-1H-indole-2-carboxamide (40.2 mg, 24%) as a white solid.

Example 4

6-fluoro-N-isopropyl-N-(oxolan-2-ylmethyl)-1H-indole-2-carboxamide

To a mixture of isopropyl(oxolan-2-ylmethyl)amine (160 mg, 1.10 mmol), 6-fluoro-1H-indole-2-carboxylic acid (200 mg, 1.10 mmol) in N,N-dimethylformamide (4 mL) were added N-(3-dimethylaminopropyl)-N'-ethylcarbodiimide hydrochloride (321 mg, 1.80 mmol), 1-hydroxybenzotriazole (226 mg, 1.80 mmol) and triethylamine (339 mg, 3.40 mmol). The mixture was stirred at room temperature for 16 h. The mixture was diluted with water and extracted with ethyl acetate. The combined organic layers were washed with brine, dried over anhydrous sodium sulfate, filtered, and concentrated under vacuum. The residue was purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 35% B to 60% B in 8 min; 220 nm] to afford 6-fluoro-N-isopropyl-N-(oxolan-2-ylmethyl)-1H-indole-2-carboxamide (134.4 mg, 39%) as a white solid.

Example 5

6-fluoro-N-isopropyl-N-(1,2-oxazol-3-ylmethyl)-1H-indole-2-carboxamide

To a mixture of isopropyl(1,2-oxazol-3-ylmethyl)amine (75 mg, 0.50 mmol) and 6-fluoro-1H-indole-2-carboxylic acid (96 mg, 0.50 mmol) in N,N-dimethylformamide (2 mL) were added triethylamine (162 mg, 1.60 mmol), N-(3-dimethylaminopropyl)-N'-ethylcarbodiimide hydrochloride (154 mg, 0.80 mmol) and 1-hydroxybenzotriazole (108 mg, 0.80 mmol) at room temperature. The mixture was stirred at room temperature for 16 h. The resulting mixture was diluted by water and extracted with ethyl acetate. The combined organic layers were washed with water, dried over anhydrous anhydrous sodium sulfate. After filtration, the filtrate was concentrated under reduced pressure. The residue was purified by Prep-HPLC with the following conditions [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 35% B to 55% B in 8 min] to afford 6-fluoro-N-isopropyl-N-(1,2-oxazol-3-ylmethyl)-1H-indole-2-carboxamide (20.5 mg, 12%) as a white solid.

Example 6

6-fluoro-N-isopropyl-N-(1,2-oxazol-3-ylmethyl)-1H-indole-2-carboxamide

Followed the procedure of Example 5 and purified by Prep-HPLC with the following conditions [Column: XBridge Shield RP18 OBD Column, 30*150 mm, 5 um; Mobile Phase A: water (10 mmol/L ammonium bicarbonate), Mobile Phase B: acetonitrile; Flow rate: 60 mL/min; Gradient: 25% B to 50% B in 8 min] to afford 6-fluoro-N-isopropyl-N-(1,3-oxazol-5-ylmethyl)-1H-indole-2-carboxamide (37.1 mg, 20%) as a white solid from isopropyl(1,3-oxazol-5-ylmethyl)amine (85 mg, 0.60 mmol) and 6-fluoro-1H-indole-2-carboxylic acid (109 mg, 0.60 mmol).

Example 7

6-fluoro-N-isopropyl-N-(pyridin-2-ylmethyl)-1H-indole-2-carboxamide

Followed the procedure of Example 5 and purified by reverse-phase FC with 20-60% acetonitrile in water to afford 6-fluoro-N-isopropyl-N-(pyridin-2-ylmethyl)-1H-indole-2-carboxamide (206.6 mg, 59%) as a white solid from isopropyl(pyridin-2-ylmethyl)amine (168 mg, 1.10 mmol) and 6-fluoro-1H-indole-2-carboxylic acid (200 mg, 1.10 mmol).

Example 8

6-fluoro-N-isopropyl-N-(1,2-oxazol-5-ylmethyl)-1H-indole-2-carboxamide

Followed the procedure of Example 5 and purified by Prep-HPLC [Column: XBridge Shield RP18 OBD Column, 30*150 mm, 5 um; Mobile Phase A: water, Mobile Phase B: acetonitrile; Flow rate: 60 mL/min; Gradient: 30% to 50% in 10 min] to afford 6-fluoro-N-isopropyl-N-(1,2-oxazol-5-ylmethyl)-1H-indole-2-carboxamide (18.4 mg, 7%) as a white solid from isopropyl(1,2-oxazol-5-ylmethyl)amine (117 mg, 0.80 mmol) and 6-fluoro-1H-indole-2-carboxylic acid (150 mg, 0.80 mmol).

Example 9

6-fluoro-N-isopropyl-N-(pyridin-3-ylmethyl)-1H-indole-2-carboxamide

Followed the procedure of Example 5 and purified by Prep-HPLC [Column: XBridge Shield RP18 OBD Column, 30*150 mm, 5 um; Mobile Phase A: H₂O, Mobile Phase B: acetonitrile; Flow rate: 60 mL/min; Gradient: 30% B to 55% B in 8 min] to afford 6-fluoro-N-isopropyl-N-(pyridin-3-ylmethyl)-1H-indole-2-carboxamide (63.2 mg, 18%) as a white solid from isopropyl(pyridin-3-ylmethyl)amine (168 mg, 1.10 mmol) and 6-fluoro-1H-indole-2-carboxylic acid (200 mg, 1.10 mmol).

Example 10

6-fluoro-N-isopropyl-N-(pyridin-4-ylmethyl)-1H-indole-2-carboxamide

Followed the procedure of Example 5 and purified by Prep-HPLC [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 25% B to 45% B in 8 min] to afford 6-fluoro-N-isopropyl-N-(pyridin-4-ylmethyl)-1H-indole-2-carboxamide (84.2 mg, 24%) as a white solid from isopropyl(pyridin-4-ylmethyl)amine (168 mg, 1.10 mmol) and 6-fluoro-1H-indole-2-carboxylic acid (200 mg, 1.10 mmol).

Example 11

6-fluoro-N-isopropyl-N-phenyl-1H-indole-2-carboxamide

To a solution of 6-fluoro-1H-indole-2-carboxylic acid (100 mg, 0.56 mmol) and N-isopropylaniline (75 mg, 0.56 mmol) in N,N-dimethylformamide (1 mL) were added triethylamine (169 mg, 1.68 mmol) and $T_3P$ (532 mg, 1.67 mmol). The mixture was stirred at room temperature for 16 h. The resulting mixture was diluted by water and extracted with ethyl acetate. The combined organic layers were washed with water, dried over anhydrous sodium sulfate. After filtration, the filtrate was concentrated under reduced pressure. The residue was purified by Prep-HPLC [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 42% B to 70% B in 8 min] to afford 6-fluoro-N-isopropyl-N-phenyl-1H-indole-2-carboxamide (25.4 mg, 15%) as an off-white solid. $^1$H NMR (400 MHz, DMSO-$d_6$) δ 11.63 (s, 1H), 7.60-7.49 (m, 3H), 7.37-7.29 (m, 2H), 7.27 (dd, J=8.8, 5.6 Hz, 1H), 7.08 (dd, J=10.0, 2.4 Hz, 1H), 6.76-6.75 (m, 1H), 5.04-5.03 (m, 1H), 4.90 (s, 1H), 1.11 (d, J=6.8 Hz, 6H).

Example 12

6-fluoro-N-(2-methoxyethyl)-N-phenyl-1H-indole-2-carboxamide

To a solution of 6-fluoro-1H-indole-2-carboxylic acid (118 mg, 0.70 mmol) and N,N-dimethylformamide (0.02 mL) in dichloromethane (5 mL) was added a solution of oxalyl chloride (159 mg, 1.30 mmol) in dichloromethane (0.5 mL) at 0° C. The mixture was stirred at 0° C. for 1 h. The mixture was concentrated under vacuum. The residue was dissolved in dichloromethane (1 mL) was added to a solution of N,N-diisopropylethylamine (256 mg, 1.90 mmol) and N-(2-methoxyethyl)aniline (100 mg, 0.60 mmol) in dichloromethane (2 mL) at 0° C. The mixture was stirred at room temperature for 16 h. The reaction mixture was diluted with water and extracted with dichloromethane. The combined organic layers were washed with brine, dried over anhydrous sodium sulfate, filtered, and concentrated under vacuum. The residue was purified by reverse-phase FC with 40-80% acetonitrile in water to afford 6-fluoro-N-(2-methoxyethyl)-N-phenyl-1H-indole-2-carboxamide (89.6 mg, 43%) as a white solid.

Example 13

6-fluoro-N-methyl-N-(pyridin-2-yl)-1H-indole-2-carboxamide

Followed the procedure of Example 14 and purified by Prep-HPLC [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 8 min] to afford 6-fluoro-N-methyl-N-(pyridin-2-yl)-1H-indole-2-carboxamide (33.8 mg, 19%) as a white solid from 6-fluoro-1H-indole-2-carboxylic acid (127 mg, 0.70 mmol) and 6-fluoro-1H-indole-2-carboxylic acid (127 mg, 0.70 mmol).

Example 14

6-fluoro-N-methyl-N-(pyridin-3-yl)-1H-indole-2-carboxamide

Followed the procedure of Example 14 and purified by Prep-HPLC [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 25% B to 50% B in 8 min] to afford 6-fluoro-N-methyl-N-(pyridin-3-yl)-1H-indole-2-carboxamide (43.1 mg, 24%) as a white solid from 6-fluoro-1H-indole-2-carboxylic acid (116 mg, 0.60 mmol) and N-methylpyridin-3-amine (70 mg, 0.60 mmol).

Example 15

6-fluoro-N-methyl-N-(pyridin-4-yl)-1H-indole-2-carboxamide

Followed the procedure of Example 14 and purified by reverse-phase FC with 30-70% acetonitrile in water to afford 6-fluoro-N-methyl-N-(pyridin-4-yl)-1H-indole-2-carboxamide (15.1 mg, 10%) as a white solid from 6-fluoro-1H-indole-2-carboxylic acid (100 mg, 0.60 mmol) and N-methylpyridin-4-amine (60 mg, 0.60 mmol).

Example 16

N-(3-cyanophenyl)-6-fluoro-N-methyl-1H-indole-2-carboxamide

Followed the procedure of Example 14 and purified by Prep-HPLC [Column: Xselect CSH OBD Column 30*150 mm 5 um; Mobile Phase A: water (0.1% formic acid), Mobile Phase B: acetonitrile; Flow rate: 60 mL/min; Gradient: 5% B to 25% B in 8 min] to afford N-(3-cyanophenyl)-6-fluoro-N-methyl-1H-indole-2-carboxamide (22.9 mg, 13%) as a white solid from 6-fluoro-1H-indole-2-carboxylic acid (100 mg, 0.55 mmol) and 3-(methylamino)benzonitrile (73 mg, 0.55 mmol).

Example 17

N-(4-cyanophenyl)-6-fluoro-N-methyl-1H-indole-2-carboxamide

Followed the procedure of Example 14 and purified by Prep-HPLC [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 20% B to 35% B in 8 min] to afford N-(4-cyanophenyl)-6-fluoro-N-methyl-1H-indole-2-carboxamide (29.2 mg, 17%) as a white solid from 6-fluoro-1 H-indole-2-carboxylic acid (100 mg, 0.55 mmol) and 4-(methylamino) benzonitrile (110 mg, 0.80 mol).

Example 18

N-methyl-N-phenyl-1H-pyrrolo[2,3-b]pyridine-2-carboxamide

Followed the procedure of Example 5 and purified by trituration with ethyl acetate and hexane (1/10) to afford N-methyl-N-phenyl-1H-pyrrolo[2,3-b]pyridine-2-carboxamide (48.9 mg, 10%) as a white solid from methylaniline (200 mg, 1.87 mmol) and 1H-pyrrolo[2,3-b]pyridine-2-carboxylic acid (303 mg, 1.87 mmol).

Example 19

7-chloro-N-methyl-N-phenyl-1H-indole-2-carboxamide

Followed the procedure of Example 5 and purified by Prep-HPLC with the following conditions [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 40% B to 70% B in 8 min] to afford 7-chloro-N-methyl-N-phenyl-1H-indole-2-carboxamide (64.9 mg, 12%) as a white solid from methylaniline (200 mg, 1.87 mmol) and 7-chloro-1H-indole-2-carboxylic acid (365 mg, 1.87 mmol).

Example 20

7-cyano-N-cyclopentyl-N-methyl-1H-indole-2-carboxamide

Followed the procedure of Example 5 and purified by reverse phase FC with 10-70% acetonitrile in water to afford 7-cyano-N-cyclopentyl-N-methyl-1H-indole-2-carboxamide (23.3 mg, 32%) as an off-white solid from 7-cyano-1H-indole-2-carboxylic acid (50 mg, 0.27 mmol) and N-methylcyclopentanamine (27 mg, 0.27 mmol).

Example 21

7-cyano-N-methyl-N-phenyl-1H-indole-2-carboxamide

Followed the procedure of Example 5 and purified by reverse-phase FC with 10-80% acetonitrile in water to afford 7-cyano-N-methyl-N-phenyl-1H-indole-2-carboxamide (20.3 mg, 27%) as an off-white solid from 7-cyano-1H-indole-2-carboxylic acid (50 mg, 0.27 mmol) and methylaniline (29 mg, 0.27 mmol).

Example 22

3-chloro-N-methyl-N-phenyl-1H-indole-2-carboxamide

Followed the procedure of Example 5 and purified by prep-HPLC with the following conditions [Column: XBridge Shield RP18 OBD Column, 30*150 mm, 5 um; Mobile Phase A: water, Mobile Phase B: acetonitrile; Flow rate: 60 mL/min; Gradient: 35% B to 55% B in 8 min] to afford 3-chloro-N-methyl-N-phenyl-1H-indole-2-carboxamide (19.2 mg, 13%) as a white solid from methylaniline (54 mg, 0.51 mmol) and 3-chloro-1H-indole-2-carboxylic acid (100 mg, 0.51 mmol).

Example 23

5-fluoro-N-methyl-N-phenyl-3H-1,3-benzodiazole-2-carboxamide

Followed the procedure of Example 5 and purified by prep-HPLC with the following conditions [Column: XBridge Prep OBD C18 Column, 30×150 mm 5 um; Mobile Phase A: water (10 mmol/L ammonium bicarbonate+0.1% $NH_3 \cdot H_2O$), Mobile Phase B: acetonitrile; Flow rate: 60 mL/min; Gradient: 27% B to 45% B in 8 min] to afford 5-fluoro-N-methyl-N-phenyl-3H-1,3-benzodiazole-2-carboxamide (17.3 mg, 7%) as a white solid from 5-fluoro-3H-1,3-benzodiazole-2-carboxylic acid (92 mg, 0.51 mmol) and methylaniline (53 mg, 0.51 mmol).

Example 24

6-fluoro-N-methyl-N-phenyl-1-benzofuran-2-carboxamide

Followed the procedure of Example 5 and purified by prep-HPLC with the following conditions: [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 25% B to 40% B in 8 min] to afford 6-fluoro-N-methyl-N-phenyl-1-benzofuran-2-carboxamide (43.7 mg, 29%) as a white solid from 6-fluoro-1-benzofuran-2-carboxylic acid (100 mg, 0.55 mmol) and methylaniline (59 mg, 0.55 mmol).

Example 25

N-methyl-N-phenyl-7-(trifluoromethyl)-1H-indole-2-carboxamide

Followed the procedure of Example 14 and purified by prep-HPLC with the following conditions [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 45% B to 70% B in 7 min] to afford N-methyl-N-phenyl-7-(trifluoromethyl)-1H-indole-2-carboxamide (52.3 mg, 36%) as a white solid from 7-(trifluoromethyl)-1H-indole-2-carbonyl chloride (110 mg, 0.44 mmol) and methylaniline (47 mg, 0.44 mmol).

Example 26

N-methyl-N-(pyridin-2-yl)-7-(trifluoromethyl)-1H-indole-2-carboxamide

Followed the procedure of Example 12 and purified by prep-HPLC with the following conditions [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 8 min] to afford N-methyl-N-(pyridin-2-yl)-7-(trifluoromethyl)-1H- indole-2-carboxamide (59 mg, 38%) as a white solid from 2-methylaminopyridine (52 mg, 0.48 mmol).

Example 27

N-(4-cyanophenyl)-N-methyl-7-(trifluoromethyl)-1H-indole-2-carboxamide

Followed the procedure of Example 12 and purified by reverse-phase FC with 10-80% acetonitrile in water to afford N-(4-cyanophenyl)-N-methyl-7-(trifluoromethyl)-1H-indole-2-carboxamide (16.4 mg, 9%) as a yellow solid from 4-(methylamino)benzonitrile (64 mg, 0.48 mmol).

Example 28

7-chloro-N-methyl-N-(pyridin-2-yl)-1H-indole-2-carboxamide

Followed the procedure of Example 12 and purified by Prep-HPLC [Column: XBridge Prep OBD C18 Column, 30*150 mm, 5 μm; Mobile Phase A: water (10 mmol/L ammonium bicarbonate), Mobile Phase B: acetonitrile; Flow rate: 60 mL/min; Gradient: 25% B to 50% B in 8 min] to afford 7-chloro-N-methyl-N-(pyridin-2-yl)-1H-indole-2-carboxamide (35.4 mg, 26%) as an off-white solid from 7-chloro-1H-indole-2-carboxylic acid (100 mg, 0.51 mmol) and 2-methylaminopyridine (152 mg, 1.40 mmol).

Example 29

7-chloro-N,N-dimethyl-1H-indole-2-carboxamide

Followed the procedure of Example 5 and purified by Prep-HPLC [Column: XBridge Prep OBD C18 Column, 30×150 mm 5 um; Mobile Phase A: water (10 mmoL/L ammonium bicarbonate), Mobile Phase B: acetonitrile; Flow rate: 60 mL/min; Gradient: 30% to 55% in 8 min] to afford 7-chloro-N,N-dimethyl-1H-indole-2-carboxamide (36.1 mg, 31%) as an off-white solid from 7-chloro-1H-indole-2-carboxylic acid (100 mg, 0.51 mmol) and dimethylamine hydrochloride (69 mg, 0.85 mmol).

Example 30

7-chloro-N-cyclopentyl-N-methyl-1H-indole-2-carboxamide

Followed the procedure of Example 5 and purified by Prep-HPLC [Column: Xselect CSH OBD Column 30*150 mm 5 um; Mobile Phase A: water (0.1% FA), Mobile Phase B: acetonitrile; Flow rate: 60 mL/min; Gradient: 25% to 50% in 8 min] to afford 7-chloro-N-cyclopentyl-N-methyl-1H-indole-2-carboxamide (14.2 mg, 10%) as an off-white solid from 7-chloro-1H-indole-2-carboxylic acid (100 mg, 0.51 mmol) and N-methylcyclopentanamine (51 mg, 0.51 mmol).

Example 31

7-chloro-N-methyl-N-(oxolan-3-yl)-1H-indole-2-carboxamide

Followed the procedure of Example 5 and purified by Prep-HPLC [Column: XBridge Shield RP18 OBD Column, 30*150 mm, 5 um; Mobile Phase A: water (10 mmoL/L ammonium bicarbonate+0.1% ammonium hydroxide), Mobile Phase B: acetonitrile; Flow rate: 60 mL/min; Gradient: 30% to 60% in 8 min] to afford 7-chloro-N-methyl-N-(oxolan-3-yl)-1H-indole-2-carboxamide (61 mg, 42%) as an off-white solid from 7-chloro-1H-indole-2-carboxylic acid (100 mg, 0.51 mmol) and N-methyloxolan-3-amine (78 mg, 0.77 mmol).

Example 32

7-chloro-N-(cyclopropylmethyl)-N-methyl-1H-indole-2-carboxamide

Followed the procedure of Example 5 and purified by Prep-HPLC [Column: XBridge Shield RP18 OBD Column, 30*150 mm, 5 μm; Mobile Phase A: water (10 mmol/L ammonium bicarbonate+0.1% ammonium hydroxide), Mobile Phase B: acetonitrile; Flow rate: 60 mL/min; Gradient: 30% B to 65% B in 8 min] to afford 7-chloro-N-(cyclopropylmethyl)-N-methyl-1H-indole-2-carboxamide (43.0 mg, 32%) as an off-white semi-solid from 7-chloro-1H-indole-2-carboxylic acid (100 mg, 0.51 mmol) and 1-cyclopropyl-N-methylmethanamine hydrochloride (65 mg, 0.53 mmol).

Example 33

7-chloro-N-(4-cyanophenyl)-N-methyl-1H-indole-2-carboxamide

Followed the procedure of Example 12 and purified by Prep-HPLC [Column: XBridge Prep OBD C18 Column, 30*150 mm, 5 μm; Mobile Phase A: water (10 mmol/L ammonium bicarbonate), Mobile Phase B: acetonitrile; Flow rate: 60 mL/min; Gradient: 35% B to 65% B in 8 min] to afford 7-chloro-N-(4-cyanophenyl)-N-methyl-1H-indole-2-carboxamide (16.8 mg, 11%) as an off-white solid from 7-chloro-1H-indole-2-carboxylic acid (100 mg, 0.51 mmol) and 4-(methylamino)benzonitrile (185 mg, 1.40 mmol).

Example 34

7-cyano-N-(4-fluorophenyl)-N-methyl-1-benzofuran-2-carboxamide

Step 1: To a solution of 7-bromo-1-benzofuran-2-carboxylic acid (1000 mg, 0.41 mmol) and N,N-dimethylformamide (0.2 mL) in dichloromethane (10 mL) was added oxalyl chloride (790 mg, 6.20 mmol) dropwise at 0° C. The mixture was stirred at 0° C. for 2 h. The mixture was concentrated under vacuum. The residue was redissolved in dichloromethane (5 mL) and then added dropwise to a solution of triethylamine (1491 mg, 9.24 mmol) and 4-fluoro-N-methylaniline (463 mg, 3.70 mmol) in tetrahydrofuran (8 mL) at 0° C. The mixture was stirred at room temperature for 16 h. The reaction mixture was concentrated under vacuum. The residue was purified by FC with 0-100% ethyl acetate in petroleum ether to afford 7-bromo-N-(4-fluorophenyl)-N-methyl-1-benzofuran-2-carboxamide (500 mg, 46%) as a yellow solid. MS m/z 348.0, 350.

Step 2: A degassed mixture of 7-bromo-N-(4-fluorophenyl)-N-methyl-1-benzofuran-2-carboxamide (200 mg, 0.57 mmol), palladium(0)tetrakis(triphenylphosphine) (66 mg, 0.057 mmol) and zinc cyanide (101 mg, 0.86 mmol) in N,N-dimethylformamide (2 mL) was stirred at 120° C. for 16 h. The reaction mixture was diluted by water and extracted with ethyl acetate. The combined organic layers were washed with brine, dried over anhydrous sodium sulfate, filtered, and concentrated under vacuum. The residue was purified by prep-HPLC with the following conditions: [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 40% B to 55% B in 8 min] to afford 7-cyano-N-(4-fluorophenyl)-N-methyl-1-benzofuran-2-carboxamide (9 mg, 5%) as a white solid.

Example 35

7-chloro-N-(4-fluorophenyl)-N-methyl-1-benzofuran-2-carboxamide

Followed the procedure of Example 12 and purified by Prep-HPLC [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 40% B to 70% B in 8 min] to afford 7-chloro-N-(4-fluorophenyl)-N-methyl-1-benzofuran-2-carboxamide (37.6 mg, 32%) as a white solid from 7-chloro-1-benzofuran-2-carboxylic acid (75 mg, 0.38 mmol) and 4-fluoro-N-methylaniline (47 mg, 0.38 mmol).

Example 36

N-(4-fluorophenyl)-N-methyl-7-(trifluoromethyl)benzofuran-2-carboxamide

Followed the procedure of Example 12 and purified by prep-HPLC with the following conditions: [Column: XBridge Prep OBD C18 Column, 30×150 mm 5 um; Mobile Phase A: water (10 mmol/L ammonium bicarbonate+0.1% ammonium hydroxide), Mobile Phase B: acetonitrile; Flow rate: 60 mL/min; Gradient: 45% B to 70% B in 8 min] to afford N-(4-fluorophenyl)-N-methyl-7-(trifluoromethyl)benzofuran-2-carboxamide (5.5 mg, 4%) as a white solid from 7-(trifluoromethyl)-1-benzofuran-2-carboxylic acid (100 mg, 0.43 mmol) and 4-fluoro-N-methylaniline (50 mg, 0.40 mmol).

Example 37

7-chloro-N-methyl-N-(pyridin-2-yl)-1-benzofuran-2-carboxamide

Followed the procedure of Example 12 and purified by Prep-HPLC [Column: XBridge Prep OBD C18 Column, 30*150 mm 5 um; Mobile Phase A: water (10 mmol/L ammonium bicarbonate+0.1% ammonium hydroxide), Mobile Phase B: acetonitrile; Flow rate: 60 mL/min; Gradient: 25% B to 60% B in 7 min] to afford 7-chloro-N-methyl-N-(pyridin-2-yl)-1-benzofuran-2-carboxamide (23.4 mg, 21%) as a white solid from 7-chloro-1-benzofuran-2-carboxylic acid (75 mg, 0.38 mmol) and 2-methylaminopyridine (41 mg, 0.38 mmol).

Example 38

6-fluoro-N-methyl-N-(pyridin-2-yl)-1-benzofuran-2-carboxamide

Followed the procedure of Example 12 and purified by reverse-phase FC with 10-70% acetonitrile in water to afford 6-fluoro-N-methyl-N-(pyridin-2-yl)-1-benzofuran-2-carboxamide (26.8 mg, 16%) as an off-white solid from 6-fluoro-1-benzofuran-2-carboxylic acid (200 mg, 1.11 mmol) and 2-methylaminopyridine (65 mg, 0.60 mmol).

Example 39

6-fluoro-N-(4-fluorophenyl)-N-methyl-1-benzofuran-2-carboxamide

Followed the procedure of Example 12 and purified by reverse-phase FC with 5-70% acetonitrile in water to afford 6-fluoro-N-(4-fluorophenyl)-N-methyl-1-benzofuran-2-carboxamide (61.4 mg, 35%) as a white solid from 4-fluoro-N-methylaniline (75 mg, 0.60 mmol).

Example 40

7-chloro-N-methyl-N-(pyrrolidin-3-yl)-1H-indole-2-carboxamide trifluoroacetic acid salt Step 1: To a solution of 7-chloro-1H-indole-2-carboxylic acid (300 mg, 1.53 mmol) and N,N-dimethylformamide (0.10 mL) in dichloromethane (3 mL) was added oxalyl chloride (292 mg, 2.30 mmol) at 0° C. Then the mixture was stirred at 0° C. for 2 h. The mixture was concentrated under vacuum to afford 7-chloro-1H-indole-2-carbonyl chloride, which was re-dissolved in tetrahydrofuran (4 mL) and then added dropwise to a solution of tert-butyl 3-(methylamino)pyrrolidine-1-carboxylate (306 mg, 1.53 mmol) and triethylamine (465 mg, 4.59 mmol) in tetrahydrofuran (5 mL) at 0° C. The mixture was stirred at room temperature for 16 h. The reaction mixture was diluted by water and extracted with ethyl acetate. The combined organic layers were washed with brine, dried over anhydrous sodium sulfate, filtered, and concentrated under vacuum. The residue was purified by FC with 0-40% ethyl acetate in petroleum ether to afford tert-butyl 3-(N-methyl7-chloro-1H-indole-2-amido)pyrrolidine-1-carboxylate (526 mg, 90%) as a yellow oil. MS m/z 378.1 [M+1]$^+$.

Step 2: To a solution of tert-butyl 3-(N-methyl7-chloro-1H-indole-2-amido)pyrrolidine-1-carboxylate (526 mg, 1.39 mmol) in dichloromethane (5 mL) was added trifluoroacetic acid (4 mL). The mixture was stirred at room temperature for 2 h. The mixture was concentrated under vacuum. The residue was purified by prep-HPLC with the following conditions: [Column: XBridge Shield RP18 OBD Column, 30*150 mm, 5 um; Mobile Phase A: water (0.05% trifluoroacetic acid), Mobile Phase B: acetonitrile; Flow rate: 60 mL/min; Gradient: 15% B to 45% B in 8 min] to afford 7-chloro-N-methyl-N-(pyrrolidin-3-yl)-1H-indole-2-carboxamide trifluoroacetic acid salt (31.9 mg, 8%) as a white solid.

Example 41

7-chloro-N-(1-isopropylpyrrolidin-3-yl)-N-methyl-1H-indole-2-carboxamide

To a solution of 7-chloro-N-methyl-N-(pyrrolidin-3-yl)-1H-indole-2-carboxamide 2,2,2-trifluoroacetate (200 mg, 0.72 mmol) in dichloroethane (2 mL) were added acetone (83 mg, 1.44 mmol), sodium triacetoxyborohydride (305 mg, 1.43 mmol) and acetic acid (0.1 mL). Then the mixture was mixed at room temperature for 1 h. The reaction was quenched by water and extracted with dichloromethane. The combined organic layers were washed with brine, dried over anhydrous sodium sulfate, filtered, and concentrated under vacuum. The residue was purified by Prep-HPLC [Column: XBridge Prep OBD C18 Column, 30*150 mm, 5 μm; Mobile Phase A: water (10 mmol/L ammonium bicarbonate+0.1% ammonium hydroxide), Mobile Phase B: acetonitrile; Flow rate: 60 mL/min; Gradient: 35% B to 60% B in 8 min] to afford 7-chloro-N-(1-isopropylpyrrolidin-3-yl)-N-methyl-1H-indole-2-carboxamide (41.1 mg, 17%) as a white solid.

Example 42

7-chloro-N-methyl-N-(piperidin-3-yl)-1H-indole-2-carboxamide

Followed the procedure of Example 40 and purified by Prep-HPLC [Column: XBridge Prep OBD C18 Column, 30*150 mm 5 um; Mobile Phase A: water (10 mmol/L ammonium bicarbonate+0.1% ammonium hydroxide), Mobile Phase B: acetonitrile; Flow rate: 60 mL/min; Gradient: 25% B to 45% B in 8 min] to afford 7-chloro-N-methyl-N-(piperidin-3-yl)-1H-indole-2-carboxamide (8.8 mg, 2% over two steps) as a white solid from 7-chloro-1H-indole-2-carboxylic acid (300 mg, 1.53 mmol).

Example 43

7-chloro-N-methyl-N-(piperidin-4-yl)-1H-indole-2-carboxamide

Followed the procedure of Example 40 and purified by prep-HPLC with the following conditions: [Column: XBridge Shield RP18 OBD Column, 30*150 mm, 5 um; Mobile Phase A: water (10 mmol/L ammonium bicarbonate+0.1% ammonium hydroxide), Mobile Phase B: acetonitrile; Flow rate: 60 mL/min; Gradient: 45% B to 75% B in 8 min] to afford 7-chloro-N-methyl-N-(piperidin-4-yl)-1H-indole-2-carboxamide (6.2 mg, 2% over two steps) as a white solid from 7-chloro-1H-indole-2-carbonyl chloride (328 mg, 1.53 mmol).

Example 44

7-chloro-N-(1-isopropylpiperidin-3-yl)-N-methyl-1H-indole-2-carboxamide

Followed the procedure of Example 41 and purified by Prep-HPLC [Column: XBridge Prep OBD C18 Column, 30*150 mm 5 um; Mobile Phase A: water (10 mmol/L ammonium bicarbonate+0.1% ammonium hydroxide), Mobile Phase B: acetonitrile; Flow rate: 60 mL/min; Gradient: 35% B to 70% B in 7 min] to afford 7-chloro-N-(1-isopropylpiperidin-3-yl)-N-methyl-1H-indole-2-carboxamide (32.5 mg, 14%) as a white solid from 7-chloro-N-methyl-N-(piperidin-3-yl)-1H-indole-2-carboxamide (200 mg, 0.68 mmol).

Example 45

7-chloro-N-(1-isopropylpiperidin-4-yl)-N-methyl-1H-indole-2-carboxamide

Followed the procedure of Example 41 and purified by prep-HPLC with the following conditions: [Column: XBridge Prep OBD C18 Column, 30*150 mm 5 um; Mobile Phase A: water (10 mmol/L ammonium bicarbonate+0.1% ammonium hydroxide), Mobile Phase B: acetonitrile; Flow rate: 60 mL/min; Gradient: 30% B to 55% B in 7 min] to afford 7-chloro-N-(1-isopropylpiperidin-4-yl)-N-methyl-1H-indole-2-carboxamide (34.6 mg, 10%) as a white solid from 7-chloro-N-methyl-N-(piperidin-4-yl)-1H-indole-2-carboxamide (300 mg, 1.03 mmol).

Example 46

N-(2-aminoethyl)-7-cyano-N-(cyclopropylmethyl)-1H-indole-2-carboxamide formate

Step 1: To a mixture of tert-butyl N-[2-[(cyclopropylmethyl)amino]ethyl]carbamate (200 mg, 0.93 mmol) and 7-cyano-1H-indole-2-carboxylic acid (208 mg, 1.12 mmol) in N,N-dimethylformamide (2 mL) were added O-(7-Azabenzotriazol-1-yl)-N,N,N,N-tetramethyluronium Hexafluorophosphate (532 mg, 1.40 mmol) and N,N-diisopropylethylamine (362 mg, 2.80 mmol) at room temperature. The mixture was stirred at room temperature for 2 h. The mixture was diluted with water and extracted with ethyl acetate. The organic layers were washed with brine, dried over anhydrous sodium sulfate, filtered, and concentrated under vacuum. The residue was purified by FC with 0-100% ethyl acetate in petroleum ether to afford tert-butyl 2-(7-cyano-N-(cyclopropylmethyl)-1H-indole-2-carboxamido)ethylcarbamate (230 mg, 64%) as a colorless oil. MS m/z 383.2 [M+1]$^+$.

Step 2: To a solution of tert-butyl N-[2-[1-(7-cyano-1H-indol-2-yl)-N-(cyclopropylmethyl)formamido]ethyl]carbamate (200 mg, 0.52 mmol) in dichloromethane (10 mL) was added trifluoroacetic acid (3 mL). The mixture was stirred at room temperature for 2 h. The mixture was concentrated under vacuum. The residue was purified by Prep-HPLC [Column: Sunfire prep C18 column, 30*150 mm, 5 μm; Mobile Phase A: water (0.1% formic acid), Mobile Phase B: acetonitrile; Flow rate: 60 mL/min; Gradient: 15% B to 40% B in 8 min] to afford N-(2-aminoethyl)-7-cyano-N-(cyclopropylmethyl)-1H-indole-2-carboxamide formate (26.3 mg, 15%) as a white solid.

Example 47

N-(2-aminoethyl)-7-chloro-N-(cyclopropylmethyl)-1H-indole-2-carboxamide

Followed the procedure of Example 46 and purified by Prep-HPLC [Column: YMC-Actus Triart C18, 20*250 mm, 5 um, 12 nm; Mobile Phase A: water (10 mmol/L ammonium bicarbonate), Mobile Phase B: acetonitrile; Flow rate: 60 mL/min; Gradient: 35% B to 60% B in 8 min] to afford N-(2-aminoethyl)-7-chloro-N-(cyclopropylmethyl)-1H-indole-2-carboxamide (35 mg, 19% over two steps) as a white solid from 7-chloro-1H-indole-2-carboxylic acid (120 mg, 0.62 mmol).

Example 48

7-cyano-N-(cyclopropylmethyl)-N-(2-methoxyethyl)-1H-indole-2-carboxamide

Followed the procedure of Example 5 and purified by FC with 0-100% ethyl acetate in petroleum ether to afford 7-cyano-N-(cyclopropylmethyl)-N-(2-methoxyethyl)-1H-indole-2-carboxamide (13.6 mg, 5%) as a yellow solid from (cyclopropylmethyl)(2-methoxyethyl)amine (100 mg, 0.77 mmol) and 7-cyano-1H-indole-2-carboxylic acid (144 mg, 0.77 mmol).

Example 49

6-fluoro-N-(2-methoxyethyl)-N-(1-methylpyrazol-4-yl)-1H-indole-2-carboxamide Step 1: Followed the procedure of Example 5 and purified by FC with 0-100% ethyl acetate in petroleum ether to afford 1-(benzenesulfonyl)-6-fluoro-N-(2-methoxyethyl)-N-(1-methylpyrazol-4-yl)indole-2-carboxamide (100 mg, 30%) as a brown semi-solid from 1-(benzenesulfonyl)-6-fluoroindole-2-carboxylic acid (226 mg, 0.71 mmol). MS m/z 457.1 [M+1]$^+$.

Step 2: A mixture of 1-(benzenesulfonyl)-6-fluoro-N-(2-methoxyethyl)-N-(1-methylpyrazol-4-yl)indole-2-carboxamide (160 mg, 0.35 mmol) and tetrabutylammonium fluoride (275 mg, 1.05 mmol) in tetrahydrofuran (2 mL) was stirred at room temperature for 1 h. The mixture was diluted with ethyl acetate and washed with brine. The organic layer was dried over anhydrous sodium sulfate, filtered, and concentrated under vacuum. The residue was purified by FC with 0-100% ethyl acetate in petroleum ether to afford 6-fluoro-N-(2-methoxyethyl)-N-(1-methylpyrazol-4-yl)-1H-indole-2-carboxamide (30.7 mg, 27%) as a white solid.

Example 50

7-chloro-N-(cyclopropylmethyl)-N-(2-methoxyethyl)-1H-indole-2-carboxamide

To a mixture of (cyclopropylmethyl)(2-methoxyethyl)amine (110 mg, 0.85 mmol) and 7-chloro-1H-indole-2-carboxylic acid (167 mg, 0.85 mmol) in N,N-dimethylformamide (1 mL) were added O-(7-Azabenzotriazol-1-yl)-N,N,N,N-tetramethyluronium Hexafluorophosphate (486 mg, 1.28 mmol) and N,N-diisopropylethylamine (330 mg, 2.55 mmol). The mixture was stirred at room temperature for 16 h. The mixture was diluted with water and extracted with ethyl acetate. The organic layers were washed with brine, dried over anhydrous sodium sulfate, filtered, and concentrated under vacuum. The residue was purified by FC with 0-100% ethyl acetate in petroleum ether to afford 7-chloro-N-(cyclopropylmethyl)-N-(2-methoxyethyl)-1H-indole-2-carboxamide (49.7 mg, 20%) as a white solid.

Example 51

N-(4-cyanophenyl)-6-fluoro-N-(2-methoxyethyl)-1H-indole-2-carboxamide

Followed the procedure of Example 12 and purified by Prep-HPLC [Column: YMC-Actus Triart C18, 20*250 mm, 5 μm, 12 nm; Flow rate: 60 mL/min; Mobile Phase A: water (0.1% formic acid), Mobile Phase B: acetonitrile; Gradient: 35% B to 65% B in 8 min, 65% B to 75% B in 9 min] to afford N-(4-cyanophenyl)-6-fluoro-N-(2-methoxyethyl)-1H-indole-2-carboxamide (9.2 mg, 4.81%) as a white solid from 6-fluoro-1H-indole-2-carboxylic acid (102 mg, 0.57 mmol).

Example 52

1-(5-cyanopyridin-2-yl)-6-fluoro-N-(2-methoxyethyl)-1H-indole-2-carboxamide

Step 1: To a solution of 6-fluoro-1-(phenylsulfonyl)-1H-indole-2-carboxylic acid (300 mg, 0.94 mmol) and N,N-dimethylformamide (0.1 mL) in dichloromethane (3 mL) was added oxalyl chloride (239 mg, 1.88 mmol) at 5° C. The mixture was stirred at room temperature for 2 h. The mixture was concentrated under vacuum. The residue was added to a solution of 6-(2-methoxyethylamino)nicotinonitrile (166 mg, 0.94 mmol)) and triethylamine (285 mg, 2.82 mmol) in dichloromethane (1 mL) at room temperature. The mixture was stirred at room temperature for 16 h. The mixture was diluted with ethyl acetate and washed with brine. The organic layer was dried over anhydrous sodium sulfate, filtered, and concentrated under vacuum. The residue was purified by FC with 0-70% ethyl acetate in petroleum ether to afford N-(5-cyanopyridin-2-yl)-6-fluoro-N-(2-methoxyethyl)-1-(phenylsulfonyl)-1H-indole-2-carboxamide (410 mg, 91%) as a brown oil. MS m/z 479.1 [M+1]$^+$.

Step 2: A mixture of N-(5-cyanopyridin-2-yl)-6-fluoro-N-(2-methoxyethyl)-1-(phenylsulfonyl)-1H-indole-2-carboxamide (350 mg, 0.73 mmol) and tetrabutylammonium fluoride (574 mg, 2.19 mmol) in tetrahydrofuran (4 mL) was stirred at room temperature for 1 h. The mixture was diluted with ethyl acetate and washed with saturated sodium bicarbonate aqueous solution and brine. The organic layer was dried over anhydrous sodium sulfate, filtered, and concentrated under vacuum. The residue was purified by Prep-HPLC [Column: Xselect CSH OBD Column 30*150 mm 5 um; Mobile Phase A: water (0.1% formic acid), Mobile Phase B: acetonitrile; Flow rate: 60 mL/min; Gradient: 25% B to 55% B in 8 min] to afford 1-(5-cyanopyridin-2-yl)-6-fluoro-N-(2-methoxyethyl)-1H-indole-2-carboxamide (50 mg, 20%) as a white solid.

Example 53

1-(5-chloropyridin-2-yl)-6-fluoro-N-(2-methoxyethyl)-1H-indole-2-carboxamide Followed the procedure of Example 52 and purified by FC with 0-100% ethyl acetate in petroleum ether to afford N1-(5-chloropyridin-2-yl)-6-fluoro-N-(2-methoxyethyl)-1H-indole-2-carboxamide (210 mg, 37% over two steps) as a yellow solid from 1-(benzenesulfonyl)-6-fluoroindole-2-carboxylic acid (513 mg, 1.61 mmol).

Example 54

6-fluoro-N-(2-methoxyethyl)-1-(pyrimidin-2-yl)-1H-indole-2-carboxamide

Followed the procedure of Example 52 and purified by prep-HPLC with the following conditions: [Column: Xselect CSH OBD Column 30*150 mm 5 um; Mobile Phase A: water (0.1% formic acid), Mobile Phase B: acetonitrile; Flow rate: 60 mL/min; Gradient: 25% B to 55% B in 8 min] to afford 6-fluoro-N-(2-methoxyethyl)-1-(pyrimidin-2-yl)-1H-indole-2-carboxamide (29.5 mg, 8% over two steps) as a white solid from 6-fluoro-1-(phenylsulfonyl)-1H-indole-2-carboxylic acid (417 mg, 1.31 mmol).

Example 55

7-chloro-N-(4-cyanophenyl)-N-(2-methoxyethyl)-1H-indole-2-carboxamide

Followed the procedure of Example 12 and purified by prep-HPLC with the following conditions: [Column: Xselect CSH OBD Column 30*150 mm 5 um; Mobile Phase A: water (0.1% formic acid), Mobile Phase B: acetonitrile; Flow rate: 60 mL/min; Gradient: 40% B to 67% B in 8 min]

to afford 7-chloro-N-(4-cyanophenyl)-N-(2-methoxyethyl)-1H-indole-2-carboxamide (33.3 mg, 18%) as a white solid from 7-chloro-1H-indole-2-carboxylic acid (100 mg, 0.51 mmol).

Example 56

7-chloro-N-(4-cyanophenyl)-N-(cyclopropylmethyl)-1H-indole-2-carboxamide

Followed the procedure of Example 12 and purified by FC with 0-100% ethyl acetate in petroleum ether to afford 7-chloro-N-(4-cyanophenyl)-N-(cyclopropylmethyl)-1H-indole-2-carboxamide (34.7 mg, 11%) as a white solid from 7-chloro-1H-indole-2-carboxylic acid (170 mg, 0.87 mmol).

Example 57

7-chloro-N-(4-cyanophenyl)-N-(cyclopropylmethyl)-1H-indole-2-carboxamide

Followed the procedure of Example 52 and purified by prep-HPLC with the following conditions: [Column: Xselect CSH OBD Column 30*150 mm 5 um; Mobile Phase A: water (0.1% formic acid), Mobile Phase B: acetonitrile; Flow rate: 60 mL/min; Gradient: 25% B to 50% B in 8 min] to afford 6-fluoro-N-(2-methoxyethyl)-N-(1-methyl-1H-pyrazol-3-yl)-1H-indole-2-carboxamide (26.9 mg, 21%) as a white solid from 6-fluoro-1-(phenylsulfonyl)-1H-indole-2-carboxylic acid (412 mg, 1.29 mmol).

Example 58

7-chloro-N-(4-cyanophenyl)-N-(cyclopropylmethyl)-1H-indole-2-carboxamide

Followed the procedure of Example 12 and purified by prep-HPLC with the following conditions: [Column: Xselect CSH OBD Column 30*150 mm 5 um; Mobile Phase A: water (0.1% formic acid), Mobile Phase B: acetonitrile; Flow rate: 60 mL/min; Gradient: 30% B to 70% B in 9 min] to afford 7-chloro-N-(4-fluorophenyl)-N-(tetrahydrofuran-3-yl)-1H-indole-2-carboxamide (91 mg, 30%) as a white solid.

Example 59

6-fluoro-N-methyl-N-phenyl-1H-indole-2-carboxamide

Followed the procedure of Example 5 and purified by reverse-phase FC with 5-60% acetonitrile in water to afford 6-fluoro-N-methyl-N-phenyl-1H-indole-2-carboxamide (37.2 mg, 31%) as a white solid from 6-fluoro-1H-indole-2-carboxylic acid (80 mg, 0.44 mmol).

Example 60

6-fluoro-N-isopropyl-N-phenyl-1H-indole-2-carboxamide

Followed the procedure of Example 34 and purified by prep-HPLC with the following conditions [Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 37% B to 48% B in 8 min] to afford 7-((I1-azaneyl)ethynyl)-N-(cyclopropylmethyl)-N-(pyridin-2-yl)-1H-indole-2-carboxamide (80 mg, 38%) as a white solid.

Example 61 and Example 62

7-chloro-N-[(2R,3S)-2-methyloxolan-3-yl]-1H-indole-2-carboxamide and 7-chloro-N-[(2S,3S)-2-methyloxolan-3-yl]-1H-indole-2-carboxamide Step-1: To a mixture of 7-chloro-1H-indole-2-carboxylic acid (120 mg, 0.613 mmol) in DMF (4 mL) were added HATU (350 mg, 0.920 mmol) and DIEA (238 mg, 1.839 mmol). The resulting mixture was stirred at room temperature for 30 min. To the above mixture was added 2-methyloxolan-3-amine (62 mg, 0.613 mmol). The resulting mixture was stirred at room temperature overnight. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% EtOAc in PE to afford 7-chloro-N-(2-methyloxolan-3-yl)-1H-indole-2-carboxamide (70 mg, 40.93%) as a white solid. MS m/z 279.0 [M+1]$^+$ Step-2: The racemic product (65 mg) was separated by Prep-HPLC [column: DAICEL DCpak P4VP, 2*25 cm, 5 um; Mobile Phase A: CO$_2$, Mobile Phase B: IPA (0.5% 2M NH$_3$-MeOH); Flow rate: 50 mL/min; Gradient: isocratic 32% B; Column Temperature (° C.): 35; Back Pressure (bar): 100; Wave Length: 254 nm] to afford 7-chloro-N-[(2R,3S)-2-methyloxolan-3-yl]-1H-indole-2-carboxamide (27.9 mg, 39.86%) as a white solid. And 7-chloro-N-[(2S,3S)-2-methyloxolan-3-yl]-1H-indole-2-carboxamide (12.4 mg, 17.71%) as a white solid.

Example 63

7-chloro-N-(5,5-dimethyloxolan-3-yl)-1H-indole-2-carboxamide

To a mixture of 7-chloro-1H-indole-2-carboxylic acid (120 mg, 0.613 mmol) in DMF (4 mL) were added DIEA (238 mg, 1.839 mmol) and HATU (350 mg, 0.920 mmol). The resulting mixture was stirred at room temperature for 30 min. To the above mixture was added 5,5-dimethyloxolan-3-amine hydrochloride (92 mg, 0.613 mmol). The resulting mixture was stirred at room temperature overnight. The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 35 B to 46 B in 8 min, 254/220 nm] to afford 7-chloro-N-(5,5-dimethyloxolan-3-yl)-1H-indole-2-carboxamide (35.9 mg, 19.99%) as a white solid.

Example 64 and Example 65

7-chloro-N-[(3S,4S)-4-methyloxolan-3-yl]-1H-indole-2-carboxamide and 7-chloro-N-[(3S,4R)-4-methyloxolan-3-yl]-1H-indole-2-carboxamide Step-1: To a mixture of 7-chloro-1H-indole-2-carboxylic acid (120 mg, 0.613 mmol) in DMF (4 mL) were added HATU (350 mg, 0.920 mmol) and DIEA (238 mg, 1.839 mmol). The resulting mixture was stirred at room temperature for 30 min. To the above mixture was added 4-methyloxolan-3-amine (75 mg, 0.736 mmol). The resulting mixture was stirred at room temperature overnight. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% EtOAc in PE to afford 7-chloro-N-(4-methyloxolan-3-yl)-1H-indole-2-carboxamide (50 mg, 29.24%) as a white solid. as a white solid. MS m/z 279.0 [M+1]$^+$ Step-2: The mixture product (47 mg) was separated by Prep-HPLC [Column: DAICEL DCpak P4VP, 2*25 cm, 5 um; Mobile Phase A: $CO_2$, Mobile Phase B: IPA:HEX=1:1 (0.1%2M $NH_3$-MeOH); Flow rate: 50 mL/min; Gradient: isocratic 38% B; Column Temperature (° C.): 35; Back Pressure (bar): 100; Wave Length: 254 nm] to afford 7-chloro-N-[(3S,4S)-4-methyloxolan-3-yl]-1H-indole-2-carboxamide (10.8 mg, 21.60%) as a white solid. And 7-chloro-N-[(3S,4R)-4-methyloxolan-3-yl]-1H-indole-2-carboxamide (8.0 mg, 16.00%) as a white solid.

Example 66

7-cyano-N-isopropyl-N-(1,3-oxazol-5-ylmethyl)-1H-indole-2-carboxamide

To a mixture of 7-cyano-1H-indole-2-carboxylic acid (186 mg, 0.999 mmol) in DCM (3 mL) and DMF (0.3 mL) were added (COCl)$_2$ (152 mg, 1.199 mmol). The resulting mixture was stirred at 0° C. for 30 min under nitrogen atmosphere. The above mixture was added to isopropyl(1,3-oxazol-5-ylmethyl)amine (112 mg, 0.799 mmol) in NMP (3 mL). The resulting mixture was stirred at room temperature overnight. The resulting mixture was extracted with EtOAc. The combined organic layers were washed with brine, dried over anhydrous $Na_2SO_4$. After filtration, the filtrate was concentrated under reduced pressure. The residue was purified by Prep-HPLC [Column: XBridge Shield RP18 OBD Column, 19*250 mm, 10 um; Mobile Phase A: ACN, Mobile Phase B: water (10 mmol/L $NH_4HCO_3$); Flow rate: 60 mL/min; Gradient: 25 B to 45 B in 8 min; 220/254 nm] to afford 7-cyano-N-isopropyl-N-(1,3-oxazol-5-ylmethyl)-1H-indole-2-carboxamide (78.7 mg, 25.55%) as a white solid.

Example 67

7-chloro-N-isopropyl-N-(1,3-oxazol-5-ylmethyl)-1H-indole-2-carboxamide

Followed the procedure of Example 66 and purified by Prep-HPLC [Column: XBridge Shield RP18 OBD Column, 19*250 mm, 10 um; Mobile Phase A: Water (10 mmol/L $NH_4HCO_3$), Mobile Phase B: ACN; Flow rate: 60 mL/min; Gradient: 25 B to 45 B in 8 min; 220/254 nm] to afford 7-chloro-N-isopropyl-N-(1,3-oxazol-5-ylmethyl)-1H-indole-2-carboxamide (85.7 mg, 26.35%) as a white solid.

Example 68

7-chloro-N-(4-cyanophenyl)-1H-indole-2-carboxamide

Followed the procedure of Example 66 and purified by Prep-HPLC [Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 45 B to 70 B in 8 min, 220 nm] to afford 7-chloro-N-(4-cyanophenyl)-1H-indole-2-carboxamide (85.8 mg, 37.83%) as a white solid.

Example 69

7-chloro-N-cyclopentyl-1H-indole-2-carboxamide

Followed the procedure of Example 63 and purified by Prep-HPLC [Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 40 B to 55 B in 8 min; 254/220 nm] to afford 7-chloro-N-cyclopentyl-1H-indole-2-carboxamide (54.1 mg, 33.56%) as a white solid.

Example 70

7-Chloro-N-(cyclopentylmethyl)-N-methyl-1H-indole-2-carboxamide

Followed the procedure of Example 63 and purified by reverse-phase FC with 0-100% ACN in $H_2O$ to afford 7-chloro-N-(cyclopentylmethyl)-N-methyl-1H-indole-2-carboxamide (130 mg, 50.61%) as a white solid.

Example 71

7-chloro-2-(pyrrolidine-1-carbonyl)-1H-indole

Followed the procedure of Example 63 and purified by Prep-HPLC [Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 38 B to 47 B in 8 min; 254/220 nm] to afford 7-chloro-2-(pyrrolidine-1-carbonyl)-1H-indole (35.4 mg, 23.20%) as a white solid.

Example 72

7-chloro-N-methyl-N-(oxan-4-yl)-1H-indole-2-carboxamide

Followed the procedure of Example 63 and purified by Prep-HPLC [Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 35 B to 45 B in 8 min; 254/220 nm] to afford 7-chloro-N-methyl-N-(oxan-4-yl)-1H-indole-2-carboxamide (36.4 mg, 20.27%) as a white solid.

Example 73

7-chloro-N-methyl-N-(oxan-3-yl)-1H-indole-2-carboxamide

Followed the procedure of Example 63 and purified by reverse-phase FC with 0-100% ACN in $H_2O$ to afford 7-chloro-N-methyl-N-(oxan-3-yl)-1H-indole-2-carboxamide (20.2 mg, 26.97%) as a white solid.

Example 74

7-chloro-N-(2,2-dimethyloxan-4-yl)-N-methyl-1H-indole-2-carboxamide

Followed the procedure of Example 66 and purified by Prep-HPLC [Column: Xselect CSH OBD Column 30*150 mm 5 um; Mobile Phase A: Water (10 mmol/L NH$_4$HCO$_3$), Mobile Phase B: ACN; Flow rate: 60 mL/min; Gradient: 43 B to 52 B in 8 min, 254/220 nm] to afford 7-chloro-N-(2,2-dimethyloxan-4-yl)-N-methyl-1H-indole-2-carboxamide (29.3 mg, 17.83%) as a white solid.

Example 75

7-chloro-N-methyl-N-(2,2,6,6-tetramethylpiperidin-4-yl)-1H-indole-2-carboxamide

Followed the procedure of Example 63 and purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 25 B to 37 B in 8 min; 254/220 nm] to afford 7-chloro-N-methyl-N-(2,2,6,6-tetramethylpiperidin-4-yl)-1H-indole-2-carboxamide (6.1 mg, 3.43%) as a white solid.

Example 76

7-chloro-N-(4-cyano-3-methylphenyl)-N-(2-methoxyethyl)-1H-indole-2-carboxamide

Followed the procedure of Example 66 and purified by reverse-phase FC with 0-100% ACN in H$_2$O to afford 7-chloro-N-(4-cyano-3-methylphenyl)-N-(2-methoxyethyl)-1H-indole-2-carboxamide (30.2 mg, 19.00%) as a white solid.

Example 77

7-chloro-N-(4-cyano-2-methylphenyl)-N-(2-methoxyethyl)-1H-indole-2-carboxamide

Followed the procedure of Example 66 and purified by reverse-phase FC with 0-100% ACN in H$_2$O to afford 7-chloro-N-(4-cyano-2-methylphenyl)-N-(2-methoxyethyl)-1H-indole-2-carboxamide (33.3 mg, 21.49%) as a white solid.

Example 78

7-Chloro-N-(4-cyano-3-fluorophenyl)-N-(2-methoxyethyl)-1H-indole-2-carboxamide

Followed the procedure of Example 66 and purified by Prep-HPLC [Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 39% B to 69% B in 9 min; Wave Length: 254 nm] to afford 7-chloro-N-(4-cyano-3-fluorophenyl)-N-(2-methoxyethyl)-1H-indole-2-carboxamide (15.1 mg, 7.89%) as a white solid.

Example 79

7-chloro-N-(4-cyano-2-fluorophenyl)-N-(2-methoxyethyl)-1H-indole-2-carboxamide

Followed the procedure of Example 66 and purified by reverse-phase FC with 0-100% ACN in H$_2$O to afford 7-chloro-N-(4-cyano-2-fluorophenyl)-N-(2-methoxyethyl)-1H-indole-2-carboxamide (40.5 mg, 21.11%) as a white solid.

Example 80

7-chloro-N-methyl-N-(2-methyloxolan-3-yl)-1H-indole-2-carboxamide

Followed the procedure of Example 66 and purified by Prep-HPLC [Column: YMC-Actus Triart C18 ExRS, 30*150 mm, 5 um; Mobile Phase A: Water (10 mmol/L NH$_4$HCO$_3$), Mobile Phase B: ACN; Flow rate: 60 mL/min; Gradient: 38 B to 52 B in 11 min, 254/220 nm] to afford 7-chloro-N-methyl-N-(2-methyloxolan-3-yl)-1H-indole-2-carboxamide (38.0 mg, 25.36%) as a white solid.

Example 81

7-chloro-N-cyclohexyl-N-methyl-1H-indole-2-carboxamide

Followed the procedure of Example 63 and purified by Prep-HPLC [Column: Xselect CSH OBD Column 30*150 mm, 5 um; Mobile Phase A: Water (10 mmol/L NH4HCO3), Mobile Phase B: ACN; Flow rate: 60 mL/min; Gradient: 51 B to 73 B in 10 min, 254/220 nm] to afford 7-chloro-N-cyclohexyl-N-methyl-1H-indole-2-carboxamide (40 mg, 26.88%) as a white solid.

Example 82

N-[bicyclo[1.1.1]pentan-1-yl]-7-chloro-N-methyl-1H-indole-2-carboxamide

To a mixture of 7-chloro-1H-indole-2-carboxylic acid (100 mg, 0.511 mmol) in DMF (4 mL) was added TEA (231 mg, 2.285 mmol). The resulting mixture was stirred at room temperature for 15 min. To the above mixture was added N-methylbicyclo[1.1.1]pentan-1-amine (37 mg, 0.381 mmol) and T$_3$P (203 mg, 0.638 mmol) at 0° C. The resulting mixture was stirred at room temperature overnight under nitrogen atmosphere. The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Prep OBD C18 Column, 30×150 mm 5 um; Mobile Phase A: Water (10 mmol/L NH$_4$HCO$_3$); Mobile Phase B: ACN; Flow rate: 60 mL/min; Gradient: 15 B to 35 B in 8 min; 220 nm] to afford N-[bicyclo[1.1.1]pentan-1-yl]-7-chloro-N-methyl-1H-indole-2-carboxamide (30.2 mg, 28.86%) as a white solid.

Example 83

7-chloro-N-(4-cyanophenyl)-N-(oxolan-3-yl)-1H-indole-2-carboxamide

Followed the procedure of Example 66 and purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 34 B to 64 B in 9 min; 254 nm] to afford 7-chloro-N-(4-cyanophenyl)-N-(oxolan-3-yl)-1H-indole-2-carboxamide (41.8 mg, 10.14%) as a white solid.

Example 84

7-cyano-N-(4-fluorophenyl)-N-(oxolan-3-yl)-1H-indole-2-carboxamide

Followed the procedure of Example 66 and purified by Prep-HPLC [Column: XBridge Shield RP18 OBD Column, 19*250 mm, 10 μm; Flow rate: 60 mL/min; Gradient: 36% B to 53% B in 8 min, 53% B; Wave Length: 220/254 nm] to afford 7-cyano-N-(4-fluorophenyl)-N-(oxolan-3-yl)-1H-indole-2-carboxamide (81.9 mg, 29.07%) as a white solid.

Example 85

6-fluoro-N-(4-fluorophenyl)-N-(tetrahydrofuran-3-yl)-1H-indole-2-carboxamide

Followed the procedure of Example 66 and purified by Prep-HPLC [Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 30 B to 60 B in 8 min; 254/220 nm] to afford 6-fluoro-N-(4-fluorophenyl)-N-(tetrahydrofuran-3-yl)-1H-indole-2-carboxamide (83.5 mg, 18.44%) as an off-white solid.

Example 86

7-chloro-N-[3-cyanobicyclo[1.1.1]pentan-1-yl]-N-methyl-1H-indole-2-carboxamide

Step-1: To a mixture of 7-chloro-1-[[2-(trimethylsilyl)ethoxy]methyl]indole-2-carboxylic acid (662 mg, 2.032 mmol) in DMF (3 mL) were added DIEA (788 mg, 6.095 mmol). The resulting mixture was stirred at room temperature for 30 min. To the above mixture was added HATU (1158 mg, 3.047 mmol) and 3-aminobicyclo[1.1.1]pentane-1-carbonitrile (219 mg, 2.032 mmol). The resulting mixture was stirred at room temperature overnight. The resulting mixture was extracted with EtOAc. The combined organic layers were washed with water brine, dried over anhydrous $Na_2SO_4$. After filtration, the filtrate was concentrated under reduced pressure. The residue was purified by FC with 0-50% ethyl acetate in PE to afford 7-chloro-N-[3-cyanobicyclo[1.1.1]pentan-1-yl]-1-[[2-(trimethylsilyl)ethoxy]methyl]indole-2-carboxamide (500 mg, 59.16%) as a colorless oil. MS m/z 416.2 [M+1]$^+$ Step-2: To a mixture of 7-chloro-N-[3-cyanobicyclo[1.1.1]pentan-1-yl]-1-[[2-(trimethylsilyl)ethoxy]methyl]indole-2-carboxamide (500 mg, 1.202 mmol) in DMF (3 mL) was added NaH (58 mg, 2.404 mmol). The resulting mixture was stirred at 0° C. for 30 min under nitrogen atmosphere. To the above mixture was added $CH_3I$ (205 mg, 1.442 mmol). The resulting mixture was stirred at room temperature for 2 h. The reaction was quenched by the addition of water. The resulting mixture was extracted with EtOAc. The combined organic layers were washed with water brine, dried over anhydrous $Na_2SO_4$. After filtration, the filtrate was concentrated under reduced pressure. The residue was purified by FC with 0-50% ethyl acetate in PE to afford 7-chloro-N-[3-cyanobicyclo[1.1.1]pentan-1-yl]-N-methyl-1-[[2-(trimethylsilyl)ethoxy]methyl]indole-2-carboxamide (390 mg, 75.46%) as a yellow oil. MS m/z 430.1 [M+1]$^+$ Step-3: To a mixture of 7-chloro-N-[3-cyanobicyclo[1.1.1]pentan-1-yl]-N-methyl-1-[[2-(trimethylsilyl)ethoxy]methyl]indole-2-carboxamide (200 mg, 0.465 mmol) and ethane-1,2-diamine (84 mg, 1.395 mmol) in tetrahydrofuran (4 mL) was added TBAF (84 mg, 1.395 mmol) and 4AMS (200 mg, 0.465 mmol). The resulting mixture was stirred at 80° C. overnight under nitrogen atmosphere. The residue was purified by Prep-HPLC [Column: YMC-Actus Triart C18 ExRS, 30 mm*150 mm, 5 urn; Mobile Phase A: Water (10 mmol/L $NH_4HCO_3$), Mobile Phase B: ACN; Flow rate: 60 mL/min; Gradient: 45% B to 65% B in 8 min, 65% B; Wave Length: 254 nm] to afford 7-chloro-N-[3-cyanobicyclo[1.1.1]pentan-1-yl]-N-methyl-1H-indole-2-carboxamide (77.1 mg, 55.30%) as a white solid.

Example 87

7-chloro-N-methyl-N-[3-(methylcarbamoyl)bicyclo[1.1.1]pentan-1-yl]-1H-indole-2-carboxamide Step-1: To a mixture of 7-chloro-1H-indole-2-carboxylic acid (60 mg, 0.307 mmol) in DCM (4 mL) and DMF (0.4 mL) were added $(COCl)_2$ (0.18 mL, 0.368 mmol) at 0° C. under nitrogen atmosphere. The resulting mixture was stirred at room temperature for 30 min. Then methyl 3-(methylamino)bicyclo[1.1.1]pentane-1-carboxylate (57 mg, 0.368 mmol) in NMP (2 mL) was added to the above mixture. The resulting mixture was stirred at room temperature overnight under nitrogen atmosphere. The resulting mixture was extracted with EtOAc. The combined organic layers were washed with brine, dried over anhydrous $Na_2SO_4$. After filtration, the filtrate was concentrated under reduced pressure. The crude product was purified by Prep-HPLC [Column: Sunfire prep C18 column, 30*150, 5 um; Mobile Phase ACN, Mobile Phase B: Water (0.05% FA); Flow rate: 60 mL/min; Gradient: 40 B to 40 B in 25 min, 254 nm] to afford methyl 3-(N-methyl7-chloro-1H-indole-2-amido)bicyclo[1.1.1]pentane-1-carboxylate (25 mg, 36.74%) as a white solid. MS m/z 333.1 [M+1]$^+$ Step-2: To a mixture of methyl 3-(N-methyl7-chloro-1H-indole-2-amido)bicyclo[1.1.1]pentane-1-carboxylate (20 mg, 0.06 mmol) in $CH_3NH_2$/MeOH (3 mL). The resulting mixture was stirred at room temperature for 3 h. The resulting mixture was concentrated under vacuum. The residue was purified by Prep-HPLC [Column: XBridge Prep OBD C18 Column, 30×150 mm 5 urn; Mobile Phase A: Water (10 mmol/L $NH_4HCO_3$), Mobile Phase B: ACN; Flow rate: 60 mL/min; Gradient: 23 B to 50 B in 8 min; 254/220 nm] to afford 7-chloro-N-methyl-N-[3-(methylcarbamoyl)bicyclo[1.1.1]pentan-1-yl]-1H-indole-2-carboxamide (7.2 mg, 36.11%) as a white solid.

Example 88

7-chloro-N-(3-hydroxybicyclo[1.1.1]pentan-1-yl)-1-((2-(trimethylsilyl)ethoxy)methyl)-1H-indole-2-carboxamide Followed the procedure of Example 63 and purified by Prep-HPLC [Column: XBridge Shield RP18 OBD Column, 19*250 mm, 10 μm; Mobile Phase A: Water (0.1% FA), Mobile Phase B: MeOH-HPLC; Flow rate: 25 mL/min; Gradient: 75% B to 75% B in 10 min, 75% B; Wave Length: 254 nm] to afford 7-chloro-N-(3-hydroxybicyclo[1.1.1]pentan-1-yl)-1-((2-(trimethylsilyl)ethoxy)methyl)-1H-indole-2-carboxamide (1.4 mg, 0.57%) as a white solid.

Example 89

N-[bicyclo[1.1.1]pentan-1-yl]-7-chloro-1H-indole-2-carboxamide

Followed the procedure of Example 82 and purified by reverse-phase FC with 0-60% ACN in $H_2O$ to afford N-[bicyclo[1.1.1]pentan-1-yl]-7-chloro-1H-indole-2-carboxamide (43.7 mg, 32.79%) as a white solid.

Example 90

N-[bicyclo[1.1.1]pentan-1-yl]-7-chloro-N-(2-methoxyethyl)-1H-indole-2-carboxamide Step-1: To a mixture of 7-chloro-1-[[2-(trimethylsilyl)ethoxy]methyl]indole-2-carboxylic acid (1 g, 3.069 mmol) in DMF (5 mL) was added DIEA (1.18 g, 9.206 mmol). The resulting mixture was stirred at room temperature for 30 min. To the above mixture was added HATU (1.75 g, 4.603 mmol) and bicyclo[1.1.1]pentan-1-amine (255 mg, 3.069 mmol). The resulting mixture was stirred at room temperature overnight. The residue was purified by FC with 0-30% ethyl acetate in PE to afford N-[bicyclo[1.1.1]pentan-1-yl]-7-chloro-1-[[2-(trimethylsilyl)ethoxy]methyl]indole-2-carboxamide (486 mg, 40.51%) as a white solid. MS m/z 391.1 [M+1]$^+$ Step-2: To a mixture of N-[bicyclo[1.1.1]pentan-1-yl]-7-chloro-1-[[2-(trimethylsilyl)ethoxy]methyl]indole-2-carboxamide (450 mg, 1.151 mmol) in DMF (3 mL) was added NaH (55 mg, 2.302 mmol). The resulting mixture was stirred at 0° C. for 30 min under nitrogen atmosphere. To the above mixture was added 2-bromoethyl methyl ether (320 mg, 2.302 mmol). The resulting mixture was stirred at room temperature overnight. The resulting mixture was stirred at room temperature overnight under nitrogen atmosphere. The resulting mixture was extracted with EtOAc. The combined organic layers were washed with brine, dried over anhydrous Na$_2$SO$_4$. After filtration, the filtrate was concentrated under reduced pressure. The residue was purified by FC with 0-50% ethyl acetate in PE to afford N-[bicyclo[1.1.1]pentan-1-yl]-7-chloro-N-(2-methoxyethyl)-1-[[2-(trimethylsilyl)ethoxy]methyl]indole-2-carboxamide (365 mg, 70.72%) as a colorless oil. MS m/z 449.2 [M+1]$^+$.

Step-3: To a mixture of N-[bicyclo[1.1.1]pentan-1-yl]-7-chloro-N-(2-methoxyethyl)-1-[[2-(trimethylsilyl)ethoxy]methyl]indole-2-carboxamide (200 mg, 0.445 mmol) and ethane-1,2-diamine (120 mg, 2.004 mmol) in THF (4 mL) were added TBAF (349 mg, 1.336 mmol) and 4AMS (200 mg). The resulting mixture was stirred at 80° C. overnight. The resulting mixture was concentrated under reduced pressure. The residue was purified by Prep-HPLC [Column: YMC-Actus Triart C18 ExRS, 30*150 mm, 5 µm; Mobile Phase A: Water (10 mmol/L NH$_4$HCO$_3$), Mobile Phase B: ACN; Flow rate: 60 mL/min; Gradient: 60% B to 70% B in 8 min, 70% B; Wave Length: 254 nm] to afford N-[bicyclo[1.1.1]pentan-1-yl]-7-chloro-N-(2-methoxyethyl)-1H-indole-2-carboxamide (51.3 mg, 36.13%) as a colorless oil.

Example 91

N-[bicyclo[1.1.1]pentan-1-yl]-7-chloro-N-(oxolan-3-yl)-1H-indole-2-carboxamide

Followed the procedure of Example 63 and purified by Prep-HPLC [Column: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min; Gradient: 30% B to 65% B in 8 min, 65% B; Wave Length: 220 nm] to afford N-[bicyclo[1.1.1]pentan-1-yl]-7-chloro-N-(oxolan-3-yl)-1H-indole-2-carboxamide (28.0 mg, 5.50%) as a white solid

Example 92

N-(3,3-difluorocyclobutyl)-6-fluoro-N-methyl-1H-indole-2-carboxamide

Followed the procedure of Example 82 and purified by reverse-phase FC with 0-50% ACN in H$_2$O to afford N-(3,3-difluorocyclobutyl)-6-fluoro-N-methyl-1H-indole-2-carboxamide (22.0 mg, 11.64%) as a yellow solid.

Example 93

N-[bicyclo[1.1.1]pentan-1-yl]-6-fluoro-N-methyl-1H-indole-2-carboxamide

Followed the procedure of Example 82 and purified by reverse-phase FC with 0-100% ACN in H$_2$O to afford N-[bicyclo[1.1.1]pentan-1-yl]-6-fluoro-N-methyl-1H-indole-2-carboxamide (26.7 mg, 18.52%) as an off-white solid.

Example 94

N-[bicyclo[1.1.1]pentan-1-yl]-7-cyano-N-methyl-1H-indole-2-carboxamide

Followed the procedure of Example 82 and purified by reverse-phase FC with 0-80% ACN in H$_2$O to afford N-[bicyclo[1.1.1]pentan-1-yl]-7-cyano-N-methyl-1H-indole-2-carboxamide (26.0 mg, 18.24%) as a white solid.

Example 95

N-[bicyclo[1.1.1]pentan-1-yl]-7-chloro-N-methyl-1H-pyrrolo[2,3-c]pyridine-2-carboxamide Followed the procedure of Example 82 and purified by reverse-phase FC with 0-80% ACN in H$_2$O to afford N-[bicyclo[1.1.1]pentan-1-yl]-7-chloro-N-methyl-1H-pyrrolo[2,3-c]pyridine-2-carboxamide (32.3 mg, 28.87%) as a white solid.

Example 96

N-[bicyclo[1.1.1]pentan-1-yl]-7-methoxy-N-methyl-1H-pyrrolo[2,3-c]pyridine-2-carboxamide To a mixture of 7-methoxy-1H-pyrrolo[2,3-c]pyridine-2-carboxylic acid (130 mg, 0.676 mmol) and N-methylbicyclo[1.1.1]pentan-1-amine (66 mg, 0.676 mmol) in DMF (3 mL) were added TEA (151 mg, 1.487 mmol) and TBTU (261 mg, 0.811 mmol). The resulting mixture was stirred at room temperature overnight. The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Prep OBD C18 Column, 30×150 mm 5 um; Mobile Phase A: Water (10 mmol/L NH$_4$HCO$_3$), Mobile Phase B: ACN; Flow rate: 60 mL/min; Gradient: 20 B to 55 B in 8 min, 254/220 nm] to afford N-[bicyclo[1.1.1]pentan-1-yl]-7-methoxy-N-methyl-1H-pyrrolo[2,3-c]pyridine-2-carboxamide (14 mg, 7.63%) as a white solid.

Example 97

7-chloro-N-methyl-N-[(4-methyl-1,3-oxazol-5-yl)methyl]-1H-indole-2-carboxamide

Followed the procedure of Example 66 and purified by reverse-phase FC with 0-80% ACN in H$_2$O to afford 7-chloro-N-methyl-N-[(4-methyl-1,3-oxazol-5-yl)methyl]-1H-indole-2-carboxamide (2.3 mg, 1.48%) as a white solid.

Example 98

7-chloro-N-[3-fluorobicyclo[1.1.1]pentan-1-yl]-N-methyl-1H-pyrrolo[2,3-c]pyridine-2-carboxamide Step-1: To a mixture of 7-chloro-1-[[2-(trimethylsilyl)ethoxy]methyl]pyrrolo[2,3-c]pyridine-2-carboxylic acid (500 mg, 1.53 mmol) in DMF (10 mL) was added TEA (928 mg, 9.179 mmol). The resulting mixture was stirred at room temperature for 30 min under nitrogen atmosphere. To the above mixture were added 3-fluorobicyclo[1.1.1]pentan-1-amine (154 mg, 1.53 mmol) and $T_3P$ (730 mg, 2.295 mmol). The resulting mixture was stirred at room temperature overnight under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by FC with 0-25% ethyl acetate in PE to afford 7-chloro-N-[3-fluorobicyclo[1.1.1]pentan-1-yl]-1-[[2-(trimethylsilyl)ethoxy]methyl]pyrrolo[2,3-c]pyridine-2-carboxamide (340 mg, 48.79%) as a white solid. MS (ESI) calc'd for ($C_{19}H_{25}ClFN_3O_2Si$) [M+1]$^+$, 410.1, found 410.1. $^1$H NMR (400 MHz, Methanol-$d_4$) δ 8.07-8.01 (m, 1H), 7.70-7.65 (m, 1H), 7.12 (s, 1H), 6.30 (s, 2H), 3.52-3.44 (m, 2H), 2.52-2.47 (m, 6H), 0.86-0.78 (m, 2H), −0.09 (s, 9H).

Step-2: To a mixture of 7-chloro-N-{3-fluorobicyclo[1.1.1]pentan-1-yl}-1-{[2-(trimethylsilyl)ethoxy]methyl}pyrrolo[2,3-c]pyridine-2-carboxamide (300 mg, 0.732 mmol) in DMF (10 mL) was added NaH (35 mg, 1.464 mmol). The resulting mixture was stirred at room temperature for 30 min under nitrogen atmosphere. To the above mixture was added $CH_3I$ (208 mg, 1.464 mmol). The resulting mixture was stirred at room temperature for 1 h. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% ethyl acetate in PE to afford 7-chloro-N-{3-fluorobicyclo[1.1.1]pentan-1-yl}-N-methyl-1-{[2-(trimethylsilyl)ethoxy]methyl}pyrrolo[2,3-c]pyridine-2-carboxamide (290 mg, 84.12%) as a brown oil. MS m/z 424.2 [M+1]$^+$ Step-3: To a mixture of 7-chloro-N-[3-fluorobicyclo[1.1.1]pentan-1-yl]-N-methyl-1-[[2-(trimethylsilyl)ethoxy]methyl]pyrrolo[2,3-c]pyridine-2-carboxamide (300 mg, 0.708 mmol) in THF (10 mL) were added TBAF (555 mg, 2.123 mmol), ethane-1,2-diamine (191 mg, 3.184 mmol) and 4AMS (300 mg). The resulting mixture was stirred at 80° C. for 2 h under nitrogen atmosphere. The resulting mixture was concentrated under reduced pressure. The residue was purified by reverse-phase FC with 0-100% ACN in $H_2O$ to afford 7-chloro-N-[3-fluorobicyclo[1.1.1]pentan-1-yl]-N-methyl-1H-pyrrolo[2,3-c]pyridine-2-carboxamide (33.6 mg, 16.12%) as a white solid.

Example 99

7-chloro-N-[3-fluorobicyclo[1.1.1]pentan-1-yl]-1H-pyrrolo[2,3-c]pyridine-2-carboxamide Followed the procedure of Example 82 and purified by reverse-phase FC with 0-100% ACN in $H_2O$ to afford 7-chloro-N-[3-fluorobicyclo[1.1.1]pentan-1-yl]-1H-pyrrolo[2,3-c]pyridine-2-carboxamide (28.7 mg, 18.28%) as a white solid.

Example 100

7-chloro-N-(3,3-difluorocyclobutyl)-1H-pyrrolo[2,3-c]pyridine-2-carboxamide

Followed the procedure of Example 82 and purified by reverse-phase FC with 0-60% ACN in $H_2O$ to afford 7-chloro-N-(3,3-difluorocyclobutyl)-1H-pyrrolo[2,3-c]pyridine-2-carboxamide (52.7 mg, 32.97%) as a white solid.

Example 101

7-chloro-N-(3,3-difluorocyclobutyl)-N-methyl-1H-pyrrolo[2,3-c]pyridine-2-carboxamide Followed the procedure of Example 82 and purified by reverse-phase FC with 0-70% ACN in $H_2O$ to afford 7-chloro-N-(3,3-difluorocyclobutyl)-N-methyl-1H-pyrrolo[2,3-c]pyridine-2-carboxamide (24.9 mg, 14.80%) as a white solid.

Example 102

N-[bicyclo[1.1.1]pentan-1-yl]-7-chloro-3-methyl-1H-indole-2-carboxamide

Followed the procedure of Example 82 and purified by reverse-phase FC with 0-100% ACN in $H_2O$ to afford N-[bicyclo[1.1.1]pentan-1-yl]-7-chloro-3-methyl-1H-indole-2-carboxamide (32.7 mg, 24.77%) as a white solid.

Example 103

N-[bicyclo[1.1.1]pentan-1-yl]-1H-pyrrolo[2,3-c]pyridine-2-carboxamide

Followed the procedure of Example 82 and purified by Prep-HPLC [Column: XBridge Prep C18 OBD Column, 30*50 mm, 5 μm 13 nm; Mobile Phase A: Water (10 mmol/L $NH_4HCO_3$), Mobile Phase B: ACN; Flow rate: 60 mL/min; Gradient: 15% B to 35% B in 8 min, 35% B; Wave Length: 254 nm] to afford N-[bicyclo[1.1.1]pentan-1-yl]-1H-pyrrolo[2,3-c]pyridine-2-carboxamide (18.3 mg, 10.92%) as a white solid.

Example 104

N-[bicyclo[1.1.1]pentan-1-yl]-7-chloro-N,3-dimethyl-1H-indole-2-carboxamide

Followed the procedure of Example 82 and purified by reverse-phase FC with 0-80% ACN in $H_2O$ to afford N-[bicyclo[1.1.1]pentan-1-yl]-7-chloro-N,3-dimethyl-1H-indole-2-carboxamide (31.1 mg, 22.58%) as a white solid.

Example 105

N-[bicyclo[1.1.1]pentan-1-yl]-7-chloro-3-cyclopropyl-1H-indole-2-carboxamide Followed the procedure of Example 82 and purified by Prep-HPLC [Column: YMC-Actus Triart C18 ExRS, 30*150 mm, 5 μm; Mobile Phase A: Water (10 mmol/L $NH_4HCO_3$), Mobile Phase B: ACN; Flow rate: 60 mL/min; Gradient: 64% B to 74% B in 8 min; Wave Length: 220 nm]

Example 106

N-[bicyclo[1.1.1]pentan-1-yl]-3,7-dichloro-1H-indole-2-carboxamide

Followed the procedure of Example 82 and purified by reverse-phase FC with 0-100% ACN in H$_2$O to afford N-{bicyclo[1.1.1]pentan-1-yl}-3,7-dichloro-1H-indole-2-carboxamide (9.1 mg, 4.43%) as a white solid.

Example 107

N-[bicyclo[1.1.1]pentan-1-yl]-7-chloro-3-(1-methylpyrazol-3-yl)-1H-indole-2-carboxamide Followed the procedure of Example 82 and purified by reverse-phase FC with 0-80% ACN in H$_2$O to afford N-[bicyclo[1.1.1]pentan-1-yl]-7-chloro-3-(1-methylpyrazol-3-yl)-1H-indole-2-carboxamide (82.2 mg, 44.33%) as a white solid.

Example 108

N-[bicyclo[1.1.1]pentan-1-yl]-7-chloro-3-phenyl-1H-indole-2-carboxamide

Followed the procedure of Example 82 and purified by reverse-phase FC with 0-50% ACN in H$_2$O to afford N-[bicyclo[1.1.1]pentan-1-yl]-7-chloro-3-phenyl-1H-indole-2-carboxamide (34.4 mg, 27.75%) as a white solid.

Example 109

7-chloro-N-[3-fluorobicyclo[1.1.1]pentan-1-yl]-3-methyl-1H-indole-2-carboxamide

Followed the procedure of Example 82 and purified by Prep-HPLC [Column: YMC-Actus Triart C18 ExRS, 30*150 mm, 5 µm; Mobile Phase A: Water (10 mmol/L NH$_4$HCO$_3$), Mobile Phase B: ACN; Flow rate: 60 mL/min; Gradient: 50% B to 65% B in 8 min, Wave Length: 254/220 nm] to afford 7-chloro-N-[3-fluorobicyclo[1.1.1]pentan-1-yl]-3-methyl-1H-indole-2-carboxamide (41.5 mg, 29.72%) as a white solid.

Example 110

7-chloro-N-[3-fluorobicyclo[1.1.1]pentan-1-yl]-1-methylpyrrolo[2,3-c]pyridine-2-carboxamide Followed the procedure of Example 82 and purified by reverse-phase FC with 0-60% ACN in H$_2$O to afford 7-chloro-N-[3-fluorobicyclo[1.1.1]pentan-1-yl]-1-methylpyrrolo[2,3-c]pyridine-2-carboxamide (77.9 mg, 46.55%) as a yellow solid.

Example 111

7-chloro-1-ethyl-N-[3-fluorobicyclo[1.1.1]pentan-1-yl]pyrrolo[2,3-c]pyridine-2-carboxamide Followed the procedure of Example 82 and purified by reverse-phase FC with 0-50% ACN in H$_2$O to afford 7-chloro-1-ethyl-N-[3-fluorobicyclo[1.1.1]pentan-1-yl]pyrrolo[2,3-c]pyridine-2-carboxamide (42.5 mg, 25.85%) as a white solid.

Example 112

7-chloro-N-{3-fluorobicyclo[1.1.1]pentan-1-yl}-1-isopropylpyrrolo[2,3-c]pyridine-2-carboxamide Followed the procedure of Example 63 and purified by reverse-phase FC with 0-80% ACN in H$_2$O to afford 7-chloro-N-{3-fluorobicyclo[1.1.1]pentan-1-yl}-1-isopropylpyrrolo[2,3-c]pyridine-2-carboxamide (26.8 mg, 49.70%) as a white solid.

Example 113

7-chloro-1-(cyclopropylmethyl)-N-{3-fluorobicyclo[1.1.1]pentan-1-yl}pyrrolo[2,3-c]pyridine-2-carboxamide Followed the procedure of Example 82 and purified by reverse-phase FC with 0-70% ACN in H$_2$O to afford 7-chloro-1-(cyclopropylmethyl)-N-{3-fluorobicyclo[1.1.1]pentan-1-yl}pyrrolo[2,3-c]pyridine-2-carboxamide (31.8 mg, 19.88%) as a white solid.

Example 114

7-chloro-N-{3-fluorobicyclo[1.1.1]pentan-1-yl}-1-methylindole-2-carboxamide

Followed the procedure of Example 82 and purified by reverse-phase FC with 0-100% ACN in H$_2$O to afford 7-chloro-N-{3-fluorobicyclo[1.1.1]pentan-1-yl}-1-methylindole-2-carboxamide (56.3 mg, 22.40%) as a white solid.

Example 115

7-chloro-N-[3-hydroxybicyclo[1.1.1]pentan-1-yl]-1H-indole-2-carboxamide

Followed the procedure of Example 82 and purified by reverse-phase FC with 0-100% ACN in H$_2$O to afford 7-chloro-N-[3-hydroxybicyclo[1.1.1]pentan-1-yl]-1H-indole-2-carboxamide (40.8 mg, 28.84%) as a off-white solid.

Example 116

7-chloro-N-{3-hydroxybicyclo[1.1.1]pentan-1-yl}-1H-pyrrolo[2,3-c]pyridine-2-carboxamide Followed the procedure of Example 82 and purified by Prep-HPLC [Column: XBridge Prep OBD C18 Column, 19*250 mm, 5 µm; Mobile Phase A: Water (10 mmol/L NH$_4$HCO$_3$), Mobile Phase B: MeOH-HPLC; Flow rate: 25 mL/min; Gradient: 38% B to 38% B in 10 min, 38% B; Wave Length: 254 nm] to afford 7-chloro-N-{3-hydroxybicyclo[1.1.1]pentan-1-yl}-1H-pyrrolo[2,3-c]pyridine-2-carboxamide (10.2 mg, 7.22%) as a white solid.

to afford N-[bicyclo[1.1.1]pentan-1-yl]-7-chloro-3-cyclopropyl-1H-indole-2-carboxamide (16.4 mg, 5.64%) as a white solid.

Example 117

7-chloro-N-ethyl-N-{3-fluorobicyclo[1.1.1]pentan-1-yl}-1H-pyrrolo[2,3-c]pyridine-2-carboxamide Step-1: To a mixture of 7-chloro-N-{3-fluorobicyclo[1.1.1]pentan-1-yl}-1-{[2-(trimethylsilyl)ethoxy]methyl}pyrrolo[2,3-c]pyridine-2-carboxamide (300 mg, 0.732 mmol) in DMF (15 mL) was added NaH (35 mg, 1.463 mmol). The resulting mixture was stirred at 0° C. for 30 min under nitrogen atmosphere. To the above mixture was added iodoethane (228 mg, 1.464 mmol). The resulting mixture was stirred at room temperature for 1 h. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% ethyl acetate in PE to afford 7-chloro-N-ethyl-N-{3-fluorobicyclo[1.1.1]pentan-1-yl}-1-{[2-(trimethylsilyl)ethoxy]methyl}pyrrolo[2,3-c]pyridine-2-carboxamide (250 mg, 70.20%) as a yellow oil. MS m/z 438.2 [M+1]$^+$ Step-2: To a mixture of 7-chloro-N-ethyl-N-{3-fluorobicyclo[1.1.1]pentan-1-yl}-1-{[2-(trimethylsilyl)ethoxy]methyl}pyrrolo[2,3-c]pyridine-2-carboxamide (300 mg, 0.685 mmol) in THF (20 mL) were added 1,2-ethylenediamine (185 mg, 3.083 mmol), 4AMS (300 mg) and TBAF (537 mg, 2.055 mmol). The resulting mixture was stirred at 80° C. for 1 h under nitrogen atmosphere. The resulting mixture was concentrated under reduced pressure. The residue was purified by reverse-phase FC with 0-100% ACN in $H_2O$ to afford 7-chloro-N-ethyl-N-{3-fluorobicyclo[1.1.1]pentan-1-yl}-1H-pyrrolo[2,3-c]pyridine-2-carboxamide (47.2 mg, 22.19%) as a white solid.

Example 118

N-{3-fluorobicyclo[1.1.1]pentan-1-yl}-7-methoxy-1-methylpyrrolo[2,3-c]pyridine-2-carboxamide Followed the procedure of Example 82 and purified by reverse FC with 0-100% ACN in $H_2O$ to afford N-{3-fluorobicyclo[1.1.1]pentan-1-yl}-7-methoxy-1-methylpyrrolo[2,3-c]pyridine-2-carboxamide (13.4 mg, 9.55%) as a white solid.

Example 119

7-cyclopropoxy-N-{3-fluorobicyclo[1.1.1]pentan-1-yl}-1-methylpyrrolo[2,3-c]pyridine-2-carboxamide Followed the procedure of Example 82 and purified by reverse-phase FC with 0-100% ACN in $H_2O$ to afford 7-cyclopropoxy-N-{3-fluorobicyclo[1.1.1]pentan-1-yl}-1-methylpyrrolo[2,3-c]pyridine-2-carboxamide (20.0 mg, 47.43%) as a white solid.

Example 120

7-cyclopropyl-N-{3-fluorobicyclo[1.1.1]pentan-1-yl}-1-methylpyrrolo[2,3-c]pyridine-2-carboxamide Followed the procedure of Example 82 and purified by reverse-phase FC with 0-70% ACN in $H_2O$ to afford 7-cyclopropyl-N-{3-fluorobicyclo[1.1.1]pentan-1-yl}-1-methylpyrrolo[2,3-c]pyridine-2-carboxamide (43 mg, 31.06%) as a white solid.

Example 121

N-{3-fluorobicyclo[1.1.1]pentan-1-yl}-7-methoxy-1H-pyrrolo[2,3-c]pyridine-2-carboxamide Followed the procedure of Example 63 and purified by reverse-phase FC with 0-100% ACN in $H_2O$ to afford N-{3-fluorobicyclo[1.1.1]pentan-1-yl}-7-methoxy-1H-pyrrolo[2,3-c]pyridine-2-carboxamide (5.5 mg, 3.34%) as a white solid.

Example 122

7-cyclopropoxy-N-{3-fluorobicyclo[1.1.1]pentan-1-yl}-1H-pyrrolo[2,3-c]pyridine-2-carboxamide Step-1: To a mixture of 7-cyclopropoxy-1-{[2-(trimethylsilyl)ethoxy]methyl}pyrrolo[2,3-c]pyridine-2-carboxylic acid (180 mg, 0.517 mmol) in DMF (5 mL) were added HATU (216 mg, 0.569 mmol) and DIEA (267 mg, 2.068 mmol). The resulting mixture was stirred at room temperature for 30 min. To the above mixture was added 3-fluorobicyclo[1.1.1]pentan-1-amine hydrochloride (71 mg, 0.517 mmol). The resulting mixture was stirred at room temperature overnight. The resulting mixture was extracted with EtOAc. The combined organic layers were washed with brine, dried over anhydrous $Na_2SO_4$. After filtration, the filtrate was concentrated under reduced pressure. The residue was purified by FC with 0-40% EtOAc in PE to afford 7-cyclopropoxy-N-{3-fluorobicyclo[1.1.1]pentan-1-yl}-1-{[2-(trimethylsilyl)ethoxy]methyl}pyrrolo[2,3-c]pyridine-2-carboxamide (170 mg, 76.26%) as a white solid. MS m/z 432.2 [M+1]$^+$.

Step-2: To a mixture of 7-cyclopropoxy-N-{3-fluorobicyclo[1.1.1]pentan-1-yl}-1-{[2-(trimethylsilyl)ethoxy]methyl}pyrrolo[2,3-c]pyridine-2-carboxamide (100 mg, 0.232 mmol) in DCM (6 mL) was added 2,2,2-trifluoroacetic acid (2 mL). The resulting mixture was stirred at 50° C. overnight. The resulting mixture was concentrated under vacuum. The residue was purified by reverse-phase FC with 0-100% ACN in $H_2O$ to afford 7-cyclopropoxy-N-{3-fluorobicyclo[1.1.1]pentan-1-yl}-1H-pyrrolo[2,3-c]pyridine-2-carboxamide (10.6 mg, 15.18%) as a white solid.

Example 123

N-{bicyclo[1.1.1]pentan-1-yl}-7-chloro-1H-pyrrolo[2,3-c]pyridine-2-carboxamide Followed the procedure of Example 63 and purified by reverse-phase chromatography with 0-80% ACN in $H_2O$ to afford N-{bicyclo[1.1.1]pentan-1-yl}-7-chloro-1H-pyrrolo[2,3-c]pyridine-2-carboxamide (6.5 mg, 4.88%) as a white solid.

Example 124

N-{3-fluorobicyclo[1.1.1]pentan-1-yl}-1-methyl-7-(methylamino)pyrrolo[2,3-c]pyridine-2-carboxamide Followed the procedure of Example 63 and purified by Prep-HPLC [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 20% B to 35% B in 8 min, 35% B; Wave Length: 254 nm] to afford N-{3-fluorobicyclo[1.1.1]pentan-1-yl}-1- methyl-7-(methylamino)pyrrolo[2,3-c]pyridine-2-carboxamide (7.4 mg, 17.38%) as a white solid.

Example 125

7-(dimethylamino)-N-{3-fluorobicyclo[1.1.1]pentan-1-yl}-1-methylpyrrolo[2,3-c]pyridine-2-carboxamide Followed the procedure of Example 63 and purified by reverse-phase FC with 0-100% ACN in $H_2O$ to afford 7-(dimethylamino)-N-{3-fluorobicyclo[1.1.1]pentan-1-yl}-1-methylpyrrolo[2,3-c]pyridine-2-carboxamide (42.9 mg, 51.85%) as a pink solid.

Example 126

7-cyclopropoxy-N-{3-fluorobicyclo[1.1.1]pentan-1-yl}-N-methyl-1H-pyrrolo[2,3-c]pyridine-2-carboxamide Step-1: To a mixture of ethyl 7-chloro-N-{3-fluorobicyclo[1.1.1]pentan-1-yl}-1-{[2-(trimethylsilyl)ethoxy]methyl}pyrrolo[2,3-c]pyridine-2-carboxamide (400 mg, 0.976 mmol) and cyclopropanol (567 mg, 9.760 mmol) in toluene (20 mL) were added $Cs_2CO_3$ (477 mg, 1.464 mmol), t-BuBrettPhos (95 mg, 0.195 mmol) and [Pd(allyl)Cl]$_2$ (36 mg, 0.098 mmol). The resulting mixture was stirred at 80° C. for 1 h under nitrogen atmosphere. The resulting mixture was concentrated under vacuum. The residue was purified by FC with 0-20% EtOAc in PE to afford 7-cyclopropoxy-N-{3-fluorobicyclo[1.1.1]pentan-1-yl}-1-{[2-(trimethylsilyl)ethoxy]methyl}pyrrolo[2,3-c]pyridine-2-carboxamide (110 mg, 26.12%) as a yellow solid. MS m/z 432.2 [M+1]$^+$.

Step-2: To a mixture of 7-cyclopropoxy-N-{3-fluorobicyclo[1.1.1]pentan-1-yl}-1-{[2-(trimethylsilyl)ethoxy]methyl}pyrrolo[2,3-c]pyridine-2-carboxamide (100 mg, 0.232 mmol) in DMF (5 mL) were added NaH (12 mg, 0.464 mmol) at 0° C. The resulting mixture was stirred at 0° C. for 30 min under nitrogen atmosphere. To the above mixture was added $CH_3I$ (66 mg, 0.464 mmol). The resulting mixture was stirred at room temperature for 16 h. The reaction was then quenched by the addition of water. The resulting mixture was extracted with EtOAc. The combined organic layers were washed with brine, dried over anhydrous $Na_2SO_4$. After filtration, the filtrate was concentrated under reduced pressure. The residue was purified by FC with 0-20% ethyl acetate in PE to afford 7-cyclopropoxy-N-{3-fluorobicyclo[1.1.1]pentan-1-yl}-N-methyl-1-{[2-(trimethylsilyl)ethoxy]methyl}pyrrolo[2,3-c]pyridine-2-carboxamide (80 mg, 77.48%) as a yellow solid. MS m/z 446.2 [M+1]$^+$.

Step-3: To a mixture of 7-cyclopropoxy-N-{3-fluorobicyclo[1.1.1]pentan-1-yl}-N-methyl-1-{[2-(trimethylsilyl)ethoxy]methyl}pyrrolo[2,3-c]pyridine-2-carboxamide (80 mg, 0.180 mmol) in DCM (20 mL) was added $SnCl_4$ (936 mg, 3.600 mmol) at 0° C. The resulting mixture was stirred at 0° C. for 1 h. To the above mixture was added NaOH in MeOH (4%) at 0° C. The resulting mixture was stirred at 0° C. for 1 h. The resulting mixture was concentrated under vacuum. The residue was purified by reverse-phase FC with 0-100% ACN in $H_2O$ to afford 7-cyclopropoxy-N-{3-fluorobicyclo[1.1.1]pentan-1-yl}-N-methyl-1H-pyrrolo[2,3-c]pyridine-2-carboxamide (16.1 mg, 28.38%) as a white solid.

Example 127

N-{3-fluorobicyclo[1.1.1]pentan-1-yl}-7-methoxy-N-methyl-1H-pyrrolo[2,3-c]pyridine-2-carboxamide Step-1: To a mixture of 7-chloro-N-[3-fluorobicyclo[1.1.1]pentan-1-yl]-N-methyl-1-[[2-(trimethylsilyl)ethoxy]methyl]pyrrolo[2,3-c]pyridine-2-carboxamide (200 mg, 0.472 mmol) in THF (10 mL) were added TBAF (370 mg, 1.416 mmol), ethane-1,2-diamine (128 mg, 2.124 mmol) and 4AMS (200 mg). The resulting mixture was stirred at 80° C. for 1 h under nitrogen atmosphere. The resulting mixture was concentrated under reduced pressure. The residue was purified by reverse-phase FC with 0-100% ACN in $H_2O$ to afford 7-chloro-N-[3-fluorobicyclo[1.1.1]pentan-1-yl]-N-methyl-1H-pyrrolo[2,3-c]pyridine-2-carboxamide (140 mg, 90.94%) as a white solid. MS m/z 294.1 [M+1]$^+$ Step-2: To a mixture of 7-chloro-N-{3-fluorobicyclo[1.1.1]pentan-1-yl}-N-methyl-1H-pyrrolo[2,3-c]pyridine-2-carboxamide (160 mg, 0.545 mmol) and $CH_3OH$ (0.4 mL) in Toluene (10 mL) were added [Pd(allyl)Cl]$_2$ (8 mg, 0.022 mmol), t-BuBrettPhos (26 mg, 0.055 mmol) and $Cs_2CO_3$ (266 mg, 0.818 mmol). The resulting mixture was stirred at 80° C. for 1 h under nitrogen atmosphere. The resulting mixture was concentrated under reduced pressure. The residue was purified by reverse-phase FC with 0-100% ACN in $H_2O$ to afford N-{3-fluorobicyclo[1.1.1]pentan-1-yl}-7-methoxy-N-methyl-1H-pyrrolo[2,3-c]pyridine-2-carboxamide (25.9 mg, 15.94%) as a white solid.

Example 128

7-chloro-N-{3-fluorobicyclo[1.1.1]pentan-1-yl}-N,1-dimethylpyrrolo[2,3-c]pyridine-2-carboxamide To a mixture of 7-chloro-N-{3-fluorobicyclo[1.1.1]pentan-1-yl}-1-methylpyrrolo[2,3-c]pyridine-2-carboxamide (100 mg, 0.340 mmol) in DMF (2 mL) was added NaH (16 mg, 0.680 mmol) at 0° C. The resulting mixture was stirred at 0° C. for 30 min under nitrogen atmosphere. To the above mixture was added $CH_3I$ (58 mg, 0.408 mmol). The resulting mixture was stirred for 1 h at room temperature. The resulting mixture was extracted with EtOAc. The combined organic layers were washed with brine, dried over anhydrous $Na_2SO_4$. After filtration, the filtrate was concentrated under reduced pressure. The residue was purified by Prep-HPLC [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 43% B in 8 min, 43% B; Wave Length: 254 nm] to afford 7-chloro-N-{3-fluorobicyclo[1.1.1]pentan-1-yl}-N,1-dimethylpyrrolo[2,3-c]pyridine-2-carboxamide (31.4 mg, 29.97%) as a white solid.

Example 129

7-chloro-N-{3-fluorobicyclo[1.1.1]pentan-1-yl}-1,3-dimethylpyrrolo[2,3-c]pyridine-2-carboxamide Followed the procedure of Example 63 and purified by Prep-HPCL [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 26% B to 56% B in 8 min, 56% B; Wave Length:

254 nm] to afford 7-chloro-N-{3-fluorobicyclo[1.1.1]pentan-1-yl}-1,3-dimethylpyrrolo[2,3-c]pyridine-2-carboxamide (16.5 mg, 23.29%) as a white solid.

Example 130

N-{3-fluorobicyclo[1.1.1]pentan-1-yl}-1,7-dimethylpyrrolo[2,3-c]pyridine-2-carboxamide Followed the procedure of Example 82 and purified by Prep-HPLC [Column: YMC-Actus Triart C18 ExRS, 30 mm×150 mm, 5 um; Mobile Phase A: Water (10 mmol/L $NH_4HCO_3$), Mobile Phase B: ACN; Flow rate: 60 mL/min; Gradient: 35 B to 40 B in 11 min, 254 nm] to afford N-{3-fluorobicyclo[1.1.1]pentan-1-yl}-1,7-dimethylpyrrolo[2,3-c]pyridine-2-carboxamide (26.3 mg, 34.81%) as a white solid.

Example 131

7-cyano-N-{3-fluorobicyclo[1.1.1]pentan-1-yl}-1-methylpyrrolo[2,3-c]pyridine-2-carboxamide To a mixture of 7-chloro-N-{3-fluorobicyclo[1.1.1]pentan-1-yl}-1-methylpyrrolo[2,3-c]pyridine-2-carboxamide (100 mg, 0.352 mmol) in DMA (4 mL) were added $Zn(CN)_2$ (83 mg, 0.704 mmol), Zn (12 mg, 0.176 mmol), dppf (39 mg, 0.07 mmol) and $Pd_2(dba)_3$ (32 mg, 0.035 mmol). The resulting mixture was stirred at 120° C. for 1 h under nitrogen atmosphere. The resulting mixture was extracted with EtOAc. The combined organic layers were washed with brine, dried over anhydrous $Na_2SO_4$. After filtration, the filtrate was concentrated under reduced pressure. The crude product was purified by Prep-HPLC with the following conditions [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 31%, B to 41%, B in 8 min, 41%, B; Wave Length: 254 nm] to afford 7-cyano-N-{3-fluorobicyclo[1.1.1]pentan-1-yl}-1-methylpyrrolo[2,3-c]pyridine-2-carboxamide (20 mg, 20.00%) as a white solid.

Example 132

N-{3-fluorobicyclo[1.1.1]pentan-1-yl}-N,1,7-trimethylpyrrolo[2,3-c]pyridine-2-carboxamide Step-1: To a stirred mixture of 1,7-dimethylpyrrolo[2,3-c]pyridine-2-carboxylic acid (150 mg, 0.851 mmol) in DMF (2 mL) was added TEA (517 mg, 5.106 mmol). The resulting mixture was stirred at room temperature for 30 min under nitrogen atmosphere. To the above mixture was added 3-fluorobicyclo[1.1.1]pentan-1-amine hydrochloride (108 mg, 0.851 mmol) and $T_3P$ (406 mg, 1.276 mmol). The resulting mixture was stirred at room temperature overnight. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% ethyl acetate in PE to afford N-{3-fluorobicyclo[1.1.1]pentan-1-yl}-1,7-dimethylpyrrolo[2,3-c]pyridine-2-carboxamide (181 mg, 77.78%) as a yellow solid. MS m/z 274.1 [M+1]+

Step-2: To a mixture of N-{3-fluorobicyclo[1.1.1]pentan-1-yl}-1,7-dimethylpyrrolo[2,3-c]pyridine-2-carboxamide (160 mg, 0.585 mmol) in DMF (2 mL) was added NaH (28 mg, 1.170 mmol) at 0° C. under nitrogen atmosphere. The resulting mixture was stirred at 0° C. for 30 min. To the above mixture was added $CH_3I$ (100 mg, 0.702 mmol). The resulting mixture was stirred at room temperature for 1 h. The resulting mixture was extracted with EtOAc. The combined organic layers were washed with brine, dried over anhydrous $Na_2SO_4$. After filtration, the filtrate was concentrated under reduced pressure. The residue was purified by Prep-HPLC [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 20% B to 40% B in 8 min, 40% B; Wave Length: 254/220 nm] to afford N-{3-fluorobicyclo[1.1.1]pentan-1-yl}-N,1,7-trimethylpyrrolo[2,3-c]pyridine-2-carboxamide (32.6 mg, 19.38%) as a white solid.

Example 133

7-cyano-N-{3-fluorobicyclo[1.1.1]pentan-1-yl}-N,1-dimethylpyrrolo[2,3-c]pyridine-2-carboxamide To a mixture of 7-chloro-N-{3-fluorobicyclo[1.1.1]pentan-1-yl}-N,1-dimethylpyrrolo[2,3-c]pyridine-2-carboxamide (150 mg, 0.487 mmol) in DMA (5 mL) were added Zn (16 mg, 0.243 mmol), dppf (54 mg, 0.097 mmol), $Zn(CN)_2$ (114 mg, 0.974 mmol) and $Pd_2(dba)_3$ (45 mg, 0.049 mmol). The resulting mixture was stirred at 120° C. for 1 h under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by Prep-HPLC [Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 31% B to 41% B in 8 min, 41% B; Wave Length: 254 nm] to afford 7-cyano-N-{3-fluorobicyclo[1.1.1]pentan-1-yl}-N,1-dimethylpyrrolo[2,3-c]pyridine-2-carboxamide (30.8 mg, 21.18%) as a white solid.

Example 134

7-chloro-N-isopropyl-N,1-dimethylpyrrolo[2,3-c]pyridine-2-carboxamide

Step-1: To a mixture of 7-chloro-1H-pyrrolo[2,3-c]pyridine-2-carboxylic acid (160 mg, 0.814 mmol) in DMF (5 mL) were added DIEA (316 mg, 2.442 mmol) and HATU (465 mg, 1.221 mmol). The resulting mixture was stirred at room temperature for 30 min. To the above mixture was added isopropylamine (481 mg, 8.14 mmol). The resulting mixture was stirred at room temperature overnight. The resulting mixture was extracted with EtOAc. The combined organic layers were washed with brine, dried over anhydrous $Na_2SO_4$. After filtration, the filtrate was concentrated under reduced pressure. The residue was purified by FC with 0-50% ethyl acetate in PE to afford 7-chloro-N-isopropyl-1H-pyrrolo[2,3-c]pyridine-2-carboxamide (90 mg, 46.52%) as a yellow solid. MS m/z 238.1 [M+1]+

Step-2: To a mixture of 7-chloro-N-isopropyl-1H-pyrrolo[2,3-c]pyridine-2-carboxamide (70 mg, 0.295 mmol) in DMF (5 mL) was added NaH (14 mg, 0.59 mmol). The resulting mixture was stirred at 0° C. for 30 min under nitrogen atmosphere. To the above mixture was added $CH_3I$ (167 mg, 1.18 mmol) at 0° C. The resulting mixture was stirred at room temperature for 2 h. The residue was purified by Prep-HPLC [Column: XBridge Prep Phenyl OBD Column, 19*250 mm, 5 μm; Mobile Phase A: Water (10 mmol/L $NH_4HCO_3$), Mobile Phase B: ACN; Flow rate: 25 mL/min;

Gradient: 35% B to 50% B in 10 min, Wave Length: 254 nm] to afford 7-chloro-N-isopropyl-N,1-dimethylpyrrolo[2,3-c]pyridine-2-carboxamide (17.2 mg, 21.98%) as a white solid.

Example 135

7-chloro-N-isopropyl-1-methylpyrrolo[2,3-c]pyridine-2-carboxamide

Followed the procedure of Example 82 and purified by reverse-phase FC with 0-100% ACN in H₂O to afford 7-chloro-N-isopropyl-1-methylpyrrolo[2,3-c]pyridine-2-carboxamide (11.2 mg, 11.71%) as a white solid.

Example 136

7-chloro-1-methyl-N-(sec-butyl)pyrrolo[2,3-c]pyridine-2-carboxamide

Followed the procedure of Example 82 and purified by reverse-phase chromatography with 0-80% ACN in H₂O to afford 7-chloro-1-methyl-N-(sec-butyl)pyrrolo[2,3-c]pyridine-2-carboxamide (27.5 mg, 27.25%) as a white solid.

Example 137

1-(2-aminoethyl)-7-chloro-N-{3-fluorobicyclo[1.1.1]pentan-1-yl}pyrrolo[2,3-c]pyridine-2-carboxamide Step-1: To a mixture of 1-{2-[(tert-butoxycarbonyl)amino]ethyl}-7-chloropyrrolo[2,3-c]pyridine-2-carboxylic acid (100 mg, 0.294 mmol) in DMF (4 mL) was added TEA (179 mg, 1.764 mmol). The resulting mixture was stirred at room temperature for 30 min under nitrogen atmosphere. To the above mixture were added 3-fluorobicyclo[1.1.1]pentan-1-amine hydrochloride (48 mg, 0.353 mmol) and T₃P (140.46 mg, 0.441 mmol) at 0° C. The resulting mixture was stirred at room temperature overnight. The resulting mixture was extracted with EtOAc. The combined organic layers were washed with brine, dried over anhydrous Na₂SO₄. After filtration, the filtrate was concentrated under reduced pressure. The residue was purified by FC with 0-50% ethyl acetate in PE to afford tert-butyl N-{2-[7-chloro-2-({3-fluorobicyclo[1.1.1]pentan-1-yl}carbamoyl)pyrrolo[2,3-c]pyridin-1-yl]ethyl}carbamate (50 mg, 40.17%) as a white solid. MS m/z 423.1 [M+1]⁺

Step-2: To a mixture of tert-butyl N-{2-[7-chloro-2-({3-fluorobicyclo[1.1.1]pentan-1-yl}carbamoyl)pyrrolo[2,3-c]pyridin-1-yl]ethyl}carbamate (50 mg, 0.118 mmol) in HCl (gas) in 1,4-dioxane (3 mL) at 0° C. The resulting mixture was stirred at room temperature for 1 h. The residue was purified by reverse-phase FC with 0-100% ACN in H₂O to afford 1-(2-aminoethyl)-7-chloro-N-{3-fluorobicyclo[1.1.1]pentan-1-yl}pyrrolo[2,3-c]pyridine-2-carboxamide (10.8 mg, 28.30%) as a white solid.

Example 138

7-chloro-N-{3-fluorobicyclo[1.1.1]pentan-1-yl}-1-(2-hydroxyethyl)pyrrolo[2,3-c]pyridine-2-carboxamide Followed the procedure of Example 63 and purified by reverse-phase FC with 0-70% ACN in H₂O to afford 7-chloro-N-{3-fluorobicyclo[1.1.1]pentan-1-yl}-1-(2-hydroxyethyl)pyrrolo[2,3-c]pyridine-2-carboxamide (13.4 mg, 5.88%) as a white solid.

Example 139

7-chloro-N-{3-fluorobicyclo[1.1.1]pentan-1-yl}-1-(2-methoxyethyl)pyrrolo[2,3-c]pyridine-2-carboxamide Followed the procedure of Example 63 and purified by reverse-phase FC with 0-100% ACN in H₂O to afford 7-chloro-N-{3-fluorobicyclo[1.1.1]pentan-1-yl}-1-(2-methoxyethyl)pyrrolo[2,3-c]pyridine-2-carboxamide (30.5 mg, 22.70%) as a white solid.

Example 140

7-chloro-3-fluoro-N-{3-fluorobicyclo[1.1.1]pentan-1-yl}-1-methylpyrrolo[2,3-c]pyridine-2-carboxamide Followed the procedure of Example 63 and purified by Prep-HPLC [Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 40% B to 50% B in 8 min, 50% B; Wave Length: 254 nm] to afford 7-chloro-3-fluoro-N-{3-fluorobicyclo[1.1.1]pentan-1-yl}-1-methylpyrrolo[2,3-c]pyridine-2-carboxamide (35.1 mg, 32.18%) as a white solid.

Example 141

7-chloro-N-{3-fluorobicyclo[1.1.1]pentan-1-yl}-1-[2-(morpholin-4-yl)ethyl]pyrrolo[2,3-c]pyridine-2-carboxamide Followed the procedure of Example 63 and purified by reverse-phase FC with 0-100% ACN in H₂O to afford 7-chloro-N-{3-fluorobicyclo[1.1.1]pentan-1-yl}-1-[2-(morpholin-4-yl)ethyl]pyrrolo[2,3-c]pyridine-2-carboxamide (44.3 mg, 34.93%) as a white solid.

Example 142

7-chloro-1-methyl-N-{3-methylbicyclo[1.1.1]pentan-1-yl}pyrrolo[2,3-c]pyridine-2-carboxamide Followed the procedure of Example 63 and purified by reverse-phase FC with 0-70% ACN in H₂O to afford 7-chloro-1-methyl-N-{3-methylbicyclo[1.1.1]pentan-1-yl}pyrrolo[2,3-c]pyridine-2-carboxamide (31.5 mg, 22.83%) as a white solid.

Example 143

7-chloro-N-cyclobutyl-1-methylpyrrolo[2,3-c]pyridine-2-carboxamide

Followed the procedure of Example 63 and purified by reverse-phase FC with 0-70% ACN in H₂O to afford 7-chloro-N-cyclobutyl-1-methylpyrrolo[2,3-c]pyridine-2-carboxamide (26.5 mg, 21.14%) as a white solid.

Example 144

N-{bicyclo[2.1.1]hexan-1-yl}-7-chloro-1-methylpyrrolo[2,3-c]pyridine-2-carboxamide Followed the procedure of Example 63 and purified by reverse-phase FC with 0-60% ACN in H₂O to afford N-{bicyclo[2.1.1]hexan-1-yl}-7-chloro-1-methylpyrrolo[2,3-c]
pyridine-2-carboxamide (28.8 mg, 20.70%) as a white solid.

Example 145

7-chloro-N-(3,3-difluorocyclobutyl)-1-methylpyr-
rolo[2,3-c]pyridine-2-carboxamide Followed the procedure of Example 63 and purified by reverse-phase FC with 0-80% ACN in H$_2$O to afford 7-chloro-N-(3,3-difluorocyclobutyl)-1-methylpyrrolo[2,3-c]pyridine-2-carboxamide (28 mg, 19.64%) as a white solid.

Example 146

7-chloro-1-methyl-N-(oxolan-3-yl)pyrrolo[2,3-c]
pyridine-2-carboxamide

Followed the procedure of Example 63 and purified by reverse-phase FC with 0-80% ACN in H$_2$O to afford 7-chloro-1-methyl-N-(oxolan-3-yl)pyrrolo[2,3-c]pyridine-2-carboxamide (20.2 mg, 15.16%) as a white solid.

Example 147

7-chloro-1-methyl-N-(1-methylcyclobutyl)pyrrolo[2,
3-c]pyridine-2-carboxamide

Followed the procedure of Example 63 and purified by reverse-phase FC with 0-80% ACN in H$_2$O to afford 7-chloro-1-methyl-N-(1-methylcyclobutyl)pyrrolo[2,3-c]pyridine-2-carboxamide (27.7 mg, 20.92%) as a white solid.

Example 148

N-tert-butyl-7-chloro-1-methylpyrrolo[2,3-c]pyri-
dine-2-carboxamide

Followed the procedure of Example 82 and purified by reverse-phase FC with 0-100% ACN in H$_2$O to afford N-tert-butyl-7-chloro-1-methylpyrrolo[2,3-c]pyridine-2-carboxamide (45.4 mg, 29.99%) as a white solid.

Example 149

7-chloro-1-methyl-N-{spiro[2.3]hexan-5-yl}pyrrolo
[2,3-c]pyridine-2-carboxamide

Followed the procedure of Example 63 and purified by reverse-phase FC with 0-70% ACN in H$_2$O to afford 7-chloro-1-methyl-N-{spiro[2.3]hexan-5-yl}pyrrolo[2,3-c]pyridine-2-carboxamide (30.5 mg, 21.88%) as a white solid.

Example 150

7-chloro-1-methyl-N-{spiro[3.3]heptan-2-yl}pyrrolo
[2,3-c]pyridine-2-carboxamide Followed the procedure of Example 63 and purified by reverse-phase FC with 0-70% ACN in H$_2$O to afford 7-chloro-1-methyl-N-{spiro[3.3]heptan-2-yl}pyrrolo[2,3-c]pyridine-2-carboxamide (28.3 mg, 19.33%) as a white solid.

Example 151

7-cyano-1-ethyl-N-(3-fluorobicyclo[1.1.1]pentan-1-
yl)-N-methyl-1H-pyrrolo[2,3-c]pyridine-2-carbox-
amide Step-1: To a mixture of 7-chloro-1-ethyl-N-{3-fluorobicyclo[1.1.1]pentan-1-yl}pyrrolo[2,3-c]pyridine-2-carboxamide (300 mg, 0.975 mmol) in DMF (4 mL) was added NaH (47 mg, 1.950 mmol). The resulting mixture was stirred at room temperature for 30 min under nitrogen atmosphere. To the above mixture was added CH$_3$I (277 mg, 1.950 mmol) at 0° C. The resulting mixture was stirred at room temperature for 2 h. The resulting mixture was extracted with EtOAc. The combined organic layers were washed with brine, dried over anhydrous Na$_2$SO$_4$. After filtration, the filtrate was concentrated under reduced pressure. The residue was purified by flash column chromatography with 0-50% ethyl acetate in PE to afford 7-chloro-1-ethyl-N-{3-fluorobicyclo[1.1.1]pentan-1-yl}-N-methylpyrrolo[2,3-c]pyridine-2-carboxamide (180 mg, 57.38%) as a white solid. MS m/z 322.1 [M+1]$^+$ Step-2: To a mixture of 7-chloro-1-ethyl-N-{3-fluorobicyclo[1.1.1]pentan-1-yl}-N-methylpyrrolo[2,3-c]pyridine-2-carboxamide (165 mg, 0.513 mmol) and in DMA (4 mL) was added Zn(CN)$_2$ (120 mg, 1.026 mmol), Zn (17 mg, 0.257 mmol), Dppf (57 mg, 0.103 mmol), and Pd$_2$(dba)$_3$ (47 mg, 0.051 mmol). The resulting mixture was stirred at 80° C. for 2 h under nitrogen atmosphere. The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC [Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 35% B to 55% B in 8 min; Wave Length: 254 nm] to afford 7-cyano-1-ethyl-N-{3-fluorobicyclo[1.1.1]pentan-1-yl}-N-methylpyrrolo[2,3-c]pyridine-2-carboxamide (33.5 mg, 20.92%) as a white solid.

Example 152

N-(bicyclo[2.1.1]hexan-1-yl)-1,7-dimethyl-1H-pyr-
rolo[2,3-c]pyridine-2-carboxamide Followed the procedure of Example 63 and purified by Prep-HPLC [Column: YMC-Actus Triart C18 ExRS, 30 mm×150 mm, 5 um; Mobile Phase A: water (10 mmol/L NH$_4$HCO$_3$), Mobile Phase B: ACN; Flow rate: 60 mL/min; Gradient: 35 B to 40 B in 11 min, 254 nm] to afford N-{bicyclo[2.1.1]hexan-1-yl}-1,7-dimethylpyrrolo[2,3-c]pyridine-2-carboxamide (32.3 mg, 14.81%) as a white solid.

Example 153

7-chloro-1-ethyl-N-(3-fluorobicyclo[1.1.1]pentan-1-
yl)-N-methyl-1H-pyrrolo[2,3-c]pyridine-2-carbox-
amide To a mixture of 7-chloro-1-ethyl-N-{3-fluorobicyclo[1.1.1]pentan-1-yl}pyrrolo[2,3-c]pyridine-2-carboxamide (200 mg, 0.651 mmol) in DMF (10 mL) was added NaH (31 mg, 1.302 mmol). The resulting mixture was stirred at room temperature for 30 min under nitrogen atmosphere. To the above mixture was added CH₃I (185 mg, 1.302 mmol) at 0° C. The resulting mixture was stirred at room temperature for 1 h. The resulting mixture was extracted with EtOAc. The combined organic layers were washed with brine, dried over anhydrous Na₂SO₄. After filtration, the filtrate was concentrated under reduced pressure. The residue was purified by reverse flash chromatography with 0-100% ACN in H₂O to afford 7-chloro-1-ethyl-N-{3-fluorobicyclo[1.1.1]pentan-1-yl}-N-methylpyrrolo[2,3-c]pyridine-2-carboxamide (125.3 mg, 59.80%) as a yellow solid.

Example 154

N-(3-fluorobicyclo[1.1.1]pentan-1-yl)-1-methyl-7-(trifluoromethyl)-1H-pyrrolo[2,3-c]pyridine-2-carboxamide Followed the procedure of Example 63 and purified by reverse flash chromatography with 0-100% ACN in H₂O to afford N-{3-fluorobicyclo[1.1.1]pentan-1-yl}-1-methyl-7-(trifluoromethyl)pyrrolo[2,3-c]pyridine-2-carboxamide (11.8 mg, 17.61%) as a white solid.

Example 155

N-(bicyclo[1.1.1]pentan-1-yl)-6-cyano-1-methyl-1H-indole-2-carboxamide

Followed the procedure of Example 63 and purified by reverse flash chromatography with 0-100% ACN in H₂O to afford N-{bicyclo[1.1.1]pentan-1-yl}-6-cyano-1-methylindole-2-carboxamide (82.9 mg, 40.12%) as a white solid.

Example 156

N-(bicyclo[1.1.1]pentan-1-yl)-1-methyl-1H-pyrrolo[2,3-c]pyridine-2-carboxamide

Followed the procedure of Example 63 and purified by reverse flash chromatography with 0-80% ACN in H₂O to afford N-{bicyclo[1.1.1]pentan-1-yl}-1-methylpyrrolo[2,3-c]pyridine-2-carboxamide (14.8 mg, 18.01%) as a white solid.

Example 157

N-(bicyclo[1.1.1]pentan-1-yl)-6-fluoro-1-methyl-1H-indole-2-carboxamide

Followed the procedure of Example 63 and purified by reverse flash chromatography with 0-100% ACN in H₂O to afford N-{bicyclo[1.1.1]pentan-1-yl}-6-fluoro-1-methylindole-2-carboxamide (21.0 mg, 26.18%) as a white solid.

Example 158

4-chloro-N-(3-fluorobicyclo[1.1.1]pentan-1-yl)thieno[3,2-c]pyridine-2-carboxamide Followed the procedure of Example 63 and purified by reverse flash chromatography with 0-100% ACN in H₂O to afford 4-chloro-N-{3-fluorobicyclo[1.1.1]pentan-1-yl}thieno[3,2-c]pyridine-2-carboxamide (69.1 mg, 49.15%) as a yellow solid.

TABLE 1

| Ex. | Structure | 1H NMR | LCMS |
| --- | --- | --- | --- |
| 1 | 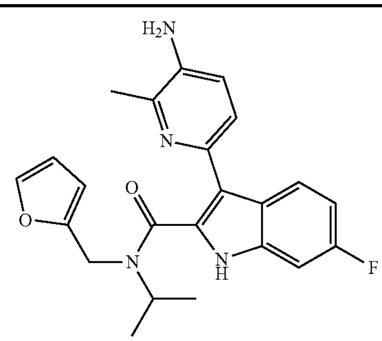 | 1H NMR (400 MHz, DMSO-d6) δ 11.68 (s, 1H), 8.24-8.09 (m, 1H), 7.61 (s, 1H), 7.13-7.10 (m, 1H), 7.03-6.81 (m, 3H), 6.45-6.41 (m, 1H), 6.25 and 5.89 (s, 1H), 5.07-4.86 (m, 2H), 4.59 (s, 2H), 3.98-3.71 (m, 1H), 2.30 (s, 3H), 1.11 and 0.89 (d, J = 6.8 Hz, 6H). | MS (ESI) calcd for (C23H23FN4O2) [M + 1]+, 407.1; found, 407.1. |
| 2 | 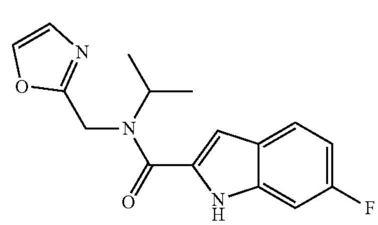 [SMILES: CC(C)N(Cc1ncco1)C(=O)c1cc2ccc(F)cc2[nH]1] | 1H NMR (400 MHz, DMSO-d6) δ 11.70 (s, 1H), 8.06 (s, 1H), 7.68-7.58 (m, 1H), 7.25-7.09 (m, 2H), 6.99-6.76 (m, 2H), 4.81 (s, 3H), 1.23 (d, J = 6.4 Hz, 6H). | MS (ESI) calcd for (C16H16FN3O2) [M + 1]+, 302.1; found, 302.3. |

TABLE 1-continued

| Ex. | Structure | 1H NMR | LCMS |
|---|---|---|---|
| 3 | (furan-2-ylmethyl)-N-isopropyl-7-cyano-1H-indole-2-carboxamide | 1H NMR (400 MHz, DMSO-d6) δ 12.52 (s, 1H), 7.96 (d, J = 8.4 Hz, 1H), 7.68 (d, J = 7.6 Hz, 1H), 7.60 (s, 1H), 7.20 (t, J = 8.0 Hz, 1H), 6.88 (s, 1H), 6.42-6.41 (m, 1H), 6.34 (s, 1H), 4.65 (s, 2H), 4.46-4.42 (m, 1H), 1.17 (d, J = 6.4 Hz, 6H). | MS (ESI) calcd for (C18H17N3O2) [M + 1]+, 308.1; found, 308.1. |
| 4 | (tetrahydrofuran-2-ylmethyl)-N-isopropyl-6-fluoro-1H-indole-2-carboxamide | 1H NMR (400 MHz, DMSO-d6) δ 11.59 (s, 1H), 7.64-7.60 (m, 1H), 7.14-7.11 (m, 1H), 6.94-6.88 (m, 1H), 6.76 (s, 1H), 4.56 (br, 1H), 4.12-4.09 (m, 1H), 3.74-3.72 (m, 1H), 3.65-3.64 (m, 1H), 3.62-3.60 (m, 1H), 3.56-3.54 (m, 1H), 1.98-1.92 (m, 1H), 1.83-1.77 (m, 2H), 1.54 (br, 1H), 1.28-1.24 (m, 6H). | MS (ESI) calcd for (C17H21FN2O2) [M + 1]+, 305.2; found, 305.1. |
| 5 | (isoxazol-3-ylmethyl)-N-isopropyl-6-fluoro-1H-indole-2-carboxamide | 1H NMR (400 MHz, DMSO-d6) δ 11.70 (s, 1H), 8.86 (s, 1H), 7.67-7.59 (m, 1H), 7.18-7.11 (m, 1H), 6.97-6.87 (m, 1H), 6.81 (s, 1H), 6.53 (d, J = 1.6 Hz, 1H), 4.80-4.70 (m, 3H), 1.24 (d, J = 6.8 Hz, 6H). | MS (ESI) calcd for (C16H16FN3O2) [M + 1]+, 302.1; found, 302.1. |
| 6 | (oxazol-5-ylmethyl)-N-isopropyl-6-fluoro-1H-indole-2-carboxamide | 1H NMR (400 MHz, DMSO-d6) δ 11.68 (s, 1H), 8.30 (s, 1H), 7.67-7.59 (m, 1H), 7.17-7.10 (m, 1H), 7.08 (s, 1H), 6.97-6.87 (m, 1H), 6.85-6.80 (m, 1H), 4.76-4.75 (m, 3H), 1.24 (d, J = 6.8 Hz, 6H). | MS (ESI) calcd for (C16H16FN3O2) [M + 1]+, 302.1; found, 302.1. |
| 7 | (pyridin-2-ylmethyl)-N-isopropyl-6-fluoro-1H-indole-2-carboxamide | 1H NMR (400 MHz, DMSO-d6) δ 11.72 (s, 1H), 8.55 (s, 1H), 7.76 (t, J = 7.6 Hz, 1H), 7.59 (br, 1H), 7.37 (d, J = 8.0 Hz, 1H), 7.30-7.24 (m, 1H), 7.17-7.12 (m, 1H), 6.91-6.87 (m, 1H), 6.81 (br, 1H), 4.81-4.80 (m, 3H), 1.19 (d, J = 6.0 Hz, 6H). | MS (ESI) calcd for (C18H18FN3O) [M + 1]+, 312.1; found, 312.1. |
| 9 | N-methyl-N-phenyl-6-fluoro-1H-indole-2-carboxamide | 1H NMR (400 MHz, DMSO-d6) δ 11.67 (s, 1H), 7.55-7.29 (m, 6H), 7.10 (dd, J = 10.0, 2.4 Hz, 1H), 6.81-6.76 (m, 1H), 5.26 (s, 1H), 3.39 (s, 3H). | MS (ESI) calcd for (C16H13FN2O) [M + 1]+, 269.1; found, 269.1. |
| 8 | (isoxazol-5-ylmethyl)-N-isopropyl-6-fluoro-1H-indole-2-carboxamide | 1H NMR (400 MHz, DMSO-d6) δ 11.72 (s, 1H), 8.50 (d, J = 1.6 Hz, 1H), 7.64 (dd, J = 8.8, 5.6 Hz, 1H), 7.13 (dd, J = 9.8, 2.4 Hz, 1H), 6.92-6.90 (m, 1H), 6.82 (s, 1H), 6.39 (s, 1H), 4.85-4.81 (m, 3H), 1.24 (d, J = 6.4 Hz, 6H). | MS (ESI) calcd for (C16H16FN3O2) [M + 1]+, 302.1; found, 302.1. |

TABLE 1-continued

| Ex. | Structure | 1H NMR | LCMS |
|---|---|---|---|
| 9 | 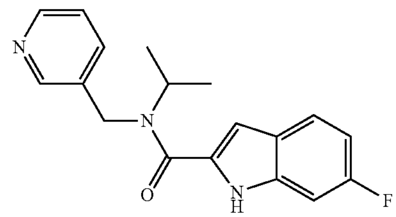 [SMILES: CC(C)N(Cc1cccnc1)C(=O)c1cc2ccc(F)cc2[nH]1] | 1H NMR (400 MHz, DMSO-d6) δ 11.72 (s, 1H), 8.58 (d, J = 2.4 Hz, 1H), 8.46-8.44 (m, 1H), 7.74-7.71 (m, 1H), 7.61 (d, J = 8.0 Hz, 1H), 7.38-7.32 (m, 1H), 71.7-7.13 (m, 1H), 6.94-6.91 (m, 1H), 6.80 (s, 1H), 4.79-4.73 (m, 3H), 1.21 (d, J = 6.4 Hz, 6H). | MS (ESI) calcd for (C18H18FN3O) [M + 1]+, 312.1; found, 312.1. |
| 10 | 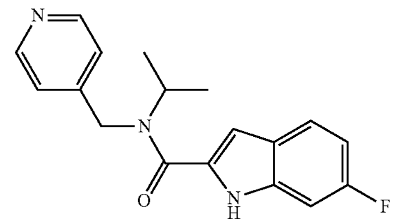 [SMILES: CC(C)N(Cc1ccncc1)C(=O)c1cc2ccc(F)cc2[nH]1] | 1H NMR (400 MHz, DMSO-d6) δ 11.71 (s, 1H), 8.52 (d, J = 5.2 Hz, 2H), 7.62-7.61 (m, 1H), 7.33 (d, J = 5.2 Hz, 2H), 7.17-7.13 (m, 1H), 6.94-6.90 (m, 2H), 4.77-4.73 (m, 3H), 1.21 (d, J = 6.8 Hz, 6H). | MS (ESI) calcd for (C18H18FN3O) [M + 1]+, 312.1; found, 312.2. |
| 11 | 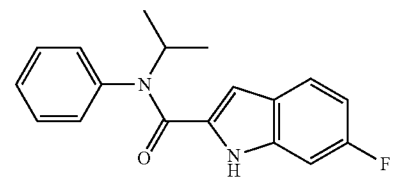 [SMILES: CC(C)N(C(=O)c1cc2ccc(F)cc2[nH]1)c1ccccc1] | 1H NMR (400 MHz, DMSO-d6) δ 11.63 (s, 1H), 7.60-7.49 (m, 3H), 7.37-7.29 (m, 2H), 7.27 (dd, J = 8.8, 5.6 Hz, 1H), 7.08 (dd, J = 10.0, 2.4 Hz, 1H), 6.76-6.75 (m, 1H), 5.04-5.03 (m, 1H), 4.90 (s, 1H), 1.11 (d, J = 6.8 Hz, 6H). | MS (ESI) calcd for (C18H17FN2O) [M + 1]+, 297.1; found, 297.0. |
| 12 | 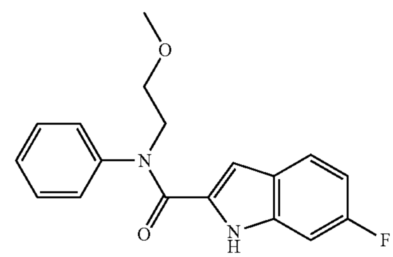 [SMILES: COCCN(C(=O)c1cc2ccc(F)cc2[nH]1)c1ccccc1] | 1H NMR (400 MHz, DMSO-d6) δ 11.69 (s, 1H), 7.55-7.45 (m, 3H), 7.43-7.35 (m, 2H), 7.33-7.29 (m, 1H), 7.12-7.05 (m, 1H), 6.83-6.75 (m, 1H), 5.14 (s, 1H), 3.98 (t, J = 6.0 Hz, 2H), 3.52 (t, J = 6.0 Hz, 2H), 3.24 (s, 3H). | MS (ESI) calcd for (C18H17FN2O2) [M + 1]+, 313.1; found, 313.0. |
| 13 | 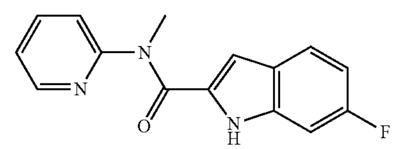 [SMILES: CN(C(=O)c1cc2ccc(F)cc2[nH]1)c1ccccn1] | 1H NMR (400 MHz, DMSO-d6) δ 11.77 (s, 1H), 8.53-8.49 (m, 1H), 7.88-7.82 (m, 1H), 7.44-7.34 (m, 3H), 7.14-7.06 (m, 1H), 6.87-6.79 (m, 1H), 5.59 (s, 1H), 3.33 (s, 3H). | MS (ESI) calcd for (C15H12FN3O) [M + 1]+, 270.1; found, 270.1. |
| 14 | 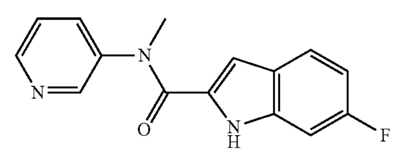 [SMILES: CN(C(=O)c1cc2ccc(F)cc2[nH]1)c1cccnc1] | 1H NMR (400 MHz, DMSO-d6) δ 11.75 (s, 1H), 8.65-8.56 (m, 2H), 7.93-7.89 (m, 1H), 7.58-7.50 (m, 1H), 7.43-7.37 (m, 1H), 7.15-7.09 (m, 1H), 6.86-6.78 (m, 1H), 5.37 (s, 1H), 3.43 (s, 3H). | MS (ESI) calcd for (C15H12FN3O) [M + 1]+, 270.1; found, 270.1. |
| 15 | 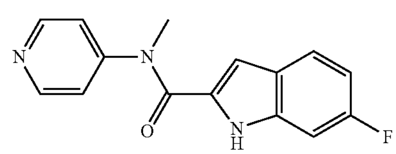 [SMILES: CN(C(=O)c1cc2ccc(F)cc2[nH]1)c1ccncc1] | 1H NMR (400 MHz, DMSO-d6) δ 11.79 (s, 1H), 8.59 (d, J = 6.0, 2H), 7.51-7.39 (m, 3H), 7.14-7.11 (m, 1H), 6.90-7.80 (m, 1H), 5.92 (s, 1H), 3.46 (s, 3H). | MS (ESI) calcd for (C15H12FN3O) [M + 1]+, 270.1; found, 270.1. |
| 16 | 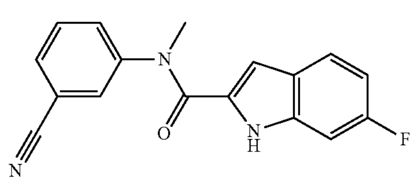 [SMILES: CN(C(=O)c1cc2ccc(F)cc2[nH]1)c1cccc(C#N)c1] | 1H NMR (400 MHz, DMSO-d6) δ 11.73 (s, 1H), 8.04 (d, J = 1.6 Hz, 1H), 7.92-8.96 (m, 1H), 7.76-7.72 (m, 1H), 7.67-7.64 (m, 1H), 7.46-7.38 (m, 1H), 7.15-7.07 (m, 1H), 6.86-6.78 (m, 1H), 5.46 (s, 1H), 3.41 (s, 3H). | MS (ESI) calcd for (C17H12FN3O) [M + 1]+, 294.1; found, 294.1. |

TABLE 1-continued

| Ex. | Structure | 1H NMR | LCMS |
|---|---|---|---|
| 17 | 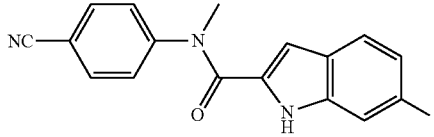 | 1H NMR (400 MHz, DMSO-d6) δ 11.75 (s, 1H), 7.97-7.89 (m, 2H), 7.64-7.56 (m, 2H), 7.48-7.42 (m, 1H), 7.15-7.07 (m, 1H), 6.85-6.81 (m, 1H), 5.64 (s, 1H), 3.43 (s, 3H). | MS (ESI) calcd for (C17H12FN3O) [M + 1]+, 294.1; found, 294.1. |
| 18 | 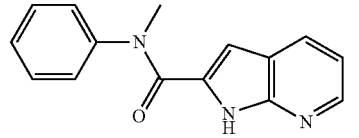 [SMILES: CN(C(=O)c1cc2cccnc2[nH]1)c1ccccc1] | 1H NMR (400 MHz, DMSO-d6) δ 12.09 (s, 1H), 8.27-8.26 (m, 1H), 7.83-7.76 (m, 1H), 7.50-7.33 (m, 5H), 7.04-7.96 (m, 1H), 5.45 (s, 1H), 3.40 (s, 3H). | MS (ESI) calcd for (C15H13N3O) [M + 1]+, 252.1; found, 252.1. |
| 19 | 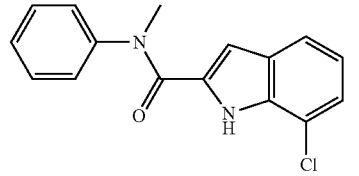 [SMILES: CN(C(=O)c1cc2cccc(Cl)c2[nH]1)c1ccccc1] | 1H NMR (400 MHz, DMSO-d6) δ 11.62 (s, 1H), 7.47-7.38 (m, 2H), 7.40-7.29 (m, 4H), 7.24-7.18 (m, 1H), 6.98-6.90 (m, 1H), 5.66 (s, 1H), 3.41 (s, 3H). | MS (ESI) calcd for (C16H13ClN2O) [M + 1]+, 285.0; found, 285.1. |
| 20 | 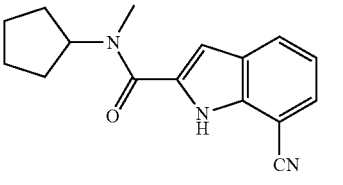 [SMILES: CN(C(=O)c1cc2cccc(C#N)c2[nH]1)C1CCCC1] | 1H NMR (400 MHz, DMSO-d6) δ 12.43 (s, 1H), 7.98 (d, J = 8.0 Hz, 1H), 7.69 (dd, J = 7.4, 1.2 Hz, 1H), 7.22 (t, J = 7.6 Hz, 1H), 6.90 (s, 1H), 4.65 (br, 1H), 2.97 (s, 3H), 1.84-1.80 (m, 2H) 1.69-1.68 (m, 4H), 1.53-1.52 (m, 2H). | MS (ESI) calcd for (C16H17N3O) [M + 1]+, 268.1; found, 268.1. |
| 21 | 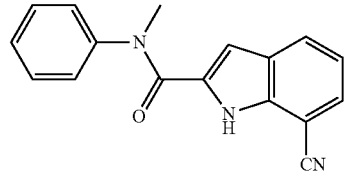 | 1H NMR (400 MHz, DMSO-d6) δ 12.42 (s, 1H), 7.73 (d, J = 8.0 Hz, 1H), 7.65 (dd, J = 7.4, 1.2 Hz, 1H), 7.48-7.30 (m, 5H), 7.09 (t, J = 7.8 Hz, 1H), 5.71 (s, 1H), 3.41 (s, 3H). | MS (ESI) calcd for (C17H13N3O) [M + 1]+, 276.1; found, 276.0. |
| 22 | 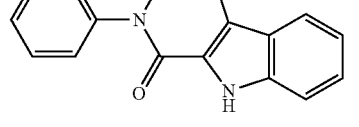 | 1H NMR (400 MHz, DMSO-d6) δ 11.82 (s, 1H), 7.4-7.3 (m, 2H), 7.28-7.16 (m, 5H), 7.14-7.12 (m, 1H), 7.08-7.04 (m, 1H), 3.43 (s, 3H). | MS (ESI) calcd for (C16H13ClN2O) [M + 1]+, 285.1; found, 285.0. |
| 23 | 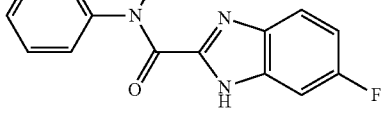 | 1H NMR (400 MHz, DMSO-d6) δ 13.17 (s, 1H), 8.03-6.26 (m, 8H), 3.60 (s, 3H) | MS (ESI) calcd for (C15H12FN3O) [M + 1]+, 270.1; found, 270.1. |
| 24 | 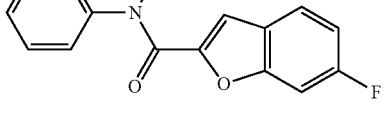 | 1H NMR (400 MHz, DMSO-d6) δ 7.65-7.550 (m, 1H), 7.54-7.27 (m, 6H), 7.17-7.07 (m, 1H), 6.37 (s, 1H), 3.39 (s, 3H). | MS (ESI) calcd for (C16H12FNO2) [M + 1]+, 270.1; found, 270.1. |
| 25 | 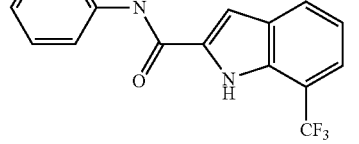 | 1H NMR (400 MHz, DMSO-d6) δ 11.31 (s, 1H), 7.70 (d, J = 8.0 Hz, 1H), 7.50 (d, J = 7.2 Hz, 1H), 7.47-7.38 (m, 2H), 7.37-7.25 (m, 3H), 7.12 (t, J = 7.6 Hz, 1H), 5.87 (s, 1H), 3.42 (s, 3H). | MS (ESI) calcd for (C17H13F3N2O) [M + 1]+, 319.1; found, 319.0. |

TABLE 1-continued

| Ex. | Structure | 1H NMR | LCMS |
|---|---|---|---|
| 26 | 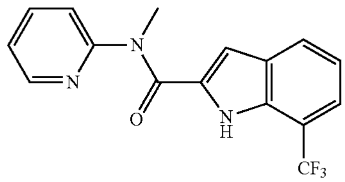 [SMILES: CN(C(=O)c1cc2cccc(C(F)(F)F)c2[nH]1)c1ccccn1] | 1H NMR (400 MHz, DMSO-d6) δ 11.67 (br, 1H), 8.45-8.44 (m, 1H), 7.94-7.71 (m, 2H), 7.52 (d, J = 7.2 Hz, 1H), 7.36-7.16 (m, 2H), 7.14 (d, J = 7.6 Hz, 1H), 6.12 (s, 1H), 3.48 (s, 3H). | MS (ESI) calcd for (C16H12F3N3O) [M + 1]+, 320.1; found, 320.1. |
| 27 | 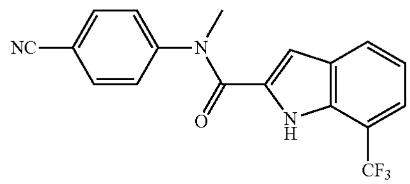 [SMILES: CN(C(=O)c1cc2cccc(C(F)(F)F)c2[nH]1)c1ccc(C#N)cc1] | 1H NMR (400 MHz, DMSO-d6) δ 11.54 (s, 1H), 7.85-7.74 (m, 3H), 7.61-7.38 (m, 3H), 7.16 (t, J = 8.0 Hz, 1H), 6.21 (s, 1H), 3.46 (s, 3H). | MS (ESI) calcd for (C18H12F3N3O) [M + 1]+, 344.1; found, 344.1. |
| 28 | 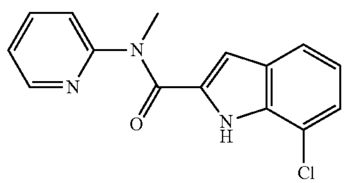 | 1H NMR (400 MHz, DMSO-d6) δ 11.86 (s, 1H), 8.46-8.45 (m, 1H), 7.81-7.79 (m, 1H), 7.38 (d, J = 8.0 Hz, 1H), 7.31-7.29 (m, 2H), 7.24 (dd, J = 7.6, 0.8 Hz, 1H), 6.97 (t, J = 7.6 Hz, 1H), 5.93 (s, 1H), 3.33 (s, 3H). | MS (ESI) calc'd for (C15H12ClN3O) [M + 1]+, 286.1; found, 286.1. |
| 29 | 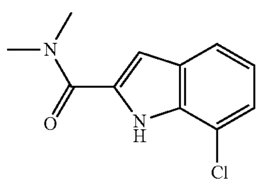 | 1H NMR (400 MHz, DMSO-d6) δ 11.69 (s, 1H), 7.59 (d, J = 8.0 Hz, 1H), 7.27 (dd, J = 7.6, 0.8 Hz, 1H), 7.06 (t, J = 7.6 Hz, 1H), 6.87 (s, 1H), 3.19 (s, 3H), 3.05 (s, 3H). | MS (ESI) calc'd for (C11H11ClN2O) [M + 1]+, 223.1; found, 223.1. |
| 30 | 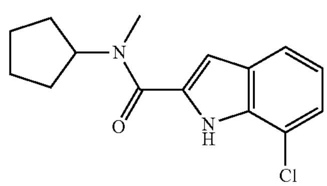 [SMILES: CN(C(=O)c1cc2cccc(Cl)c2[nH]1)C1CCCC1] | 1H NMR (400 MHz, DMSO-d6) δ 11.74 (s, 1H), 7.59 (d, J = 8.0 Hz, 1H), 7.25 (dd, J = 7.6, 0.9 Hz, 1H), 7.06 (t, J = 7.6 Hz, 1H), 6.81 (s, 1H), 4.70 (br, 1H), 2.97 (s, 3H), 1.83-1.81 (m, 2H), 1.72-1.66 (m, 4H), 1.53-1.52 (m, 2H). | MS (ESI) calc'd for (C15H17ClN2O) [M + 1]+, 277.1; found, 277.1. |
| 31 | 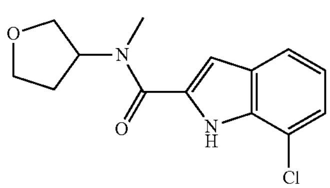 [SMILES: CN(C(=O)c1cc2cccc(Cl)c2[nH]1)C1CCOC1] | 1H NMR (400 MHz, DMSO-d6) δ 11.74 (s, 1H), 7.60 (d, J = 8.0 Hz, 1H), 7.27 (dd, J = 7.6, 0.8 Hz, 1H), 7.07 (t, J = 7.6 Hz, 1H), 6.84 (s, 1H), 5.05 (br, 1H), 4.01-3.95 (m, 1H), 3.83-3.71 (m, 2H), 3.60-3.58 (m, 1H), 3.03 (s, 3H), 2.25-2.20 (m, 1H), 2.02-1.94 (m, 1H). | MS (ESI) calcd for (C14H15ClN2O2) [M + 1]+, 279.1; found, 279.1. |
| 32 | 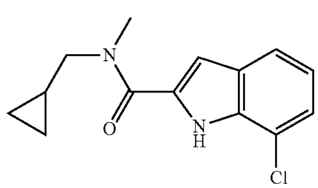 [SMILES: CN(CC1CC1)C(=O)c1cc2cccc(Cl)c2[nH]1] | 1H NMR (400 MHz, DMSO-d6) δ 11.25 (br, 1H), 7.62-7.56 (m, 1H), 7.26 (d, J = 7.6 Hz, 1H), 7.06 (t, J = 7.6 Hz, 1H), 6.88-6.86 (m, 1H), 3.41 (d, J = 7.6 Hz, 2H), 3.25-3.12 (m, 3H), 1.07-0.94 (m, 1H), 0.51 (d, J = 4.4 Hz, 2H), 0.17-0.11 (m, 2H). | MS (ESI) calc'd for (C14H15ClN2O) [M + 1]+, 263.1; found, 263.1. |
| 33 | 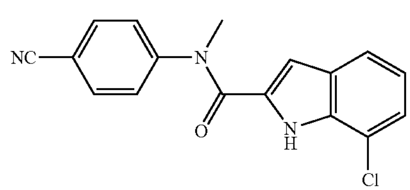 [SMILES: CN(C(=O)c1cc2cccc(Cl)c2[nH]1)c1ccc(C#N)cc1] | 1H NMR (400 MHz, DMSO-d6) δ 11.79 (s, 1H), 7.90-7.82 (m, 2H), 7.56-7.48 (m, 2H), 7.42 (d, J = 8.0 Hz, 1H), 7.25 (dd, J = 7.6, 0.8 Hz, 1H), 6.98 (t, J = 7.8 Hz, 1H), 6.02 (s, 1H), 3.46 (s, 3H). | MS (ESI) calcd for (C17H12ClN3O) [M + 1]+, 310.1; found, 310.1. |

TABLE 1-continued

| Ex. | Structure | 1H NMR | LCMS |
|---|---|---|---|
| 34 | 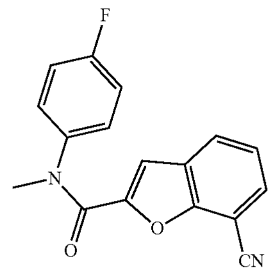 [SMILES: CN(C(=O)c1cc2cccc(C#N)c2o1)c1ccc(F)cc1] | 1H NMR (400 MHz, DMSO-d6) δ 8.05-8.00 (m, 1H), 7.90-7.88 (m, 1H), 7.51-7.39 (m, 3H), 7.31-7.21 (m, 2H), 6.91 (s, 1H), 3.40 (s, 3H). | MS (ESI) calcd for (C17H11FN2O2) [M + 1]+, 295.1; found, 295.1. |
| 35 | 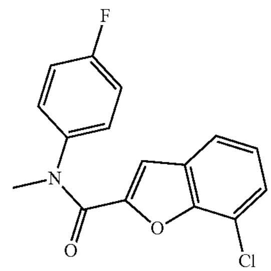 [SMILES: CN(C(=O)c1cc2cccc(Cl)c2o1)c1ccc(F)cc1] | 1H NMR (400 MHz, DMSO-d6) δ 7.63-7.61 (m, 1H), 7.51-7.40 (m, 3H), 7.32-7.22 (m, 3H), 6.86 (s, 1H), 3.39 (s, 3H). | MS (ESI) calcd for (C16H11ClFNO2) [M + 1]+, 304.0; found, 304.0. |
| 36 | 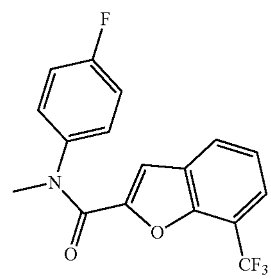 [SMILES: CN(C(=O)c1cc2cccc(C(F)(F)F)c2o1)c1ccc(F)cc1] | 1H NMR (400 MHz, DMSO-d6) δ 7.99 (d, J = 7.8 Hz, 1H), 7.70 (d, J = 7.6 Hz, 1H), 7.48-7.38 (m, 3H), 7.29-7.19 (m, 3H), 3.39 (s, 3H). | MS (ESI) calcd for (C17H11F4NO2) [M + 1]+, 338.0; found, 338.1. |
| 37 | 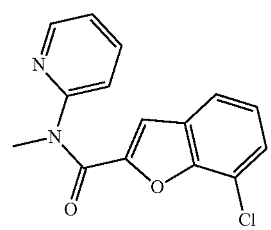 [SMILES: CN(C(=O)c1cc2cccc(Cl)c2o1)c1ccccn1] | 1H NMR (400 MHz, DMSO-d6) δ 8.38-3.37 (m, 1H), 7.89-7.85 (m, 1H), 7.64 (dd, J = 8.0, 1.2 Hz, 1H), 7.50-7.43 (m, 2H), 7.34-7.28 (m, 1H), 7.28-6.87 (m, 2H), 3.47 (s, 3H). | MS (ESI) calcd for (C15H11ClN2O2) [M + 1]+, 287.0; found, 286.9. |
| 39 | | 1H NMR (400 MHz, DMSO-d6) δ 8.45-8.35 (m, 1H), 7.89-7.79 (m, 1H), 7.69-7.58 (m, 1H), 7.44-7.23 (m, 3H), 7.21-7.11 (m, 1H), 6.95 (s, 1H), 3.46 (s, 3H). | MS (ESI) calcd for (C15H11FN2O2) [M + 1]+, 271.1; found, 271.1. |
| 39 | | 1H NMR (400 MHz, DMSO-d6) δ 7.65 (dd, J = 8.8, 5.6 Hz, 1H), 7.47-7.42 (m, 3H), 7.32-7.24 (m, 2H), 7.16-7.11 (m, 1H), 6.48 (s, 1H), 3.37 (s, 3H). | MS (ESI) calcd for (C16H11F2NO2) [M + 1]+, 288.1; found, 288.1. |

TABLE 1-continued

| Ex. | Structure | 1H NMR | LCMS |
|---|---|---|---|
| 40 | 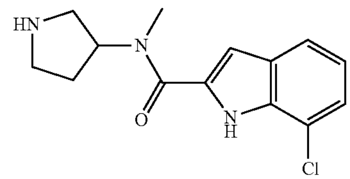 [SMILES: CN(C(=O)c1cc2cccc(Cl)c2[nH]1)C1CCNC1] | 1H NMR (400 MHz, Methanol-d4) δ 7.62 (dd, J = 8.0, 0.8 Hz, 1H), 7.30 (dd, J = 7.8, 1.0 Hz, 1H), 7.10 (t, J = 7.8 Hz, 1H), 7.02 (s, 1H), 4.71 (s, 1H), 3.76-3.71 (m, 1H), 3.66-3.50 (m, 2H), 3.40 (s, 3H), 3.31-3.20 (m, 1H), 2.57-2.48 (m, 1H), 2.42-2.30 (m, 1H). | MS (ESI) calcd for (C14H16ClN3O) [M + 1]+, 278.0; found, 278.0. |
| 41 | 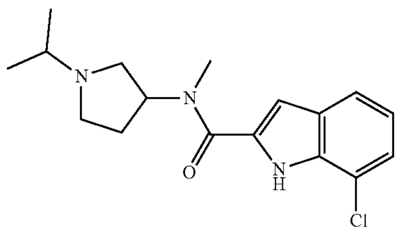 [SMILES: CC(C)N1CCC(N(C)C(=O)c2cc3cccc(Cl)c3[nH]2)C1] | 1H NMR (400 MHz, Methanol-d4) δ 7.60 (d, J = 8.0 Hz, 1H), 7.26 (d, J = 7.6 Hz, 1H), 7.08 (t, J = 7.6 Hz, 1H), 6.92-6.87 (m, 1H), 5.10 (br, 1H), 3.21 (s, 3H), 2.96-2.87 (m, 3H), 2.82-2.80 (m, 1H), 2.67-2.63 (m, 1H), 2.23-2.21 (m, 1H), 2.04-2.01 (m, 1H), 1.16 (d, J = 6.8 Hz, 6H). | MS (ESI) calcd for (C17H22ClN3O) [M + 1]+, 320.1; found, 320.1. |
| 42 | 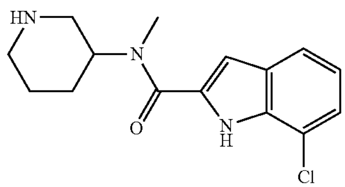 [SMILES: CN(C(=O)c1cc2cccc(Cl)c2[nH]1)C1CCCNC1] | 1H NMR (400 MHz, DMSO-d6) δ 11.70 (s, 1H), 7.62-7.56 (m, 1H), 7.27-7.25 (m, 1H), 7.07 (t, J = 7.6 Hz, 1H), 6.81 (s, 1H), 4.37-4.02 (br, 2H), 3.06-2.67 (m, 6H), 2.51-2.40 (m, 1H), 1.80-1.71 (m, 3H), 1.44-1.24 (m, 1H). | MS (ESI) calcd for (C15H18ClN3O) [M + 1]+, 292.1; found, 292.0 |
| 43 | 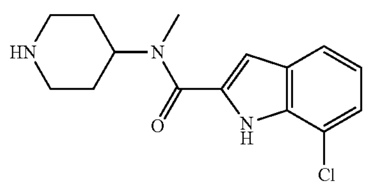 [SMILES: CN(C(=O)c1cc2cccc(Cl)c2[nH]1)C1CCNCC1] | 1H NMR (400 MHz, DMSO-d6) δ 11.70 (s, 1H), 7.64-7.54 (m, 1H), 7.31-7.21 (m, 1H), 7.06 (t, J = 7.6 Hz, 1H), 6.81 (s, 1H), 4.39 (s, 1H), 3.00 (s, 6H), 1.70 (d, J = 11.2 Hz, 1H), 1.64 (s, 4H). | MS (ESI) calcd for (C15H18ClN3O) [M + 1]+, 292.1; found, 292.1 |
| 44 | 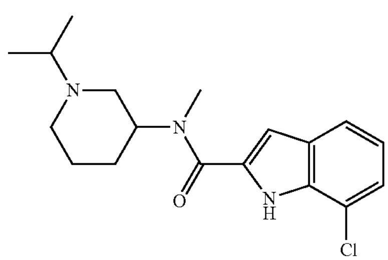 [SMILES: CC(C)N1CCCC(N(C)C(=O)c2cc3cccc(Cl)c3[nH]2)C1] | 1H NMR (400 MHz, DMSO-d6) δ 11.72 (s, 1H), 7.64-7.54 (m, 1H), 7.31-7.21 (m, 1H), 7.06 (t, J = 7.6 Hz, 1H), 6.81 (br, 1H), 4.39-3.97 (m, 1H), 3.01-2.96 (m, 3H), 2.82-2.67 (m, 3H), 2.29-2.16 (m, 1H), 2.03-1.91 (m, 1H), 1.74-1.44 (m, 4H), 0.98-0.96 (m, 6H). | MS (ESI) calcd for (C18H24ClN3O) [M + 1]+, 334.1; found, 334.1 |
| 45 | 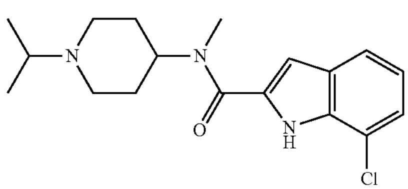 [SMILES: CC(C)N1CCC(N(C)C(=O)c2cc3cccc(Cl)c3[nH]2)CC1] | 1H NMR (400 MHz, DMSO-d6) δ 11.73 (s, 1H), 7.59 (d, J = 8.0 Hz, 1H), 7.27-7.25 (m, 1H), 7.06 (t, J = 7.6 Hz, 1H), 6.80 (s, 1H), 4.29-3.90 (m, 1H), 2.99-2.67 (m, 6H), 2.32-1.98 (m, 2H), 1.81-1.66 (m, 4H), 0.95 (s, 6H). | MS (ESI) calcd for (C18H24ClN3O) [M + 1]+, 334.1; found, 334.1 |
| 46 | 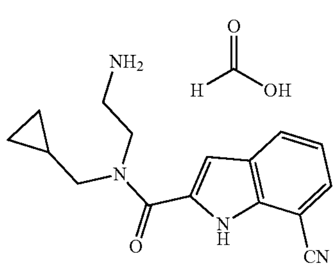 | 1H NMR (400 MHz, Methanol-d4) δ 8.56 (s, 1H), 8.01 (dd, J = 8.0, 1.2 Hz, 1H), 7.69 (dd, J = 7.6, 1.2 Hz, 1H), 7.26 (t, J = 7.8 Hz, 1H), 7.07 (s, 1H), 3.97 (t, J = 6.2 Hz, 2H), 3.63 (d, J = 6.8 Hz, 2H), 3.30 (t, J = 6.2 Hz, 2H), 1.21-1.13 (m, 1H), 0.72-0.63 (m, 2H), 0.32-0.31 (m, 2H). | MS (ESI) calcd for (C16H18N4O) [M + 1]+, 283.1; found, 283.1. |

TABLE 1-continued

| Ex. | Structure | 1H NMR | LCMS |
|---|---|---|---|
| 47 | 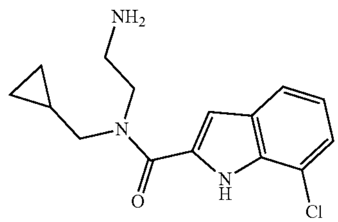 [SMILES: NCCN(CC1CC1)C(=O)c1cc2cccc(Cl)c2[nH]1] | 1H NMR (400 MHz, Methanol-d4) δ 7.59 (dd, J = 8.0, 0.8 Hz, 1H), 7.32-7.22 (m, 1H), 7.07 (t, J = 7.6 Hz, 1H), 6.93 (s, 1H), 3.79 (t, J = 6.4 Hz, 2H), 3.53 (d, J = 6.4 Hz, 2H), 3.03 (t, J = 6.4 Hz, 2H), 1.16-1.15 (m, 1H), 0.67-0.55 (m, 2H), 0.30-0.29 (m, 2H). | MS (ESI) calcd for (C15H18ClN3O) [M + 1]+, 292.1; found, 292.2. |
| 48 | 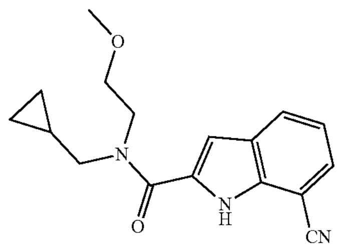 [SMILES: COCCN(CC1CC1)C(=O)c1cc2cccc(C#N)c2[nH]1] | 1H NMR (400 MHz, DMSO-d6) δ 12.48 (br, 1H), 8.02-7.96 (m, 1H), 7.70 (d, J = 7.4 Hz, 1H), 7.22 (t, J = 7.8 Hz, 1H), 6.93 (s, 1H), 3.76-3.75 (m, 2H), 3.60 (t, J = 6.0 Hz, 2H), 3.43 (d, J = 6.8 Hz, 2H), 3.22 (s, 3H), 1.12-1.10 (m, 1H), 0.54-0.46 (m, 2H). 0.30-0.14 (m, 2H). | MS (ESI) calcd for (C17H19N3O2) [M + 1]+, 298.1; found, 298.1. |
| 49 | 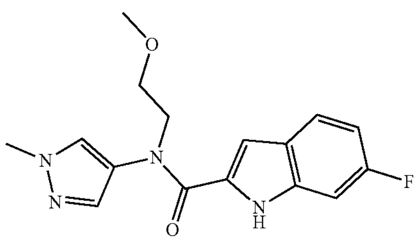 [SMILES: COCCN(C(=O)c1cc2ccc(F)cc2[nH]1)c1cnn(C)c1] | 1H NMR (400 MHz, DMSO-d6) δ 11.64 (s, 1H), 7.89 (s, 1H), 7.48-7.43 (m, 2H), 7.11 (dd, J = 9.8, 2.4 Hz, 1H), 6.86-6.81 (m, 1H), 5.56 (br, 1H), 3.90-3.72 (m, 5H), 3.52 (t, J = 5.8 Hz, 2H), 3.27 (s, 3H). | MS (ESI) calcd for (C16H17FN4O2) [M + 1]+, 317.1; found, 317.1. |
| 50 | 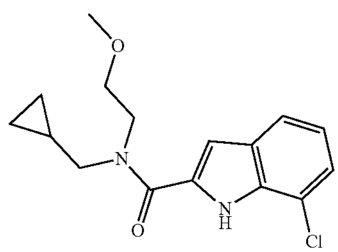 [SMILES: COCCN(CC1CC1)C(=O)c1cc2cccc(Cl)c2[nH]1] | 1H NMR (400 MHz, DMSO-d6) δ 11.74 (s, 1H), 7.59 (d, J = 8.0 Hz, 1H), 7.26 (d, J = 7.6 Hz, 1H), 7.06 (t, J = 7.8 Hz, 1H), 6.85 (s, 1H), 3.77 (t, J = 6.0 Hz, 2H), 3.60 (t, J = 5.8 Hz, 2H), 3.43 (d, J = 6.4 Hz, 2H), 3.31 (s, 3H), 1.08-1.02 (m, 1H), 0.55-0.44 (m, 2H), 0.29-0.14 (m, 2H). | MS (ESI) calcd for (C16H19ClN2O2) [M + 1]+, 307.1; found, 307.1. |
| 51 | 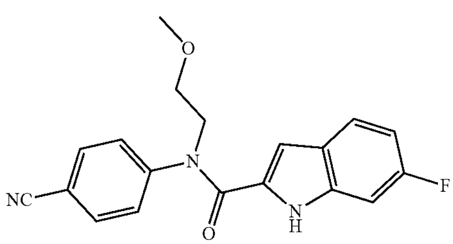 [SMILES: COCCN(C(=O)c1cc2ccc(F)cc2[nH]1)c1ccc(C#N)cc1] | 1H NMR (400 MHz, DMSO-d6) δ 11.76 (s, 1H), 7.97-7.89 (m, 2H), 7.62-7.55 (m, 2H), 7.43 (dd, J = 8.8, 5.6 Hz, 1H), 7.11 (dd, J = 10.0, 2.4 Hz, 1H), 6.84-6.81 (m, 1H), 5.47 (s, 1H), 4.04 (t, J = 5.6 Hz, 2H), 3.53 (t, J = 5.6 Hz, 2H), 3.22 (s, 3H). | MS (ESI) calcd for (C19H16FN3O2) [M + 1]+, 338.1; found, 338.3. |
| 52 | 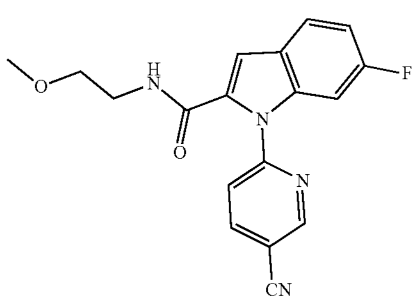 [SMILES: COCCNC(=O)c1cc2ccc(F)cc2n1-c1ccc(C#N)cn1] | 1H NMR (400 MHz, DMSO-d6) δ 9.06 (dd, J = 2.4, 0.8 Hz, 1H), 8.81 (t, J = 5.6 Hz, 1H), 8.48 (dd, J = 8.4, 2.4 Hz, 1H), 7.80 (dd, J = 8.4, 5.6 Hz, 1H), 7.60 (dd, J = 8.4, 0.8 Hz, 1H), 7.43 (dd, J = 10.4, 2.4 Hz, 1H), 7.29 (d, J = 0.8 Hz, 1H), 7.18-7.09 (m, 1H), 3.45-3.43 (m, 2H), 3.40-3.32 (m, 2H), 3.29 (s, 3H). | MS (ESI) calcd for (C18H15FN4O2) [M + 1]+, 339.1; found, 339.1. |

TABLE 1-continued

| Ex. | Structure | 1H NMR | LCMS |
|---|---|---|---|
| 53 | 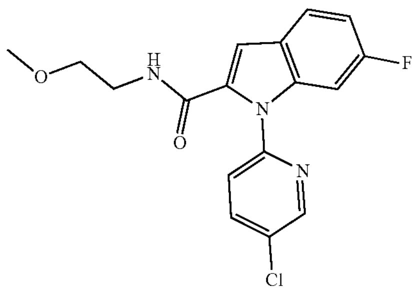 [SMILES: COCCNC(=O)c1cc2ccc(F)cc2n1-c1ccc(Cl)cn1] | 1H NMR (400 MHz, DMSO-d6) δ 8.72 (t, J = 5.8 Hz, 1H), 8.63 (dd, J = 2.8, 0.6 Hz, 1H), 8.12 (dd, J = 8.6, 2.8 Hz, 1H), 7.78 (dd, J = 8.8, 5.6 Hz, 1H), 7.47 (dd, J = 8.6, 0.8 Hz, 1H), 7.28-7.20 (m, 2H), 7.09-7.06 (m, 1H), 3.44-3.42 (m, 2H), 3.38-3.30 (m, 2H), 3.28 (s, 3H). 1 less H | MS (ESI) calcd for (C17H15ClFN3O2) [M + 1]+, 348.1; found, 348.1. |
| 54 | 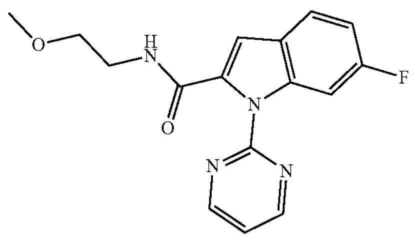 [SMILES: COCCNC(=O)c1cc2ccc(F)cc2n1-c1ncccn1] | 1H NMR (400 MHz, DMSO-d6) δ 8.90 (d, J = 4.8 Hz, 2H), 8.67-8.65 (m, 1H), 7.87-8.86 (m, 1H), 7.76-7.74 (m, 1H), 7.49-7.46 (m, 1H), 7.15-7.12 (m, 1H), 7.08 (d, J = 0.8 Hz, 1H), 3.49-3.42 (m, 2H), 3.37-3.35 (m, 2H), 3.30 (s, 3H). | MS (ESI) calcd for (C16H15FN4O2) [M + 1]+, 315.1; found, 315.1. |
| 55 | 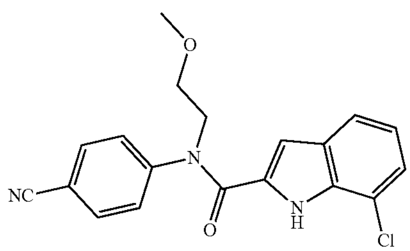 [SMILES: COCCN(C(=O)c1cc2cccc(Cl)c2[nH]1)c1ccc(C#N)cc1] | 1H NMR (400 MHz, DMSO-d6) δ 11.82 (s, 1H), 7.90-7.83 (m, 2H), 7.55-7.47 (m, 2H), 7.44-7.37 (m, 1H), 7.28-7.21 (m, 1H), 6.97 (t, J = 7.6 Hz, 1H), 5.87 (s, 1H), 4.08 (t, J = 5.6 Hz, 2H), 3.54 (t, J = 5.6 Hz, 2H), 3.22 (s, 3H). | MS (ESI) calcd for (C19H16ClN3O2) [M + 1]+,354.1; found,354.0. |
| 60 | 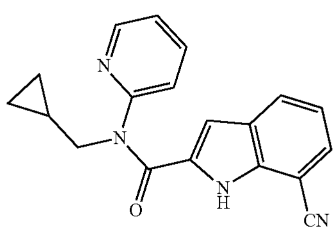 [SMILES: N#Cc1cccc2cc(C(=O)N(CC3CC3)c3ccccn3)[nH]c12] | 1H NMR (400 MHz, DMSO-d6) δ 12.59 (s, 1H), 8.48 (dd, J = 4.8, 2.0 Hz, 1H), 7.79-7.77 (m, 2H), 7.66 (dd, J = 7.4, 1.2 Hz, 1H), 7.36-7.28 (m, 1H), 7.25 (d, J = 8.0 Hz, 1H), 7.12 (t, J = 7.8 Hz, 1H), 5.87 (s, 1H), 3.88 (d, J = 7.0 Hz, 2H), 1.10-1.07 (m, 1H), 0.45-0.36 (m, 2H), 0.16-0.13 (m, 2H). | MS (ESI) calcd for (C19H16N4O) [M + 1]+, 317.1; found, 317.1. |
| 56 | 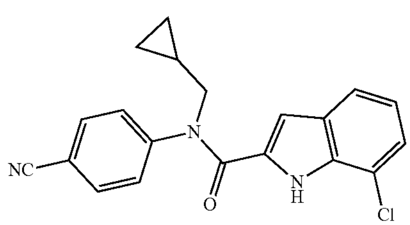 [SMILES: N#Cc1ccc(N(CC2CC2)C(=O)c2cc3cccc(Cl)c3[nH]2)cc1] | 1H NMR (400 MHz, DMSO-d6) δ 11.81 (s, 1H), 7.92-7.84 (m, 2H), 7.56-7.48 (m, 2H), 7.40 (d, J = 8.0 Hz, 1H), 7.24 (d, J = 7.6 Hz, 1H), 6.97 (t, J = 7.6 Hz, 1H), 5.88 (s, 1H), 3.82 (d, J = 7.2 Hz, 2H), 1.24-1.06 (m, 1H), 0.46-0.36 (m, 2H), 0.18-0.10 (m, 2H). | MS (ESI) calcd for (C20H16ClN3O) [M + 1]+, 350.1; found, 350.1. |
| 57 | 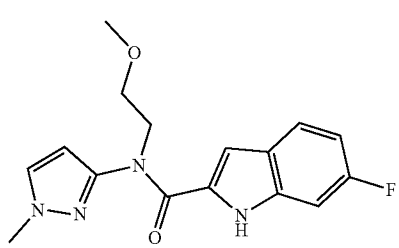 [SMILES: COCCN(C(=O)c1cc2ccc(F)cc2[nH]1)c1ccn(C)n1] | 1H NMR (400 MHz, DMSO-d6) δ 11.65 (s, 1H), 7.80 (d, J = 2.4 Hz, 1H), 7.46-7.44 (m, 1H), 7.11-7.09 (m, 1H), 6.88-6.78 (m, 1H), 6.21 (d, J = 2.4 Hz, 1H), 5.57 (s, 1H), 3.88 (t, J = 6.4 Hz, 2H), 3.87 (s, 3H), 3.53 (t, J = 6.4 Hz, 2H), 3.26 (s, 3H). | MS (ESI) calcd for (C16H17FN4O2) [M + 1]+, 317.1; found, 317.1. |

TABLE 1-continued

| Ex. | Structure | 1H NMR | LCMS |
|---|---|---|---|
| 58 | 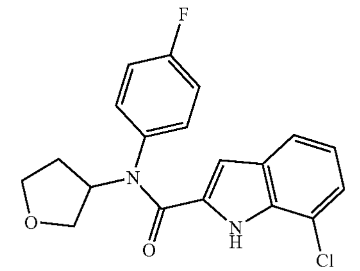 [SMILES: O=C(c1cc2cccc(Cl)c2[nH]1)N(c1ccc(F)cc1)C1CCOC1] | 1H NMR (400 MHz, DMSO-d6) δ 11.51 (s, 1H), 7.50-7.40 (m, 2H), 7.36 (d, J = 8.0 Hz, 1H), 7.30 (t, J = 8.8 Hz, 2H), 7.22 (d, J = 7.6 Hz, 1H), 6.95 (t, J = 7.6 Hz, 1H), 5.53 (s, 1H), 5.23-5.18 (m, 1H), 3.94-3.92 (m, 1H), 3.78-3.76 (m, 1H), 3.63-3.61 (m, 1H), 3.47-3.41 (m, 1H), 2.24-2.17 (m, 1H), 1.94-1.81 (m, 1H). | MS (ESI) calcd for (C19H16ClFN2O2) [M + 1]+, 359.0; found, 359.0. |
| 61 | 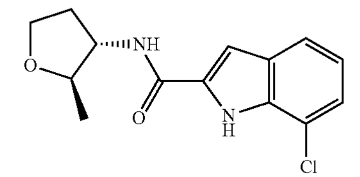 [SMILES: C[C@H]1OCC[C@@H]1NC(=O)c1cc2cccc(Cl)c2[nH]1] | 1H NMR (300 MHz, Methanol-d4) δ 7.62-7.53 (m, 1H), 7.31-7.23 (m, 1H), 7.25 (s, 1H), 7.11-7.00 (m, 1H), 4.74-4.62 (m, 1H), 4.17-3.93 (m, 2H), 3.82-3.67 (m, 1H), 2.52-2.34 (m, 1H), 2.10-1.93 (m, 1H), 1.28-1.20 (m, 3H). | MS (ESI) calc'd for (C14H15ClN2O2) [M + 1]+, 279.0; found, 279.0. |
| 62 | 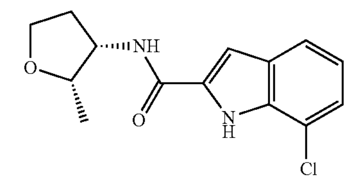 [SMILES: C[C@@H]1OCC[C@@H]1NC(=O)c1cc2cccc(Cl)c2[nH]1] | 1H NMR (300 MHz, Methanol-d4) δ 7.62-7.53 (m, 1H), 7.27-7.25 (m, 1H), 7.25-7.21 (m, 1H), 7.08-7.03 (m, 1H), 4.29-4.16 (m, 1H), 4.02-3.86 (m, 3H), 2.48-2.30 (m, 1H), 2.07-1.90 (m, 1H), 1.31-1.28 (m, 3H). | MS (ESI) calc'd for (C14H15ClN2O2) [M + 1]+, 279.0; found, 279.0. |
| 63 | 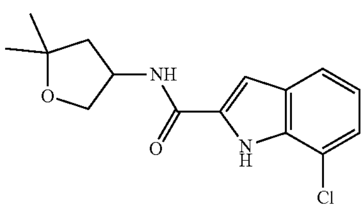 [SMILES: CC1(C)CC(NC(=O)c2cc3cccc(Cl)c3[nH]2)CO1] | 1H NMR (400 MHz, DMSO-d6) δ 11.62 (s, 1H), 8.64-8.58 (m, 1H), 7.62 (d, J = 8.0 Hz, 1H), 7.31 (d, J = 7.6 Hz, 1H), 7.23 (s, 1H), 7.11-7.03 (m, 1H), 4.62-4.52 (m, 1H), 4.08-4.00 (m, 1H), 3.70-3.62 (m, 1H), 2.21-2.11 (m, 1H), 1.85-1.75 (m, 1H), 1.32 (s, 3H), 1.21 (s, 3H). | MS (ESI) calc'd for (C15H17ClN2O2) [M + 1]+, 293.1; found, 293.1. |
| 64 | 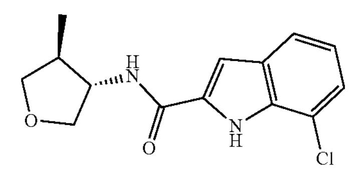 [SMILES: C[C@@H]1COC[C@H]1NC(=O)c1cc2cccc(Cl)c2[nH]1] | 1H NMR (300 MHz, Methanol-d4) δ 7.62-7.52 (m, 1H), 7.31-7.22 (m, 2H), 7.12-7.00 (m, 1H), 4.81-4.70 (m, 1H), 4.16-4.06 (m, 1H), 4.06-3.96 (m, 1H), 3.85-3.75 (m, 1H), 3.58-3.46 (m, 1H), 2.68-2.47 (m, 1H), 1.28-1.03 (m, 3H). | MS (ESI) calc'd for (C14H15ClN2O2) [M + 1]+, 279.0; found, 279.0. |
| 65 | 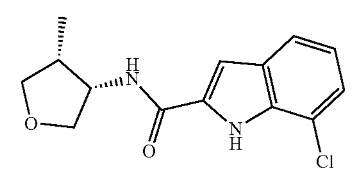 [SMILES: C[C@H]1COC[C@H]1NC(=O)c1cc2cccc(Cl)c2[nH]1] | 1H NMR (300 MHz, Methanol-d4) δ 7.62-7.53 (m, 1H), 7.31-7.19 (m, 2H), 7.11-7.00 (m, 1H), 4.29-4.18 (m, 1H), 4.18-4.05 (m, 2H), 3.76-3.65 (m, 1H), 3.58-3.39 (m, 1H), 2.45-2.30 (m, 1H), 1.28-1.15 (m, 3H). | MS (ESI) calc'd for (C14H15ClN2O2) [M + 1]+, 279.0; found, 279.0. |
| 66 | 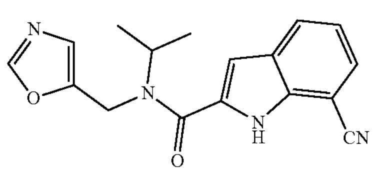 [SMILES: CC(C)N(Cc1cnco1)C(=O)c1cc2cccc(C#N)c2[nH]1] | 1H NMR (400 MHz, DMSO-d6) δ 12.50 (s, 1H), 8.30 (s, 1H), 7.99-7.97 (m, 1H), 7.70-7.69 (m, 1H), 7.23-7.20 (m, 1H), 7.10 (s, 1H), 6.89 (s, 1H), 4.71 (s, 2H), 4.46-4.44 (m, 1H), 1.22-1.20 (m, 6H). | MS (ESI) calc'd for (C17H16N4O2) [M + 1]+, 309.1; found, 309.0. |

TABLE 1-continued

| Ex. | Structure | 1H NMR | LCMS |
|---|---|---|---|
| 67 | 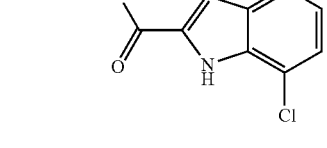 | 1H NMR (400 MHz, DMSO-d6) δ 11.83 (s, 1H), 8.31 (s, 1H), 7.62-7.55 (m, 1H), 7.30-7.23 (m, 1H), 7.16-6.99 (m, 2H), 6.81 (s, 1H), 4.72 (s, 2H), 4.54-4.43 (m, 1H), 1.22 (d, J = 6.8 Hz, 6H). | MS (ESI) calc'd for (C16H16ClN3O2) [M + 1]+, 318.0; found, 318.0. |
| 68 | 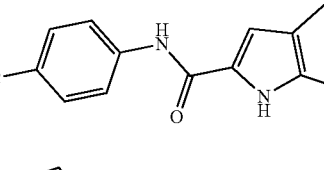 | 1H NMR (400 MHz, DMSO-d6) δ 11.98 (s, 1H), 10.67 (s, 1H), 8.05-7.98 (m, 2H), 7.90-7.83 (m, 2H), 7.70 (d, J = 8.0 Hz, 1H), 7.51 (s, 1H), 7.36 (d, J = 7.6 Hz, 1H), 7.18-7.08 (m, 1H). | MS (ESI) calc'd for (C16H10ClN3O) [M + 1]+, 296.0; found, 296.0. |
| 69 | 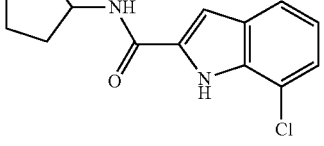 | 1H NMR (400 MHz, DMSO-d6) δ 11.56 (s, 1H), 8.40-8.34 (m, 1H), 7.61 (d, J = 8.0 Hz, 1H), 7.29 (d, J = 7.6 Hz, 1H), 7.20 (s, 1H), 7.11-7.02 (m, 1H), 4.31-4.21 (m, 1H), 2.01-1.88 (m, 2H), 1.75-1.70 (m, 2H), 1.65-1.49 (m, 4H). | MS (ESI) calc'd for (C14H15ClN2O) [M + 1]+, 263.1; found, 263.2. |
| 70 | 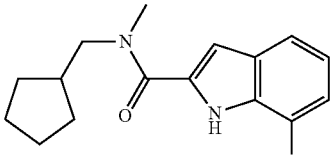 | 1H NMR (300 MHz, Methanol-d4) δ 7.70-7.54 (m, 1H), 7.41-7.15 (m, 1H), 7.13-7.01 (m, 1H), 6.90 (s, 1H), 3.79-3.57 (m, 2H), 3.57-3.31 (m, 2H), 3.13-2.83 (m, 1H), 2.33 (s, 1H), 1.96-1.56 (m, 6H), 1.31-0.88 (m, 2H). | MS (ESI) calc'd for (C16H19ClN2O) [M + 1]+, 291.1; found, 291.0. |
| 71 | 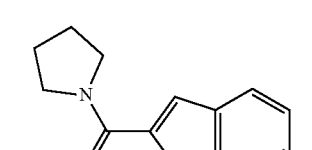 | 1H NMR (400 MHz, DMSO-d6) δ 11.52 (s, 1H), 7.65-7.58 (m, 1H), 7.32-7.25 (m, 1H), 7.11-7.02 (m, 2H), 3.81-3.74 (m, 2H), 3.59-3.52 (m, 2H), 1.99-1.85 (m, 4H). | MS (ESI) calc'd for (C13H13ClN2O) [M + 1]+, 249.1; found, 249.15. |
| 72 | 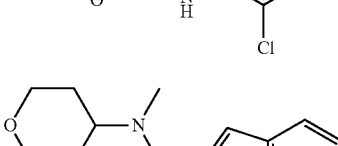 | 1H NMR (400 MHz, DMSO-d6) δ 11.73 (s, 1H), 7.63-7.56 (m, 1H), 7.30-7.23 (m, 1H), 7.11-7.02 (m, 1H), 6.84 (s, 1H), 4.48 (s, 1H), 3.97-3.90 (m, 2H), 3.55-3.33 (m, 2H), 3.01 (s, 3H), 1.92-1.80 (m, 2H), 1.68-1.60 (m, 2H). | MS (ESI) calc'd for (C15H17ClN2O2) [M + 1] +, 293.1; found, 293.1. |
| 73 | 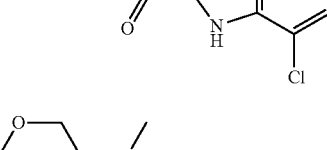 | 1H NMR (300 MHz, Methanol-d4) δ 7.63-7.54 (m, 1H), 7.30-7.21 (m, 1H), 7.13-7.01 (m, 1H), 6.88 (s, 1H), 4.45 (s, 1H), 4.02-3.91 (m, 1H), 3.91-3.82 (m, 1H), 3.67-3.54 (m, 1H), 3.47-3.36 (m, 1H), 3.17 (s, 3H), 2.07-1.94 (m, 2H), 1.79 (s, 2H). | MS (ESI) calc'd for (C15H17ClN2O2) [M + 1]+, 293.1; found, 293.2. |
| 74 | 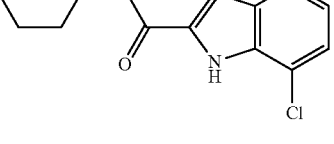 | 1H NMR (300 MHz, DMSO-d6) δ 11.71 (s, 1H), 7.61-7.52 (m, 1H), 7.28-7.20 (m, 1H), 7.09-6.98 (m, 1H), 6.80 (s, 1H), 4.68 (s, 1H), 3.67-3.60 (m, 2H), 2.95 (s, 3H), 1.67-1.50 (m, 4H), 1.17 (s, 6H). | MS (ESI) calc'd for (C17H21ClN2O2) [M + 1]+, 321.1; found, 321.0. |

TABLE 1-continued

| Ex. | Structure | 1H NMR | LCMS |
|---|---|---|---|
| 75 | 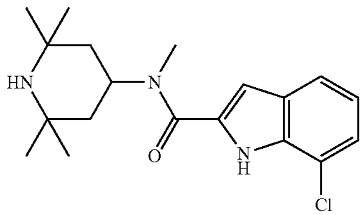 [SMILES: CN(C(=O)c1cc2cccc(Cl)c2[nH]1)C1CC(C)(C)NC(C)(C)C1] | 1H NMR (400 MHz, DMSO-d6) δ 11.53 (s, 1H), 7.59-7.52 (m, 1H), 7.26-7.19 (m, 1H), 7.08-7.00 (m, 1H), 6.74 (s, 1H), 4.60 (s, 1H), 2.93 (s, 3H), 1.60-1.52 (m, 2H), 1.47-1.36 (m, 2H), 1.06 (s, 13H). | MS (ESI) calc'd for (C19H26ClN3O) [M + 1]+, 348.1; found, 348.1. |
| 76 | 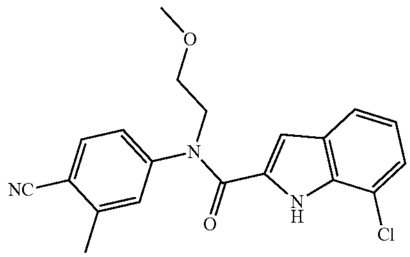 [SMILES: COCCN(C(=O)c1cc2cccc(Cl)c2[nH]1)c1ccc(C#N)c(C)c1] | 1H NMR (300 MHz, DMSO-d6) δ 12.01-11.46 (m, 1H), 7.80-7.71 (m, 1H), 7.53-7.47 (m, 1H), 7.47-7.36 (m, 1H), 7.30-7.19 (m, 2H), 7.02-6.91 (m, 1H), 5.89 (s, 1H), 4.10-4.00 (m, 2H), 3.57-3.47 (m, 2H), 3.22 (s, 3H), 2.49-2.38 (m, 3H). | MS (ESI) calc'd for (C20H18ClN3O2) [M + 1]+, 368.1, found 368.0. |
| 77 | 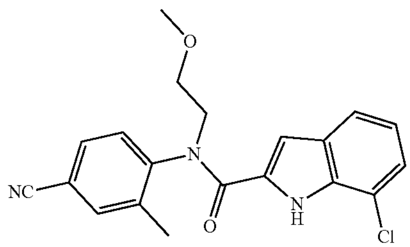 [SMILES: COCCN(C(=O)c1cc2cccc(Cl)c2[nH]1)c1ccc(C#N)cc1C] | 1H NMR (300 MHz, DMSO-d6) δ 11.76 (s, 1H), 7.87-7.74 (m, 2H), 7.67-7.58 (m, 1H), 7.40-7.31 (m, 1H), 7.27-7.19 (m, 1H), 7.00-6.92 (m, 1H), 5.54 (s, 1H), 4.17-4.07 (m, 1H), 3.92-3.81 (m, 1H), 3.54 (s, 2H), 3.21 (s, 3H), 2.13 (s, 3H). | MS (ESI) calc'd for (C20H18ClN3O2) [M + 1]+, 368.1; found, 368.0. |
| 78 | 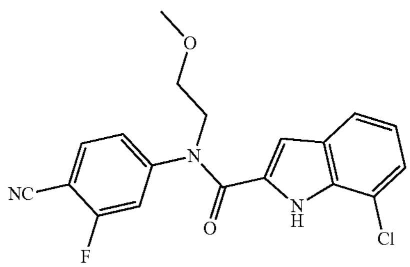 [SMILES: COCCN(C(=O)c1cc2cccc(Cl)c2[nH]1)c1ccc(C#N)c(F)c1] | 1H NMR (300 MHz, Methanol-d4) δ 7.78-7.67 (m, 1H), 7.56-7.46 (m, 1H), 7.42-7.34 (m, 1H), 7.34-7.26 (m, 1H), 7.26-7.18 (m, 1H), 7.04-6.92 (m, 1H), 6.01 (s, 1H), 4.19-4.09 (m, 2H), 3.71-3.61 (m, 2H), 3.34 (s, 3H). | MS (ESI) calc'd for (C19H15ClFN3O2) [M + 1]+, 372.1; found, 372.0. |
| 79 | 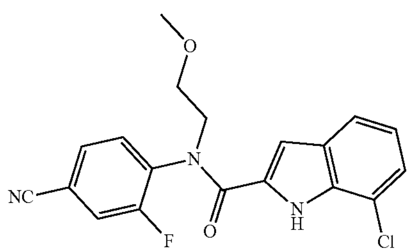 [SMILES: COCCN(C(=O)c1cc2cccc(Cl)c2[nH]1)c1ccc(C#N)cc1F] | 1H NMR (300 MHz, Methanol-d4) δ 7.85-7.74 (m, 1H), 7.74-7.64 (m, 1H), 7.64-7.55 (m, 1H), 7.38-7.29 (m, 1H), 7.26-7.18 (m, 1H), 7.02-6.91 (m, 1H), 5.93 (s, 1H), 4.10 (s, 2H), 3.71-3.62 (m, 2H), 3.29 (s, 3H). | MS (ESI) calc'd for (C19H15ClFN3O2) [M + 1]+, 372.1; found, 372.0. |
| 80 | 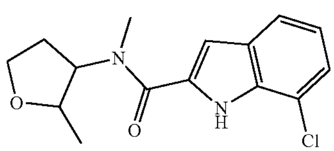 [SMILES: CC1OCCC1N(C)C(=O)c1cc2cccc(Cl)c2[nH]1] | 1H NMR (300 MHz, Methanol-d4) δ 7.62-7.53 (m, 1H), 7.29-7.20 (m, 1H), 7.11-7.00 (m, 1H), 6.90 (s, 1H), 5.19 (s, 1H), 4.21-3.92 (m, 1H), 3.90 (s, 1H), 3.71 (s, 1H), 3.25 (s, 3H), 2.52-2.34 (m, 1H), 2.28 (s, 1H), 1.83-1.26 (m, 3H). | MS (ESI) calc'd for (C15H17ClN2O2) [M + 1]+, 293.1; found, 293.1. |
| 81 | 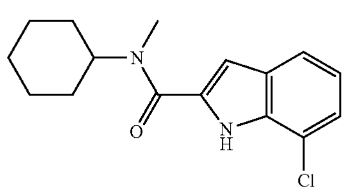 [SMILES: CN(C(=O)c1cc2cccc(Cl)c2[nH]1)C1CCCCC1] | 1H NMR (300 MHz, DMSO-d6) δ 11.70 (s, 1H), 7.59-7.56 (m, 1H), 7.29-7.20 (m, 1H), 7.11-6.99 (m, 1H), 6.78 (s, 1H), 4.29 (s, 1H), 2.97 (s, 3H), 1.96-1.43 (m, 7H), 1.13 (s, 3H). | MS (ESI) calc'd for (C16H19ClN2O) [M + 1]+, 291.1; found, 291.1. |

TABLE 1-continued

| Ex. | Structure | 1H NMR | LCMS |
|---|---|---|---|
| 82 | 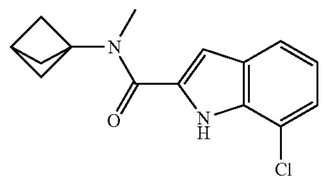 [SMILES: CN(C(=O)c1cc2cccc(Cl)c2[nH]1)C12CC(C1)C2] | 1H NMR (400 MHz, Methanol-d4) δ 7.61-7.55 (m, 1H), 7.28-7.22 (m, 1H), 7.11-7.03 (m, 1H), 6.84 (s, 1H), 3.19 (s, 3H), 2.45 (s, 1H), 2.13 (s, 6H). | MS (ESI) calc'd for (C15H15ClN2O) [M + 1]+, 275.0; found, 275.1. |
| 83 | 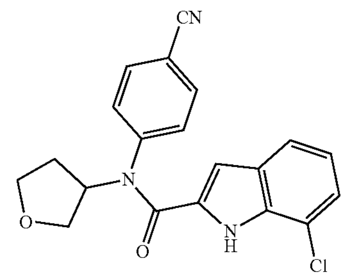 [SMILES: N#Cc1ccc(N(C(=O)c2cc3cccc(Cl)c3[nH]2)C2CCOC2)cc1] | 1H NMR (300 MHz, DMSO-d6) δ 7.96-7.87 (m, 2H), 7.64-7.55 (m, 2H), 7.37 (d, J = 8.1 Hz, 1H), 7.21 (d, J = 7.5 Hz, 1H), 7.00-6.89 (m, 1H), 5.67 (s, 1H), 5.20 (s, 1H), 3.98-3.86 (m, 1H), 3.86-3.76 (m, 1H), 3.66-3.44 (m, 2H), 2.30-2.15 (m, 1H), 1.97-1.80 (m, 1H). | MS (ESI) calc'd for (C20H16ClN3O2) [M + 1]+, 366.1; found, 366.1. |
| 84 | 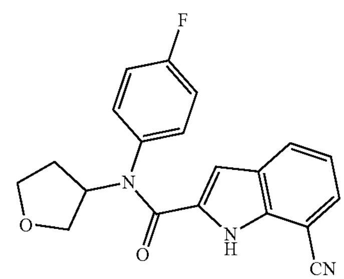 [SMILES: N#Cc1cccc2cc(C(=O)N(c3ccc(F)cc3)C3CCOC3)[nH]c12] | 1H NMR (400 MHz, DMSO-d6) δ 12.25 (s, 1H), 7.80-7.73 (m, 1H), 7.68-7.62 (m, 1H), 7.50-7.40 (m, 2H), 7.36-7.25 (m, 2H), 7.14-7.05 (m, 1H), 5.55 (s, 1H), 5.27-5.17 (m, 1H), 3.98-3.90 (m, 1H), 3.83-3.75 (m, 1H), 3.66-3.55 (m, 1H), 3.52-3.42 (m, 1H), 2.29-2.15 (m, 1H), 1.94-1.81 (m, 1H). | MS (ESI) calc'd for (C20H16FN3O2) [M + 1]+, 350.1; found, 350.2. |
| 85 | 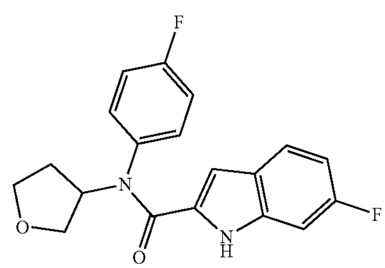 [SMILES: O=C(c1cc2ccc(F)cc2[nH]1)N(c1ccc(F)cc1)C1CCOC1] | 1H NMR (400 MHz, DMSO-d6) δ 11.71-11.66 (m, 1H), 7.53-7.44 (m, 2H), 7.42-7.32 (m, 3H), 7.12-7.07 (m, 1H), 6.84-6.75 (m, 1H), 5.30-5.19 (m, 1H), 5.04-4.99 (m, 1H), 3.97-3.88 (m, 1H), 3.79-3.71 (m, 1H), 3.65-3.54 (m, 1H), 3.50-3.40 (m, 1H), 2.26-2.13 (m, 1H), 1.91-1.79 (m, 1H). | MS (ESI) calc'd for (C19H16F2N2O2) [M + 1]+, 343.1; found, 343.1. |
| 86 | 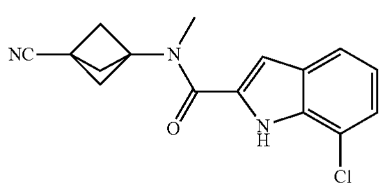 [SMILES: CN(C(=O)c1cc2cccc(Cl)c2[nH]1)C12CC(C#N)(C1)C2] | 1H NMR (400 MHz, DMSO-d6) δ 11.79 (s, 1H), 7.60-7.58 (m, 1H), 7.29-7.27 (m, 1H), 7.09-7.05 (m, 1H), 6.89 (s, 1H), 3.18-3.08 (m, 3H), 2.67-2.60 (m, 6H). | MS (ESI) calc'd for (C16H14ClN3O) [M + 1]+, 300.1, found 300.1. |
| 87 | 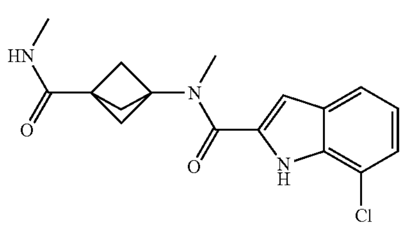 [SMILES: CNC(=O)C12CC(N(C)C(=O)c3cc4cccc(Cl)c4[nH]3)(C1)C2] | 1H NMR (400 MHz, Methanol-d4) δ 7.62-7.56 (m, 1H), 7.29-7.23 (m, 1H), 7.12-7.03 (m, 1H), 6.88 (s, 1H), 3.21 (s, 3H), 2.72 (s, 3H), 2.35 (s, 6H). | MS (ESI) calc'd for (C17H18ClN3O2) [M + 1]+, 332.1, found 332.1. |

| Ex. | Structure | 1H NMR | LCMS |
|---|---|---|---|
| 88 | 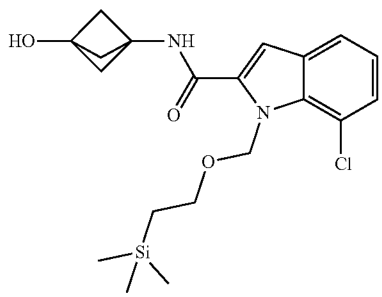 [SMILES: C[Si](C)(C)CCOCn1c(C(=O)NC23CC(O)(C2)C3)cc2cccc(Cl)c21] | 1H NMR (400 MHz, Methanol-d4) δ 7.65-7.58 (m, 1H), 7.36-7.30 (m, 1H), 7.18-7.09 (m, 2H), 6.29 (s, 2H), 3.60-3.51 (m, 2H), 3.49-3.41 (m, 2H), 3.22-3.12 (m, 2H), 1.75 (s, 2H), 0.85-0.76 (m, 2H), −0.10 (s, 9H). | MS (ESI) calc'd for (C20H27ClN2O3Si) [M + 1]+, 407.2, found 407.1. |
| 89 | 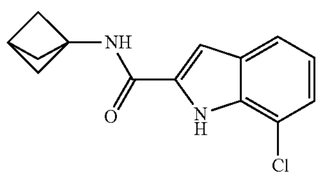 [SMILES: O=C(NC12CC(C1)C2)c1cc2cccc(Cl)c2[nH]1] | 1H NMR (300 MHz, Methanol-d4) δ 7.61-7.52 (m, 1H), 7.31-7.22 (m, 1H), 7.15 (s, 1H), 7.11-7.00 (m, 1H), 2.50 (s, 1H), 2.22 (s, 6H). | MS (ESI) calc'd for (C14H13ClN2O) [M + 1]+, 261.1; found, 261.1. |
| 90 | 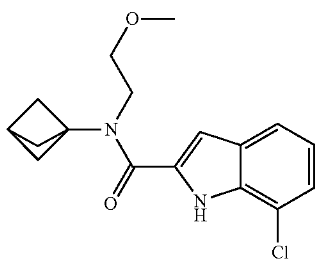 [SMILES: COCCN(C(=O)c1cc2cccc(Cl)c2[nH]1)C12CC(C1)C2] | 1H NMR (400 MHz, DMSO-d6) δ 7.58-7.56 (m, 1H), 7.26-7.24 (m, 1H), 7.07-7.03 (m, 1H), 6.77 (s, 1H), 3.67-3.64 (m, 2H), 3.50-3.48 (m, 2H), 3.33-3.27 (m, 3H), 2.42 (s, 1H), 2.04 (s, 6H). | MS (ESI) calc'd for (C17H19ClN2O2) [M + 1]+, 319.1, found 319.1. |
| 91 | 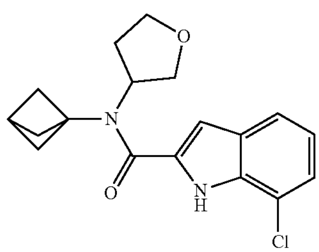 [SMILES: O=C(c1cc2cccc(Cl)c2[nH]1)N(C1CCOC1)C12CC(C1)C2] | 1H NMR (400 MHz, DMSO-d6) δ 11.87 (s, 1H), 7.58-7.57 (m, 1H), 7.26-7.24 (m, 1H), 7.07-7.03 (m, 1H), 6.71 (s, 1H), 4.64-4.52 (m, 1H), 4.06-3.96 (m, 1H), 3.90-3.78 (m, 2H), 3.70-3.60 (m, 1H), 2.36 (s, 1H), 2.28-2.09 (m, 2H), 2.08-1.97 (m, 6H). | MS (ESI) calc'd for C18H19ClN2O2 [M + 1]+, 331.1, found 331.0. |
| 92 | 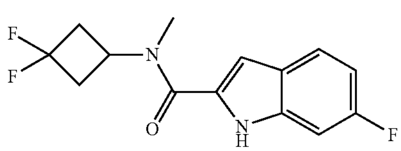 [SMILES: CN(C(=O)c1cc2ccc(F)cc2[nH]1)C1CC(F)(F)C1] | 1H NMR (400 MHz, Methanol-d4) δ 7.68-7.60 (m, 1H), 7.18-7.10 (m, 1H), 6.95-6.84 (m, 2H), 4.81 (s, 1H), 3.28 (s, 3H), 3.02-2.86 (m, 4H). | MS (ESI) calc'd for (C14H13F3N2O) [M + 1]+, 283.1; found, 283.1. |
| 93 | 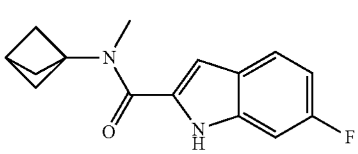 [SMILES: CN(C(=O)c1cc2ccc(F)cc2[nH]1)C12CC(C1)C2] | 1H NMR (400 MHz, Methanol-d4) δ 7.65-7.57 (m, 1H), 7.17-7.09 (m, 1H), 6.93-6.83 (m, 2H), 3.25 (s, 3H), 2.49 (s, 1H), 2.20 (s, 6H). | MS (ESI) calc'd for (C15H15FN2O) [M + 1]+, 259.1; found, 259.1. |
| 94 | 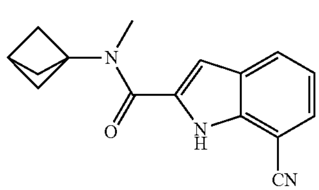 [SMILES: CN(C(=O)c1cc2cccc(C#N)c2[nH]1)C12CC(C1)C2] | 1H NMR (400 MHz, DMSO-d6) δ 11.79 (s, 1H), 7.98 (d, J = 8.0 Hz, 1H), 7.69 (d, J = 7.2 Hz, 1H), 7.26-7.17 (m, 1H), 6.89 (s, 1H), 3.05 (s, 3H), 2.43 (s, 1H), 2.03 (s, 6H). | MS (ESI) calc'd for (C16H15N3O) [M + 1]+, 266.1; found, 266.2. |

TABLE 1-continued

| Ex. | Structure | 1H NMR | LCMS |
|---|---|---|---|
| 95 | 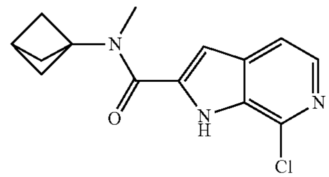 [SMILES: CN(C(=O)c1cc2ccnc(Cl)c2[nH]1)C12CC(C1)C2] | 1H NMR (400 MHz, Methanol-d4) δ 7.96-7.94 (m, 1H), 7.64-7.62 (m, 1H), 6.85 (s, 1H), 3.14 (s, 3H), 2.53-1.30 (s, 7H). | MS (ESI) calc'd for (C14H14ClN3O) [M + 1]+, 276.1; found, 276.2. |
| 96 | 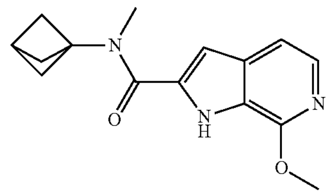 [SMILES: COc1nccc2cc(C(=O)N(C)C34CC(C3)C4)[nH]c12] | 1H NMR (400 MHz, Methanol-d4) δ 7.66-7.65 (m, 1H), 7.20-7.19 (m, 1H), 6.73 (s, 1H), 4.10 (s, 3H), 3.15 (s, 3H), 2.43 (s, 1H), 2.10-2.05 (m, 6H). | MS (ESI) calc'd for (C15H17N3O2) [M + 1]+, 272.1; found, 272.1. |
| 97 | 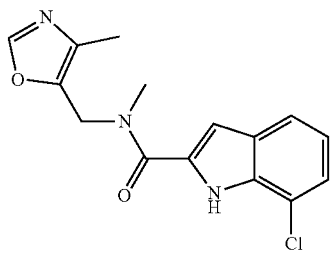 [SMILES: Cc1ncoc1CN(C)C(=O)c1cc2cccc(Cl)c2[nH]1] | 1H NMR (400 MHz, Methanol-d4) δ 8.14 (s, 1H), 7.63-7.56 (m, 1H), 7.31-7.24 (m, 1H), 7.12-7.04 (m, 1H), 6.99 (s, 1H), 4.90 (s, 2H), 3.57-3.33 (m, 1H), 3.02-2.96 (m, 2H), 2.23 (s, 3H). | MS (ESI) calc'd for (C15H14ClN3O2) [M + 1]+, 304.1, found 304.0. |
| 98 | 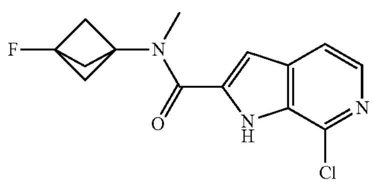 [SMILES: CN(C(=O)c1cc2ccnc(Cl)c2[nH]1)C12CC(F)(C1)C2] | 1H NMR (400 MHz, Methanol-d4) δ 7.99-7.93 (m, 1H), 7.67-7.61 (m, 1H), 6.92 (s, 1H), 3.21 (s, 3H), 2.47 (s, 6H). | MS (ESI) calc'd for (C14H13ClFN3O) [M + 1]+, 294.1, found 294.1. |
| 99 | 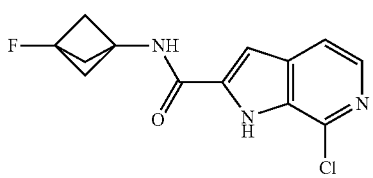 | 1H NMR (400 MHz, DMSO-d6) δ 12.29 (s, 1H), 9.40 (s, 1H), 7.96-7.95 (m, 1H), 7.67-7.66 (m, 1H), 7.23 (s, 1H), 2.67-2.33 (m, 6H). | MS (ESI) calc'd for (C13H11ClFN3O) [M + 1]+, 280.1; found, 280.1. |
| 100 | 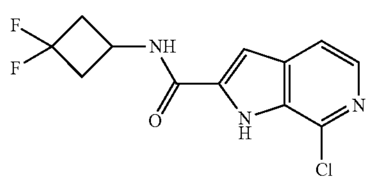 [SMILES: O=C(NC1CC(F)(F)C1)c1cc2ccnc(Cl)c2[nH]1] | 1H NMR (400 MHz, DMSO-d6) δ 12.34 (s, 1H), 9.07-9.06 (m, 1H), 7.97-7.96 (m, 1H), 7.68-7.67 (m, 1H), 7.25 (s, 1H), 4.38-4.26 (m, 1H), 3.10-2.95 (m, 2H), 2.87-2.69 (m, 2H). | MS (ESI) calc'd for (C12H10ClF2N3O) [M + 1]+, 286.0; found, 286.1. |
| 101 | 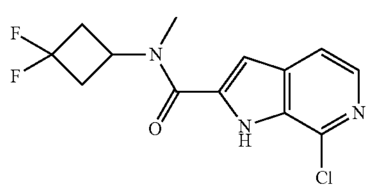 [SMILES: CN(C(=O)c1cc2ccnc(Cl)c2[nH]1)C1CC(F)(F)C1] | 1H NMR (400 MHz, DMSO-d6) δ 12.34 (s, 1H), 9.97-9.96 (m, 1H), 7.64-7.62 (m, 1H), 6.91 (s, 1H), 4.70-4.60 (m, 1H), 3.07 (s, 3H), 2.95-2.87 (m, 4H). | MS (ESI) calc'd for (C13H12ClF2N3O) [M + 1]+, 300.0; found, 300.1. |
| 102 | 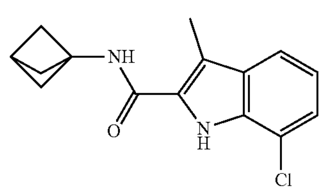 [SMILES: Cc1c(C(=O)NC23CC(C2)C3)[nH]c2c(Cl)cccc12] | 1H NMR (400 MHz, DMSO-d6) δ 11.15 (s, 1H), 8.82 (s, 1H), 7.60-7.58 (m, 1H), 7.32-7.30 (m, 1H), 7.08-7.04 (m, 1H), 2.67-2.50 (m, 4H), 2.15-2.08 (m, 6H). | MS (ESI) calc'd for (C15H15ClN2O) [M + 1]+, 275.0; found, 275.1. |

TABLE 1-continued

| Ex. | Structure | 1H NMR | LCMS |
|---|---|---|---|
| 103 | 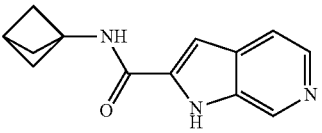 [SMILES: O=C(NC12CC(C1)C2)c1cc2ccncc2[nH]1] | 1H NMR (400 MHz, Methanol-d4) δ 8.82-8.77 (s, 1H), 8.24-8.04 (m, 1H), 7.69-7.63 (m, 1H), 7.14-7.10 (m, 1H), 2.54-2.49 (s, 1H), 2.26-2.21 (s, 6H). | MS (ESI) calc'd for (C13H13N3O) [M + 1]+, 228.1, found 228.1. |
| 104 | 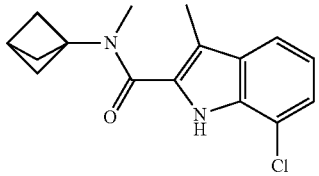 [SMILES: Cc1c(C(=O)N(C)C23CC(C2)C3)[nH]c2c(Cl)cccc12] | 1H NMR (400 MHz, Methanol-d4) δ 7.52-7.50 (m, 1H), 7.22-7.20 (m, 1H), 7.08-7.04 (m, 1H), 3.06 (s, 3H), 2.35 (s, 1H), 2.30 (s, 3H), 1.97 (s, 6H). | MS (ESI) calc'd for (C16H17ClN2O2) [M + 1]+ , 289.1; found, 289.2. |
| 105 | 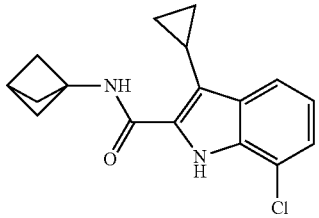 [SMILES: O=C(NC12CC(C1)C2)c1[nH]c2c(Cl)cccc2c1C1CC1] | 1H NMR (400 MHz, DMSO-d6) δ 11.17 (s, 1H), 8.73 (s, 1H), 7.52-7.50 (m, 1H), 7.28-7.26 (m, 1H), 7.03-6.99 (m, 1H), 2.71-2.60 (m, 2H), 2.13-2.08 (m, 6H), 0.97-0.93 (m, 4H). | MS (ESI) calc'd for (C17H17ClN2O) [M + 1]+, 301.1, found 301.1. |
| 106 | 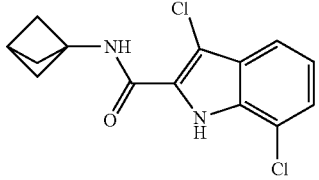 [SMILES: O=C(NC12CC(C1)C2)c1[nH]c2c(Cl)cccc2c1Cl] | 1H NMR (400 MHz, Methanol-d4) δ 7.61-7.55 (m, 1H), 7.40-7.34 (m, 1H), 7.22-7.14 (m, 1H), 2.53 (s, 1H), 2.25 (s, 6H) | MS (ESI) calc'd for (C14H12Cl2N2O) [M + 1]+, 295.0, found 294.9. |
| 107 | 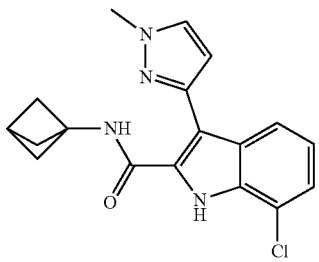 [SMILES: Cn1ccc(-c2c(C(=O)NC34CC(C3)C4)[nH]c3c(Cl)cccc23)n1] | 1H NMR (400 MHz, Methanol-d4) δ 7.87-7.81 (m, 1H), 7.81-7.76 (m, 1H), 7.38-7.31 (m, 1H), 7.19-7.11 (m, 1H), 6.80-6.75 (m, 1H), 4.02 (s, 3H), 2.54 (s, 1H), 2.24 (s, 6H). | MS (ESI) calc'd for (C18H17ClN4O) [M + 1]+, 341.1; found, 341.1. |
| 108 | 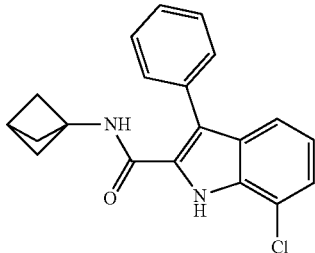 [SMILES: O=C(NC12CC(C1)C2)c1[nH]c2c(Cl)cccc2c1-c1ccccc1] | 1H NMR (400 MHz, Methanol-d4) δ 7.54-7.47 (m, 4H), 7.50-7.38 (m, 2H), 7.34-7.28 (m, 1H), 7.13-7.04 (m, 1H), 2.45 (s, 1H), 2.09 (s, 6H). | MS (ESI) calc'd for (C20H17ClN2O) [M + 1]+, 337.1; found, 337.1. |
| 109 | 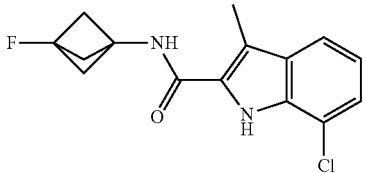 [SMILES: Cc1c(C(=O)NC23CC(F)(C2)C3)[nH]c2c(Cl)cccc12] | 1H NMR (400 MHz, Methanol-d4) δ 7.61-7.54 (m, 1H), 7.32-7.25 (m, 1H), 7.12-7.03 (m, 1H), 2.57 (s, 3H), 2.50-2.49 (m, 6H). | MS (ESI) calc'd for (C15H14ClFN2O) [M + 1]+, 293.1, found 293.2. |

TABLE 1-continued

| Ex. | Structure | 1H NMR | LCMS |
|---|---|---|---|
| 110 | 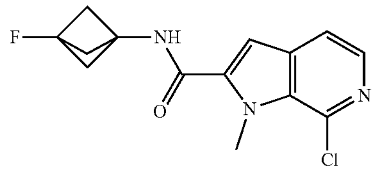 | 1H NMR (400 MHz, DMSO-d6) δ 9.51 (s, 1H), 7.97-7.96 (m, 1H), 7.67-7.65 (m, 1H), 7.12 (s, 1H), 4.30-4.27 (s, 3H), 2.33 (s, 6H). | MS (ESI) calc'd for (C14H13ClFN3O) [M + 1]+, 294.1, found 294.3. |
| 111 | 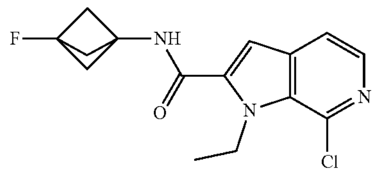 [SMILES: CCn1c(C(=O)NC23CC(F)(C2)C3)cc2ccnc(Cl)c21] | 1H NMR (400 MHz, Methanol-d4) δ 7.95-7.94 (m, 1H), 7.62-7.61 (m, 1H), 7.04 (s, 1H), 4,96-4.94 (m, 2H), 2.52-2.49 (m, 6H), 1.47-1.43 (m, 3H). | MS (ESI) calc'd for (C15H15ClFN3O) [M + 1]+, 308.1, found 308.3. |
| 112 | 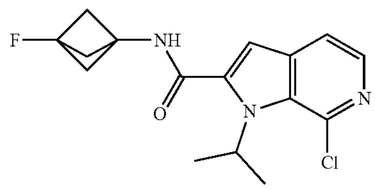 [SMILES: CC(C)n1c(C(=O)NC23CC(F)(C2)C3)cc2ccnc(Cl)c21] | 1H NMR (400 MHz, Methanol-d4) δ 7.97-7.91 (m, 1H), 7.63-7.57 (m, 1H), 6.87 (s, 1H), 5.90-5.79 (m, 1H), 2.52-2.47 (m, 6H), 1.72-1.66 (m, 6H). | MS (ESI) calc'd for (C16H17ClFN3O) [M + 1]+, 322.1; found, 322.1. |
| 113 | 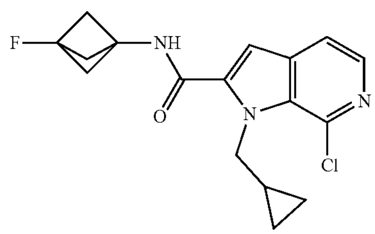 [SMILES: O=C(NC12CC(F)(C1)C2)c1cc2ccnc(Cl)c2n1CC1CC1] | 1H NMR (400 MHz, Methanol-d4) δ 8.00-7.94 (m, 1H), 7.68-7.62 (m, 1H), 7.05 (s, 1H), 4.95-4.89 (m, 2H), 2.52-2.47 (m, 6H), 1.32-1.17 (m, 1H), 0.52-0.41 (m, 2H), 0.43-0.31 (m, 2H). | MS (ESI) calc'd for (C17H17ClFN3O) [M + 1]+, 334.1; found, 334.0. |
| 114 | 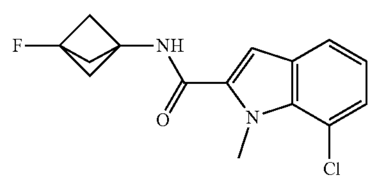 [SMILES: Cn1c(C(=O)NC23CC(F)(C2)C3)cc2cccc(Cl)c21] | 1H NMR (400 MHz, Methanol-d4) δ 7.59-7.52 (m, 1H), 7.29-7.23 (m, 1H), 7.08-7.00 (m, 1H), 6.99 (s, 1H), 4.31 (s, 3H), 2.48 (d, J = 2.4 Hz, 6H). | MS (ESI) calc'd for (C15H14ClFN2O) [M + 1]+, 293.1, found 293.2. |
| 115 | 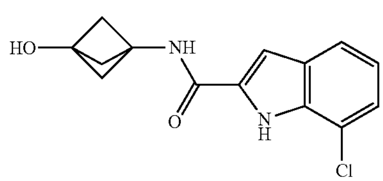 [SMILES: O=C(NC12CC(O)(C1)C2)c1cc2cccc(Cl)c2[nH]1] | 1H NMR (400 MHz, DMSO-d6) δ 10.69 (s, 1H), 8.99 (s, 1H), 7.61-7.59 (m, 1H), 7.30-7.28 (m, 1H), 7.16 (s, 1H), 7.08-7.04 (m, 1H), 6.27 (s, 1H), 2.16-2.02 (m, 6H). | MS (ESI) calc'd for (C14H13ClN2O2) [M + 1]+, 277.1, found 277.3. |
| 116 | 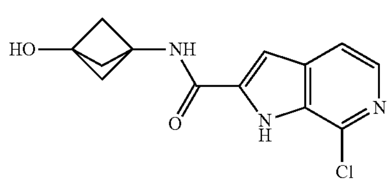 [SMILES: O=C(NC12CC(O)(C1)C2)c1cc2ccnc(Cl)c2[nH]1] | 1H NMR (400 MHz, Methanol-d4) δ 7.97-7.92 (m, 1H), 7.65-7.60 (m, 1H), 7.19 (s, 1H), 2.30 (s, 6H). | MS (ESI) calc'd for (C13H12ClN3O2) [M + 1]+, 278.1; found, 278.0. |
| 117 | 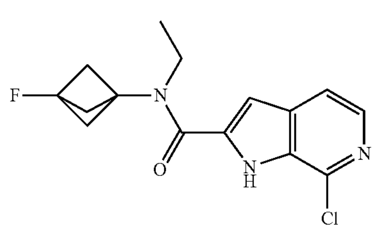 [SMILES: CCN(C(=O)c1cc2ccnc(Cl)c2[nH]1)C12CC(F)(C1)C2] | 1H NMR (400 MHz, Methanol-d4) δ 7.99-7.93 (m, 1H), 7.67-7.61 (m, 1H), 6.86 (s, 1H), 3.69-3.59 (m, 2H), 2.47 (s, 6H), 1.31-1.23 (m, 3H). | MS (ESI) calc'd for (C15H15ClFN3O) [M + 1]+, 308.1, found 308.2. |

TABLE 1-continued

| Ex. | Structure | 1H NMR | LCMS |
|---|---|---|---|
| 118 | 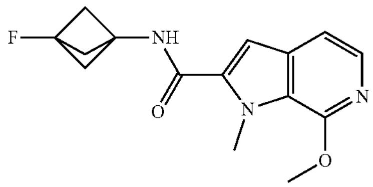 [SMILES: COc1nccc2cc(C(=O)NC34CC(F)(C3)C4)n(C)c12] | 1H NMR (400 MHz, Methanol-d4) δ 7.64-7.63 (m, 1H), 7.15-7.14 (m, 1H), 6.91 (s, 1H), 4.25 (s, 3H), 4.08 (s, 3H), 2.48-2.47 (m, 6H). | MS (ESI) calc'd for (C15H16FN3O2) [M + 1]+, 290.1; found, 290.1. |
| 119 | 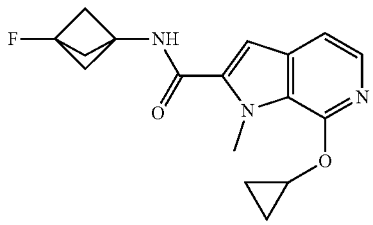 [SMILES: Cn1c(C(=O)NC23CC(F)(C2)C3)cc2ccnc(OC3CC3)c21] | 1H NMR (400 MHz, Methanol-d4) δ 7.70-7.64 (m, 1H), 7.23-7.17 (m, 1H), 6.93 (s, 1H), 4.44-4.35 (m, 1H), 4.18 (s, 3H), 2.50-2.45 (m, 6H), 0.95-0.80 (m, 4H). | MS (ESI) calc'd for (C17H18FN3O2) [M + 1]+, 316.1, found 316.2. |
| 120 | 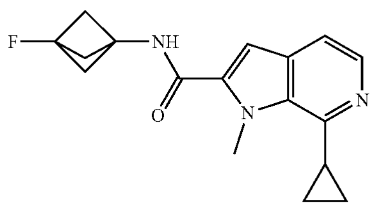 [SMILES: Cn1c(C(=O)NC23CC(F)(C2)C3)cc2ccnc(C3CC3)c21] | 1H NMR (400 MHz, Methanol-d4) δ 7.98-7.92 (m, 1H), 7.45-7.39 (m, 1H), 6.94 (s, 1H), 4.40 (s, 3H), 2.80-2.69 (m, 1H), 2.52-2.47 (m, 6H), 1.22-1.13 (m, 2H), 1.17-1.07 (m, 2H). | MS (ESI) calc'd for (C17H18FN3O) [M + 1]+, 300.1, found 300.2. |
| 121 | 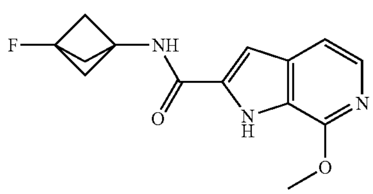 [SMILES: COc1nccc2cc(C(=O)NC34CC(F)(C3)C4)[nH]c12] | 1H NMR (400 MHz, Methanol-d4) δ 7.66-7.65 (m, 1H), 7.19-7.18 (m, 1H), 7.05 (s, 1H), 4.10 (s, 3H), 2.49-2.46 (m, 6H). | MS (ESI) calc'd for (C14H14FN3O2) [M + 1]+ , 276.1; found, 275.9. |
| 122 | 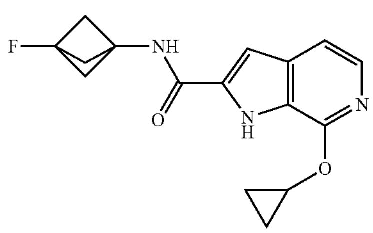 [SMILES: O=C(NC12CC(F)(C1)C2)c1cc2ccnc(OC3CC3)c2[nH]1] | 1H NMR (400 MHz, Methanol-d4) δ 7.13-7.11 (m, 1H), 6.95 (s, 1H), 6.68-6.66 (m, 1H), 6.06-5.96 (m, 1H), 5.23-5.21 (m, 1H), 5.15-5.11 (m, 1H), 4.76-4.66 (m, 2H), 2.64-2.47 (m, 6H). | MS (ESI) calc'd for (C16H16FN3O2) [M + 1]+, 302.1; found, 302.2. |
| 123 | 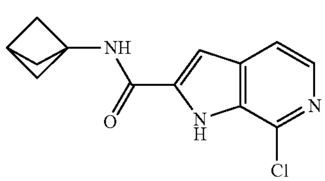 [SMILES: O=C(NC12CC(C1)C2)c1cc2ccnc(Cl)c2[nH]1] | 1H NMR (400 MHz, Methanol-d4) δ 7.95-7.94 (m, 3H), 7.63-7.62 (m, 1H), 7.18 (s, 1H), 2.52 (s, 1H), 2.24 (s, 6H). | MS (ESI) calc'd for (C13H12ClN3O) [M + 1]+, 262.1; found, 362.2. |
| 124 | 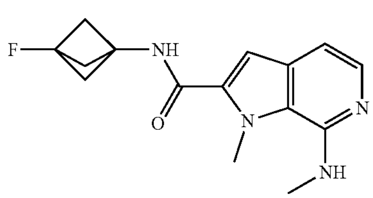 [SMILES: CNc1nccc2cc(C(=O)NC34CC(F)(C3)C4)n(C)c12] | 1H NMR (400 MHz, Methanol-d4) δ 7.54-7.52 (m, 1H), 6.91-6.86 (m, 2H), 4.26 (s, 3H), 3.05 (s, 3H), 2.48-2.47 (m, 6H). | MS (ESI) calc'd for (C15H17FN4O) [M + 1]+, 289.1; found, 289.2. |

TABLE 1-continued

| Ex. | Structure | 1H NMR | LCMS |
|---|---|---|---|
| 125 | 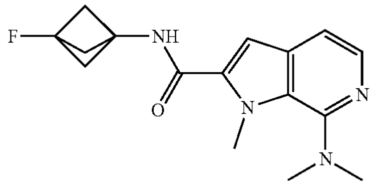 [SMILES: CN(C)c1nccc2cc(C(=O)NC34CC(F)(C3)C4)n(C)c12] | 1H NMR (400 MHz, Methanol-d4) δ 7.78-7.76 (m, 1H), 7.24-7.22 (m, 1H), 6.99 (s, 1H), 4.22 (s, 3H), 2.90 (s, 6H), 2.49-2.48 (m, 6H). | MS (ESI) calc'd for (C16H19FN4O) [M + 1]+, 303.2; found, 303.2 |
| 126 | 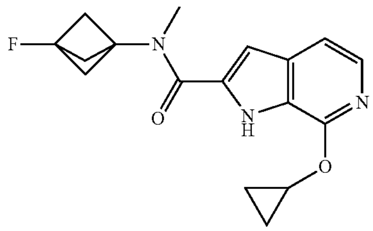 [SMILES: CN(C(=O)c1cc2ccnc(OC3CC3)c2[nH]1)C12CC(F)(C1)C2] | 1HNMR (400 MHz, Methanol-d4) δ 7.71-7.69 (m, 1H), 7.25-7.24 (m, 1H), 6.81 (s, 1H), 4.41-4.37 (m, 1H), 3.23 (s, 3H), 2.47 (s, 6H), 0.91-0.86 (m, 4H). | MS (ESI) calc'd for (C17H18FN3O2) [M + 1]+, 316.1; found, 316.1. |
| 127 | 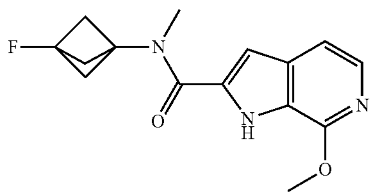 [SMILES: COc1nccc2cc(C(=O)N(C)C34CC(F)(C3)C4)[nH]c12] | 1H NMR (400 MHz, Methanol-d4) δ 7.70-7.64 (m, 1H), 7.24-7.18 (m, 1H), 6.81 (s, 1H), 4.10 (s, 3H), 3.24 (s, 3H), 2.48 (s, 6H). | MS (ESI) calc'd for (C15H16FN3O2) [M + 1]+, 290.1, found 290.3. |
| 128 | 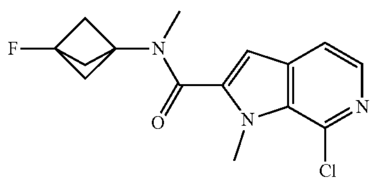 [SMILES: CN(C(=O)c1cc2ccnc(Cl)c2n1C)C12CC(F)(C1)C2] | 1H NMR (400 MHz, Methanol-d4) δ 7.98-7.92 (m, 1H), 7.65-7.59 (m, 1H), 6.77 (s, 1H), 4.12 (s, 3H), 3.12 (s, 3H), 2.47 (s, 6H). | MS (ESI) calc'd for (C15H15ClFN3O) [M + 1]+, 308.1, found 308.1. |
| 129 | 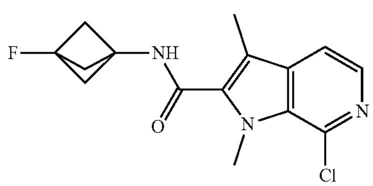 [SMILES: Cc1c(C(=O)NC23CC(F)(C2)C3)n(C)c2c(Cl)nccc12] | 1H NMR (400 MHz, Methanol-d4) δ 7.96-7.90 (m, 1H), 7.62-7.56 (m, 1H), 4.14 (s, 3H), 2.55-2.48 (m, 6H), 2.37 (s, 3H). | MS (ESI) calc'd for (C15H15ClFN3O) [M + 1]+, 308.1, found 308.1. |
| 130 | 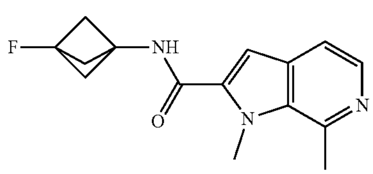 [SMILES: Cc1nccc2cc(C(=O)NC34CC(F)(C3)C4)n(C)c12] | 1H NMR (400 MHz, Methanol-d4) δ 7.99-7.93 (s, 1H), 7.50-7.44 (s, 1H), 6.96-6.92 (s, 1H), 4.30-4.25 (s, 3H), 3.02-2.98 (s, 3H), 2.52-2.47 (s, 6H). | MS (ESI) calc'd for (C15H16FN3O) [M + 1]+, 274.1, found 273.9. |
| 131 | 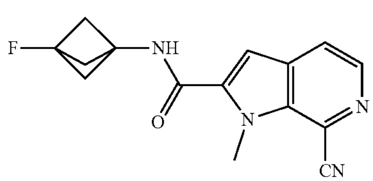 [SMILES: Cn1c(C(=O)NC23CC(F)(C2)C3)cc2ccnc(C#N)c21] | 1H NMR (400 MHz, DMSO-d6) δ 9.58 (s, 1H), 8.41-8.34 (m, 1H), 8.06-8.01 (m, 1H), 7.26 (s, 1H), 4.30 (s, 3H), 2.51-2.42 (m, 6H). | MS (ESI) calc'd for (C15H13FN4O2) [M + 1]+, 285.1, found 285.0. |
| 132 | 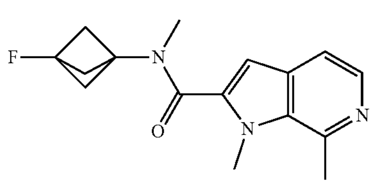 [SMILES: Cc1nccc2cc(C(=O)N(C)C34CC(F)(C3)C4)n(C)c12] | 1H NMR (400 MHz, Methanol-d4) δ 8.01-7.95 (m, 1H), 7.51-7.45 (m, 1H), 6.65 (s, 1H), 4.05 (s, 3H), 3.12 (s, 3H), 3.01 (s, 3H), 2.39 (s, 6H). | MS (ESI) calc'd for (C16H18FN3O) [M + 1]+, 288.1, found 288.1. |

TABLE 1-continued

| Ex. | Structure | 1H NMR | LCMS |
|---|---|---|---|
| 133 | 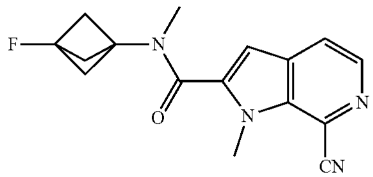 | 1H NMR (400 MHz, DMSO-d6) δ 8.39-8.33 (m, 1H), 8.00-7.94 (m, 1H), 6.92 (s, 1H), 4.02 (s, 3H), 3.32 (s, 3H), 3.03 (s, 1H), 2.18 (s, 3H). | MS (ESI) calc'd for (C16H15FN4O) [M + 1]+ 299.1; found, 299.1. |
| 134 | 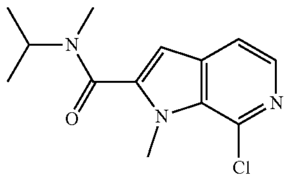 [SMILES: CC(C)N(C)C(=O)c1cc2ccnc(Cl)c2n1C] | 1H NMR (400 MHz, Methanol-d4) δ 7.94-7.92 (m, 1H), 7.60-7.59 (m, 1H), 6.74-6.73 (m, 1H), 4.29-4.11 (m, 3H), 4.07-4.00 (m, 1H), 3.05 (s, 2H), 2.92 (s, 1H), 1.35-1.16 (m, 6H). | MS (ESI) calc'd for (C13H16ClN3O) [M + 1]+, 266.1, found 266.1. |
| 135 | 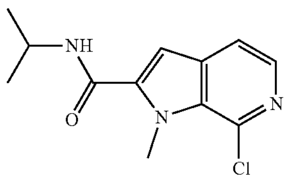 [SMILES: CC(C)NC(=O)c1cc2ccnc(Cl)c2n1C] | 1H NMR (400 MHz, Methanol-d4) δ 7.93-7.92 (m, 1H), 7.61-7.60 (m, 1H), 6.97 (s, 1H), 4.32-4.26 (m, 3H), 4.25-4.20 (m, 1H), 1.30-1.28 (m, 6H), | MS (ESI) calc'd for (C12H14ClN3O) [M + 1]+, 252.1; found, 252.0. |
| 136 | 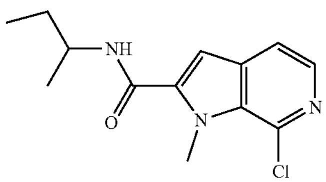 [SMILES: CCC(C)NC(=O)c1cc2ccnc(Cl)c2n1C] | 1H NMR (400 MHz, Methanol-d4) δ 7.93-7.91 (m, 1H), 7.61-7.60 (m, 1H), 6.97 (s, 1H), 4.32 (s, 3H), 4.10-4.01 (m, 1H), 1.69-1.58 (m, 2H), 1.30-1.26 (m, 3H), 1.06-0.97 (m, 3H). | MS (ESI) calc'd for (C13H16ClN3O) [M + 1]+, 266.1; found, 266.1. |
| 137 | 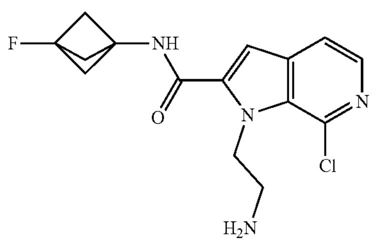 [SMILES: NCCn1c(C(=O)NC23CC(F)(C2)C3)cc2ccnc(Cl)c21] | 1H NMR (400 MHz, Methanol-d4) δ 8.01-7.95 (m, 1H), 7.68-7.62 (m, 1H), 7.08 (s, 1H), 4.98-4.90 (m, 2H), 3.19-3.11 (m, 2H), 2.53-2.48 (m, 6H). | MS (ESI) calc'd for (C15H16ClFN4O) [M + 1]+, 323.1, found 323.0. |
| 138 | 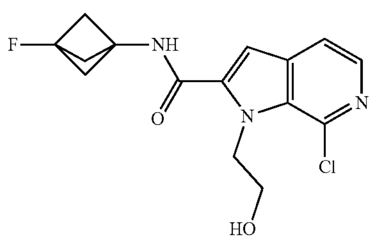 [SMILES: O=C(NC12CC(F)(C1)C2)c1cc2ccnc(Cl)c2n1CCO] | 1H NMR (400 MHz, Methanol-d4) δ 7.97-7.96 (m, 1H), 7.65-7.63 (m, 1H), 7.04 (s, 1H), 5.08-5.05 (m, 2H), 3.90-3.87 (m, 2H), 2.53-2.47 (m, 6H). | MS (ESI) calc'd for (C15H15ClFN3O2) [M + 1]+, 324.1; found, 324.1. |
| 139 | 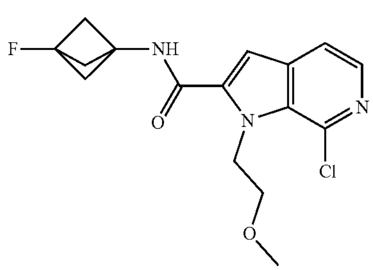 [SMILES: COCCn1c(C(=O)NC23CC(F)(C2)C3)cc2ccnc(Cl)c21] | 1H NMR (400 MHz, Methanol-d4) δ 7.97-7.96 (m, 1H), 7.63-7.62 (m, 1H), 7.00 (s, 1H), 5.18-5.15 (m, 2H), 3.68-3.65 (m, 2H), 3.23 (s, 3H), 2.49-2.48 (m, 6H) | MS (ESI) calc'd for (C16H17ClFN3O2) [M + 1]+, 338.1; found, 338.1. |

TABLE 1-continued

| Ex. | Structure | 1H NMR | LCMS |
|---|---|---|---|
| 140 | 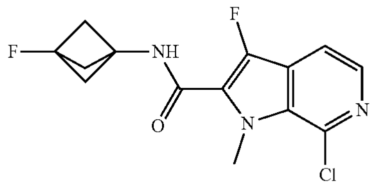 [SMILES: Cn1c(C(=O)NC23CC(F)(C2)C3)c(F)c2ccnc(Cl)c21] | 1H NMR (400 MHz, Methanol-d4) δ 8.01-7.95 (m, 1H), 7.66-7.60 (m, 1H), 4.27-4.23 (m, 3H), 2.54-2.49 (m, 6H). | MS (ESI) calc'd for (C14H12ClF2N3O) [M + 1]+, 312.1; found, 312.1. |
| 141 | 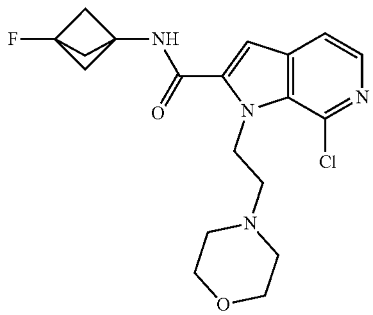 [SMILES: O=C(NC12CC(F)(C1)C2)c1cc2ccnc(Cl)c2n1CCN1CCOCC1] | 1H NMR (400 MHz, Methanol-d4) δ 7.98-7.95 (m, 1H), 7.63-7.62 (m, 1H), 7.04 (s, 1H), 5.12-5.09 (m, 2H), 3.63-3.59 (m, 4H), 2.74-2.71 (m, 2H), 2.52-2.49 (m, 6H), 2.49-2.42 (m, 4H). | MS (ESI) calc'd for (C19H22ClFN4O2) [M + 1]+, 393.1; found, 393.2. |
| 142 | 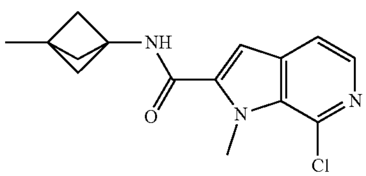 [SMILES: Cn1c(C(=O)NC23CC(C)(C2)C3)cc2ccnc(Cl)c21] | 1H NMR (400 MHz, Methanol-d4) δ 7.92-7.91 (m, 1H), 7.60-7.58 (m, 1H), 6.97 (s, 1H), 4.32 (s, 3H), 2.07 (s, 6H), 1.29 (s, 3H). | MS (ESI) calc'd for (C15H16ClN3O) [M + 1]+, 290.1; found, 290.1. |
| 143 | 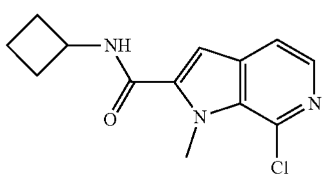 [SMILES: Cn1c(C(=O)NC2CCC2)cc2ccnc(Cl)c21] | 1H NMR (400 MHz, Methanol-d4) δ 7.93-7.92 (m, 1H), 7.61-7.60 (m, 1H), 7.00 (s, 1H), 4.57-4.31 (m, 1H), 4.31 (s, 3H), 2.43-2.35 (m, 2H), 2.20-2.10 (m, 2H), 1.86-1.82 (m, 2H). | MS (ESI) calc'd for (C13H14ClN3O) [M + 1]+, 264.0; found, 264.1. |
| 144 | 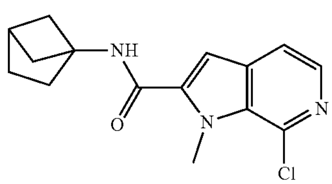 [SMILES: Cn1c(C(=O)NC23CCC(C2)C3)cc2ccnc(Cl)c21] | 1H NMR (400 MHz, Methanol-d4) δ 7.92-7.91 (m, 1H), 7.60-7.59 (m, 1H), 6.97 (s, 1H), 4.32 (s, 3H), 2.47-2.40 (m, 1H), 1.98-1.91 (m, 4H), 1.79-1.75 (m, 2H), 1.61-1.56 (m, 2H). | MS (ESI) calc'd for (C15H16ClN3O) [M + 1]+, 290.1; found, 290.1 |
| 145 | 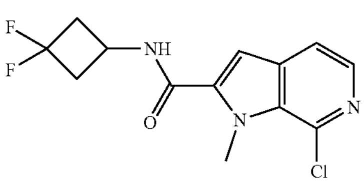 [SMILES: Cn1c(C(=O)NC2CC(F)(F)C2)cc2ccnc(Cl)c21] | 1H NMR (400 MHz, Methanol-d4) δ 7.94-7.92 (m, 1H), 7.62-7.60 (m, 1H), 7.05 (s, 1H), 4.40-4.33 (m, 4H), 3.09-2.99 (m, 2H), 2.82-2.76 (m, 2H). | MS (ESI) calc'd for (C13H12ClF2N3O) [M + 1]+, 300.1; found, 300.1 |
| 146 | 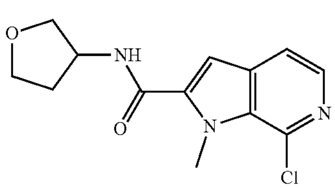 [SMILES: Cn1c(C(=O)NC2CCOC2)cc2ccnc(Cl)c21] | 1H NMR (400 MHz, Methanol-d4) δ 7.93-7.92 (m, 1H), 7.61-7.59 (m, 1H), 7.01 (s, 1H), 4.64-4.59 (m, 1H), 4.32 (s, 3H), 4.03-3.97 (m, 2H), 3.88-3.83 (m, 1H), 3.83-3.77 (m, 1H), 2.39-2.30 (m, 1H), 2.09-1.97 (m, 1H). | MS (ESI) calc'd for (C13H14ClN3O2) [M + 1]+, 280.1; found, 280.1. |

TABLE 1-continued

| Ex. | Structure | 1H NMR | LCMS |
|---|---|---|---|
| 147 | 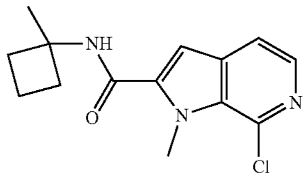 [SMILES: Cn1c(C(=O)NC2(C)CCC2)cc2ccnc(Cl)c21] | 1H NMR (400 MHz, Methanol-d4) δ 7.92-7.91 (m, 1H), 7.60-7.59 (m, 1H), 6.96 (s, 1H), 4.31 (s, 3H), 2.50-2.42 (m, 2H), 2.17-2.11 (m, 2H), 1.99-1.93 (m, 2H), 1.60 (s, 3H). | MS (ESI) calc'd for (C14H16ClN3O) [M + 1]+, 278.1; found, 278.1 |
| 148 | 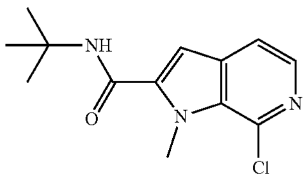 [SMILES: Cn1c(C(=O)NC(C)(C)C)cc2ccnc(Cl)c21] | 1H NMR (400 MHz, Methanol-d4) δ 7.95-7.89 (m, 1H), 7.63-7.57 (m, 1H), 6.90 (s, 1H), 4.27 (s, 3H), 1.50 (s, 9H). | MS (ESI) calc'd for (C13H16ClN3O) [M + 1]+, 266.1, found 266.1. |
| 149 | 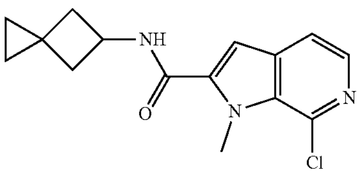 [SMILES: Cn1c(C(=O)NC2CC3(CC3)C2)cc2ccnc(Cl)c21] | 1H NMR (400 MHz, DMSO-d6) δ 9.11-9.09 (m, 1H), 7.97-7.96 (m, 1H), 7.67-7.66 (m, 1H), 7.11 (s, 1H), 4.62-4.56 (m, 1H), 4.26 (s, 3H), 2.43-2.38 (m, 2H), 2.29-2.22 (m, 2H), 0.52-0.49 (m, 2H), 0.46-0.37 (m, 2H). | MS (ESI) calc'd for (C15H16ClN3O) [M + 1]+, 290.1; found, 290.1. |
| 150 | 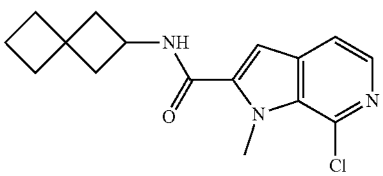 [SMILES: Cn1c(C(=O)NC2CC3(CCC3)C2)cc2ccnc(Cl)c21] | 1H NMR (400 MHz, DMSO-d6) δ 8.94-8.92 (m, 1H), 7.96-7.95 (m, 1H), 7.65-7.64 (m, 1H), 7.07 (s, 1H), 4.32-4.24 (m, 4H), 2.37-2.32 (m, 2H), 2.07-2.03 (m, 4H), 1.95-1.91 (m, 2H), 1.84-1.77 (m, 2H). | MS (ESI) calc'd for (C16H18ClN3O) [M + 1]+, 304.1; found, 304.1 |
| 151 | 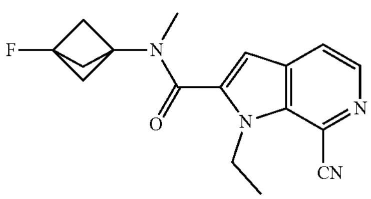 [SMILES: CCn1c(C(=O)N(C)C23CC(F)(C2)C3)cc2ccnc(C#N)c21] | $^1$H NMR (400 MHz, Methanol-d$_4$) δ 8.37-8.32 (m, 1H), 7.97-7.92 (m, 1H), 6.89 (s, 1H), 4.87 (s, 2H), 3.13 (s, 3H), 2.48 (s, 6H), 1.56-1.48 (m, 3H). | MS (ESI) calculated for (C$_{17}$H$_{17}$FN$_4$O) [M + 1]$^+$, 313.2; found, 313.2. |
| 152 | 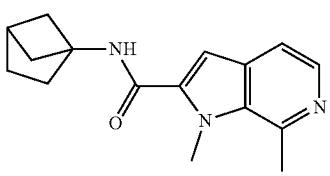 [SMILES: Cc1nccc2cc(C(=O)NC34CCC(C3)C4)n(C)c12] | $^1$H NMR (400 MHz, DMSO-d$_6$) δ 9.02-8.98 (s, 1H), 8.00-7.94 (s, 1H), 7.43-7.37 (s, 1H), 6.97-6.92 (s, 1H), 4.23-4.18 (s, 3H), 2.95-2.91 (s, 3H), 2.37-2.33 (s, 1H), 1.91-1.87 (s, 2H), 1.86-1.78 (s, 2H), 1.69-1.63 (s, 2H), 1.47-1.42 (m, 2H). | MS (ESI) calc'd for (C$_{16}$H$_{19}$N$_3$O) [M + 1]$^+$, 270.1, found 270.0. |
| 153 | 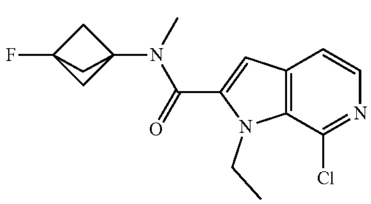 | $^1$H NMR (400 MHz, Methanol-d$_4$) δ 8.00-7.94 (m, 1H), 7.66-7.60 (m, 1H), 6.77 (s, 1H), 4.85 (s, 2H), 3.11 (s, 3H), 2.45 (s, 6H), 1.49-1.41 (m, 3H). | MS (ESI) calc'd for (C$_{16}$H$_{17}$ClFN$_3$O) [M + 1]$^+$, 322.1, found 322.1. |
| 154 | 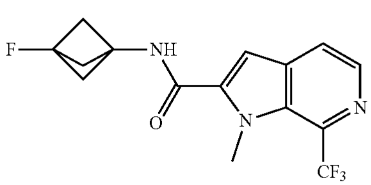 [SMILES: Cn1c(C(=O)NC23CC(F)(C2)C3)cc2ccnc(C(F)(F)F)c21] | $^1$H NMR (400 MHz, Methanol-d$_4$) δ 8.31-8.26 (m, 1H), 7.96-7.90 (m, 1H), 7.14 (s, 1H), 4.16-4.10 (m, 3H), 2.53-2.48 (m, 6H). | MS (ESI) calculated for (C$_{15}$H$_{13}$F$_4$N$_3$O) [M + 1]$^+$, 328.1; found, 328.0. |

TABLE 1-continued

| Ex. | Structure | 1H NMR | LCMS |
|---|---|---|---|
| 155 | 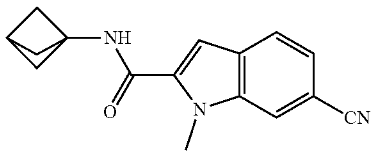 [SMILES: Cn1c(C(=O)NC23CC(C2)C3)cc2ccc(C#N)cc21] | ¹H NMR (400 MHz, Methanol-d₄) δ 8.01-7.96 (m, 1H), 7.81-7.74 (m, 1H), 7.41-7.34 (m, 1H), 7.10-7.05 (m, 1H), 4.05 (s, 3H), 2.51 (s, 1H), 2.22 (s, 6H). | MS (ESI) calc'd for (C₁₆H₁₅N₃O) [M + 1]⁺, 266.1, found 266.2. |
| 156 | 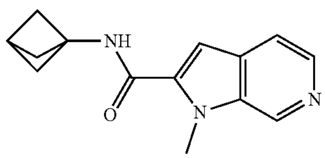 [SMILES: Cn1c(C(=O)NC23CC(C2)C3)cc2ccncc21] | ¹H NMR (400 MHz, Methanol-d₄) δ 8.89-8.84 (m, 1H), 8.19-8.13 (m, 1H), 7.68-7.61 (m, 1H), 7.05-7.00 (m, 1H), 4.12 (s, 3H), 2.52 (s, 1H), 2.23 (s, 6H). | MS (ESI) calc'd for (C₁₄H₁₅N₃O) [M + 1]⁺, 242.3, found 242.0. |
| 157 | 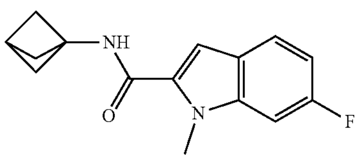 [SMILES: Cn1c(C(=O)NC23CC(C2)C3)cc2ccc(F)cc21] | ¹H NMR (400 MHz, Methanol-d₄) δ 7.63-7.55 (m, 1H), 7.23-7.15 (m, 1H), 7.01 (s, 1H), 6.95-6.86 (m, 1H), 3.96 (s, 3H), 2.50 (s, 1H), 2.21 (s, 6H). | MS (ESI) calculated for (C₁₅H₁₅FN₂O) [M + 1]⁺, 259.1; found, 259.0. |
| 158 | 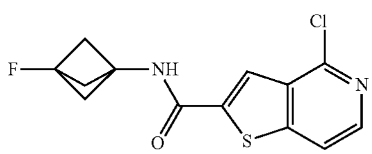 [SMILES: O=C(NC12CC(F)(C1)C2)c1cc2c(Cl)nccc2s1] | ¹H NMR (400 MHz, Methanol-d₄) δ 8.30-8.24 (m, 1H), 8.21-8.15 (m, 1H), 8.01-7.94 (m, 1H), 2.55-2.47 (m, 6H). | MS (ESI) calc'd for (C₁₃H₁₀ClFN₂OS) [M + 1]⁺, 297.0, found 297.0. |
| 159 | 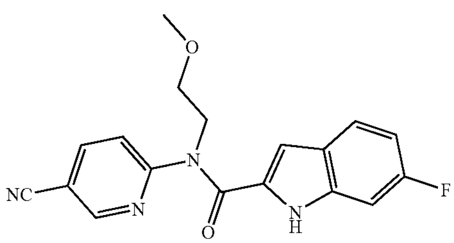 [SMILES: COCCN(C(=O)c1cc2ccc(F)cc2[nH]1)c1ccc(C#N)cn1] | | |
| 160 | 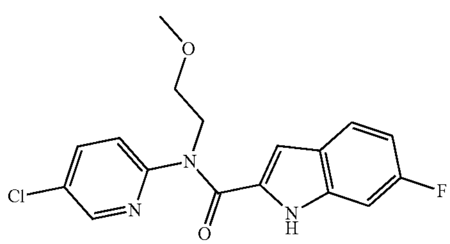 [SMILES: COCCN(C(=O)c1cc2ccc(F)cc2[nH]1)c1ccc(Cl)cn1] | | |
| 161 | 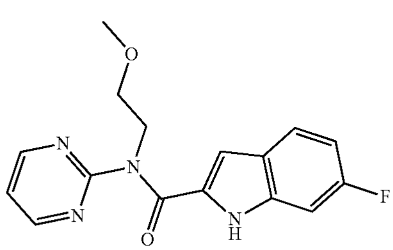 [SMILES: COCCN(C(=O)c1cc2ccc(F)cc2[nH]1)c1ncccn1] | | |

Example B: Biological Assay

LNCaP cells expressing ARR2PB-FireflyLuc and CMV-RenillaLuc were treated with indicated concentrations of test compounds, enzalutamide (negative control), or DHT (positive control)+/−0.5 nM DHT for 48 h at 37° C. Fluorescent signals were read with the ImageXpress Micro Confocal System. Remaining activity (antagonist mode) was calculated as % Remaining Activity=100×[(Read$_{Sample}$−LC$_{ave}$)/(HC$_{ave}$−LC$_{ave}$)] where HC is cells treated with 0.5 nM DHT only and LC is cells treated with 10 uM enzalutamide+0.5 nM DHT. Activation (agonist mode) was calculated as % Activation=100×[(ReadSample−LC$_{ave}$)/(HC$_{ave}$−LC$_{ave}$)] where HO is cells treated with 1 uM DHT and LC is cells treated with DMSO. Dose response curves and IC$_{50}$ values were calculated using non-linear regression analysis in XLfit.

IC$_{50}$ values for the compounds provided herein are shown in Table 4 below. The designation "A" indicates an IC$_{50}$ value of >10 μM, "B" indicates an IC$_{50}$ value between 1 μM and 10 μM; "C" indicates an IC$_{50}$ value between 100 nM and 1 μM; and "D" indicates an IC$_{50}$ value of less than 100 nM.

TABLE 2

| Cmpd No. | LNCap Antagonist Archive: IC$_{50}$ (nM) |
|---|---|
| 1 | A |
| 2 | A |
| 3 | B |
| 4 | A |
| 5 | B |
| 6 | B |
| 7 | A |
| 8 | B |
| 9 | B |
| 10 | B |
| 11 | C |
| 12 | B |
| 13 | B |
| 14 | A |
| 15 | A |
| 16 | A |
| 17 | B |
| 19 | C |
| 20 | B |
| 21 | C |
| 22 | A |
| 23 | A |
| 24 | B |
| 25 | C |
| 26 | C |
| 27 | B |
| 28 | B |
| 29 | B |
| 30 | C |
| 31 | C |
| 32 | B |
| 33 | B |
| 34 | A |
| 35 | B |
| 36 | B |
| 37 | A |
| 38 | A |
| 39 | B |
| 40 | A |
| 41 | A |
| 42 | A |
| 43 | A |
| 44 | A |
| 45 | A |
| 47 | A |
| 49 | A |
| 51 | B |
| 52 | A |
| 53 | A |
| 54 | A |
| 55 | C |
| 56 | C |
| 57 | A |
| 58 | C |
| 59 | C |
| 60 | A |
| 61 | C |
| 62 | B |
| 63 | A |
| 64 | B |
| 65 | B |
| 66 | B |
| 67 | C |
| 68 | B |
| 69 | A |
| 70 | B |
| 71 | A |
| 72 | A |
| 73 | A |
| 74 | B |
| 75 | A |
| 76 | B |
| 77 | A |
| 78 | B |
| 79 | B |
| 80 | B |
| 81 | B |
| 82 | C |
| 83 | D |
| 84 | C |
| 85 | D |
| 86 | B |
| 88 | B |
| 89 | C |
| 90 | B |
| 92 | C |
| 93 | C |
| 94 | B |
| 95 | C |
| 96 | B |
| 97 | A |
| 98 | C |
| 99 | B |
| 100 | C |
| 101 | B |
| 102 | C |
| 103 | A |
| 104 | A |
| 105 | B |
| 106 | B |
| 107 | A |
| 108 | B |
| 109 | C |
| 110 | C |
| 111 | D |
| 113 | C |
| 114 | D |
| 115 | A |
| 116 | A |
| 117 | C |
| 118 | B |
| 119 | A |
| 120 | B |
| 122 | A |
| 124 | A |
| 125 | B |
| 126 | A |
| 128 | D |
| 128 | C |
| 129 | A |
| 130 | B |
| 131 | C |
| 132 | B |
| 133 | C |
| 134 | C |

TABLE 2-continued

| Cmpd No. | LNCap Antagonist Archive: IC$_{50}$ (nM) |
|---|---|
| 137 | A |
| 138 | B |
| 139 | B |
| 140 | C |
| 141 | A |
| 142 | B |
| 143 | C |
| 146 | C |
| 146 | B |
| 147 | C |
| 148 | C |
| 149 | B |
| 150 | B |
| 151 | C |
| 152 | B |
| 153 | D |
| 154 | B |
| 155 | B |
| 156 | C |
| 157 | B |
| 158 | C |
| 159 | B |
| 160 | B |
| 161 | B |
| 162 | C |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A compound of Formula I:

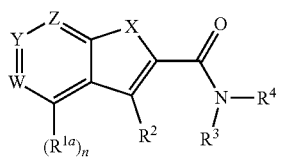

(I)

or a pharmaceutically acceptable salt thereof;
wherein
X is O, S, or NR$^5$;
W, Y, and Z are each independently selected from the group consisting of CH, CR$^1$, and N;
each R$^1$ is independently selected from the group consisting of halo, CN, C$_{1-6}$ alkyl, C$_{1-6}$ haloalkyl, C$_{1-6}$ alkoxy, C$_{1-6}$ alkyl-NH$_2$, C$_{3-10}$ cycloalkyl, O(C$_{3-10}$ cycloalkyl), NH$_2$, NH(C$_{1-6}$ alkyl), and N(C$_{1-6}$ alkyl)$_2$;
R$^{1a}$ is selected from the group consisting of halo, CN, C$_{1-6}$ alkyl, C$_{1-6}$ haloalkyl, C$_{1-6}$ alkoxy, C$_{1-6}$ alkyl-NH$_2$, C$_{3-10}$ cycloalkyl, O(C$_{3-10}$ cycloalkyl), NH$_2$, NH(C$_{1-6}$ alkyl), and N(C$_{1-6}$ alkyl)$_2$;
R$^2$ is selected from the group consisting of H, halo, C$_{1-6}$ alkyl, 5-10 membered heteroaryl, C$_{3-10}$ cycloalkyl, C$_{6-10}$ aryl, wherein heteroaryl, cycloalkyl, and aryl are each optionally substituted one, two, or three times with R$^6$;
R$^3$ is selected from the group consisting of H, C$_{1-6}$ alkyl, 3-10 membered heterocycloalkyl, wherein C$_{1-6}$ alkyl is optionally substituted one, two, or three times with R$^7$;
R$^4$ is

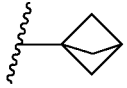

optionally substituted one, two, three or four times with R$^8$;
R$^5$ is selected from the group consisting of H, C$_{1-6}$ alkyl, C$_{1-6}$ alkyl-O—C$_{1-6}$ alkyl-TMS, C$_{1-6}$ alkyl-C$_{3-10}$ cycloalkyl, C$_{1-6}$ alkyl-OH, C$_{1-6}$ alkyl-O—C$_{1-6}$ alkyl, C$_{1-6}$ alkyl-(3-10 membered heterocycloalkyl), and C$_{1-6}$ alkyl-NH$_2$;
alternatively, when Z is CR$^1$, then R$^5$ and R$^1$, together with the atoms to which they are attached, optionally form a 4-7 membered heterocyclic ring;
each R$^6$ is independently selected from the group consisting of C$_{1-6}$ alkyl, NH$_2$, NH(C$_{1-6}$ alkyl), and N(C$_{1-6}$ alkyl)$_2$;
each R$^7$ is independently selected from the group consisting of O—C$_{1-6}$ alkyl, NH$_2$, NH(C$_{1-6}$ alkyl), N(C$_{1-6}$ alkyl)$_2$, and C$_{3-10}$ cycloalkyl;
each R$^8$ is independently selected from the group consisting of 5-10 membered heteroaryl, 3-10 membered heterocycloalkyl, C$_{3-10}$ cycloalkyl, CN, halo, C$_{1-6}$ alkyl, and OH, wherein heteroaryl is optionally substituted with C$_{1-4}$ alkyl; and
n is 0 or 1.

2. The compound of claim 1, wherein
X is NR$^5$;
W, Y, and Z are each independently selected from the group consisting of CH, CR$^1$, and N;
each R$^1$ is independently selected from the group consisting of halo, CN, and C$_{1-6}$ alkoxy;
R$^{1a}$ is halo;
R$^2$ is H;
R$^3$ is selected from the group consisting of H, C$_{1-6}$ alkyl, 3-10 membered heterocycloalkyl, wherein C$_{1-6}$ alkyl is optionally substituted one, two, or three times with R$^7$;
R$^4$ is

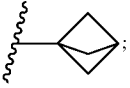

wherein R$^4$ is optionally substituted with one, two, three, or four substituents selected from the group consisting of CN, halo, C$_{1-4}$ alkyl, and OH;
R$^5$ is H or C$_{1-6}$ alkyl;
each R$^7$ is independently selected from the group consisting of O—C$_{1-6}$ alkyl, NH$_2$, NH(C$_{1-6}$ alkyl), N(C$_{1-6}$ alkyl)$_2$, and C$_{3-10}$ cycloalkyl;
and
n is 0 or 1.

3. The compound of claim 1, wherein each R$^1$ is independently selected from the group consisting of halo, CN, and C$_{1-6}$ alkoxy.

4. The compound of claim 1, wherein R$^{1a}$ is halo.

5. The compound of claim 1, wherein n is 0.

6. The compound of claim 1, wherein R$^2$ is selected from the group consisting of H, halo, C$_{1-3}$ alkyl, C$_{3-6}$ cycloalkyl, 5-membered heteroaryl, and phenyl, wherein heteroaryl is optionally substituted with C$_{1-3}$ alkyl.

7. The compound of claim 1, wherein $R^3$ is H, $C_{1-4}$ alkyl, $C_{1-6}$ alkyl-O—$C_{1-3}$ alkyl, $C_{1-6}$ alkyl-NH$_2$, $C_{1-6}$ alkyl-$C_{3-6}$ cycloalkyl, and 5-membered heteroaryl.

8. The compound of claim 1, wherein $R^5$ is selected from the group consisting of H, $C_{1-6}$ alkyl, $C_{1-3}$ alkyl-O—$C_{1-3}$ alkyl-TMS, $C_{1-3}$ alkyl-cyclopropyl, $C_{1-3}$ alkyl-OH, $C_{1-3}$ alkyl-O—$C_{1-3}$ alkyl, $C_{1-3}$ alkyl(5-7 membered heterocycloalkyl), and $C_{1-3}$ alkyl-NH$_2$.

9. The compound of claim 1, wherein the compound of Formula I is a compound of Formula Ia:

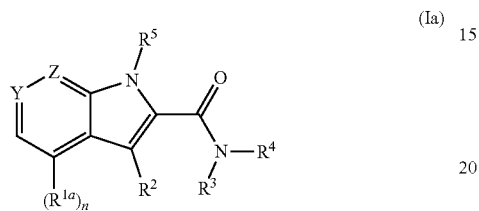

or a pharmaceutically acceptable salt thereof.

10. The compound of claim 1, wherein the compound of Formula I is a compound of Formula Ic:

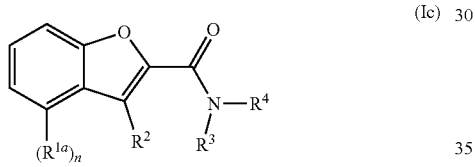

or a pharmaceutically acceptable salt thereof.

11. The compound of claim 1, wherein the compound of Formula I is selected from the group consisting of or a pharmaceutically acceptable salt thereof

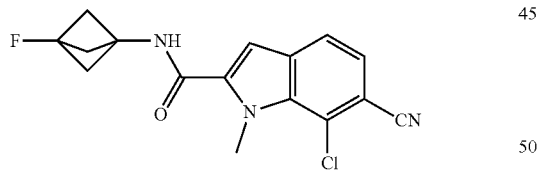

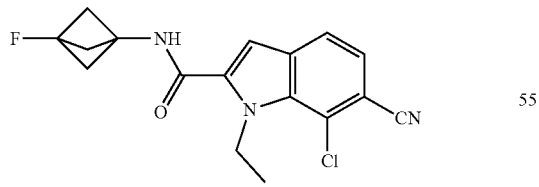

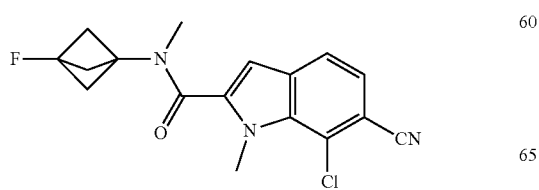

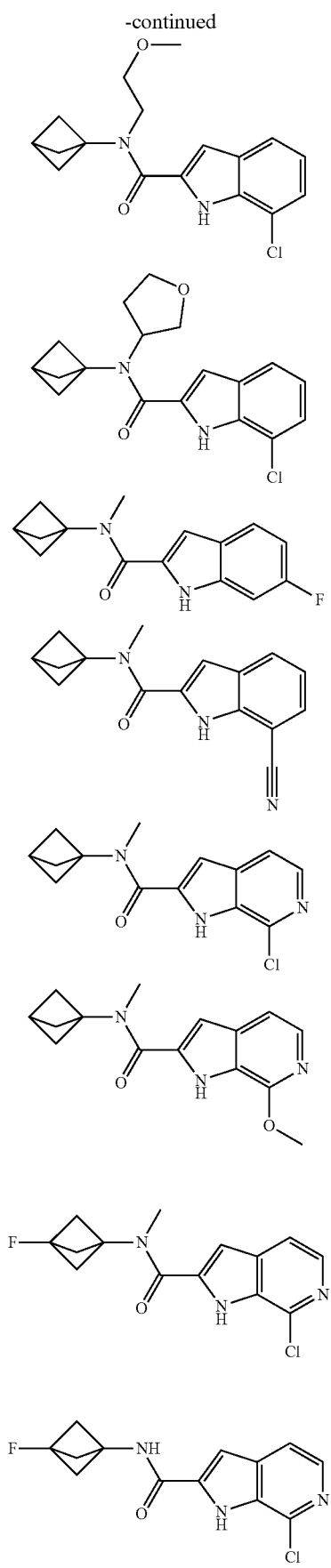
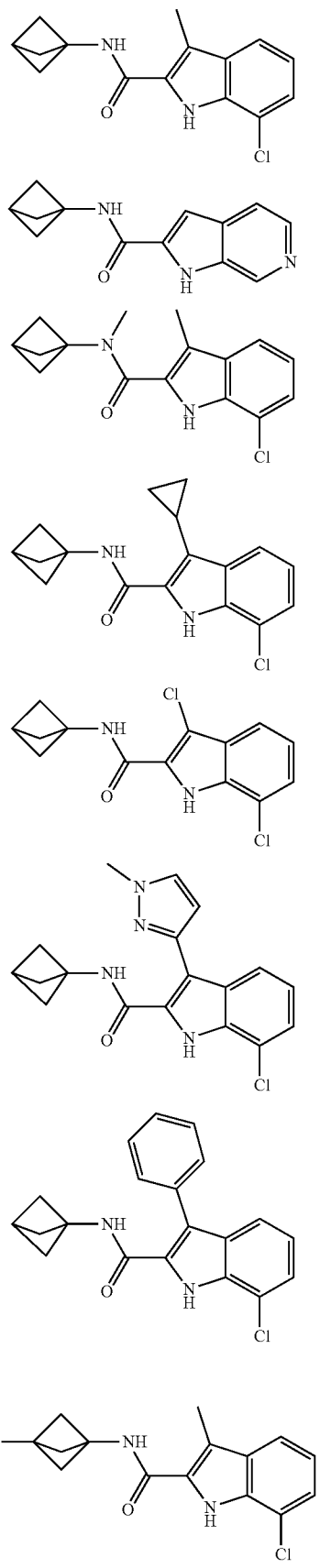

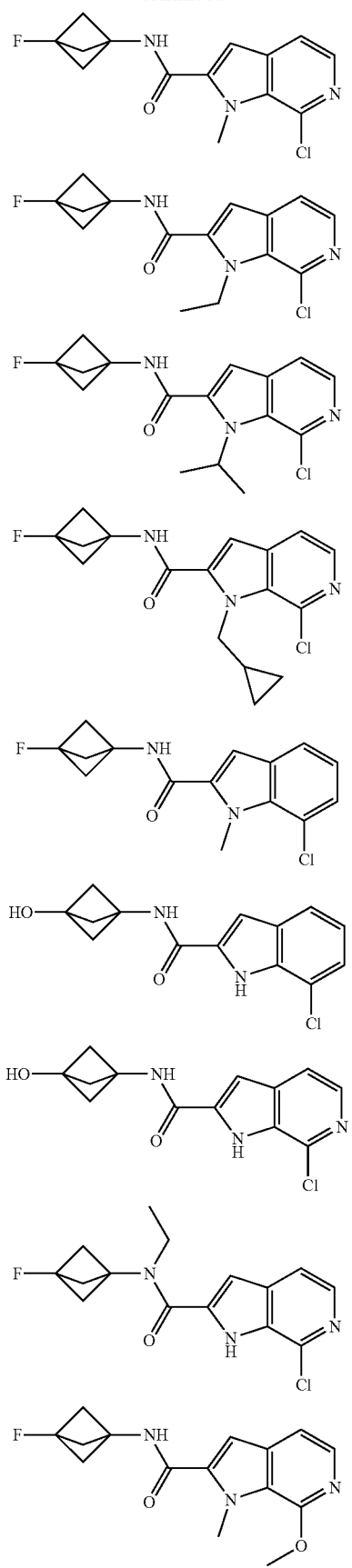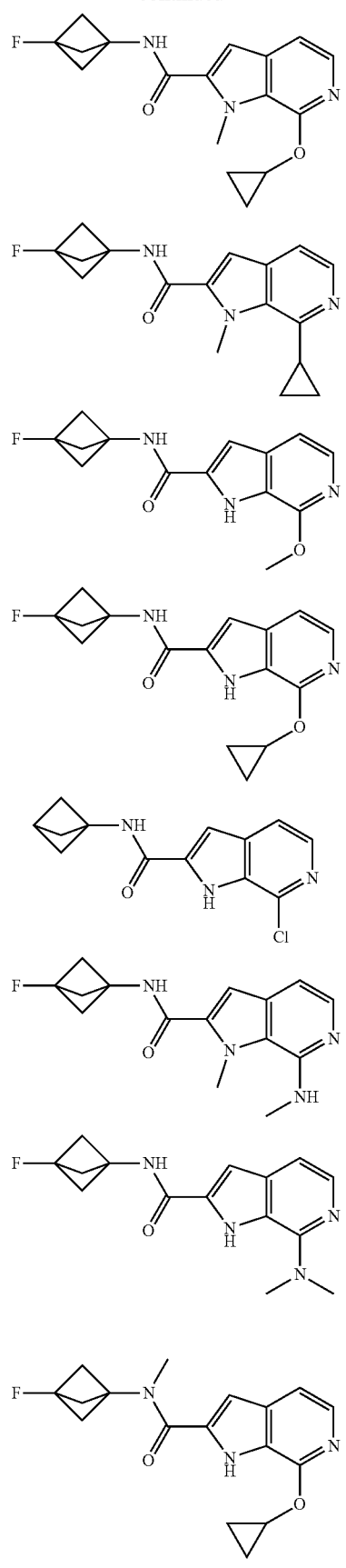

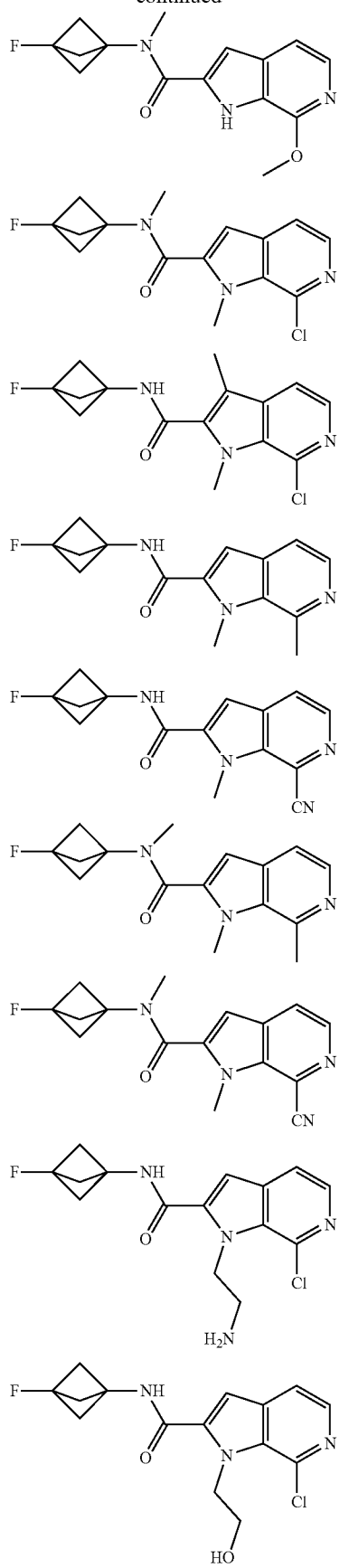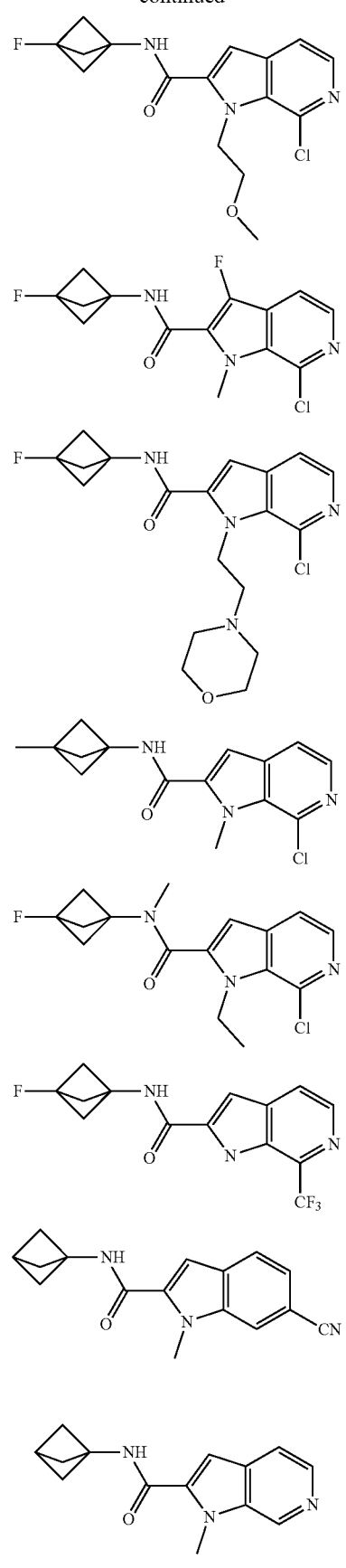

-continued
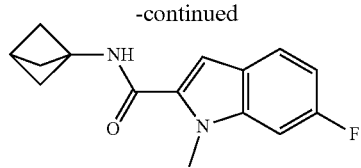
5
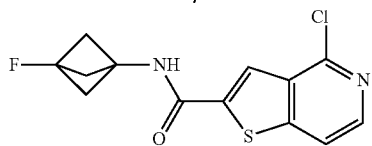
10
12. The compound of claim 1, wherein the compound of Formula I is
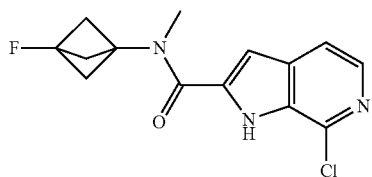 [SMILES: CN(C(=O)c1cc2ccnc(Cl)c2[nH]1)C12CC(F)(C1)C2]
or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 12,012,398 B2 |
| APPLICATION NO. | : 17/811731 |
| DATED | : June 18, 2024 |
| INVENTOR(S) | : Bakary-Barry Toure et al. |

It is certified that error appears in the above-identified patent and that said Letters Patent is hereby corrected as shown below:

In the Claims

Claim 11, Column 149, Lines 41-42 should read:
-- Formula I is selected from the group consisting of --

Claim 11, Column 157, Line 13 should read:
-- or a pharmaceutically acceptable salt thereof. --

Signed and Sealed this
Twenty-seventh Day of August, 2024

Katherine Kelly Vidal
*Director of the United States Patent and Trademark Office*